United States Patent
Nielsen et al.

(10) Patent No.: US 11,512,300 B2
(45) Date of Patent: *Nov. 29, 2022

(54) XANTHAN LYASE VARIANTS AND POLYNUCLEOTIDES ENCODING SAME

(71) Applicant: NOVOZYMES A/S, Bagsvaerd (DK)

(72) Inventors: Jens Erik Nielsen, Bagsvaerd (DK); Allan Svendsen, Hoersholm (DK); Lars Anderson, Malmoe (SE); Rune Nygaard Monrad, Hileroed (DK); Rajendra Kulothungan Sainathan, Bangalore (IN); Pernille F. Jensen, Taastrup (DK); Kasper D. Rand, Frederiksberg (DK); Geetha Hiremath Mendez, Bangalore (IN); Sohel Dalal, Ahmedabad (IN); Shilpi Agarwal, Bangalore (IN)

(73) Assignee: NOVOZYMES A/S, Bagsvaerd (DK)

( * ) Notice: Subject to any disclaimer, the term of this patent is extended or adjusted under 35 U.S.C. 154(b) by 0 days.

This patent is subject to a terminal disclaimer.

(21) Appl. No.: 16/327,051

(22) PCT Filed: Aug. 24, 2017

(86) PCT No.: PCT/EP2017/071277
§ 371 (c)(1),
(2) Date: Feb. 21, 2019

(87) PCT Pub. No.: WO2018/037061
PCT Pub. Date: Mar. 1, 2018

(65) Prior Publication Data
US 2019/0185841 A1   Jun. 20, 2019

(30) Foreign Application Priority Data

Aug. 24, 2016   (IN) .............................. 201641028779

(51) Int. Cl.
| | | |
|---|---|---|
| *C12N 9/88* | (2006.01) | |
| *C11D 3/386* | (2006.01) | |
| *C09K 8/035* | (2006.01) | |

(52) U.S. Cl.
CPC ................ *C12N 9/88* (2013.01); *C09K 8/035* (2013.01); *C11D 3/38636* (2013.01); *C12Y 402/02012* (2013.01)

(58) Field of Classification Search
CPC . C12N 7/64; C12N 9/16; C12N 15/52; C12N 15/70
See application file for complete search history.

(56) References Cited

U.S. PATENT DOCUMENTS 9,458,441 B2 * 10/2016 Segura ................. C12N 9/2437

FOREIGN PATENT DOCUMENTS

| WO | 2013/167581 A1 | 11/2013 |
| WO | 2015/001017 A2 | 1/2015 |

OTHER PUBLICATIONS

Ruijssenaars et al., Appl.Environ. Microb., 66(9), 3945-3950, 2000.*
Hashimoto et al., 2002, The J of Biological Chem 278(9), 7663-7673.
Henrissat, 1991, Biochem J 280(2), 309-316.
Li et al., 2008, Appl Biochem Biotechnol 159(1), 24-32.
Ruijssenaars et al., 1999, Appl Environ Microbiol 65(6), 2446-2452.
Ruijssenaars et al., 2000, Appl Environ Microbiol 66(9), 3945-3950.
Sutherland, 1987, J Gen Microbiol 133, 3129-3134.
Jia et al, 2011, Modem scientific instruments 5, 171-173.

* cited by examiner

*Primary Examiner* — Maryam Monshipouri
(74) *Attorney, Agent, or Firm* — Kelly Reynolds

(57) ABSTRACT

The present invention relates to xanthan lyase variants and methods for obtaining xanthan lyase variants. The present invention also relates to polynucleotides encoding the variants; nucleic acid constructs, vectors, and host cells comprising the polynucleotides; and methods of using the variants.

21 Claims, No Drawings
Specification includes a Sequence Listing.

SEQUENCE LISTING

<160> NUMBER OF SEQ ID NOS: 2

<210> SEQ ID NO 1
<211> LENGTH: 3111
<212> TYPE: DNA
<213> ORGANISM: Paenibacillus sp.
<220> FEATURE:
<221> NAME/KEY: CDS
<222> LOCATION: (1)..(3111)
<220> FEATURE:
<221> NAME/KEY: mat_peptide
<222> LOCATION: (1)..(3111)

<400> SEQUENCE: 1

```
gac gag ttt gac acg cta agg gaa aag tat aag gcc atg ctg aac gga      48
Asp Glu Phe Asp Thr Leu Arg Glu Lys Tyr Lys Ala Met Leu Asn Gly
1               5                   10                  15 ggg aca acc tat aat ctc tcc gac ccg gat ata gcg gcg cgt gtt aat      96
Gly Thr Thr Tyr Asn Leu Ser Asp Pro Asp Ile Ala Ala Arg Val Asn
                20                  25                  30 gcc att acg gtg act gcc cag gga tac tgg gac tcc atg ctt aaa gat     144
Ala Ile Thr Val Thr Ala Gln Gly Tyr Trp Asp Ser Met Leu Lys Asp
            35                  40                  45 ccg aac cgt aac cgt ctt tgg aac gat gca ccc ttt ggc tcg gat tcg     192
Pro Asn Arg Asn Arg Leu Trp Asn Asp Ala Pro Phe Gly Ser Asp Ser
        50                  55                  60 act tcc atc acc acg acc tac aga cac ctt tat gat atg gcg cta gct     240
Thr Ser Ile Thr Thr Thr Tyr Arg His Leu Tyr Asp Met Ala Leu Ala
65                  70                  75                  80 tat acg act tat ggc tcc agt ctg cag ggc aat gcc gca ctt aaa gcg     288
Tyr Thr Thr Tyr Gly Ser Ser Leu Gln Gly Asn Ala Ala Leu Lys Ala
                85                  90                  95 gat att atc agc ggt ttg gac tgg atg aat gcc aat caa ttt tat aat     336
Asp Ile Ile Ser Gly Leu Asp Trp Met Asn Ala Asn Gln Phe Tyr Asn
                100                 105                 110 ggc tgc agc caa tat caa aac tgg tgg cac tgg caa att ggc ggt ccc     384
Gly Cys Ser Gln Tyr Gln Asn Trp Trp His Trp Gln Ile Gly Gly Pro
            115                 120                 125 atg gcc ttg aat gat atc gtg gca tta atg tac acg gag cta acc gca     432
Met Ala Leu Asn Asp Ile Val Ala Leu Met Tyr Thr Glu Leu Thr Ala
        130                 135                 140 aca caa att tcc aat tac atg gcg gcc att tat tac acc caa gcg agt     480
Thr Gln Ile Ser Asn Tyr Met Ala Ala Ile Tyr Tyr Thr Gln Ala Ser
145                 150                 155                 160 gtt acg atg acg ggg gca aac cgg cta tgg gaa agt cag gtt att gcc     528
Val Thr Met Thr Gly Ala Asn Arg Leu Trp Glu Ser Gln Val Ile Ala
                165                 170                 175
```

-continued

| | |
|---|---|
| atc tcc gga atc ttg aat aag gat tcc gcc aga gtt gcc gct ggt cgg<br>Ile Ser Gly Ile Leu Asn Lys Asp Ser Ala Arg Val Ala Ala Gly Arg<br>            180                      185                      190 | 576 |
| gat ggc atc agc gct ttg ctg ccg tat gtc gcc aag ggt gac gga ttt<br>Asp Gly Ile Ser Ala Leu Leu Pro Tyr Val Ala Lys Gly Asp Gly Phe<br>           195                     200               205 | 624 |
| tac aac gat gga tca ttc gtt cag cat act tat tat gct tac aac ggt<br>Tyr Asn Asp Gly Ser Phe Val Gln His Thr Tyr Tyr Ala Tyr Asn Gly<br>210                      215                     220 | 672 |
| ggt tat ggt tca gag ctg tta tct ggc att gca gac ttg ata ttt att<br>Gly Tyr Gly Ser Glu Leu Leu Ser Gly Ile Ala Asp Leu Ile Phe Ile<br>225                      230                     235               240 | 720 |
| ttg aat ggc tct tca tgg cag gta acg gat cct aat aaa aac aat gta<br>Leu Asn Gly Ser Ser Trp Gln Val Thr Asp Pro Asn Lys Asn Asn Val<br>                    245                     250                     255 | 768 |
| tac cgt tgg att tat gat tcc tac gag cct ttc atc tat aaa ggg aat<br>Tyr Arg Trp Ile Tyr Asp Ser Tyr Glu Pro Phe Ile Tyr Lys Gly Asn<br>260                      265                     270 | 816 |
| ctg atg gac atg gtc cgc ggt aga gag atc tca agg cat gga ttg cag<br>Leu Met Asp Met Val Arg Gly Arg Glu Ile Ser Arg His Gly Leu Gln<br>           275                     280               285 | 864 |
| gac gat aag gca gcc gtg act gtg atg gca tcg atc att cgt ctg tca<br>Asp Asp Lys Ala Ala Val Thr Val Met Ala Ser Ile Ile Arg Leu Ser<br>290                      295                     300 | 912 |
| caa acc gct gct tcc gcc gat gct acc gca ttt aag aga atg gtg aaa<br>Gln Thr Ala Ala Ser Ala Asp Ala Thr Ala Phe Lys Arg Met Val Lys<br>305                      310                     315               320 | 960 |
| tat tgg ctg ctg ctg gat acg gat aag act ttc ctt aaa gca gta tcg<br>Tyr Trp Leu Leu Leu Asp Thr Asp Lys Thr Phe Leu Lys Ala Val Ser<br>                    325                     330               335 | 1008 |
| att gat ctg att att gcc gcg aac caa ctg gtg aac gat tcc acc gtt<br>Ile Asp Leu Ile Ile Ala Ala Asn Gln Leu Val Asn Asp Ser Thr Val<br>                  340                     345               350 | 1056 |
| acc tct cga ggg gag cta gtg aaa tat aaa caa ttc tcc gga atg gac<br>Thr Ser Arg Gly Glu Leu Val Lys Tyr Lys Gln Phe Ser Gly Met Asp<br>           355                     360               365 | 1104 |
| cgc gct gta cag ctt aga cct ggc ttc ggt ttt ggg ctt agc atg ttt<br>Arg Ala Val Gln Leu Arg Pro Gly Phe Gly Phe Gly Leu Ser Met Phe<br>370                      375                     380 | 1152 |
| tcc agc cgg atc ggt aat tat gag tcg att aat gca gag aac aac aaa<br>Ser Ser Arg Ile Gly Asn Tyr Glu Ser Ile Asn Ala Glu Asn Asn Lys<br>385                      390                     395               400 | 1200 |
| ggc tgg cat acc ggc gac ggc atg acc tac ctt tac aat act gac ctg<br>Gly Trp His Thr Gly Asp Gly Met Thr Tyr Leu Tyr Asn Thr Asp Leu<br>                    405                     410               415 | 1248 |
| agt cag ttc aat gac cat ttc tgg gca act gtg gat aat tac cga ttg<br>Ser Gln Phe Asn Asp His Phe Trp Ala Thr Val Asp Asn Tyr Arg Leu<br>                  420                     425               430 | 1296 |
| ccg ggt acc aca gtg ctc cag aac acg acg caa acc gcg aac agc cgc<br>Pro Gly Thr Thr Val Leu Gln Asn Thr Thr Gln Thr Ala Asn Ser Arg<br>           435                     440               445 | 1344 |
| agc gac aaa agc tgg gcc gga gga acg gat att ctt ggg caa tat ggt<br>Ser Asp Lys Ser Trp Ala Gly Gly Thr Asp Ile Leu Gly Gln Tyr Gly<br>450                      455                     460 | 1392 |
| gtt tcc ggc atg gaa ctg cat acc gta ggt aag agc ctg aca gcc aag<br>Val Ser Gly Met Glu Leu His Thr Val Gly Lys Ser Leu Thr Ala Lys<br>465                      470                     475               480 | 1440 |
| aaa tcc tgg ttc atg ttt gac gat gag atc gtc gcg ctg ggt tca ggt<br>Lys Ser Trp Phe Met Phe Asp Asp Glu Ile Val Ala Leu Gly Ser Gly<br>                    485                     490               495 | 1488 |

```
att gcc agc acc gat ggc atc gca acc gaa acg att gta gag aat cga      1536
Ile Ala Ser Thr Asp Gly Ile Ala Thr Glu Thr Ile Val Glu Asn Arg
            500                 505                 510 aag ctc aat agc agc ggc aat aat gca ttg att gtt aac ggg acg gcg      1584
Lys Leu Asn Ser Ser Gly Asn Asn Ala Leu Ile Val Asn Gly Thr Ala
            515                 520                 525 aag ccg ggc tcc ctt gga tgg tcg gaa aca atg acc gga acc aat tat      1632
Lys Pro Gly Ser Leu Gly Trp Ser Glu Thr Met Thr Gly Thr Asn Tyr
        530                 535                 540 att cat cta gcc ggc agc gta ccc ggc tcc gat atc ggt tat tat ttt      1680
Ile His Leu Ala Gly Ser Val Pro Gly Ser Asp Ile Gly Tyr Tyr Phe
545                 550                 555                 560 cct ggt gga gca gca gtc aaa ggc ttg cgt gaa gcc cgg tcg gga agc      1728
Pro Gly Gly Ala Ala Val Lys Gly Leu Arg Glu Ala Arg Ser Gly Ser
                565                 570                 575 tgg agc tcg ctg aat tcc tcc gca tcc tgg aag gac tcg aca ttg cat      1776
Trp Ser Ser Leu Asn Ser Ser Ala Ser Trp Lys Asp Ser Thr Leu His
            580                 585                 590 aca cgc aac ttt atg acg ctt tgg ttc gat cat ggc atg aac ccg aca      1824
Thr Arg Asn Phe Met Thr Leu Trp Phe Asp His Gly Met Asn Pro Thr
        595                 600                 605 aac ggt agt tat tct tat gtg ctg ctt ccg aat aag acc agc agt gcg      1872
Asn Gly Ser Tyr Ser Tyr Val Leu Leu Pro Asn Lys Thr Ser Ser Ala
610                 615                 620 gtg gcc agc tat gct gca acg cct cag atc agc att ctg gag aat tct      1920
Val Ala Ser Tyr Ala Ala Thr Pro Gln Ile Ser Ile Leu Glu Asn Ser
625                 630                 635                 640 agc tcg gcg caa gcg gtg aag gag acg caa ttg aat gtc acc gga att      1968
Ser Ser Ala Gln Ala Val Lys Glu Thr Gln Leu Asn Val Thr Gly Ile
                645                 650                 655 aac ttt tgg aac gat gag cca acc acg gtg ggc ctg gtt act tcc aat      2016
Asn Phe Trp Asn Asp Glu Pro Thr Thr Val Gly Leu Val Thr Ser Asn
            660                 665                 670 cgg aaa gca tcc gtt atg aca aaa gaa acg gct agt gat ttc gag ata      2064
Arg Lys Ala Ser Val Met Thr Lys Glu Thr Ala Ser Asp Phe Glu Ile
        675                 680                 685 tcc gtt tcc gac ccg acc caa agt aat gtg ggg acc atc tat att gat      2112
Ser Val Ser Asp Pro Thr Gln Ser Asn Val Gly Thr Ile Tyr Ile Asp
    690                 695                 700 gtc aac aaa agt gca acc gga ttg att tcg aag gat aat gaa ata acg      2160
Val Asn Lys Ser Ala Thr Gly Leu Ile Ser Lys Asp Asn Glu Ile Thr
705                 710                 715                 720 gtc att cag tac tac cca acc atg aag ttt aaa gtc aat gta aac aat      2208
Val Ile Gln Tyr Tyr Pro Thr Met Lys Phe Lys Val Asn Val Asn Asn
                725                 730                 735 tct ggc ggg aag tcc tat aaa gta aag ttt agc ctg aca gga aca ccc      2256
Ser Gly Gly Lys Ser Tyr Lys Val Lys Phe Ser Leu Thr Gly Thr Pro
            740                 745                 750 ggc agc aac ccg tct cca atc ccg ata ccg aat cct tac gaa gcg gaa      2304
Gly Ser Asn Pro Ser Pro Ile Pro Ile Pro Asn Pro Tyr Glu Ala Glu
        755                 760                 765 gct ttg cca att aac gct ctg aca gat act ccc gtg gtt tac aat gat      2352
Ala Leu Pro Ile Asn Ala Leu Thr Asp Thr Pro Val Val Tyr Asn Asp
    770                 775                 780 gcc aat gcc agt ggt ggc aag aag ctt ggc ttc aat aac aat gca gtg      2400
Ala Asn Ala Ser Gly Gly Lys Lys Leu Gly Phe Asn Asn Asn Ala Val
785                 790                 795                 800 gat gat tat gtg gag ttc agt ctg gac gtc aca cag ccc ggc acc tac      2448
Asp Asp Tyr Val Glu Phe Ser Leu Asp Val Thr Gln Pro Gly Thr Tyr
                805                 810                 815
```

| | | |
|---|---|---|
| gat gtc aaa tcc cgg att atg aaa tca acg aac agc ggg att tat cag<br>Asp Val Lys Ser Arg Ile Met Lys Ser Thr Asn Ser Gly Ile Tyr Gln<br>820                         825                     830 | 2496 |
| ctg tct att aat ggg acc aac gta ggg agc gcg cag gat atg ttc tgg<br>Leu Ser Ile Asn Gly Thr Asn Val Gly Ser Ala Gln Asp Met Phe Trp<br>835                         840                     845 | 2544 |
| acg acc tcc gag ctg tct aag gag ttt act atg ggc tca tac agc ttc<br>Thr Thr Ser Glu Leu Ser Lys Glu Phe Thr Met Gly Ser Tyr Ser Phe<br>850                         855                     860 | 2592 |
| agc aca ccc ggg agc tat ttg ttc cga tta aaa aca acc ggc aag aat<br>Ser Thr Pro Gly Ser Tyr Leu Phe Arg Leu Lys Thr Thr Gly Lys Asn<br>865                         870                     875                     880 | 2640 |
| gtc agt tct tca gga tat aag ctg atg ctg gac aat ttt agt ctg gta<br>Val Ser Ser Ser Gly Tyr Lys Leu Met Leu Asp Asn Phe Ser Leu Val<br>885                         890                     895 | 2688 |
| tca aca ggt att gat aca acg gtg att gtg gac aat gcc gat gca gct<br>Ser Thr Gly Ile Asp Thr Thr Val Ile Val Asp Asn Ala Asp Ala Ala<br>900                         905                     910 | 2736 |
| ggt gtt acg aag gtg ggt act tgg acc gga acc aat acg cag acc gat<br>Gly Val Thr Lys Val Gly Thr Trp Thr Gly Thr Asn Thr Gln Thr Asp<br>915                         920                     925 | 2784 |
| cgg tac ggc gcc gac tac att cac gat ggg aac acg ggg aaa ggt acg<br>Arg Tyr Gly Ala Asp Tyr Ile His Asp Gly Asn Thr Gly Lys Gly Thr<br>930                         935                     940 | 2832 |
| aag agc gtt acc ttt act cca aat gta cct atc agt gga act tat cag<br>Lys Ser Val Thr Phe Thr Pro Asn Val Pro Ile Ser Gly Thr Tyr Gln<br>945                         950                     955                     960 | 2880 |
| gtt tac atg atg tgg gct gcc cat acg aat agg gca acg aat gtt ccc<br>Val Tyr Met Met Trp Ala Ala His Thr Asn Arg Ala Thr Asn Val Pro<br>965                         970                     975 | 2928 |
| gta gac gta acg cat tca ggc ggt aca gca acg cta aat gtt aac caa<br>Val Asp Val Thr His Ser Gly Gly Thr Ala Thr Leu Asn Val Asn Gln<br>980                         985                     990 | 2976 |
| caa ggt aat ggt ggt gtg tgg aat tta ctg ggt acg tat agc ttt aat<br>Gln Gly Asn Gly Gly Val Trp Asn Leu Leu Gly Thr Tyr Ser Phe Asn<br>995                         1000                  1005 | 3024 |
| gct ggg tcc acg ggg gct atc aag atc cgt acg gac gcg acg aat<br>Ala Gly Ser Thr Gly Ala Ile Lys Ile Arg Thr Asp Ala Thr Asn<br>1010                    1015                  1020 | 3069 |
| gga tat gtt gta gcc gat gcc gtg aag ctg gta aag gtc cca<br>Gly Tyr Val Val Ala Asp Ala Val Lys Leu Val Lys Val Pro<br>1025                    1030                  1035 | 3111 |

<210> SEQ ID NO 2
<211> LENGTH: 1037
<212> TYPE: PRT
<213> ORGANISM: Paenibacillus sp.

<400> SEQUENCE: 2

Asp Glu Phe Asp Thr Leu Arg Glu Lys Tyr Lys Ala Met Leu Asn Gly
1               5                   10                 15

Gly Thr Thr Tyr Asn Leu Ser Asp Pro Asp Ile Ala Ala Arg Val Asn
               20                   25                   30

Ala Ile Thr Val Thr Ala Gln Gly Tyr Trp Asp Ser Met Leu Lys Asp
        35                   40                   45

Pro Asn Arg Asn Arg Leu Trp Asn Asp Ala Pro Phe Gly Ser Asp Ser
    50                   55                   60

Thr Ser Ile Thr Thr Thr Tyr Arg His Leu Tyr Asp Met Ala Leu Ala
65              70                   75                   80

```
Tyr Thr Thr Tyr Gly Ser Ser Leu Gln Gly Asn Ala Ala Leu Lys Ala
                85                  90                  95

Asp Ile Ile Ser Gly Leu Asp Trp Met Asn Ala Asn Gln Phe Tyr Asn
            100                 105                 110

Gly Cys Ser Gln Tyr Gln Asn Trp Trp His Trp Gln Ile Gly Gly Pro
        115                 120                 125

Met Ala Leu Asn Asp Ile Val Ala Leu Met Tyr Thr Glu Leu Thr Ala
    130                 135                 140

Thr Gln Ile Ser Asn Tyr Met Ala Ala Ile Tyr Tyr Thr Gln Ala Ser
145                 150                 155                 160

Val Thr Met Thr Gly Ala Asn Arg Leu Trp Glu Ser Gln Val Ile Ala
                165                 170                 175

Ile Ser Gly Ile Leu Asn Lys Asp Ser Ala Arg Val Ala Ala Gly Arg
            180                 185                 190

Asp Gly Ile Ser Ala Leu Leu Pro Tyr Val Ala Lys Gly Asp Gly Phe
        195                 200                 205

Tyr Asn Asp Gly Ser Phe Val Gln His Thr Tyr Tyr Ala Tyr Asn Gly
    210                 215                 220

Gly Tyr Gly Ser Glu Leu Leu Ser Gly Ile Ala Asp Leu Ile Phe Ile
225                 230                 235                 240

Leu Asn Gly Ser Ser Trp Gln Val Thr Asp Pro Asn Lys Asn Asn Val
                245                 250                 255

Tyr Arg Trp Ile Tyr Asp Ser Tyr Glu Pro Phe Ile Tyr Lys Gly Asn
            260                 265                 270

Leu Met Asp Met Val Arg Gly Arg Glu Ile Ser Arg His Gly Leu Gln
        275                 280                 285

Asp Asp Lys Ala Ala Val Thr Val Met Ala Ser Ile Ile Arg Leu Ser
    290                 295                 300

Gln Thr Ala Ala Ser Ala Asp Ala Thr Ala Phe Lys Arg Met Val Lys
305                 310                 315                 320

Tyr Trp Leu Leu Leu Asp Thr Asp Lys Thr Phe Leu Lys Ala Val Ser
                325                 330                 335

Ile Asp Leu Ile Ile Ala Ala Asn Gln Leu Val Asn Asp Ser Thr Val
            340                 345                 350

Thr Ser Arg Gly Glu Leu Val Lys Tyr Lys Gln Phe Ser Gly Met Asp
        355                 360                 365

Arg Ala Val Gln Leu Arg Pro Gly Phe Gly Phe Gly Leu Ser Met Phe
    370                 375                 380

Ser Ser Arg Ile Gly Asn Tyr Glu Ser Ile Asn Ala Glu Asn Asn Lys
385                 390                 395                 400

Gly Trp His Thr Gly Asp Gly Met Thr Tyr Leu Tyr Asn Thr Asp Leu
                405                 410                 415

Ser Gln Phe Asn Asp His Phe Trp Ala Thr Val Asp Asn Tyr Arg Leu
            420                 425                 430

Pro Gly Thr Thr Val Leu Gln Asn Thr Thr Gln Thr Ala Asn Ser Arg
        435                 440                 445

Ser Asp Lys Ser Trp Ala Gly Thr Asp Ile Leu Gly Gln Tyr Gly
    450                 455                 460

Val Ser Gly Met Glu Leu His Thr Val Gly Lys Ser Leu Thr Ala Lys
465                 470                 475                 480

Lys Ser Trp Phe Met Phe Asp Asp Glu Ile Val Ala Leu Gly Ser Gly
                485                 490                 495
```

```
Ile Ala Ser Thr Asp Gly Ile Ala Thr Glu Thr Ile Val Glu Asn Arg
                500                 505                 510

Lys Leu Asn Ser Ser Gly Asn Asn Ala Leu Ile Val Asn Gly Thr Ala
            515                 520                 525

Lys Pro Gly Ser Leu Gly Trp Ser Glu Thr Met Thr Gly Thr Asn Tyr
        530                 535                 540

Ile His Leu Ala Gly Ser Val Pro Gly Ser Asp Ile Gly Tyr Tyr Phe
545                 550                 555                 560

Pro Gly Gly Ala Ala Val Lys Gly Leu Arg Glu Ala Arg Ser Gly Ser
                565                 570                 575

Trp Ser Ser Leu Asn Ser Ser Ala Ser Trp Lys Asp Ser Thr Leu His
            580                 585                 590

Thr Arg Asn Phe Met Thr Leu Trp Phe Asp His Gly Met Asn Pro Thr
        595                 600                 605

Asn Gly Ser Tyr Ser Tyr Val Leu Leu Pro Asn Lys Thr Ser Ser Ala
        610                 615                 620

Val Ala Ser Tyr Ala Ala Thr Pro Gln Ile Ser Ile Leu Glu Asn Ser
625                 630                 635                 640

Ser Ser Ala Gln Ala Val Lys Glu Thr Gln Leu Asn Val Thr Gly Ile
                645                 650                 655

Asn Phe Trp Asn Asp Glu Pro Thr Thr Val Gly Leu Val Thr Ser Asn
            660                 665                 670

Arg Lys Ala Ser Val Met Thr Lys Glu Thr Ala Ser Asp Phe Glu Ile
        675                 680                 685

Ser Val Ser Asp Pro Thr Gln Ser Asn Val Gly Thr Ile Tyr Ile Asp
        690                 695                 700

Val Asn Lys Ser Ala Thr Gly Leu Ile Ser Lys Asp Asn Glu Ile Thr
705                 710                 715                 720

Val Ile Gln Tyr Tyr Pro Thr Met Lys Phe Lys Val Asn Val Asn Asn
                725                 730                 735

Ser Gly Gly Lys Ser Tyr Lys Val Lys Phe Ser Leu Thr Gly Thr Pro
            740                 745                 750

Gly Ser Asn Pro Ser Pro Ile Pro Ile Pro Asn Pro Tyr Glu Ala Glu
        755                 760                 765

Ala Leu Pro Ile Asn Ala Leu Thr Asp Thr Pro Val Val Tyr Asn Asp
        770                 775                 780

Ala Asn Ala Ser Gly Gly Lys Lys Leu Gly Phe Asn Asn Ala Val
785                 790                 795                 800

Asp Asp Tyr Val Glu Phe Ser Leu Asp Val Thr Gln Pro Gly Thr Tyr
                805                 810                 815

Asp Val Lys Ser Arg Ile Met Lys Ser Thr Asn Ser Gly Ile Tyr Gln
            820                 825                 830

Leu Ser Ile Asn Gly Thr Asn Val Gly Ser Ala Gln Asp Met Phe Trp
        835                 840                 845

Thr Thr Ser Glu Leu Ser Lys Glu Phe Thr Met Gly Ser Tyr Ser Phe
        850                 855                 860

Ser Thr Pro Gly Ser Tyr Leu Phe Arg Leu Lys Thr Thr Gly Lys Asn
865                 870                 875                 880

Val Ser Ser Ser Gly Tyr Lys Leu Met Leu Asp Asn Phe Ser Leu Val
                885                 890                 895

Ser Thr Gly Ile Asp Thr Val Ile Val Asp Asn Ala Asp Ala Ala
            900                 905                 910
```

```
Gly Val Thr Lys Val Gly Thr Trp Thr Gly Thr Asn Thr Gln Thr Asp
        915             920                 925

Arg Tyr Gly Ala Asp Tyr Ile His Asp Gly Asn Thr Gly Lys Gly Thr
930                     935                 940

Lys Ser Val Thr Phe Thr Pro Asn Val Pro Ile Ser Gly Thr Tyr Gln
945             950                 955                     960

Val Tyr Met Met Trp Ala Ala His Thr Asn Arg Ala Thr Asn Val Pro
                965                 970                 975

Val Asp Val Thr His Ser Gly Gly Thr Ala Thr Leu Asn Val Asn Gln
                980              985                 990

Gln Gly Asn Gly Gly Val Trp Asn  Leu Leu Gly Thr Tyr Ser Phe Asn
        995             1000                 1005

Ala Gly Ser Thr Gly Ala Ile  Lys Ile Arg Thr Asp  Ala Thr Asn
    1010                1015               1020

Gly Tyr Val Val Ala Asp Ala Val Lys Leu Val Lys  Val Pro
    1025            1030                1035
```

XANTHAN LYASE VARIANTS AND POLYNUCLEOTIDES ENCODING SAME

CROSS-REFERENCE TO RELATED APPLICATIONS

This application is a 35 U.S.C. 371 national application of international application no. PCT/EP2017/071277 filed Aug. 24, 2017, which claims priority or the benefit under 35 U.S.C. 119 of Indian application no. 201641028779, filed Aug. 24, 2016, the contents of which are fully incorporated herein by reference.

REFERENCE TO A JOINT RESEARCH AGREEMENT

The embodiments claimed in the present application were made under a joint research agreement between Henkel AG & Co. KGaA and Novozymes A/S.

REFERENCE TO A SEQUENCE LISTING

This application contains a Sequence Listing in computer readable form, which is incorporated herein by reference.

BACKGROUND OF THE INVENTION

Field of the Invention

The present invention relates to novel xanthan lyase variants exhibiting alterations relative to the parent xanthan lyase in one or more properties including: detergent stability (e.g. improved stability in a detergent composition, e.g. in the presence of a chelator, e.g. EDTA or citrate) and/or storage stability (e.g. improved storage stability in a detergent composition, e.g. in the presence of a chelator, e.g. EDTA or citrate). The present invention further relates to novel xanthan lyase variants having activity on xanthan gum. The invention also relates to nucleic acid constructs, vectors, and host cells comprising polynucleotides encoding variants of the invention as well as methods for producing and using variants of the invention. Variants of the invention are suitable for use in cleaning processes and detergent compositions, such as laundry compositions and dish wash compositions, including hand wash and automatic dish wash compositions. The invention further relates to compositions comprising variants of the invention and/or endoglucanases for use in detergents and in the drilling and oil industries.

Description of the Related Art

Xanthan gum is a polysaccharide derived from the bacterial coat of *Xanthomonas campestris*. It is produced by the fermentation of glucose, sucrose, or lactose by the *Xanthomonas campestris* bacterium. After a fermentation period, the polysaccharide is precipitated from a growth medium with isopropyl alcohol, dried, and ground into a fine powder. Later, it is added to a liquid medium to form the gum. Xanthan gum is a natural polysaccharide consisting of different sugars which are connected by several different bonds, such as β-D-mannosyl-β-D-1,4-glucuronosyl bonds and β-D-glucosyl-β-D-1,4-glucosyl bonds. Xanthan gum is at least partly soluble in water and forms highly viscous solutions or gels. Complete enzymatic degradation of xanthan gum requires several enzymatic activities including xanthan lyase activity and endo-β-1,4-glucanase activity. Xanthan lyases are enzymes that cleave the β-D-mannosyl-β-D-1,4-glucuronosyl bond of xanthan and have been described in the literature. Xanthan degrading enzymes are known in the art, e.g. two xanthan lyases have been isolated from *Paenibacillus alginolyticus* XL-1 (e.g. Ruijssenaars et al. (1999) 'A pyruvated mannose-specific xanthan lyase involved in xanthan degradation by *Paenibacillus alginolyticus* XL-1', *Appl. Environ. Microbiol.* 65(6): 2446-2452, and Ruijssenaars et al. (2000), 'A novel gene encoding xanthan lyase of *Paenibacillus alginolyticus* strain XL-1', *Appl. Environ. Microbiol.* 66(9): 3945-3950). Glycoside hydrolases are enzymes that catalyse the hydrolysis of the glycosyl bond to release smaller sugars. There are over 100 classes of glycoside hydrolases which have been classified, see Henrissat et al. (1991) 'A classification of glycosyl hydrolases based on amino-acid sequence similarities', *J. Biochem.* 280: 309-316 and the Uniprot website at cazy.org. The glycoside hydrolase family 9 (GH9) consists of over 70 different enzymes that are mostly endo-glucanases (EC 3.2.1.4), cellobiohydrolases (EC 3.2.1.91), β-glucosidases (EC 3.2.1.21) and exo-β-glucosaminidase (EC 3.2.1.165). In recent years xanthan gum has been used as an ingredient in many consumer products including foods (e.g. as thickening agent in salad dressings and dairy products) and cosmetics (e.g. as stabilizer and thickener in toothpaste and make-up, creams and lotions to prevent ingredients from separating and to provide the right texture of the product). Further, xanthan gum has found use in the oil industry as an additive to regulate the viscosity of drilling fluids etc. The widespread use of xanthan gum has led to a desire to degrade solutions, gels or mixtures containing xanthan gum thereby allowing easier removal of the by-products. Xanthan lyases and endoglucanases for the degradation of xanthan gum and the use of such enzymes for cleaning purposes, such as the removal of xanthan gum containing stains, and in the drilling and oil industries are known in the art, e.g. WO2013167581A1.

The known xanthan lyase having SEQ ID NO: 2 was found to be sensitive to the presence of detergents with chelators. To improve applicability and/or cost and/or the performance of such enzymes there is an ongoing search for variants with altered properties, such as increased stability, e.g. improved stability in a detergent composition, e.g. in the presence of a chelator, e.g. EDTA or citrate, etc. However, mutagenesis of large enzymes followed by purification and functional analysis of mutant libraries can be very expensive and laborious.

SUMMARY OF THE INVENTION

Since the known xanthan lyase having SEQ ID NO: 2 is a large enzyme (>1000 residues), it is difficult and expensive to randomly target its properties for improvement of, e.g., stability in a detergent composition, e.g., in the presence of a chelator.

In some aspects, the present invention identifies chelator-induced instability regions in the protein sequence/structure of the known xanthan lyase having SEQ ID NO: 2 that are affected when the molecule is incubated in a buffer with EDTA, and therefore provides an important guidance on where to mutate a xanthan lyase in order to stabilize the molecule in a detergent, e.g., detergent composition comprising a chelator.

In some aspects, the present invention relates to a xanthan lyase variant, comprising an alteration (e.g., a substitution, deletion or insertion) at one or more positions in a chelator-induced instability region selected from the group consisting of: region 1 corresponding to amino acids 154 to 176 of SEQ ID NO: 2, region 2 corresponding to amino acids 614 to 658 of SEQ ID NO: 2, region 3 corresponding to amino acids 731 to 803 of SEQ ID NO: 2, region 4 corresponding to amino acids 807 to 846 of SEQ ID NO: 2, region 5 corresponding to amino acids 872 to 885 of SEQ ID NO: 2, and region 6 corresponding to amino acids 903 to 1004 of SEQ ID NO: 2.

In some aspects, the present invention relates to a xanthan lyase variant, comprising an alteration (e.g., a substitution, deletion or insertion) at one or more positions in a chelator-induced instability region selected from the group consisting of: region 1 corresponding to amino acids 154 to 176 of SEQ ID NO: 2, region 2 corresponding to amino acids 614 to 658 of SEQ ID NO: 2, region 3 corresponding to amino acids 731 to 803 of SEQ ID NO: 2, region 4 corresponding to amino acids 807 to 846 of SEQ ID NO: 2, region 5 corresponding to amino acids 872 to 885 of SEQ ID NO: 2, and region 6 corresponding to amino acids 903 to 1004 of SEQ ID NO: 2, wherein said variant has at least 60% and less than 100% sequence identity to SEQ ID NO: 2, preferably said xanthan lyase variant having an activity on xanthan gum.

In some aspects, the present invention defines a chelator-induced instability region of a parent xanthan lyase (e.g., SEQ ID NO: 2) having one or more of the following features: in the presence of a chelator is less conformationally stable than one or more or all of its adjacent regions; and/or in the presence of a chelator is more exposed to said chelator than one or more or all of its adjacent regions; and/or in the presence of a chelator is more accessible to said chelator than one or more or all of its adjacent regions; and/or in the presence of a chelator is more conformationally dynamic than one or more or all of its adjacent regions; and/or in the presence of a chelator is more receptive to deuterium incorporation than one or more or all of its adjacent regions.

In some aspects, the present invention relates to a xanthan lyase variant having at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 2.

In some aspects, the present invention relates to a xanthan lyase variant comprising an alteration (e.g., a substitution, deletion or insertion) at one or more positions in a region selected from the group consisting of:

i) region 1 corresponding to amino acids 154 to 176 of SEQ ID NO: 2, e.g., said alteration at one or more positions selected from the group consisting of positions: 154, 155, 156, 157, 158, 159, 160, 161, 162, 163, 164, 165, 166, 167, 168, 169, 170, 171, 172, 173, 174, 175, 176, wherein said positions correspond to amino acid positions of SEQ ID NO: 2 (e.g., using the numbering of SEQ ID NO: 2), ii) region 2 corresponding to amino acids 614 to 658 of SEQ ID NO: 2, e.g., said alteration at one or more positions selected from the group consisting of positions: 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, wherein said positions correspond to amino acid positions of SEQ ID NO: 2 (e.g., using the numbering of SEQ ID NO: 2), iii) region 3 corresponding to amino acids 731 to 803 of SEQ ID NO: 2, e.g., said alteration at one or more positions selected from the group consisting of positions: 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, wherein said positions correspond to amino acid positions of SEQ ID NO: 2 (e.g., using the numbering of SEQ ID NO: 2), iv) region 4 corresponding to amino acids 807 to 846 of SEQ ID NO: 2, e.g., said alteration at one or more positions selected from the group consisting of positions: 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, wherein said positions correspond to amino acid positions of SEQ ID NO: 2 (e.g., using the numbering of SEQ ID NO: 2), v) region 5 corresponding to amino acids 872 to 885 of SEQ ID NO: 2, e.g., said alteration at one or more positions selected from the group consisting of positions: 872, 873, 874, 875, 876, 877, 878, 879, 880, 881, 882, 883, 884, 885, wherein said positions correspond to amino acid positions of SEQ ID NO: 2 (e.g., using the numbering of SEQ ID NO: 2), vi) region 6 corresponding to amino acids 903 to 1004 of SEQ ID NO: 2, e.g., said alteration at one or more positions selected from the group consisting of positions: 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, wherein said positions correspond to amino acid positions of SEQ ID NO: 2 (e.g., using the numbering of SEQ ID NO: 2).

In some aspects, the present invention relates to a xanthan lyase variant comprising an alteration (e.g., a substitution, deletion or insertion) at one or more positions in two or more regions selected from the group consisting of:

i) region 1 corresponding to amino acids 154 to 176 of SEQ ID NO: 2,
ii) region 2 corresponding to amino acids 614 to 658 of SEQ ID NO: 2,
iii) region 3 corresponding to amino acids 731 to 803 of SEQ ID NO: 2,
iv) region 4 corresponding to amino acids 807 to 846 of SEQ ID NO: 2,
v) region 5 corresponding to amino acids 872 to 885 of SEQ ID NO: 2,
vi) region 6 corresponding to amino acids 903 to 1004 of SEQ ID NO: 2.

In some aspects, the present invention relates to a xanthan lyase variant having an alteration (e.g., a substitution, deletion or insertion) at one or more positions selected from the group consisting of positions: 155, 159, 620, 624, 626, 631, 635, 645, 649, 650, 656, 738, 745, 746, 748, 752, 753, 754, 757, 764, 769, 774, 775, 777, 779, 782, 785, 786, 789, 792, 796, 799, 800, 801, 819, 824, 843, 845, 903, 911, 912, 915, 919, 921, 923, 925, 927, 928, 930, 932, 933, 941, 966, 967, 991 and 998 of SEQ ID NO: 2.

In some aspects, the present invention relates to a xanthan lyase variant having one or more substitutions selected from the group consisting of: Y155E, A159P, K620R, A624E, A626G, T631N, T631E, S635E, S635T, S635Q, A645S, T649V, T649K, T649R, Q650G, I656V, G738L, K745R, F746L, L748T, P752R, P752K, G753E, G753Q, G753S, S754E, S754L, S754Q, S754R, S757D, S757P, S757E, P764V, P764K, A769D, A769T, A769R, A769S, A769E, A769Q, A769*, A774V, L775M, L775Y, L775A, L775I, L775S, L775F, L775Q, D777K, D777R, P779V, Y782I, A785T, N786K, G789R, K792W, K792Y, K792V, K792A, N796Q, A799H, V800P, D801G, K819R, K819T, K824R, A843P, D845E, 875T, K875E, T903A, T903Q, A911V, A911M, A911S, A912T, A912I, A912Y, T915Q, T915S, T915V, T915A, T919F, T919G, T919D, T921R, T921S, T923H, T923D, T925Q, T925D, T925R, T927K, D928W, Y930H, Y930L, Y930F, A932P, D933M, G941E, G941D, A966P, A967D, N991D and V998K.

In some aspects, the present invention relates to a xanthan lyase variant having an alteration (e.g., a substitution, deletion or insertion) at one or more positions selected from the group consisting of: 624, 635, 649, 656, 738, 753, 754, 757, 769, 775, 777, 801, 843 and 875.

In some aspects, the present invention relates to a xanthan lyase variant having one or more substitutions selected from the group consisting of: A624E, S635E, T649K, I656V, G738L, G753E, S754E, S754R, S757D, A769D, L775A, D777R, D801G, A843P and K875T.

In some aspects, the xanthan lyase variant of the invention comprises an alteration at one or more positions in at least one chelator-induced instability region as well as an alteration at one or more positions in at least one adjacent region. Thus, in some aspects the xanthan lyase variant of the invention, in addition to an alteration in one or more positions in at least one region selected from the group consisting regions 1, 2, 3, 4, 5 and 6 as set forth above and elsewhere herein, further comprises an alteration (e.g., a substitution, deletion or insertion) at one or more positions in at least one region selected from the group consisting of:

vii) region 7 corresponding to amino acids 1 to 153 of SEQ ID NO: 2, viii) region 8 corresponding to amino acids 177 to 613 of SEQ ID NO: 2, ix) region 9 corresponding to amino acids 659 to 730 of SEQ ID NO: 2, x) region 10 corresponding to amino acids 804 to 806 of SEQ ID NO: 2, xi) region 11 corresponding to amino acids 847 to 871 of SEQ ID NO: 2, xii) region 12 corresponding to amino acids 886 to 902 of SEQ ID NO: 2, and xiii) region 13 corresponding to amino acids 1005 to 1037 of SEQ ID NO: 2.

The xanthan lyase variant may e.g. comprise an alteration at one or more positions in each of two or more regions selected from the group consisting of regions 7, 8, 9, 10, 11, 12 and 13.

In some aspects, the alteration at one or more positions in at least one region selected from the group consisting of regions 7, 8, 9, 10, 11, 12 and 13 is an alteration at one or more positions selected from the group consisting of: 9, 15, 18, 46, 58, 66, 89, 95, 100, 106, 109, 183, 188, 190, 203, 204, 221, 229, 234, 238, 240, 242, 243, 257, 258, 284, 291, 293, 316, 317, 320, 324, 329, 333, 339, 341, 352, 354, 360, 372, 377, 399, 400, 419, 440, 450, 451, 454, 458, 481, 492, 505, 533, 567, 568, 576, 578, 579, 582, 664, 672, 703, 722, 726, 727, 728, 851, 855, 856, 867, 887, 892, 899, 900, 901, 902, 915, 1008 and 1016 of SEQ ID NO: 2. The xanthan lyase variant may e.g. comprise an alteration at two or more of these positions, e.g. at three, four, five, six, seven, eight, nine or ten of these positions.

In some aspects, the alteration at one or more positions in at least one region selected from the group consisting of regions 7, 8, 9, 10, 11, 12 and 13 comprises one or more substitutions selected from the group consisting of: K9R, N15T, T18D, L46D, A58L, S66H, Q89Y, K95E, S100D, N106Y, Q109R, Q109D, Q109F, Q109K, Q109A, K183Q, K183R, V188I, A190Q, A203P, K204R, A221P, E229N, E229S, E229V, I234V, I238W, I238L, I238M, I240W, N242S, G243V, Y257W, R258E, R284G, K291R, A293G, A293P, K316R, R317K, K320R, L324Q, K329R, K333R, L339M, I341P, V352I, S354P, K360G, K360R, Q372H, F377Y, N399K, K400R, F419Y, N440K, D450P, K451E, K451R, A454V, D458S, K481R, A492H, A492L, T505I, L533I, K567R, G568A, S578K, S578N, S578R, S579R, S579K, S582K, T664K, N672D, 1703L, 1722F, P726Q, T727P, M728V, S851F, K855R, E856D, P867S, K887R, N892Y, N892W, N892F, G899S, 1900G, D901A, T902F, N1008D and K1016T of SEQ ID NO: 2. The xanthan lyase variant may e.g. comprise two or more of these substitutions, e.g. three, four, five, six, seven, eight, nine or ten of said substitutions.

In some aspects, the xanthan lyase variant of the invention comprises an alteration at one or more positions in at least one region selected from the group consisting of regions 1, 2, 3, 4, 5 and 6, and an alteration at one or more positions in at least one region selected from the group consisting of regions 7, 8, 9, 10, 11, 12 and 13. In one aspect, the variant comprises an alteration at one or more positions selected from the group consisting of positions 624, 631, 635, 649, 656, 738, 752, 753, 754, 757, 769, 775, 777, 800, 801, 843, 875, 911 and 915, and an alteration at one or more positions selected from the group consisting of positions 89, 100, 190, 229, 234, 352, 360, 399, 440, 458, 492, 567, 582, 664, 672, 703, 728, 892, 1008 and 1016 of SEQ ID NO: 2.

The variant may, for example, comprise an alteration at two or more positions, e.g. three, four, five or more positions, selected from the group consisting of positions 624, 631, 635, 649, 656, 738, 752, 753, 754, 757, 769, 775, 777, 800, 801, 843, 875, 911 and 915, and an alteration at two or more positions, e.g. two, three, four, five or more positions, selected from the group consisting of positions 89, 100, 190, 229, 234, 352, 360, 399, 440, 458, 492, 567, 582, 664, 672, 703, 728, 892, 1008 and 1016 of SEQ ID NO: 2.

Preferred positions for alteration in this aspect include one or more positions selected from the group consisting of positions 624, 635, 649, 656, 738, 753, 754, 757, 769, 775, 777, 801, 843 and 875, and one or more positions selected from the group consisting of positions 100, 190, 229, 234, 360, 399, 440, 458, 492, 567, 582, 672, 892 and 1008 of SEQ ID NO: 2.

In one embodiment of this aspect, the xanthan lyase variant comprises one or more substitutions selected from the group consisting of Q89Y, S100D, A190Q, E229S, I234V, V352I, K360G, N399K, N440K, D458S, A492H, A492L, K567R, S582K, T664K, N672D, 1703L, M728V, N892Y N1008D and K1016T, and one or more substitutions selected from the group consisting of A624E, T631N, S635E, T649K, I656V, G738L, P752K, P752R, G753E, S754E, S754R, S757D, A769D, L775A, D777R, V800P, D801G, A843P, K875T, A911V and T915A. The variant may, for example, comprise two or more substitutions, e.g. three, four, five or more substitutions, selected from the group consisting of Q89Y, S100D, A190Q, E229S, I234V, V352I, K360G, N399K, N440K, D458S, A492H, A492L, K567R, S582K, T664K, N672D, I703L, M728V, N892Y N1008D and K1016T, and two or more substitutions, e.g. three, four, five or more substitutions, selected from the group consisting of A624E, T631N, S635E, T649K, I656V, G738L, P752K, P752R, G753E, S754E, S754R, S757D, A769D, L775A, D777R, V800P, D801G, A843P, K875T, A911V and T915A. Preferred substitutions in this embodiment include one or more substitutions selected from the group consisting of S100D, A190Q, E229S, I234V, K360G, N399K, N440K, D458S, A492H, K567R, S582K, N672D, N892Y and N1008D, and one or more substitutions selected from the group consisting of A624E, S635E, T649K, I656V, G738L, G753E, S754E, S754R, S757D, A769D, L775A, D777R, D801G, A843P and K875T.

Non-limiting examples of such variants include:

A190Q, E229S, S635E, T649K, I656V, N672D, I703L, G753E, S754E, S757D, A769D, L775A, D801G, K875T, N892Y, N1008D

E229S, S635E, T649K, I656V, N672D, I703L, G753E, S754E, A769D, L775A, D801G, K875T, N892Y, N1008D

E229S, V352I, S635E, T649K, I656V, N672D, G753E, S754E, A769D, L775A, V800P, D801G, K875T, N892Y

E229S, K360G, D458S, S582K, N672D, G753E, S754E, A769D, L775A, D801G, K875T, N892Y, N1008D

S100D, E229S, K360G, D458S, S582K, T664K, N672D, G753E, S754E, S757D, A769D, L775A, D801G, A843P, K875T, N892Y, A911V, N1008D, K1016T

E229S, I234V, S582K, N672D, G753E, S754E, A769D, L775A, V800P, D801G, K875T, N892Y

Q89Y, E229S, N440K, S582K, A624E, N672D, G753E, S754E, A769D, L775A, D801G, K875T, N892Y

E229S, S635E, T649K, I656V, N672D, P752K, G753E, A769D, L775A, D801G, A843P, K875T, N892Y

E229S, S635E, T649K, I656V, N672D, G753E, S754E, S757D, A769D, L775A, D801G, K875T, N892Y

E229S, N440K, S582K, N672D, G753E, S754E, A769D, L775A, D801G, A843P, K875T, N892Y, N1008D

E229S, N440K, S582K, A624E, N672D, G753E, S754E, A769D, L775A, V800P, D801G, K875T, N892Y

A190Q, E229S, S635E, T649K, I656V, N672D, P752K, G753E, A769D, L775A, D801G, A843P, K875T, N892Y

A190Q, E229S, S582K, N672D, G753E, S754E, A769D, L775A, D801G, K875T, N892Y

E229S, N440K, S582K, N672D, P752R, G753E, S754E, S757D, A769D, L775A, D801G, K875T, N892Y, N1008D

E229S, S582K, S635E, N672D, P752R, G753E, S754E, A769D, L775A, D801G, K875T, N892Y, N1008D

A190Q, E229S, N440K, S582K, A624E, S635E, N672D, G753E, S754E, A769D, L775A, D801G, K875T, N892Y

E229S, I234V, A492L, S582K, N672D, G753E, S754E, A769D, L775A, D801G, K875T, N892Y

A190Q, E229S, K360G, D458S, S582K, T664K, N672D, G753E, S754E, A769D, L775A, D801G, K875T, N892Y, N1008D

S100D, E229S, K360G, D458S, S582K, N672D, G753E, S754E, S757D, A769D, L775A, D801G, A843P, K875T, N892Y, T915A, N1008D

E229S, N440K, S582K, A624E, N672D, G738L, G753E, S754E, S757D, A769D, L775A, D801G, K875T, N892Y

S100D, E229S, K360G, D458S, S582K, N672D, G753E, S754E, A769D, L775A, D801G, K875T, N892Y, N1008D

A190Q, E229S, D458S, T631N, N672D, G753E, S754E, A769D, L775A, D801G, A843P, K875T, N892Y

A190Q, E229S, K360G, D458S, S582K, N672D, G753E, S754E, A769D, L775A, D801G, K875T, N892Y, N1008D

E229S, S635E, T649K, I656V, N672D, G753E, S754R, S757D, A769D, L775A, D801G, A843P, K875T, N892Y

E229S, D458S, S582K, T631N, S635E, N672D, M728V, G753E, S754E, S757D, A769D, L775A, D801G, K875T, N892Y

A190Q, E229S, K360G, D458S, S582K, N672D, G753E, S754E, S757D, A769D, L775A, D801G, K875T, N892Y, N1008D

E229S, A492L, S635E, T649K, I656V, N672D, G753E, S757D, A769D, L775A, D801G, K875T, N892Y

S100D, A190Q, E229S, K360G, D458S, S582K, N672D, G753E, S754E, A769D, L775A, D801G, K875T, N892Y, N1008D

A190Q, E229S, I234V, S582K, N672D, G753E, S754E, S757D, A769D, L775A, D801G, K875T, N892Y

E229S, N399K, D458S, A492H, K567R, S582K, S635E, T649K, N672D, G753E, S754E, A769D, L775A, D777R, D801G, K875T, N892Y

E229S, D458S, A492L, T631N, N672D, G753E, S754E, S757D, A769D, L775A, D801G, K875T, N892Y

E229S, D458S, A492H, K567R, S582K, S635E, N672D, G753E, S754E, A769D, L775A, D777R, D801G, K875T, N892Y

S100D, E229S, K360G, D458S, S582K, N672D, G753E, S754E, S757D, A769D, L775A, D801G, A843P, K875T, N892Y, N1008D

E229S, N399K, D458S, K567R, S582K, S635E, N672D, G753E, S754E, A769D, L775A, D777R, D801G, K875T, N892Y.

In some aspects, the present invention relates to a xanthan lyase variant having activity on xanthan gum; preferably said activity comprises xanthan lyase EC 4.2.2.12 activity, further preferably said activity is xanthan lyase EC 4.2.2.12 activity.

In some aspects, the present invention relates to a xanthan lyase variant having an improved stability in a detergent composition compared to a parent xanthan lyase (e.g., with SEQ ID NO: 2).

In some aspects, the present invention relates to a xanthan lyase variant having a half-life improvement factor (HIF) of >1.0 relative to a parent xanthan lyase.

In some aspects, the present invention relates to a composition comprising at least one xanthan lyase variant of the invention. In another aspect, the invention relates to a composition comprising an isolated xanthan lyase variant having activity on xanthan gum according to the invention. In a further aspect, the composition further comprises an isolated polypeptide having GH9 endoglucanase activity.

In another aspect, the present invention relates to a composition comprising at least one xanthan lyase variant of the invention, wherein said composition is a detergent composition. In another aspect, a detergent composition of the invention comprises one or more detergent components for degrading xanthan gum.

In some aspects, the present invention relates to use of a composition of the present invention or a xanthan lyase variant of the present invention, wherein said use is selected from the group consisting of: use for degrading xanthan gum, use in a cleaning process, such as laundry or hard surface cleaning such as dish wash, and use for controlling the viscosity of drilling fluids.

In some aspects, the present invention further relates to the use of a composition of the invention for degrading xanthan gum, for washing or cleaning textiles and/or hard surfaces, such as dish wash, wherein the composition has an enzyme detergency benefit, or for controlling the viscosity of drilling fluids.

In some aspects, the present invention also relates to methods of degrading xanthan gum using variants and compositions of the invention, wherein xanthan gum is on the surface of a hard surface or textile, wherein xanthan gum is used in fracturing of a subterranean formation perpetrated by a well bore, or wherein the xanthan gum is a component in borehole filtercake.

In some aspects, the present invention relates to a method for obtaining (or producing) a xanthan lyase, comprising introducing into a parent xanthan lyase (e.g., with SEQ ID NO: 2) an alteration (e.g., a substitution, deletion or insertion) at one or more positions in a chelator-induced instability region selected from the group consisting of: region 1 corresponding to amino acids 154 to 176 of SEQ ID NO: 2, region 2 corresponding to amino acids 614 to 658 of SEQ ID NO: 2, region 3 corresponding to amino acids 731 to 803 of SEQ ID NO: 2, region 4 corresponding to amino acids 807 to 846 of SEQ ID NO: 2, region 5 corresponding to amino acids 872 to 885 of SEQ ID NO: 2, and region 6 corresponding to amino acids 903 to 1004 of SEQ ID NO: 2, wherein said variant has at least 60% and less than 100% sequence identity to SEQ ID NO: 2, and recovering said variant.

In some aspects, the present invention relates to a method for obtaining or producing a xanthan lyase variant, comprising introducing into a parent xanthan lyase (e.g., with SEQ ID NO: 2 or other parent xanthan lyase) an alteration (e.g., a substitution, deletion or insertion) at one or more positions in a region selected from the group consisting of:

i) region 1 corresponding to amino acids 154 to 176 of SEQ ID NO: 2,
ii) region 2 corresponding to amino acids 614 to 658 of SEQ ID NO: 2,
iii) region 3 corresponding to amino acids 731 to 803 of SEQ ID NO: 2,
iv) region 4 corresponding to amino acids 807 to 846 of SEQ ID NO: 2,
v) region 5 corresponding to amino acids 872 to 885 of SEQ ID NO: 2, and
vi) region 6 corresponding to amino acids 903 to 1004 of SEQ ID NO: 2.

In some aspects, the present invention relates to the method for obtaining (or producing) a xanthan lyase variant according to the invention having an alteration (e.g., a substitution, deletion or insertion) at one or more positions selected from the group consisting of positions: 155, 159, 620, 624, 626, 631, 635, 645, 649, 650, 656, 738, 745, 746, 748, 752, 753, 754, 757, 764, 769, 774, 775, 777, 779, 782, 785, 786, 789, 792, 796, 799, 800, 801, 819, 824, 843, 845, 875, 903, 911, 912, 915, 919, 921, 923, 925, 927, 928, 930, 932, 933, 941, 966, 967, 991 and 998.

In some aspects, the present invention relates to a method for obtaining (or producing) a xanthan lyase variant according to the invention having one or more substitutions selected from the group consisting of: Y155E, A159P, K620R, A624E, A626G, T631N, T631E, S635E, S635T, S635Q, A645S, T649V, T649K, T649R, Q650G, I656V, G738L, K745R, F746L, L748T, P752R, P752K, G753E, G753Q, G753S, S754E, S754L, S754Q, S754R, S757D, S757P, S757E, P764V, P764K, A769D, A769T, A769R, A769S, A769E, A769Q, A769*, A774V, L775M, L775Y, L775A, L775I, L775S, L775F, L775Q, D777K, D777R, P779V, Y782I, A785T, N786K, G789R, K792W, K792Y, K792V, K792A, N796Q, A799H, V800P, D801G, K819R, K819T, K824R, A843P, D845E, K875T, K875E, T903A, T903Q, A911V, A911M, A911S, A912T, A912I, A912Y, T915Q, T915S, T915V, T915A, T919F, T919G, T919D, T921R, T921S, T923H, T923D, T925Q, T925D, T925R, T927K, D928W, Y930H, Y930L, Y930F, A932P, D933M, G941E, G941D, A966P, A967D, N991D and V998K.

In some aspects, the present invention relates to a method for obtaining (or producing) a xanthan lyase variant according to the invention having an alteration at one or more positions in at least one region selected from the group consisting regions 1, 2, 3, 4, 5 and 6 as set forth above, and further having an alteration (e.g., a substitution, deletion or insertion) at one or more positions in at least one region selected from the group consisting of:

vii) region 7 corresponding to amino acids 1 to 153 of SEQ ID NO: 2,
viii) region 8 corresponding to amino acids 177 to 613 of SEQ ID NO: 2,
ix) region 9 corresponding to amino acids 659 to 730 of SEQ ID NO: 2,
x) region 10 corresponding to amino acids 804 to 806 of SEQ ID NO: 2,
xi) region 11 corresponding to amino acids 847 to 871 of SEQ ID NO: 2,
xii) region 12 corresponding to amino acids 886 to 902 of SEQ ID NO: 2, and
xiii) region 13 corresponding to amino acids 1005 to 1037 of SEQ ID NO: 2.

In some aspects, the present invention relates to a method for obtaining (or producing) a xanthan lyase variant according to the invention having an alteration (e.g., a substitution, deletion or insertion) at one or more positions, said method providing a variant having a half-life improvement factor (HIF) of >1.0 relative to a parent xanthan lyase.

In some aspects, the present invention also relates to isolated polynucleotides encoding the variant polypeptides of the present invention; as well as to nucleic acid constructs; recombinant expression vectors; and recombinant host cells comprising said variant polynucleotides.

OVERVIEW OF SEQUENCE LISTING

SEQ ID NO: 1 is the DNA sequence of the parent mature xanthan lyase from a strain of a *Paenibacillus* sp.
SEQ ID NO: 2 is the amino acid sequence of the mature polypeptide encoded by SEQ ID NO: 1.

Definitions cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Cleaning or Detergent Application: the term "cleaning or detergent application" means applying the xanthan lyase of the application in any composition for the purpose of cleaning or washing, by hand, machine or automated, a hard surface or a textile.

Cleaning Composition: the term "cleaning composition" refers to compositions that find use in the removal of undesired compounds from items to be cleaned, such as textiles, dishes, and hard surfaces. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish wash detergents). In addition to the xanthan lyase, the detergent formulation may contain one or more additional enzymes (such as xanthan lyases, proteases, amylases, lipases, cutinases, cellulases, xanthan lyases, xyloglucanases, pectinases, pectin lyases, xanthanases, peroxidases, haloperoxygenases, catalases and mannanases, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti corrosion agents, enzyme inhibitors or stabilizers, enzyme activators, transferase(s), hydrolytic enzymes, oxido reductases, bluing agents and fluorescent dyes, antioxidants, and solubilizers.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Colour clarification: During washing and wearing loose or broken fibers can accumulate on the surface of the fabrics. One consequence can be that the colours of the fabric appear less bright or less intense because of the surface contaminations. Removal of the loose or broken fibers from the textile will partly restore the original colours and looks of the textile. By the term "colour clarification", as used herein, is meant the partial restoration of the initial colours of textile.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Corresponding to: The term "corresponding to" as used herein, refers to a way of determining the specific amino acid of a sequence wherein reference is made to a specific amino acid sequence. E.g. for the purposes of the present invention, when references are made to specific amino acid positions, the skilled person would be able to align another amino acid sequence to said amino acid sequence that reference has been made to, in order to determine which specific amino acid may be of interest in said another amino acid sequence. Alignment of another amino acid sequence with e.g. the sequence as set forth in SEQ ID NO: 2, or any other amino acid sequence listed herein, has been described elsewhere herein. Alternative alignment methods may be used, and are well-known for the skilled person.

Degrading xanthan gum and xanthan gum degrading activity: The terms "degrading xanthan gum" and "xanthan gum degrading activity" are used interchangeably and are defined as the depolymerisation, degradation or breaking down of xanthan gum into smaller components. The degradation of xanthan gum can either be the removal of one or more side chain saccharides, the cutting of the backbone of xanthan gum into smaller components or the removal of one or more side chain saccharides and the cutting of the backbone of xanthan gum into smaller components. A preferred assay for measuring degradation of xanthan gum is described in example 4 herein. Non-limiting examples of the xanthan gum degrading activity include xanthan lyase EC 4.2.2.12 activity.

Delta remission value (ΔRem): The terms "Delta remission" or "Delta remission value" are defined herein as the result of a reflectance or remission measurement at 460 nm. The swatch is measured with one swatch of similar colour as background, preferably a swatch from a repetition wash. A swatch representing each swatch type is measured before wash. The Delta remission is the remission value of the washed swatch minus the remission value of the unwashed swatch.

Delta enzyme performance value (ΔRem enzyme value): The term "Delta enzyme remission value" is defined herein as the result of a reflectance or remission measurement at 460 nm. The swatch is measured with one swatch of similar colour as background, preferably a swatch from a repetition wash. A swatch representing each swatch type is measured before wash. The Delta remission is the remission value of the swatch washed in detergent with an enzyme present minus the remission value of a similar swatch washed in a detergent without enzyme present.

Delta enzyme intensity value (ΔInt enzyme value): The terms "Delta enzyme intensity" or "Delta enzyme intensity value" are defined herein as the result of an enzyme intensity value as defined in AMSA assay. The Delta intensity is the intensity value of the swatch area washed in detergent with an enzyme present minus the intensity value of the swatch area washed in detergent without enzyme present.

Detergent component: the term "detergent component" is defined herein to mean the types of chemicals which can be used in detergent compositions. Examples of detergent components are surfactants, hydrotropes, builders, co-builders, chelators or chelating agents, bleaching system or bleach components, polymers, fabric hueing agents, fabric conditioners, foam boosters, suds suppressors, dispersants, dye transfer inhibitors, fluorescent whitening agents, perfume, optical brighteners, bactericides, fungicides, soil suspending agents, soil release polymers, anti-redeposition agents, enzyme inhibitors or stabilizers, enzyme activators, antioxidants, and solubilizers. The detergent composition may comprise of one or more of any type of detergent component.

Detergent composition: the term "detergent composition" refers to compositions that find use in the removal of undesired compounds from items to be cleaned, such as textiles, dishes, and hard surfaces. The detergent composition may be used to e.g. clean textiles, dishes and hard surfaces for both household cleaning and industrial cleaning. The terms encompass any materials/compounds selected for the particular type of cleaning composition desired and the form of the product (e.g., liquid, gel, powder, granulate, paste, or spray compositions) and includes, but is not limited to, detergent compositions (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish wash detergents). In addition to containing a xanthan lyase of the invention and/or a GH9 endoglucanase, the detergent formulation may contain one or more additional enzymes (such as endoglucanases, xanthan lyases, proteases, amylases, lichenases, lipases, cutinases, cellulases, xanthan lyases, xyloglucanases, pectinases, pectin lyases, xanthanases, peroxidases, haloperoxygenases, catalases and mannanases, or any mixture thereof), and/or components such as surfactants, builders, chelators or chelating agents, bleach system or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

Dish wash: The term "dish wash" refers to all forms of washing dishes, e.g. by hand or automatic dish wash. Washing dishes includes, but is not limited to, the cleaning of all forms of crockery such as plates, cups, glasses, bowls, all forms of cutlery such as spoons, knives, forks and serving utensils as well as ceramics, plastics, metals, china, glass and acrylics.

Dish washing composition: The term "dish washing composition" refers to all forms of compositions for cleaning hard surfaces. The present invention is not restricted to any particular type of dish wash composition or any particular detergent.

Endoglucanase: The term "endoglucanase" or "EG" means an endo-1,4- or endo-1,3;1,4-beta-D-glucan 4-glucanohydrolase (e.g., EC 3.2.1.4) that catalyses endohydrolysis of 1,4-beta-D-glycosidic linkages in cellulose, cellulose derivatives (such as carboxymethyl cellulose and hydroxyethyl cellulose), lichenin, beta-1,4 bonds in mixed beta-1,3/beta-1,4 glucans such as cereal beta-D-glucans, xyloglucans, xanthans and other plant material containing cellulosic components. Endoglucanase activity can be determined by measuring reduction in substrate viscosity or increase in reducing ends determined by a reducing sugar assay (Zhang et al., 2006, Biotechnology Advances 24: 452-481).

Enzyme detergency benefit: The term "enzyme detergency benefit" is defined herein as the advantageous effect an enzyme may add to a detergent compared to the same detergent without the enzyme. Important detergency benefits which can be provided by enzymes are stain removal with no or very little visible soils after washing and or cleaning, prevention or reduction of redeposition of soils released in the washing process an effect that also is termed anti-redeposition, restoring fully or partly the whiteness of textiles, which originally were white but after repeated use and wash have obtained a greyish or yellowish appearance an effect that also is termed whitening. Textile care benefits, which are not directly related to catalytic stain removal or prevention of redeposition of soils are also important for enzyme detergency benefits. Examples of such textile care benefits are prevention or reduction of dye transfer from one fabric to another fabric or another part of the same fabric an effect that is also termed dye transfer inhibition or anti-backstaining, removal of protruding or broken fibers from a fabric surface to decrease pilling tendencies or remove already existing pills or fuzz an effect that also is termed anti-pilling, improvement of the fabric-softness, colour clarification of the fabric and removal of particulate soils which are trapped in the fibers of the fabric or garment. Enzymatic bleaching is a further enzyme detergency benefit where the catalytic activity generally is used to catalyze the formation of bleaching component such as hydrogen peroxide or other peroxides.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Fragment: The term "fragment" means a polypeptide having one or more amino acids absent from the amino and/or carboxyl terminus of a mature polypeptide; wherein the fragment has xanthan lyase activity. In one aspect, a fragment contains at least 85%, 86%, 87%, 88%, 89%, 90%, 91%, 92%, 93%, 94% or 95% of the number of amino acids of the mature polypeptide.

Endoglucanase variant having activity on xanthan gum pre-treated with xanthan lyase: The term "Endoglucanase variant having activity on xanthan gum pre-treated with xanthan lyase" or an "endoglucanase having activity on xanthan gum pre-treated with xanthan lyase and belonging to the GH9 class of glycosyl hydrioases" is defined as a polypeptide comprising a domain belonging to the GH9 class of glycosyl hydrolases, and having activity (e.g., enzymatic activity, xanthan degrading activity, endoglucanase EC 3.2.1.4 activity) on xanthan gum pre-treated with xanthan lyase.

Xanthan lyase variant having activity on xanthan gum: The term "Xanthan lyase variant having activity on xanthan gum" is defined as a polypeptide having any kind of activity (e.g., enzymatic activity, xanthan gum degrading activity, xanthan lyase EC 4.2.2.12 activity) on xanthan gum. A preferred assay for measuring activity on xanthan gum is disclosed in example 4 herein.

Half-life: The term "half-life" refers to the time it takes for an enzyme to lose half of its enzymatic activity under a given set of conditions.

Half-life improvement factor: The term "Half-life improvement factor" or "HIF" can be defined according to the following formula: HIF=T½ (variant)/(Wild-type), wherein T½ (variant)=(Ln (0.5)/Ln (RA-variant/100)) *Time, wherein T½ (Wild-type)=(Ln (0.5)/Ln (RA-Wild-type/100))*Time, wherein "RA" is residual activity in percent and "Time" is the incubation time. A preferred way of calculating HIF is also described in example 4 herein. The half-life improvement factor may also be calculated based on the half-life of a parent xanthan lyase (see the definition of "parent" below) that is not necessarily a wild-type.

Hard surface cleaning: The term "Hard surface cleaning" is defined herein as cleaning of hard surfaces wherein hard surfaces may include floors, tables, walls, roofs etc. as well as surfaces of hard objects such as cars (car wash) and dishes (dish wash). Dish washing includes but are not limited to cleaning of plates, cups, glasses, bowls, and cutlery such as spoons, knives, forks, serving utensils, ceramics, plastics, metals, china, glass and acrylics.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Improved property: The term "improved property" means a characteristic associated with a variant that is improved compared to the parent. Such improved properties include, but are not limited to, catalytic efficiency, catalytic rate, chemical stability, oxidation stability, pH activity, pH stability, specific activity, stability under storage conditions, chelator stability, substrate binding, substrate cleavage, substrate specificity, substrate stability, surface properties, thermal activity, and thermostability.

Improved wash performance: The term "improved wash performance" is defined herein as a (variant) enzyme (also a blend of enzymes, not necessarily only variants but also backbones, and in combination with certain cleaning composition etc.) displaying an alteration of the wash performance of a protease variant relative to the wash performance of the parent protease variant e.g. by increased stain removal. The term "wash performance" includes wash performance in laundry but also e.g. in dish wash.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., multiple copies of a gene encoding the substance; use of a stronger promoter than the promoter naturally associated with the gene encoding the substance). An isolated substance may be present in a fermentation broth sample.

Laundering: The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand.

Mature polypeptide: The term "mature polypeptide" means a polypeptide in its final form following translation and any post-translational modifications, such as N-terminal processing, C-terminal truncation, glycosylation, phosphorylation, etc. In one aspect, the mature polypeptide is amino acids 1 to 1037 of SEQ ID NO: 2.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having enzymatic activity such as activity on xanthan gum pre-treated with xanthan lyase or xanthan lyase activity. In one aspect, the mature polypeptide coding sequence is nucleotides 1 to 3111 of SEQ ID NO: 1.

Mutant: The term "mutant" means a polynucleotide encoding a variant.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Operably linked: The term "operably linked" means a configuration in which a control sequence is placed at an appropriate position relative to the coding sequence of a polynucleotide such that the control sequence directs expression of the coding sequence.

Parent: The term "parent" or "parent xanthan lyase" means any polypeptide with xanthan lyase activity to which an alteration is made to produce the enzyme variants of the present invention. In one aspect, the parent is a xanthan lyase having the identical amino acid sequence of the variant, but not having the alterations at one or more of the specified positions. It will be understood, that the expression "having identical amino acid sequence" relates to 100% sequence identity. Non-limiting examples of parent xanthan lyases include the mature parent xanthan lyase having SEQ ID NO: 2.

Sequence identity: The relatedness between two amino acid sequences or between two nucleotide sequences is described by the parameter "sequence identity". For purposes of the present invention, the sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

(Identical Residues×100)/(Length of Alignment– Total Number of Gaps in Alignment)

For purposes of the present invention, the sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 5.0.0 or later. The parameters used are gap open penalty of 10, gap extension penalty of 0.5, and the EDNAFULL (EMBOSS version of NCBI NUC4.4) substitution matrix. The output of Needle labelled "longest identity" (obtained using the –nobrief option) is used as the percent identity and is calculated as follows:

(Identical Deoxyribonucleotides×100)/(Length of Alignment–Total Number of Gaps in Alignment)

Stringency conditions: The different stringency conditions are defined as follows.

The term "very low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 45° C.

The term "low stringency conditions" means for probes of at least 100 nucleotides in length, prehybridization and hybridization at 42° C. in 5×SSPE, 0.3% SDS, 200 micrograms/ml sheared and denatured salmon sperm DNA, and 25% formamide, following standard Southern blotting procedures for 12 to 24 hours. The carrier material is finally washed three times each for 15 minutes using 2×SSC, 0.2% SDS at 50° C.

The term "medium stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 55° C.

The term "medium-high stringency conditions" means for probes of at least 100 nucleotides in length, prehybridization and hybridization at 42° C. in 5×SSPE, 0.3% SDS, 200 micrograms/ml sheared and denatured salmon sperm DNA, and 35% formamide, following standard Southern blotting procedures for 12 to 24 hours. The carrier material is finally washed three times each for 15 minutes using 2×SSC, 0.2% SDS at 60° C.

The term "high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 65° C.

The term "very high stringency conditions" means for probes of at least 100 nucleotides in length, prehybridization and hybridization at 42° C. in 5×SSPE, 0.3% SDS, 200 micrograms/ml sheared and denatured salmon sperm DNA, and 50% formamide, following standard Southern blotting procedures for 12 to 24 hours. The carrier material is finally washed three times each for 15 minutes using 2×SSC, 0.2% SDS at 70° C.

Subsequence: The term "subsequence" means a polynucleotide having one or more nucleotides absent from the 5' and/or 3' end of a mature polypeptide coding sequence; wherein the subsequence encodes a fragment having enzymatic activity, such as activity on xanthan gum pre-treated with xanthan lyase or xanthan lyase activity.

Textile: The term "textile" means any textile material including yarns, yarn intermediates, fibers, non-woven materials, natural materials, synthetic materials, and any other textile material, fabrics made of these materials and products made from fabrics (e.g., garments and other articles). The textile or fabric may be in the form of knits, wovens, denims, non-wovens, felts, yarns, and towelling. The textile may be cellulose based such as natural cellulosics, including cotton, flax/linen, jute, ramie, sisal or coir or manmade cellulosics (e.g. originating from wood pulp) including viscose/rayon, ramie, cellulose acetate fibers (tricell), lyocell or blends thereof. The textile or fabric may also be non-cellulose based such as natural polyamides including wool, camel, cashmere, mohair, rabit and silk or synthetic polymer such as nylon, aramid, polyester, acrylic, polypropylen and spandex/elastane, or blends thereof as well as blend of cellulose based and non-cellulose based fibers. Examples of blends are blends of cotton and/or rayon/viscose with one or more companion material such as wool, synthetic fibers (e.g. polyamide fibers, acrylic fibers, polyester fibers, polyvinyl alcohol fibers, polyvinyl chloride fibers, polyurethane fibers, polyurea fibers, aramid fibers), and cellulose-containing fibers (e.g. rayon/viscose, ramie, flax/linen, jute, cellulose acetate fibers, lyocell). Fabric may be conventional washable laundry, for example stained household laundry. When the term fabric or garment is used it is intended to include the broader term textiles as well.

Textile care benefit: "Textile care benefits", which are not directly related to catalytic stain removal or prevention of redeposition of soils, are also important for enzyme detergency benefits. Examples of such textile care benefits are prevention or reduction of dye transfer from one textile to another textile or another part of the same textile an effect that is also termed dye transfer inhibition or anti-backstaining, removal of protruding or broken fibers from a textile surface to decrease pilling tendencies or remove already existing pills or fuzz an effect that also is termed anti-pilling, improvement of the textile-softness, colour clarification of the textile and removal of particulate soils which are trapped in the fibers of the textile. Enzymatic bleaching is a further enzyme detergency benefit where the catalytic activity generally is used to catalyse the formation of bleaching component such as hydrogen peroxide or other peroxides or other bleaching species.

Variant: The term "variant" means a polypeptide (e.g., a xanthan lyase polypeptide) comprising an alteration, i.e., a substitution, insertion, and/or deletion, at one or more positions. A substitution means replacement of the amino acid occupying a position with a different amino acid; a deletion means removal of the amino acid occupying a position; and an insertion means adding one or more amino acids, e.g., 1-5 amino acids adjacent to and immediately following the amino acid occupying a position. Non-limiting examples of xanthan lyase variants of the present invention include xanthan lyase variants having an activity on xanthan gum. Non-limiting examples of variants of the present invention further include variants having at least 20%, e.g., at least 40%, at least 50%, at least 60%, at least 70%, at least 80%, at least 90%, at least 95%, or at least 100% xanthan lyase activity of the mature parent xanthan lyase of SEQ ID NO: 2. A preferred assay for measuring activity on xanthan gum is disclosed in example 4 herein.

Stability: The term "stability" means resistance or the degree of resistance to change, unfolding, disintegration, denaturation or activity loss. Non-limiting examples of stability include conformational stability, storage stability and stability during use, e.g. during a wash process and reflects the stability of a polypeptide (e.g. a xanthan lyase variant according to the invention) as a function of time, e.g. how much activity is retained when said polypeptide (e.g. said xanthan lyase variant) is kept in solution, in particular in a detergent solution. The stability is influenced by many factors, e.g. presence of chelator(s), pH, temperature, detergent composition, e.g. amount of builder(s), surfactant(s), chelator(s) etc. The xanthan lyase stability may be measured using a half-life improvement factor (HIF) as described in example 4 herein.

Improved stability: The term "improved stability" or "increased stability" is defined herein as increased stability in a detergent composition (e.g., in solutions, e.g. in the presence of a chelator, e.g. EDTA or citrate), relative to the stability of the parent xanthan lyase, relative to a xanthan lyase having the identical amino acid sequence of the variant, but not having the alterations at one or more of the specified positions, or relative to SEQ ID NO: 2. The terms "improved stability" and "increased stability" includes "improved chemical stability", "detergent stability" and "improved detergent stability.

Improved chemical stability: The term "improved chemical stability" is defined herein as a variant enzyme displaying retention of enzymatic activity after a period of incubation in the presence of a chemical or chemicals, either naturally occurring or synthetic, which reduces the enzymatic activity of the parent enzyme. Improved chemical stability may also result in variants being more able (e.g., better that the parent) to catalyze a reaction in the presence of such chemicals. In a particular aspect of the invention the improved chemical stability is an improved stability in a detergent, in particular in a liquid detergent. The term "detergent stability" or "improved detergent stability is in particular an improved stability of the xanthan lyase compared to the parent xanthan lyase, when a xanthan lyase variant of the present invention is mixed into a liquid detergent formulation, especially into a liquid detergent formulation comprising a chelator (e.g. EDTA or citrate).

Conformational stability: The term "conformational stability" means a resistance or a degree of resistance to conformational change, unfolding or disintegration. Accordingly, the term "less conformationally stable" means less resistant or having lesser degree of resistance to conformational change, unfolding or disintegration.

Instability: The term "instability" means lack of stability. Non-limiting examples of instability include conformational instability, unfolding, denaturation, disintegration, activity loss.

Chelator-induced instability region: The term "chelator-induced instability region" means any region of a polypeptide contributing to instability of said polypeptide in the presence of a chelator. Non-limiting examples of chelators include EDTA (Ethylenediaminetetraacetic acid) and citrate. Non-limiting examples of chelator-induced instability regions include any region of a polypeptide having one or more of the following features: in the presence of a chelator it is less conformationally stable than one or more or all of its adjacent regions; and/or in the presence of a chelator it is more exposed to said chelator than one or more or all of its adjacent regions; and/or in the presence of a chelator it is more accessible to said chelator than one or more or all of its adjacent regions; and/or in the presence of a chelator it is more conformationally dynamic than one or more or all of its adjacent regions; and/or in the presence of a chelator it is more receptive to deuterium incorporation than one or more or all of its adjacent regions. Non-limiting examples of chelator-induced instability regions further include any region of a polypeptide responsible for chelator-induced instability. Non-limiting examples of chelator-induced instability regions of a mature xanthan lyase (e.g. having SEQ ID NO: 2) include: region 1 corresponding to amino acids 154 to 176 of SEQ ID NO: 2, region 2 corresponding to amino acids 614 to 658 of SEQ ID NO: 2, region 3 corresponding to amino acids 731 to 803 of SEQ ID NO: 2, region 4 corresponding to amino acids 807 to 846 of SEQ ID NO: 2, region 5 corresponding to amino acids 872 to 885 of SEQ ID NO: 2, and region 6 corresponding to amino acids 903 to 1004 of SEQ ID NO: 2. Non-limiting examples of regions adjacent to chelator-induced instability regions of a mature xanthan lyase (e.g. having SEQ ID NO: 2) include: region 7 corresponding to amino acids 1 to 153 of SEQ ID NO: 2, region 8 corresponding to amino acids 177 to 613 of SEQ ID NO: 2, region 9 corresponding to amino acids 659 to 730 of SEQ ID NO: 2, region 10 corresponding to amino acids 804 to 806 of SEQ ID NO: 2, region 11 corresponding to amino acids 847 to 871 of SEQ ID NO: 2, region 12 corresponding to amino acids 886 to 902 of SEQ ID NO: 2, and region 13 corresponding to amino acids 1005 to 1037 of SEQ ID NO: 2.

Adjacent region: The term "adjacent region" means any region of a polypeptide that is not a chelator-induced instability region. Non-limiting examples of adjacent regions of a mature xanthan lyase (e.g. having SEQ ID NO: 2) include: region 7 corresponding to amino acids 1 to 153 of SEQ ID NO: 2, region 8 corresponding to amino acids 177 to 613 of SEQ ID NO: 2, region 9 corresponding to amino acids 659 to 730 of SEQ ID NO: 2, region 10 corresponding to amino acids 804 to 806 of SEQ ID NO: 2, region 11 corresponding to amino acids 847 to 871 of SEQ ID NO: 2, region 12 corresponding to amino acids 886 to 902 of SEQ ID NO: 2, and region 13 corresponding to amino acids 1005 to 1037 of SEQ ID NO: 2.

Chelator exposure: The term "chelator exposure" means concentration or amount of a chelator that reaches a polypeptide. Accordingly, in the context of the present invention the term "more exposed to a chelator" means that chelator exposure of a particular region (e.g. a chelator-induced instability region) is greater than a chelator exposure of a different region (e.g. an adjacent region). In one aspect, chelator exposure can be expressed in numerical terms of concentration, duration, and frequency (e.g. for chemical agents, e.g. chelators) or intensity.

Chelator accessibility: The term "chelator accessibility" encompasses openness to the influence by a chelator and easiness of approach by chelator. Accordingly, in the context of the present invention the term "more accessible to a chelator" means that chelator accessibility of a particular region (e.g. a chelator-induced instability region) is greater than a chelator accessibility of a different region (e.g. an adjacent region).

Conformational dynamics: The term "conformational dynamics" encompasses vibrations, structural rearrangements and transitions of a polypeptide (e.g. in solution). Accordingly, in the context of the present invention the term "more conformationally dynamic" means that conformational dynamics of a particular region (e.g. a chelator-induced instability region) is greater than conformational dynamics of a different region (e.g. an adjacent region).

Receptiveness to deuterium incorporation: The term "receptiveness to deuterium incorporation" means amount of hydrogen atoms replaced by a deuterium atoms during hydrogen-deuterium exchange. Said amount can be measured in relative (e.g. compared to another amount) or absolute (e.g. expressed numerically) terms. Accordingly, in the context of the present invention the term "more receptive to deuterium incorporation" means that receptiveness to deuterium incorporation of a particular region (e.g. a chelator-induced instability region) is greater than receptiveness to deuterium incorporation of a different region (e.g. an adjacent region).

Wash performance: The term "wash performance" is used as an enzyme's ability to remove stains present on the object to be cleaned during e.g. wash or hard surface cleaning. The improvement in the wash performance may be quantified by calculating the so-called intensity value (Int) in 'Automatic Mechanical Stress Assay (AMSA) for laundry' or the remission value (Rem) as defined herein.

Whiteness: The term "Whiteness" is defined herein as a broad term with different meanings in different regions and for different customers. Loss of whiteness can e.g. be due to greying, yellowing, or removal of optical brighteners/hueing agents. Greying and yellowing can be due to soil redeposition, body soils, colouring from, e.g. iron and copper ions or dye transfer. Whiteness might include one or several issues from the list below: Colorant or dye effects; Incomplete stain removal (e.g. body soils, sebum ect.); Re-deposition (greying, yellowing or other discolorations of the object) (removed soils re-associates with other part of textile, soiled or unsoiled); Chemical changes in textile during application; and Clarification or brightening of colours.

Xanthan lyase: The term "xanthan lyase" is defined herein as an enzyme that has activity on xanthan gum (e.g., enzymatic, activity, a xanthan gum degrading activity). Non-limiting examples of xanthan lyases include an enzyme that cleaves the β-D-mannosyl-β-D-1,4-glucuronosyl bonds in xanthan gum (EC 4.2.2.12).

Conventions for Designation of Variants

For purposes of the present invention, the mature polypeptide disclosed in SEQ ID NO: 2 is used to determine the corresponding amino acid residue in another xanthan lyase. The amino acid sequence of another xanthan lyase is aligned with the mature polypeptide disclosed in SEQ ID NO: 2, and based on the alignment, the amino acid position number corresponding to any amino acid residue in the mature polypeptide disclosed in SEQ ID NO: 2 is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 5.0.0 or later. The parameters used are gap open penalty of 10, gap extension penalty of 0.5, and the EBLOSUM62 (EMBOSS version of BLOSUM62) substitution matrix.

Identification of the corresponding amino acid residue in another xanthan lyase can be determined by an alignment of multiple polypeptide sequences using several computer programs including, but not limited to, MUSCLE (multiple sequence comparison by log-expectation; version 3.5 or later; Edgar, 2004, *Nucleic Acids Research* 32: 1792-1797), MAFFT (version 6.857 or later; Katoh and Kuma, 2002, *Nucleic Acids Research* 30: 3059-3066; Katoh et al., 2005, *Nucleic Acids Research* 33: 511-518; Katoh and Toh, 2007, *Bioinformatics* 23: 372-374; Katoh et al., 2009, *Methods in Molecular Biology* 537:_39-64; Katoh and Toh, 2010, *Bioinformatics* 26:_1899-1900), and EMBOSS EMMA employing ClustalW (1.83 or later; Thompson et al., 1994, *Nucleic Acids Research* 22: 4673-4680), using their respective default parameters.

When the other enzyme has diverged from the mature polypeptide of SEQ ID NO: 2 such that traditional sequence-based comparison fails to detect their relationship (Lindahl and Elofsson, 2000, *J. Mol. Biol.* 295: 613-615), other pairwise sequence comparison algorithms can be used. Greater sensitivity in sequence-based searching can be attained using search programs that utilize probabilistic representations of polypeptide families (profiles) to search databases. For example, the PSI-BLAST program generates profiles through an iterative database search process and is capable of detecting remote homologs (Atschul et al., 1997, *Nucleic Acids Res.* 25: 3389-3402). Even greater sensitivity can be achieved if the family or superfamily for the polypeptide has one or more representatives in the protein structure databases. Programs such as GenTHREADER (Jones, 1999, *J. Mol. Biol.* 287: 797-815; McGuffin and Jones, 2003, *Bioinformatics* 19: 874-881) utilize information from a variety of sources (PSI-BLAST, secondary structure prediction, structural alignment profiles, and solvation potentials) as input to a neural network that predicts the structural fold for a query sequence. Similarly, the method of Gough et al., 2000, *J. Mol. Biol.* 313: 903-919, can be used to align a sequence of unknown structure with the superfamily models present in the SCOP database. These alignments can in turn be used to generate homology models for the polypeptide, and such models can be assessed for accuracy using a variety of tools developed for that purpose.

For proteins of known structure, several tools and resources are available for retrieving and generating structural alignments. For example the SCOP superfamilies of proteins have been structurally aligned, and those alignments are accessible and downloadable. Two or more protein structures can be aligned using a variety of algorithms such as the distance alignment matrix (Holm and Sander, 1998, *Proteins* 33: 88-96) or combinatorial extension (Shindyalov and Bourne, 1998, *Protein Engineering* 11: 739-747), and implementation of these algorithms can additionally be utilized to query structure databases with a structure of interest in order to discover possible structural homologs (e.g., Holm and Park, 2000, *Bioinformatics* 16: 566-567).

In describing the variants of the present invention, the nomenclature described below is adapted for ease of reference. The accepted IUPAC single letter or three letter amino acid abbreviation is employed.

Substitutions.

For an amino acid substitution, the following nomenclature is used: Original amino acid, position, substituted amino acid. Accordingly, the substitution of threonine at position 226 with alanine is designated as "Thr226Ala" or "T226A". Multiple mutations are separated by addition marks ("+"), e.g., "Gly205Arg+Ser411Phe" or "G205R+S411F", representing substitutions at positions 205 and 411 of glycine (G) with arginine (R) and serine (S) with phenylalanine (F), respectively.

Deletions.

For an amino acid deletion, the following nomenclature is used: Original amino acid, position, *. Accordingly, the deletion of glycine at position 195 is designated as "Gly195*" or "G195*". Multiple deletions are separated by addition marks ("+"), e.g., "Gly195*+Ser411*" or "G195*+S411*".

Insertions.

For an amino acid insertion, the following nomenclature is used: Original amino acid, position, original amino acid, inserted amino acid. Accordingly the insertion of lysine after glycine at position 195 is designated "Gly195GlyLys" or "G195GK". An insertion of multiple amino acids is designated [Original amino acid, position, original amino acid, inserted amino acid #1, inserted amino acid #2; etc.]. For example, the insertion of lysine and alanine after glycine at position 195 is indicated as "Gly195GlyLysAla" or "G195GKA". An indication of an insertion at a particular position is understood as being an insertion after the original amino acid residue. For example, an "insertion at position 195" is understood to be an insertion after the original residue in position 195.

In such cases the inserted amino acid residue(s) are numbered by the addition of lower case letters to the position number of the amino acid residue preceding the inserted amino acid residue(s). In the above example, the sequence would thus be:

| Parent: | Variant: |
|---|---|
| 195 | 195 195a 195b |
| G | G - K - A |

Multiple Alterations.

Variants comprising multiple alterations are separated by addition marks ("+"), e.g., "Arg170Tyr+Gly195Glu" or "R170Y+G195E" representing a substitution of arginine and glycine at positions 170 and 195 with tyrosine and glutamic acid, respectively.

Different Alterations.

Where different alterations can be introduced at a position, the different alterations are separated by a comma, e.g., "Arg170Tyr,Glu" represents a substitution of arginine at position 170 with tyrosine or glutamic acid. Thus, "Tyr167Gly,Ala+Arg170Gly,Ala" designates the following variants: "Tyr167Gly+Arg170Gly", "Tyr167Gly+Arg170Ala", "Tyr167Ala+Arg170Gly", and "Tyr167Ala+Arg 170Ala".

Alternatively, different alterations or may be indicated using brackets, e.g., Arg170[Tyr, Gly] or in one-letter code R170 [Y,G].

DETAILED DESCRIPTION OF THE INVENTION

The known xanthan lyase having SEQ ID NO: 2 is a large enzyme (>1000 residues), it is therefore extremely laborious and expensive to target its properties for improvement of, e.g., stability in a detergent composition, e.g. in the presence of a chelator. In some aspects, the present invention narrows down the number of residues to target when trying to stabilize xanthan lyase molecules using protein engineering to a region selected from the group consisting of: region 1 corresponding to amino acids 154 to 176 of SEQ ID NO: 2, region 2 corresponding to amino acids 614 to 658 of SEQ ID NO: 2, region 3 corresponding to amino acids 731 to 803 of SEQ ID NO: 2, region 4 corresponding to amino acids 807 to 846 of SEQ ID NO: 2, region 5 corresponding to amino acids 872 to 885 of SEQ ID NO: 2, and region 6 corresponding to amino acids 903 to 1004 of SEQ ID NO: 2.

In one embodiment the present invention dramatically narrows down the number of residues to target when trying to stabilize xanthan lyase molecules using protein engineering.

Variants

In one embodiment, the present invention relates to chelator-induced instability regions in the protein sequence of the known xanthan lyase having SEQ ID NO: 2 that are affected when the molecule is incubated in a buffer with EDTA, said regions being the following: region 1 corresponding to amino acids 154 to 176 of SEQ ID NO: 2, region 2 corresponding to amino acids 614 to 658 of SEQ ID NO: 2, region 3 corresponding to amino acids 731 to 803 of SEQ ID NO: 2, region 4 corresponding to amino acids 807 to 846 of SEQ ID NO: 2, region 5 corresponding to amino acids 872 to 885 of SEQ ID NO: 2, and region 6 corresponding to amino acids 903 to 1004 of SEQ ID NO: 2. This embodiment relates to an important guidance on where to mutate a xanthan lyase in order to stabilize the molecule in a detergent, e.g. detergent composition comprising a chelator, e.g. EDTA or citrate.

In one embodiment the present invention relates to a xanthan lyase variant, comprising an alteration (e.g., a substitution, deletion or insertion) at one or more positions in a region selected from the group consisting of: region 1 corresponding to amino acids 154 to 176 of SEQ ID NO: 2, region 2 corresponding to amino acids 614 to 658 of SEQ ID NO: 2, region 3 corresponding to amino acids 731 to 803 of SEQ ID NO: 2, region 4 corresponding to amino acids 807 to 846 of SEQ ID NO: 2, region 5 corresponding to amino acids 872 to 885 of SEQ ID NO: 2, and region 6 corresponding to amino acids 903 to 1004 of SEQ ID NO: 2, wherein said variant has at least 60% and less than 100% sequence identity to SEQ ID NO: 2; preferably said xanthan lyase variant has activity on xanthan gum, further preferably said activity is a xanthan gum degrading activity.

In one embodiment the present invention relates to a xanthan lyase variant, comprising an alteration (e.g., a substitution, deletion or insertion) at one or more positions in two or more regions selected from the group consisting of: region 1 corresponding to amino acids 154 to 176 of SEQ ID NO: 2, region 2 corresponding to amino acids 614 to 658 of SEQ ID NO: 2, region 3 corresponding to amino acids 731 to 803 of SEQ ID NO: 2, region 4 corresponding to amino acids 807 to 846 of SEQ ID NO: 2, region 5 corresponding to amino acids 872 to 885 of SEQ ID NO: 2, and region 6 corresponding to amino acids 903 to 1004 of SEQ ID NO: 2, wherein said variant has at least 60% and less than 100% sequence identity to SEQ ID NO: 2; preferably said xanthan lyase variant has activity on xanthan gum, further preferably said activity is a xanthan gum degrading activity.

In one embodiment the present invention relates to a parent xanthan lyase of the invention (e.g., SEQ ID NO: 2) having an alteration (e.g., a substitution, deletion or insertion) at one or more positions in a region selected from the group consisting of regions 1-6, wherein said region is a chelator-induced instability region, preferably said chelator-induced instability region has one or more of the following features: in the presence of a chelator it is less conformationally stable than one or more or all of its adjacent regions; and/or in the presence of a chelator it is more exposed to said chelator than one or more or all of its adjacent regions; and/or in the presence of a chelator it is more accessible to said chelator than one or more or all of its adjacent regions; and/or in the presence of a chelator it is more conformationally dynamic than one or more or all of its adjacent regions; and/or in the presence of a chelator it is more receptive to deuterium incorporation than one or more or all of its adjacent regions; further preferably said adjacent region is selected from the group consisting of: region 7 corresponding to amino acids 1 to 153 of SEQ ID NO: 2, region 8 corresponding to amino acids 177 to 613 of SEQ ID NO: 2, region 9 corresponding to amino acids 659 to 730 of SEQ ID NO: 2, region 10 corresponding to amino acids 804 to 806 of SEQ ID NO: 2, region 11 corresponding to amino acids 847 to 871 of SEQ ID NO: 2, region 12 corresponding to amino acids 886 to 902 of SEQ ID NO: 2, and region 13 corresponding to amino acids 1005 to 1037 of SEQ ID NO: 2, further most preferably said chelator is EDTA or citrate.

In one embodiment the adjacent regions of the invention can be one or more or all of the following: region 7 corresponding to amino acids 1 to 153 of SEQ ID NO: 2, region 8 corresponding to amino acids 177 to 613 of SEQ ID NO: 2, region 9 corresponding to amino acids 659 to 730 of SEQ ID NO: 2, region 10 corresponding to amino acids 804 to 806 of SEQ ID NO: 2, region 11 corresponding to amino acids 847 to 871 of SEQ ID NO: 2, region 12 corresponding to amino acids 886 to 902 of SEQ ID NO: 2, and region 13 corresponding to amino acids 1005 to 1037 of SEQ ID NO: 2.

In one embodiment the present invention relates to a xanthan lyase variant of the invention having an alteration (e.g., a substitution, deletion or insertion) at one or more positions in a region selected from the group consisting of regions 1-6 (e.g., of SEQ ID NO: 2 or another parent xanthan lyase), wherein in an aqueous solution comprising a detergent component said region (e.g., of SEQ ID NO: 2 or another parent xanthan lyase) is more accessible to said detergent component than one or more or all of its adjacent regions.

In one embodiment the present invention relates to a xanthan lyase variant of the invention having an alteration (e.g., a substitution, deletion or insertion) at one or more positions in a region selected from the group consisting of regions 1-6 (e.g., of SEQ ID NO: 2 or another parent xanthan lyase), wherein in an aqueous solution comprising a detergent component said region (e.g., of SEQ ID NO: 2 or another parent xanthan lyase) is more exposed to said detergent component than one or more or all of its adjacent regions.

In one embodiment the present invention relates to a xanthan lyase variant of the invention having an alteration (e.g., a substitution, deletion or insertion) at one or more positions in a region selected from the group consisting of regions 1-6 (e.g., of SEQ ID NO: 2 or another parent xanthan lyase), wherein in an aqueous solution comprising a detergent component said region (e.g., of SEQ ID NO: 2 or another parent xanthan lyase) is more conformationally dynamic than one or more or all of its adjacent regions.

In one embodiment the present invention relates to a xanthan lyase variant of the invention having an alteration (e.g., a substitution, deletion or insertion) at one or more positions in a region selected from the group consisting of regions 1-6 (e.g., of SEQ ID NO: 2 or another parent xanthan lyase), wherein in an aqueous solution comprising a detergent component said region (e.g., of SEQ ID NO: 2 or another parent xanthan lyase) is more receptive to deuterium incorporation than one or more or all of its adjacent regions.

In one embodiment the present invention relates to a xanthan lyase variant of the invention, comprising an alteration (e.g., a substitution, deletion or insertion) at one or more positions in two or more regions selected from the group consisting of: region 1 corresponding to amino acids 154 to 176 of SEQ ID NO: 2, region 2 corresponding to amino acids 614 to 658 of SEQ ID NO: 2, region 3 corresponding to amino acids 731 to 803 of SEQ ID NO: 2, region 4 corresponding to amino acids 807 to 846 of SEQ ID NO: 2, region 5 corresponding to amino acids 872 to 885 of SEQ ID NO: 2, and region 6 corresponding to amino acids 903 to 1004 of SEQ ID NO: 2, wherein said variant has at least 60% and less than 100% sequence identity to SEQ ID NO: 2, preferably said variant has activity on xanthan gum, further preferably said activity is a xanthan gum degrading activity.

In one embodiment the present invention relates to a xanthan lyase variant of the invention having multiple alterations (such as 2, 3, 4, 5, 6, 7, 8, 9 or 10) in one region (e.g., of SEQ ID NO: 2 or another parent xanthan lyase) selected from the group consisting of: region 1 corresponding to amino acids 154 to 176 of SEQ ID NO: 2, region 2 corresponding to amino acids 614 to 658 of SEQ ID NO: 2, region 3 corresponding to amino acids 731 to 803 of SEQ ID NO: 2, region 4 corresponding to amino acids 807 to 846 of SEQ ID NO: 2, region 5 corresponding to amino acids 872 to 885 of SEQ ID NO: 2, and region 6 corresponding to amino acids 903 to 1004 of SEQ ID NO: 2, wherein said variant has at least 60% and less than 100% sequence identity to SEQ ID NO: 2, preferably said variant has activity on xanthan gum, further preferably said activity is a xanthan gum degrading activity.

In one embodiment the present invention relates to a xanthan lyase variant of the invention having multiple alterations (e.g., 2, 3, 4, 5, 6, 7, 8, 9 or 10) in multiple regions (e.g., 2, 3, 4, 5, 6, 7, 8, 9 or 10) (e.g., of SEQ ID NO: 2 or another parent xanthan lyase) selected from the group consisting of: region 1 corresponding to amino acids 154 to 176 of SEQ ID NO: 2, region 2 corresponding to amino acids 614 to 658 of SEQ ID NO: 2, region 3 corresponding to amino acids 731 to 803 of SEQ ID NO: 2, region 4 corresponding to amino acids 807 to 846 of SEQ ID NO: 2, region 5 corresponding to amino acids 872 to 885 of SEQ ID NO: 2, and region 6 corresponding to amino acids 903 to 1004 of SEQ ID NO: 2, wherein said variant has at least 60% and less than 100% sequence identity to SEQ ID NO: 2, preferably said variant has activity on xanthan gum, further preferably said activity is a xanthan gum degrading activity.

In one embodiment the present invention relates to xanthan lyase variants, comprising an alteration (e.g., a substitution, deletion or insertion) at one or more positions of the mature parent polypeptide (e.g., SEQ ID NO: 2), wherein each alteration is independently a substitution, insertion or deletion, wherein the variant has xanthan lyase activity.

In an embodiment, the variant has sequence identity of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, or at least 99%, but less than 100%, to the amino acid sequence of the parent xanthan lyase.

In one embodiment, the variant has at least 60%, e.g., at least 65%, at least 70%, at least 75%, at least 80%, at least 85%, at least 90%, at least 91%, at least 92%, at least 93%, at least 94%, at least 95%, such as at least 96%, at least 97%, at least 98%, or at least 99%, but less than 100%, sequence identity to the mature polypeptide of SEQ ID NO: 2.

In one embodiment the present invention relates to a xanthan lyase variant of the invention, having at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 2.

In another aspect, a variant comprises an alteration at one or more positions corresponding to positions 155, 159, 620, 624, 626, 631, 635, 645, 649, 650, 656, 738, 745, 746, 748, 752, 753, 754, 757, 764, 769, 774, 775, 777, 779, 782, 785, 786, 789, 792, 796, 799, 800, 801, 819, 824, 843, 845, 875, 903, 911, 912, 915, 919, 921, 923, 925, 927, 928, 930, 932, 933, 941, 966, 967, 991 and 998. In another aspect, a variant comprises an alteration at two positions corresponding to any of positions 155, 159, 620, 624, 626, 631, 635, 645, 649, 650, 656, 738, 745, 746, 748, 752, 753, 754, 757, 764, 769, 774, 775, 777, 779, 782, 785, 786, 789, 792, 796, 799, 800, 801, 819, 824, 843, 845, 875, 903, 911, 912, 915, 919, 921, 923, 925, 927, 928, 930, 932, 933, 941, 966, 967, 991 and 998. In another aspect, a variant comprises an alteration at three positions corresponding to any of positions 155, 159, 620, 624, 626, 631, 635, 645, 649, 650, 656, 738, 745, 746, 748, 752, 753, 754, 757, 764, 769, 774, 775, 777, 779, 782, 785, 786, 789, 792, 796, 799, 800, 801, 819, 824, 843, 845, 875, 903, 911, 912, 915, 919, 921, 923, 925, 927, 928, 930, 932, 933, 941, 966, 967, 991 and 998. In another aspect, a variant comprises an alteration at four or more positions, e.g. five, six, seven, eight, nine, ten or more positions, corresponding to positions 155, 159, 620, 624, 626, 631, 635, 645, 649, 650, 656, 738, 745, 746, 748, 752, 753, 754, 757, 764, 769, 774, 775, 777, 779, 782, 785, 786, 789, 792, 796, 799, 800, 801, 819, 824, 843, 845, 875, 903, 911, 912, 915, 919, 921, 923, 925, 927, 928, 930, 932, 933, 941, 966, 967, 991 and 998.

In another aspect, the variant comprises or consists of an alteration at a position corresponding to position 155. In another aspect, the amino acid at a position corresponding to position 155 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution Y155E of the mature polypeptide of SEQ ID NO: 2.

In another aspect, the variant comprises or consists of an alteration at a position corresponding to position 159. In another aspect, the amino acid at a position corresponding to position 159 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution A159P.

In another aspect, the variant comprises or consists of an alteration at a position corresponding to position 620. In another aspect, the amino acid at a position corresponding to position 620 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K620R of the mature polypeptide of SEQ ID NO: 2.

In another aspect, the variant comprises or consists of an alteration at a position corresponding to position 624. In another aspect, the amino acid at a position corresponding to position 624 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution A624E of the mature polypeptide of SEQ ID NO: 2

In another aspect, the variant comprises or consists of an alteration at a position corresponding to position 626. In another aspect, the amino acid at a position corresponding to position 626 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution A626Q of the mature polypeptide of SEQ ID NO: 2.

In another aspect, the variant comprises or consists of an alteration at a position corresponding to position 631. In another aspect, the amino acid at a position corresponding to position 631 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T631N or T631E of the mature polypeptide of SEQ ID NO: 2. A preferred substitution at a position corresponding to position 631 is T631N.

In another aspect, the variant comprises or consists of an alteration at a position corresponding to position 635. In another aspect, the amino acid at a position corresponding to position 635 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution S635E, S635T or S635Q. A preferred substitution at a position corresponding to position 635 is S635E.

In another aspect, the variant comprises or consists of an alteration at a position corresponding to position 649. In another aspect, the amino acid at a position corresponding to position 649 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T649V, T649K or T649R of the mature polypeptide of SEQ ID NO: 2. A preferred substitution at a position corresponding to position 649 is T649K.

In another aspect, the variant comprises or consists of an alteration at a position corresponding to position 650. In another aspect, the amino acid at a position corresponding to position 650 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution Q650G of the mature polypeptide of SEQ ID NO: 2.

In another aspect, the variant comprises or consists of an alteration at a position corresponding to position 656. In another aspect, the amino acid at a position corresponding to position 656 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution I656V of the mature polypeptide of SEQ ID NO: 2.

In another aspect, the variant comprises or consists of an alteration at a position corresponding to position 738. In another aspect, the amino acid at a position corresponding to position 738 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution G738L of the mature polypeptide of SEQ ID NO: 2.

In another aspect, the variant comprises or consists of an alteration at a position corresponding to position 745. In another aspect, the amino acid at a position corresponding to position 745 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K745R of the mature polypeptide of SEQ ID NO: 2.

In another aspect, the variant comprises or consists of an alteration at a position corresponding to position 746. In another aspect, the amino acid at a position corresponding to position 746 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution F746L of the mature polypeptide of SEQ ID NO: 2.

In another aspect, the variant comprises or consists of an alteration at a position corresponding to position 748. In another aspect, the amino acid at a position corresponding to position 748 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution L748T of the mature polypeptide of SEQ ID NO: 2.

In another aspect, the variant comprises or consists of an alteration at a position corresponding to position 752. In another aspect, the amino acid at a position corresponding to position 752 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution P752R or P752K of the mature polypeptide of SEQ ID NO: 2.

In another aspect, the variant comprises or consists of an alteration at a position corresponding to position 753. In another aspect, the amino acid at a position corresponding to position 753 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution G753E, G753Q or G753S of the mature polypeptide of SEQ ID NO: 2. A preferred substitution at a position corresponding to position 753 is G753E.

In another aspect, the variant comprises or consists of an alteration at a position corresponding to position 754. In another aspect, the amino acid at a position corresponding to position 754 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution S754E, S754L, S754Q or S754R of the mature polypeptide of SEQ ID NO: 2. A preferred substitution at a position corresponding to position 754 is S754E or S754R.

In another aspect, the variant comprises or consists of an alteration at a position corresponding to position 757. In another aspect, the amino acid at a position corresponding to position 757 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution S757D, S757P or S757E of the mature polypeptide of SEQ ID NO: 2. A preferred substitution at a position corresponding to position 757 is S757D.

In another aspect, the variant comprises or consists of an alteration at a position corresponding to position 764. In another aspect, the amino acid at a position corresponding to position 764 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution P764V or P764K of the mature polypeptide of SEQ ID NO: 2. A preferred substitution at a position corresponding to position 764 is P764V.

In another aspect, the variant comprises or consists of an alteration at a position corresponding to position 769. In another aspect, the amino acid at a position corresponding to position 769 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the alteration A769D, A769T, A769R, A769S, A769E, A769Q or A769* of the mature polypeptide of SEQ ID NO: 2. A preferred substitution at a position corresponding to position 769 is A769D.

In another aspect, the variant comprises or consists of an alteration at a position corresponding to position 774. In another aspect, the amino acid at a position corresponding to position 774 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution A774V of the mature polypeptide of SEQ ID NO: 2.

In another aspect, the variant comprises or consists of an alteration at a position corresponding to position 775. In another aspect, the amino acid at a position corresponding to position 775 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution L775A or L775F or L775I or L775M or L775Q or L775S or L775Y of the mature polypeptide of SEQ ID NO: 2. A preferred substitution at a position corresponding to position 775 is L775M, L775Y or L775A.

In another aspect, the variant comprises or consists of an alteration at a position corresponding to position 779. In another aspect, the amino acid at a position corresponding to position 779 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution P779V of the mature polypeptide of SEQ ID NO: 2.

In another aspect, the variant comprises or consists of an alteration at a position corresponding to position 782. In another aspect, the amino acid at a position corresponding to position 782 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution Y782I.

In another aspect, the variant comprises or consists of an alteration at a position corresponding to position 786. In another aspect, the amino acid at a position corresponding to position 786 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution N786K.

In another aspect, the variant comprises or consists of an alteration at a position corresponding to position 789. In another aspect, the amino acid at a position corresponding to position 789 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution G789R.

In another aspect, the variant comprises or consists of an alteration at a position corresponding to position 792. In another aspect, the amino acid at a position corresponding to position 792 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K792W, K792Y, K792V or K792A of the mature polypeptide of SEQ ID NO: 2. A preferred substitution at a position corresponding to position 792 is K792W or K792Y.

In another aspect, the variant comprises or consists of an alteration at a position corresponding to position 796. In another aspect, the amino acid at a position corresponding to position 796 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution N796Q of the mature polypeptide of SEQ ID NO: 2.

In another aspect, the variant comprises or consists of an alteration at a position corresponding to position 799. In another aspect, the amino acid at a position corresponding to position 799 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution A799H of the mature polypeptide of SEQ ID NO: 2.

In another aspect, the variant comprises or consists of an alteration at a position corresponding to position 800. In another aspect, the amino acid at a position corresponding to position 800 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution V800P of the mature polypeptide of SEQ ID NO: 2.

In another aspect, the variant comprises or consists of an alteration at a position corresponding to position 801. In another aspect, the amino acid at a position corresponding to position 801 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution D801G of the mature polypeptide of SEQ ID NO: 2.

In another aspect, the variant comprises or consists of an alteration at a position corresponding to position 819. In another aspect, the amino acid at a position corresponding to position 819 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K819R or K819T of the mature polypeptide of SEQ ID NO: 2. A preferred substitution at a position corresponding to position 819 is K819R or K819T.

In another aspect, the variant comprises or consists of an alteration at a position corresponding to position 824. In another aspect, the amino acid at a position corresponding to position 824 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K824R of the mature polypeptide of SEQ ID NO: 2.

In another aspect, the variant comprises or consists of an alteration at a position corresponding to position 843. In another aspect, the amino acid at a position corresponding to position 843 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution A843P.

In another aspect, the variant comprises or consists of an alteration at a position corresponding to position 845. In another aspect, the amino acid at a position corresponding to position 845 is substituted with Ala, Arg, Asn, Asp, Cys, Gln, Glu, Gly, His, Ile, Leu, Lys, Met, Phe, Pro, Ser, Thr, Trp, Tyr, or Val. A preferred substitution at a position corresponding to position 845 is D845E.

In another aspect, the variant comprises or consists of an alteration at a position corresponding to position 875. In another aspect, the amino acid at a position corresponding to position 875 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution K875T or K875E of the mature polypeptide of SEQ ID NO: 2. A preferred substitution at a position corresponding to position 875 is K875T.

In another aspect, the variant comprises or consists of an alteration at a position corresponding to position 903. In another aspect, the amino acid at a position corresponding to position 903 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T903A or T903Q of the mature polypeptide of SEQ ID NO: 2.

In another aspect, the variant comprises or consists of an alteration at a position corresponding to position 911. In another aspect, the amino acid at a position corresponding to position 911 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution A911M, A911V or A911S of the mature polypeptide of SEQ ID NO: 2. A preferred substitution at a position corresponding to position 911 is A911V.

In another aspect, the variant comprises or consists of an alteration at a position corresponding to position 912. In another aspect, the amino acid at a position corresponding to position 912 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution A912I or A912T or A912Y of the mature polypeptide of SEQ ID NO: 2. A preferred substitution at a position corresponding to position 912 is A912T.

In another aspect, the variant comprises or consists of an alteration at a position corresponding to position 915. In another aspect, the amino acid at a position corresponding to position 915 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T915S, T915Q, T915A or T915V of the mature polypeptide of SEQ ID NO: 2.

In another aspect, the variant comprises or consists of an alteration at a position corresponding to position 919. In another aspect, the amino acid at a position corresponding to position 919 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T919D, T919F or T919G of the mature polypeptide of SEQ ID NO: 2.

In another aspect, the variant comprises or consists of an alteration at a position corresponding to position 921. In another aspect, the amino acid at a position corresponding to position 921 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T921R or T921S of the mature polypeptide of SEQ ID NO: 2.

In another aspect, the variant comprises or consists of an alteration at a position corresponding to position 923. In another aspect, the amino acid at a position corresponding to position 923 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T923D or T923H of the mature polypeptide of SEQ ID NO: 2.

In another aspect, the variant comprises or consists of an alteration at a position corresponding to position 925. In another aspect, the amino acid at a position corresponding to position 925 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T925D or T925Q or T925R of the mature polypeptide of SEQ ID NO: 2.

In another aspect, the variant comprises or consists of an alteration at a position corresponding to position 927. In another aspect, the amino acid at a position corresponding to position 927 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution T927K of the mature polypeptide of SEQ ID NO: 2.

In another aspect, the variant comprises or consists of an alteration at a position corresponding to position 928. In another aspect, the amino acid at a position corresponding to position 928 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution D928W of the mature polypeptide of SEQ ID NO: 2.

In another aspect, the variant comprises or consists of an alteration at a position corresponding to position 930. In another aspect, the amino acid at a position corresponding to position 930 is substituted with Ala, Arg, Asn, Asp, Cys, Gln, Glu, Gly, His, Ile, Leu, Lys, Met, Phe, Pro, Ser, Thr, Trp, Tyr, or Val. In another aspect, the variant comprises or consists of the substitution Y930F or Y930H or Y930L of the mature polypeptide of SEQ ID NO: 2.

In another aspect, the variant comprises or consists of an alteration at a position corresponding to position 933. In another aspect, the amino acid at a position corresponding to position 933 is substituted with Ala, Arg, Asn, Asp, Cys, Gin, Glu, Gly, His, Ile, Leu, Lys, Met, Phe, Pro, Ser, Thr, Trp, Tyr, or Val. In another aspect, the variant comprises or consists of the substitution D933M of the mature polypeptide of SEQ ID NO: 2.

In another aspect, the variant comprises or consists of an alteration at a position corresponding to position 941. In another aspect, the amino acid at a position corresponding to position 941 is substituted with Ala, Arg, Asn, Asp, Cys, Gin, Glu, Gly, His, Ile, Leu, Lys, Met, Phe, Pro, Ser, Thr, Trp, Tyr, or Val. In another aspect, the variant comprises or consists of the substitution G941D or G941E of the mature polypeptide of SEQ ID NO: 2.

In another aspect, the variant comprises or consists of an alteration at a position corresponding to position 966. In another aspect, the amino acid at a position corresponding to position 966 is substituted with Ala, Arg, Asn, Asp, Cys, Gin, Glu, Gly, His, Ile, Leu, Lys, Met, Phe, Pro, Ser, Thr, Trp, Tyr, or Val. In another aspect, the variant comprises or consists of the substitution A966P of the mature polypeptide of SEQ ID NO: 2.

In another aspect, the variant comprises or consists of an alteration at a position corresponding to position 991. In another aspect, the amino acid at a position corresponding to position 991 is substituted with Ala, Arg, Asn, Asp, Cys, Gin, Glu, Gly, His, Ile, Leu, Lys, Met, Phe, Pro, Ser, Thr, Trp, Tyr, or Val. In another aspect, the variant comprises or consists of the substitution N991D of the mature polypeptide of SEQ ID NO: 2.

In another aspect, the variant comprises or consists of an alteration at a position corresponding to position 998. In another aspect, the amino acid at a position corresponding to position 998 is substituted with Ala, Arg, Asn, Asp, Cys, Gin, Glu, Gly, His, Ile, Leu, Lys, Met, Phe, Pro, Ser, Thr, Trp, Tyr, or Val. In another aspect, the variant comprises or consists of the substitution V998K of the mature polypeptide of SEQ ID NO: 2.

In one embodiment the present invention relates to a xanthan lyase variant of the invention, having an alteration at one or more positions selected from the group consisting of positions: 155, 159, 620, 624, 626, 631, 635, 645, 649, 650, 656, 738, 745, 746, 748, 752, 753, 754, 757, 764, 769, 774, 775, 777, 779, 782, 785, 786, 789, 792, 796, 799, 800, 801, 819, 824, 843, 845, 875, 903, 911, 912, 915, 919, 921, 923, 925, 927, 928, 930, 932, 933, 941, 966, 967, 991 and 998 of SEQ ID NO: 2, wherein each position corresponds to the positions of SEQ ID NO: 2.

In one embodiment the present invention relates to a xanthan lyase variant of the invention, having an alteration at one or more positions selected from the group consisting of: Y155E, A159P, K620R, A624E, A626G, T631N, T631E, S635E, S635T, S635Q, A645S, T649V, T649K, T649R, Q650G, I656V, G738L, K745R, F746L, L748T, P752R, P752K, G753E, G753Q, G753S, S754E, S754L, S754Q, S754R, S757D, S757P, S757E, P764V, P764K, A769D, A769T, A769R, A769S, A769E, A769Q, A769*, A774V, L775M, L775Y, L775A, L775I, L775S, L775F, L775Q, D777K, D777R, P779V, Y782I, A785T, N786K, G789R, K792W, K792Y, K792V, K792A, N796Q, A799H, V800P, D801G, K819R, K819T, K824R, A843P, D845E, K875T, K875E, T903A, T903Q, A911V, A911M, A911S, A912T, A912I, A912Y, T915Q, T915S, T915V, T915A, T919F, T919G, T919D, T921R, T921S, T923H, T923D, T925Q, T925D, T925R, T927K, D928W, Y930H, Y930L, Y930F, A932P, D933M, G941E, G941D, A966P, A967D, N991D and V998K, wherein numbering is according to SEQ ID NO: 2.

In a particular embodiment, the invention relates to a xanthan lyase variant selected from the group consisting of the xanthan lyase variants set forth in Table 1 herein.

In a particular embodiment, the invention relates to a xanthan lyase variant selected from the group consisting of the xanthan lyase variants set forth in Table 2 herein.

In a particular embodiment, the invention relates to a xanthan lyase variant selected from the group consisting of the xanthan lyase variants set forth in Table 3 herein.

In a particular embodiment, the invention relates to a xanthan lyase variant selected from the group consisting of the xanthan lyase variants set forth in Table 4 herein.

In a particular embodiment, the invention relates to a xanthan lyase variant selected from the group consisting of the xanthan lyase variants set forth in Table 5 herein.

In a particular embodiment, the invention relates to a xanthan lyase variant selected from the group consisting of the xanthan lyase variants set forth in Table 6 herein.

In a particular embodiment, the invention relates to a xanthan lyase variant selected from the group consisting of the xanthan lyase variants set forth in Table 7 herein.

In a particular embodiment, the invention relates to a xanthan lyase variant selected from the group consisting of the xanthan lyase variants set forth in Table 8 herein.

In a particular embodiment, the invention relates to a xanthan lyase variant selected from the group consisting of the xanthan lyase variants set forth in Table 9 herein.

In a particular embodiment, the invention relates to a xanthan lyase variant selected from the group consisting of the xanthan lyase variants set forth in Table 10 herein.

In a particular embodiment, the invention relates to a xanthan lyase variant selected from the group consisting of the xanthan lyase variants set forth in Table 11 herein.

In a particular embodiment, the invention relates to a xanthan lyase variant selected from the group consisting of the xanthan lyase variants set forth in Table 12 herein.

In a particular embodiment, the invention relates to a xanthan lyase variant selected from the group consisting of the xanthan lyase variants set forth in Table 13 herein.

The variants may further comprise one or more additional alterations at one or more other positions.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/

Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for xanthan lyase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

In one embodiment the present invention relates to a xanthan lyase variant of the invention, having a total number of alterations compared to SEQ ID NO: 2 between 1 and 20, e.g., between 1 and 10 or between 1 and 5, such as 1, 2, 3, 4, 5, 6, 7, 8, 9 or 10 alterations.

In one embodiment the present invention relates to a xanthan lyase variant of the invention, having an activity on xanthan gum, preferably said activity on xanthan gum is a xanthan gum degrading activity, further preferably said xanthan gum degrading activity is EC 4.2.2.12 activity.

In an embodiment, the variant has an improved stability in a detergent composition compared to a parent enzyme (e.g., SEQ ID NO: 2).

In one embodiment the present invention relates to a xanthan lyase variant of the invention, having an improved stability in a detergent composition compared to the parent xanthan lyase (e.g., with SEQ ID NO: 2); preferably said detergent composition comprises a chelator; further preferably said chelator is EDTA or citrate.

In one embodiment the present invention relates to a xanthan lyase variant of the invention, having a half-life improvement factor (HIF) of 1.0; preferably having a half-life improvement factor (HIF) of >1.0, relative to a parent xanthan lyase. More preferably, the half-life improvement factor (HIF) of a variant of the invention is at least 1.2, such as at least 1.5, e.g. at least 2.0, at least 3.0, at least 4.0 or at least 5.0. A preferred way of calculating a half-life improvement factor (HIF) is described in example 4 herein.

In one embodiment the present invention relates to a xanthan lyase variant of the invention, wherein a half-life improvement factor (HIF) is determined after incubation of said xanthan lyase variant in a detergent composition at 25° C. or 30° C. for a time period from about 30 min to about 20 hours.

Parent

The parent xanthan lyase may be (a) a polypeptide having at least 60% sequence identity to the mature polypeptide of SEQ ID NO: 2; (b) a polypeptide encoded by a polynucleotide that hybridizes under low stringency conditions with (i) the mature polypeptide coding sequence of SEQ ID NO: 1, or (ii) the full-length complement of (i); or (c) a polypeptide encoded by a polynucleotide having at least 60% sequence identity to the mature polypeptide coding sequence of SEQ ID NO: 1.

In an aspect, the parent has a sequence identity to the mature polypeptide of SEQ ID NO: 2 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%, which have xanthan lyase activity. In one aspect, the amino acid sequence of the parent differs by up to 10 amino acids, e.g., 1, 2, 3, 4, 5, 6, 7, 8, 9, or 10, from the mature polypeptide of SEQ ID NO: 2.

In another aspect, the parent comprises or consists of the amino acid sequence of SEQ ID NO: 2. In another aspect, the parent comprises or consists of the mature polypeptide of SEQ ID NO: 2. In another aspect, the parent is a fragment of the mature polypeptide of SEQ ID NO: 2 containing at least 85%, 86%, 87%, 88%, 89%, 90%, 91%, 92%, 93%, 94% or 95% of the number of amino acids of SEQ ID NO: 2. In another embodiment, the parent is an allelic variant of the mature polypeptide of SEQ ID NO: 2.

In another aspect, the parent is encoded by a polynucleotide that hybridizes under very low stringency conditions, low stringency conditions, medium stringency conditions, medium-high stringency conditions, high stringency conditions, or very high stringency conditions with (i) the mature polypeptide coding sequence of SEQ ID NO: 1, or (ii) the full-length complement of (i) (Sambrook et al., 1989, Molecular Cloning, A Laboratory Manual, 2d edition, Cold Spring Harbor, New York).

The polynucleotide of SEQ ID NO: 1 or a subsequence thereof, as well as the polypeptide of SEQ ID NO: 2 or a fragment thereof, may be used to design nucleic acid probes to identify and clone DNA encoding a parent from strains of different genera or species according to methods well known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may be screened for DNA that hybridizes with the probes described above and encodes a parent. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1 or a subsequence thereof, the carrier material is used in a Southern blot.

For purposes of the present invention, hybridization indicates that the polynucleotide hybridizes to a labeled nucleic acid probe corresponding to (i) SEQ ID NO: 1; (ii) the mature polypeptide coding sequence of SEQ ID NO: 1; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one aspect, the nucleic acid probe is the mature polypeptide coding sequence of SEQ ID NO: 1. In another aspect, the nucleic acid probe is a polynucleotide that encodes the polypeptide of SEQ ID NO: 2; the mature polypeptide thereof; or a fragment thereof. In another aspect, the nucleic acid probe is SEQ ID NO: 1.

In another embodiment, the parent is encoded by a polynucleotide having a sequence identity to the mature polypeptide coding sequence of SEQ ID NO: 1 of at least 60%, e.g., at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or 100%.

The polypeptide may be a hybrid polypeptide in which a region of one polypeptide is fused at the N-terminus or the C-terminus of a region of another polypeptide.

The parent may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

The parent may be obtained from microorganisms of any genus. For purposes of the present invention, the term "obtained from" as used herein in connection with a given source shall mean that the parent encoded by a polynucleotide is produced by the source or by a strain in which the polynucleotide from the source has been inserted. In one aspect, the parent is secreted extracellularly.

The parent may be a bacterial enzyme. For example, the parent may be a Gram-positive bacterial polypeptide such as a *Bacillus*, *Clostridium*, *Enterococcus*, *Geobacillus*, *Lactobacillus*, *Lactococcus*, *Oceanobacillus*, *Staphylococcus*, *Streptococcus*, or *Streptomyces* enzyme, or a Gram-negative bacterial polypeptide such as a *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma* enzyme.

In one aspect, the parent is a *Bacillus alkalophilus*, *Bacillus amyloliquefaciens*, *Bacillus brevis*, *Bacillus circulans*, *Bacillus clausii*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* enzyme.

In another aspect, the parent is a *Streptococcus equisimilis*, *Streptococcus pyogenes*, *Streptococcus uberis*, or *Streptococcus equi* subsp. *Zooepidemicus* enzyme.

In another aspect, the parent is a *Streptomyces achromogenes*, *Streptomyces avermitilis*, *Streptomyces coelicolor*, *Streptomyces griseus*, or *Streptomyces lividans* enzyme.

The parent may be a fungal enzyme. For example, the parent may be a yeast enzyme such as a *Candida*, *Kluyveromyces*, *Pichia*, *Saccharomyces*, *Schizosaccharomyces*, or *Yarrowia* enzyme; or a filamentous fungal enzyme such as an *Acremonium*, *Agaricus*, *Alternaria*, *Aspergillus*, *Aureobasidium*, *Botryosphaeria*, *Ceriporiopsis*, *Chaetomidium*, *Chrysosporium*, *Claviceps*, *Cochliobolus*, *Coprinopsis*, *Coptotermes*, *Corynascus*, *Cryphonectria*, *Cryptococcus*, *Diplodia*, *Exidia*, *Filibasidium*, *Fusarium*, *Gibberella*, *Holomastigotoides*, *Humicola*, *Irpex*, *Lentinula*, *Leptospaeria*, *Magnaporthe*, *Melanocarpus*, *Meripilus*, *Mucor*, *Myceliophthora*, *Neocallimastix*, *Neurospora*, *Paecilomyces*, *Penicillium*, *Phanerochaete*, *Piromyces*, *Poitrasia*, *Pseudoplectania*, *Pseudotrichonympha*, *Rhizomucor*, *Schizophyllum*, *Scytalidium*, *Talaromyces*, *Thermoascus*, *Thielavia*, *Tolypocladium*, *Trichoderma*, *Trichophaea*, *Verticillium*, *Volvariella*, or *Xylaria* enzyme.

In another aspect, the parent is a *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, or *Saccharomyces oviformis* enzyme.

In another aspect, the parent is an *Acremonium cellulolyticus*, *Aspergillus aculeatus*, *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola grisea*, *Humicola insolens*, *Humicola lanuginosa*, *Irpex lacteus*, *Mucor miehei*, *Myceliophthora thermophila*, *Neurospora crassa*, *Penicillium funiculosum*, *Penicillium purpurogenum*, *Phanerochaete chrysosporium*, *Thielavia achromatica*, *Thielavia albomyces*, *Thielavia albopilosa*, *Thielavia australeinsis*, *Thielavia fimeti*, *Thielavia microspora*, *Thielavia ovispora*, *Thielavia peruviana*, *Thielavia setosa*, *Thielavia spededonium*, *Thielavia subthermophila*, *Thielavia terrestris*, *Trichoderma harzianum*, *Trichoderma koningii*, *Trichoderma longibrachiatum*, *Trichoderma reesei*, or *Trichoderma viride* enzyme.

In another aspect, the parent is a *Paenibacillus* sp. xanthan lyase, e.g., the xanthan lyase of SEQ ID NO: 2.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Preparation of Variants

The present invention also relates to methods for obtaining a variant having xanthan lyase activity, comprising: (a) introducing into a parent xanthan lyase an alteration at one or more positions corresponding to positions 155, 159, 620, 624, 626, 631, 635, 645, 649, 650, 656, 738, 745, 746, 748, 752, 753, 754, 757, 764, 769, 774, 775, 777, 779, 782, 785, 786, 789, 792, 796, 799, 800, 801, 819, 824, 843, 845, 875, 903, 911, 912, 915, 919, 921, 923, 925, 927, 928, 930, 932, 933, 941, 966, 967, 991 and 998 of the mature polypeptide of SEQ ID NO: 2, wherein the variant has xanthan lyase activity; and (b) recovering the variant.

The variants can be prepared using any mutagenesis procedure known in the art, such as site-directed mutagenesis, synthetic gene construction, semi-synthetic gene construction, random mutagenesis, shuffling, etc.

Site-directed mutagenesis is a technique in which one or more mutations are introduced at one or more defined sites in a polynucleotide encoding the parent.

Site-directed mutagenesis can be accomplished in vitro by PCR involving the use of oligonucleotide primers containing the desired mutation. Site-directed mutagenesis can also be performed in vitro by cassette mutagenesis involving the cleavage by a restriction enzyme at a site in the plasmid comprising a polynucleotide encoding the parent and subsequent ligation of an oligonucleotide containing the mutation in the polynucleotide. Usually the restriction enzyme that digests the plasmid and the oligonucleotide is the same, permitting sticky ends of the plasmid and the insert to ligate to one another. See, e.g., Scherer and Davis, 1979, *Proc. Natl. Acad. Sci. USA* 76: 4949-4955; and Barton et al., 1990, *Nucleic Acids Res.* 18: 7349-4966.

Site-directed mutagenesis can also be accomplished in vivo by methods known in the art. See, e.g., U.S. Patent Application Publication No. 2004/0171154; Storici et al., 2001, *Nature Biotechnol.* 19: 773-776; Kren et al., 1998, *Nat. Med.* 4: 285-290; and Calissano and Macino, 1996, *Fungal Genet. Newslett.* 43: 15-16.

Any site-directed mutagenesis procedure can be used in the present invention. There are many commercial kits available that can be used to prepare variants.

Synthetic gene construction entails in vitro synthesis of a designed polynucleotide molecule to encode a polypeptide of interest. Gene synthesis can be performed utilizing a number of techniques, such as the multiplex microchip-based technology described by Tian et al. (2004, *Nature* 432: 1050-1054) and similar technologies wherein oligonucleotides are synthesized and assembled upon photo-programmable microfluidic chips.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204) and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

Semi-synthetic gene construction is accomplished by combining aspects of synthetic gene construction, and/or site-directed mutagenesis, and/or random mutagenesis, and/or shuffling. Semi-synthetic construction is typified by a process utilizing polynucleotide fragments that are synthesized, in combination with PCR techniques. Defined regions of genes may thus be synthesized de novo, while other regions may be amplified using site-specific mutagenic primers, while yet other regions may be subjected to error-prone PCR or non-error prone PCR amplification. Polynucleotide subsequences may then be shuffled.

EMBODIMENTS

In one embodiment the present invention relates to a composition comprising at least one (e.g. 1, 2, 3, 4, 5, 6, 7, 8, 9 or 10) xanthan lyase variant of the invention.

In one embodiment the present invention relates to a composition comprising at least one (e.g. 1, 2, 3, 4, 5, 6, 7, 8, 9 or 10) xanthan lyase variant of the invention, wherein said composition is a detergent composition.

In one embodiment the present invention relates to a composition comprising at least one (e.g. 1, 2, 3, 4, 5, 6, 7, 8, 9 or 10) xanthan lyase variant of the invention, further comprising one or more detergent components; preferably said detergent component is a chelator; further preferably said chelator is EDTA or citrate.

In one embodiment the present invention relates to a composition comprising at least one (e.g. 1, 2, 3, 4, 5, 6, 7, 8, 9 or 10) xanthan lyase variant of the invention, wherein said composition is a detergent composition further comprising one or more detergent components; preferably said detergent component is a chelator; further preferably said chelator is EDTA or citrate.

In one embodiment the present invention relates to a composition comprising at least one (e.g. 1, 2, 3, 4, 5, 6, 7, 8, 9 or 10) xanthan lyase variant of the invention, further comprising one or more additional enzymes selected from the group comprising or consisting of: endoglucanases, proteases, amylases, lipases, cutinases, cellulases, xanthan lyases, xyloglucanases, pectinases, pectin lyases, xanthanases, peroxidases, haloperoxygenases, catalases and mannanases, or any mixture thereof.

In one embodiment the present invention relates to a composition comprising at least one (e.g. 1, 2, 3, 4, 5, 6, 7, 8, 9 or 10) xanthan lyase variant of the invention, wherein said composition is a detergent composition further comprising one or more additional enzymes selected from the group comprising or consisting of: endoglucanases, proteases, amylases, lipases, cutinases, cellulases, xanthan lyases, xyloglucanases, pectinases, pectin lyases, xanthanases, peroxidases, haloperoxygenases, catalases and mannanases, or any mixture thereof.

In one embodiment the present invention relates to a composition comprising at least one (e.g. 1, 2, 3, 4, 5, 6, 7, 8, 9 or 10) xanthan lyase variant of the invention, wherein said composition is a detergent composition further comprising one or more detergent components and one or more additional enzymes selected from the group comprising or consisting of: endoglucanases, proteases, amylases, lipases, cutinases, cellulases, xanthan lyases, xyloglucanases, pectinases, pectin lyases, xanthanases, peroxidases, haloperoxygenases, catalases and mannanases, or any mixture thereof, preferably said detergent component is a chelator; further preferably said chelator is EDTA or citrate.

In one embodiment the present invention relates to a composition comprising at least one (e.g. 1, 2, 3, 4, 5, 6, 7, 8, 9 or 10) xanthan lyase variant of the invention, wherein said composition is a detergent composition further comprising one or more detergent components, wherein said detergent composition is in form of a bar, a homogenous tablet, a tablet having two or more layers, a pouch having one or more compartments, a regular or compact powder, a granule, a paste, a gel, or a regular, compact or concentrated liquid.

In one embodiment the present invention relates to use of a composition of the invention or a xanthan lyase variant of the invention, wherein said use is selected from the group comprising or consisting of: use for degrading xanthan gum, use in a cleaning process, such as laundry or hard surface cleaning such as dish wash, and use for controlling the viscosity of drilling fluids.

In one embodiment the present invention relates to use of a composition of the invention, wherein said composition has an enzyme detergency benefit In one embodiment the present invention relates to an isolated polynucleotide encoding a xanthan lyase variant of the invention.

In one embodiment the present invention relates to a nucleic acid construct or expression vector capable of expressing a polynucleotide of the invention; preferably said nucleic acid construct or said expression vector comprising the polynucleotide of the invention operably linked to one or more control sequences that direct the production of the polypeptide in an expression host.

In one embodiment the present invention relates to a host cell (e.g., isolated host cell, isolated recombinant host cell) comprising the polynucleotide of the invention; preferably said polynucleotide is operably linked to one or more control sequences that direct the production of the polypeptide; further preferably said host cell is an isolated host cell.

In one embodiment the present invention relates to a method for obtaining (or producing) a xanthan lyase variant, comprising introducing into a parent xanthan lyase (e.g., having SEQ ID NO: 2) an alteration (e.g., a substitution, deletion or insertion) at one or more positions in a region (e.g., of SEQ ID NO: 2 or another parent xanthan lyase) selected from the group consisting of: region 1 corresponding to amino acids 154 to 176 of SEQ ID NO: 2, region 2 corresponding to amino acids 614 to 658 of SEQ ID NO: 2, region 3 corresponding to amino acids 731 to 803 of SEQ ID NO: 2, region 4 corresponding to amino acids 807 to 846 of SEQ ID NO: 2, region 5 corresponding to amino acids 872 to 885 of SEQ ID NO: 2, and region 6 corresponding to amino acids 903 to 1004 of SEQ ID NO: 2, wherein said variant has at least 60% and less than 100% sequence identity to SEQ ID NO: 2, and recovering said variant; preferably said region selected from the group consisting of regions 1-6 is a chelator-induced instability region; further preferably said method further comprises introducing into the parent xanthan lyase (e.g., with SEQ ID NO: 2) an alteration (e.g., a substitution, deletion or insertion) at one or more positions in one or more regions selected from the group consisting of regions 1-6.

In one embodiment the present invention relates to a method for obtaining (or producing) a xanthan lyase variant according to the invention having at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 2.

In one embodiment the present invention relates to a method for obtaining (or producing) a xanthan lyase variant according to the invention, having an alteration (e.g., a substitution, deletion or insertion) at one or more positions is selected from the group consisting of positions: 155, 159, 620, 624, 626, 631, 635, 645, 649, 650, 656, 738, 745, 746, 748, 752, 753, 754, 757, 764, 769, 774, 775, 777, 779, 782, 785, 786, 789, 792, 796, 799, 800, 801, 819, 824, 843, 845, 875, 903, 911, 912, 915, 919, 921, 923, 925, 927, 928, 930, 932, 933, 941, 966, 967, 991 and 998, wherein each position corresponds to the positions of SEQ ID NO: 2.

In one embodiment the present invention relates to a method for obtaining (or producing) a xanthan lyase variant according to the invention having an alteration (e.g., a substitution, deletion or insertion) at one or more positions is selected from the group consisting of: Y155E, A159P, K620R, A624E, A626G, T631N, T631E, S635E, S635T, S635Q, A645S, T649V, T649K, T649R, Q650G, I656V, G738L, K745R, F746L, L748T, P752R, P752K, G753E, G753Q, G753S, S754E, S754L, S754Q, S754R, S757D, S757P, S757E, P764V, P764K, A769D, A769T, A769R, A769S, A769E, A769Q, A769*, A774V, L775M, L775Y, L775A, L775I, L775S, L775F, L775Q, D777K, D777R, P779V, Y782I, A785T, N786K, G789R, K792W, K792Y, K792V, K792A, N796Q, A799H, V800P, D801G, K819R, K819T, K824R, A843P, D845E, K875T, K875E, T903A, T903Q, A911V, A911M, A911S, A912T, A912I, A912Y, T915Q, T915S, T915V, T915A, T919F, T919G, T919D, T921R, T921S, T923H, T923D, T925Q, T925D, T925R, T927K, D928W, Y930H, Y930L, Y930F, A932P, D933M, G941E, G941D, A966P, A967D, N991D and V998K, wherein the numbering is according to SEQ ID NO: 2.

In one embodiment the present invention relates to a method for obtaining (or producing) a xanthan lyase variant according to the invention, said variant having an alteration (e.g., a substitution, deletion or insertion) at one or more positions such that to provide a variant having a half-life improvement factor (HIF) of 1.0; preferably a half-life improvement factor (HIF) of >1.0, relative to a parent xanthan lyase.

In one embodiment the present invention relates to a method of producing a xanthan lyase variant, comprising: cultivating a host cell (e.g., isolated host cell, isolated recombinant host cell) of the invention under conditions suitable for expression of said variant; and recovering said variant.

In one embodiment the present invention relates to a method of producing a xanthan lyase variant, comprising: cultivating a host cell (e.g., isolated host cell, isolated recombinant host cell) under conditions suitable for expression of said variant; and recovering said variant, wherein said xanthan lyase variant is a variant of the invention.

In one embodiment the present invention relates to a method for degrading xanthan gum comprising: applying a composition of the invention to a xanthan gum.

In one embodiment the present invention relates to a method for degrading xanthan gum comprising: applying a composition of the invention to a xanthan gum, wherein said xanthan gum is on the surface of a textile or hard surface, such as dish wash.

In one embodiment the present invention relates to a method for degrading xanthan gum comprising: applying a composition of the invention to a xanthan gum, wherein said xanthan gum is used in fracturing of a subterranean formation perpetrated by a well bore.

In one embodiment the present invention relates to a method for degrading xanthan gum comprising: applying a composition of the invention to a xanthan gum, wherein said xanthan gum is a component in a borehole filtercake.

In one embodiment the present invention relates to use of deuterium for identification of a chelator-induced instability region of a xanthan lyase polypeptide (e.g., having SEQ ID NO: 2) or a xanthan lyase variant of the invention, preferably said chelator is EDTA or citrate, further preferably said deuterium is in the form of D2O.

In one embodiment the present invention relates to a method for identification of a chelator-induced instability region of a xanthan lyase (e.g. xanthan lyase polypeptide having SEQ ID NO: 2 or a xanthan lyase variant according to the invention), said method comprising:
i) providing in the presence of a chelator, preferably said chelator is EDTA or citrate:
  a) a xanthan lyase polypeptide (e.g. having SEQ ID NO: 2 or an xanthan lyase variant according to the invention),
ii) providing in the absence of the chelator:
  b) the xanthan lyase polypeptide according to a),
iii) providing deuterium to i) and ii), e.g. to a final deuterium concentration of 95%, for hydrogen-deuterium exchange, preferably said deuterium is in the form of $D_2O$,
iv) digesting deuterated polypeptides from step iii) with pepsin,
v) identifying peptic peptides produced in step iv),
vi) quantifying and comparing deuterium incorporation into individual peptides from step v) in the presence and absence of said chelator.

Polynucleotides

The present invention also relates to isolated polynucleotides encoding a variant of the present invention.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Applica-*

*tion*, Academic Press, New York. Other nucleic acid amplification procedures such as ligase chain reaction (LCR), ligation activated transcription (LAT) and polynucleotide-based amplification (NASBA) may be used. The polynucleotides may be cloned in a strain of *Bacillus subtilis* or *E. coli*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, Ford et al., (1991), '*Protein Expression and Purification*', 2: 95-107.

Nucleic Acid Constructs

The present invention also relates to nucleic acid constructs comprising a polynucleotide encoding a variant of the present invention operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, Scientific American 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* xanthan lyase I, *Trichoderma reesei* xanthan lyase II, *Trichoderma reesei* xanthan lyase III, *Trichoderma reesei* xanthan lyase IV, *Trichoderma reesei* xanthan lyase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* xanthan lyase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide encoding a variant of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et aL, 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide encoding a variant of the present invention operably linked to one or more control sequences that direct the production of a variant of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing (e.g., in vitro or ex vivo methods) a variant, comprising: (a) cultivating a host cell of the present invention under conditions suitable for expression of the variant; and (b) recovering the variant.

The present invention also relates to methods of producing (e.g., in vitro or ex vivo methods) a variant of the present invention, comprising (a) cultivating a cell, which in its wild-type form produces the polypeptide, under conditions conducive for production of the polypeptide; and (b) recovering the polypeptide. In a preferred aspect, the cell is a *Paenibacillus* cell, or a *Microbacterium* cell.

The present invention also relates to methods of producing (e.g., in vitro or ex vivo methods) a variant of the present invention, comprising (a) cultivating a recombinant host cell of the present invention under conditions conducive for production of the polypeptide; and (b) recovering the polypeptide.

The host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The variant polypeptide may be detected using methods known in the art that are specific for the polypeptides such as methods for determining cellulose or xanthan lyase activity. These detection methods include, but are not limited to, use of specific antibodies, formation of an enzyme product, or disappearance of an enzyme substrate. For example, an enzyme assay may be used to determine the activity of the polypeptide.

The variant polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The variant polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the variant polypeptide is not recovered, but rather a host cell of the present invention expressing the polypeptide is used as a source of the variant polypeptide.

Compositions

In one certain aspect, the variants according to the invention have improved stability in detergents compared to a parent enzyme or compared to a xanthan lyase having the identical amino acid sequence of the variant, but not having an alteration (e.g., a substitution, deletion or insertion) at one or more of the specified positions or compared to the xanthan lyase with SEQ ID NO: 2, wherein activity and/or stability in detergent is measured as disclosed in example 4 herein.

Besides enzymes the detergent compositions may comprise additional components. The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

The detergent composition may be suitable for the laundering of textiles such as e.g. fabrics, cloths or linen, or for cleaning hard surfaces such as e.g. floors, tables, or dish wash.

Detergent Compositions

In one embodiment, a variant of the present invention may be added to a detergent composition in an amount corresponding to 0.0001-200 mg of enzyme protein, such as 0.0005-100 mg of enzyme protein, preferably 0.001-30 mg of enzyme protein, more preferably 0.005-8 mg of enzyme protein, even more preferably 0.01-2 mg of enzyme protein per litre of wash liquor.

A composition for use in automatic dishwash (ADW), for example, may include 0.0001%-50%, such as 0.001%-20%, such as 0.01%-10%, such as 0.05-5% of enzyme protein by weight of the composition.

A composition for use in laundry granulation, for example, may include 0.0001%-50%, such as 0.001%-20%, such as 0.01%-10%, such as 0.05%-5% of enzyme protein by weight of the composition.

A composition for use in laundry liquid, for example, may include 0.0001%-10%, such as 0.001-7%, such as 0.1%-5% of enzyme protein by weight of the composition.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO92/19709 and WO92/19708.

In certain markets different wash conditions and, as such, different types of detergents are used. This is disclosed in e.g. EP 1 025 240. For example, In Asia (Japan) a low detergent concentration system is used, while the United States uses a medium detergent concentration system, and Europe uses a high detergent concentration system.

A low detergent concentration system includes detergents where less than about 800 ppm of detergent components are present in the wash water. Japanese detergents are typically considered low detergent concentration system as they have approximately 667 ppm of detergent components present in the wash water.

A medium detergent concentration includes detergents where between about 800 ppm and about 2000 ppm of detergent components are present in the wash water. North American detergents are generally considered to be medium detergent concentration systems as they have approximately 975 ppm of detergent components present in the wash water.

A high detergent concentration system includes detergents where greater than about 2000 ppm of detergent components are present in the wash water. European detergents are generally considered to be high detergent concentration systems as they have approximately 4500-5000 ppm of detergent components in the wash water.

Latin American detergents are generally high suds phosphate builder detergents and the range of detergents used in Latin America can fall in both the medium and high detergent concentrations as they range from 1500 ppm to 6000 ppm of detergent components in the wash water. Such detergent compositions are all embodiments of the invention.

A polypeptide of the present invention may also be incorporated in the detergent formulations disclosed in WO97/07202, which is hereby incorporated by reference.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 0% to about 10% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 0% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 0% to about 10% by weight of a zwitterionic surfactant. Non-limiting examples of zwitterionic surfactants include betaine, alkyldimethylbetaine, sulfobetaine, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favor spontaneous self-aggregation, see e.g. review by Hodgdon and Kaler (2007), Current Opinion in Colloid & Interface Science 12: 121-128. Hydrotropes do not display a critical concentration above which self-aggregation occurs as found for surfactants and lipids forming miceller, lamellar or other well defined meso-phases. Instead, many hydrotropes show a continuous-type aggregation process where the sizes of aggregates grow as concentration increases. However, many hydrotropes alter the phase behaviour, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 45% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as iminodiethanol), triethanolamine (TEA, also known as 2,2',2"-nitrilotriethanol), and carboxymethyl inulin (CMI), and combinations thereof.

The detergent composition may also contain 0-20% by weight, such as about 5% to about 10%, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra-(methylenephosphonic acid) (EDTMPA), diethylenetriaminepentakis(methylenephosphonic acid) (DTPMPA or DTMPA), N-(2-hydroxyethyl) iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N, N-diacetic acid (α-ALDA), serine-N, N-diacetic acid (SEDA), isoserine-N, N-diacetic acid (ISDA), phenylalanine-N, N-diacetic acid (PHDA), anthranilic acid-N, N-diacetic acid (ANDA), sulfanilic acid-N, N-diacetic acid (SLDA), taurine-N, N-diacetic acid (TUDA) and sulfomethyl-N, N-diacetic acid (SMDA), N-(2-hydroxyethyl)-ethylidenediamine-N, N',N'-triacetate (HEDTA), diethanolglycine (DEG), diethylenetriamine penta(methylenephosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may contain 0-50% by weight, such as about 0.1% to about 25%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone®, and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term bleach activator is meant herein as a compound which reacts with peroxygen bleach like hydrogen peroxide to form a peracid. The peracid thus formed constitutes the activated bleach. Suitable bleach activators to be used herein include those belonging to the class of esters amides, imides or anhydrides. Suitable examples are tetracetylethylene diamine (TAED), sodium 4-[(3,5,5-trimethylhexanoyl)oxy]benzene sulfonate (ISONOBS), diperoxy dodecanoic acid, 4-(dodecanoyloxy) benzenesulfonate (LOBS), 4-(decanoyloxy)benzenesulfonate, 4-(decanoyloxy)benzoate (DOBS), 4-(nonanoyloxy)-benzenesulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that it is environmental friendly as it eventually degrades into citric acid and alcohol. Furthermore acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthalimido)peroxyhexanoic acid (PAP). The bleaching system may also include a bleach catalyst. In some embodiments the bleach component may be an organic catalyst selected from the group consisting of organic catalysts having the following formulae:

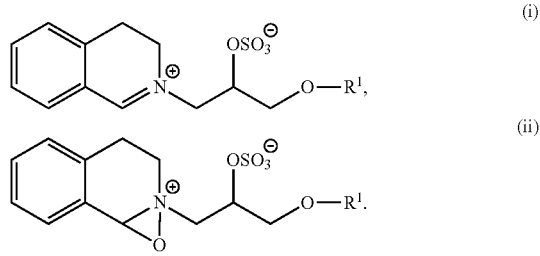

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g. in WO2007/087258, WO2007/087244, WO2007/087259 and WO2007/087242. Suitable photobleaches may for example be sulfonated zinc phthalocyanine Polymers The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly (ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly (oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g. WO 2007/087257 and WO2007/087243.

Additional Enzymes

The detergent additive as well as the detergent composition may comprise one or more [additional] enzymes such as a xanthan lyase, protease, lipase, cutinase, an amylase, lichenase, carbohydrase, cellulase, pectinase, mannanase, arabinase, galactanase, xylanase, oxidase, e.g., a laccase, and/or peroxidase.

In general the properties of the selected enzyme(s) should be compatible with the selected detergent, (i.e., pH-optimum, compatibility with other enzymatic and non-enzymatic ingredients, etc.), and the enzyme(s) should be present in effective amounts.

Cellulases:

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, 5,776,757 and WO 89/09259.

Especially suitable cellulases are the alkaline or neutral cellulases having color care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. Nos. 5,457,046, 5,686,593, 5,763,254, WO 95/24471, WO 98/12307 and PCT/DK98/00299.

Example of cellulases exhibiting endo-beta-1,4-glucanase activity (EC 3.2.1.4) are those having described in WO02/099091.

Other examples of cellulases include the family 45 cellulases described in WO96/29397, and especially variants thereof having substitution, insertion and/or deletion at one or more of the positions corresponding to the following positions in SEQ ID NO: 8 of WO 02/099091:2, 4, 7, 8, 10, 13, 15, 19, 20, 21, 25, 26, 29, 32, 33, 34, 35, 37, 40, 42, 42a, 43, 44, 48, 53, 54, 55, 58, 59, 63, 64, 65, 66, 67, 70, 72, 76, 79, 80, 82, 84, 86, 88, 90, 91, 93, 95, 95d, 95h, 95j, 97, 100, 101, 102, 103, 113, 114, 117, 119, 121, 133, 136, 137, 138, 139, 140a, 141, 143a, 145, 146, 147, 150e, 150j, 151, 152, 153, 154, 155, 156, 157, 158, 159, 160c, 160e, 160k, 161, 162, 164, 165, 168, 170, 171, 172, 173, 175, 176, 178, 181, 183, 184, 185, 186, 188, 191, 192, 195, 196, 200, and/or 20, preferably selected among P19A, G20K, Q44K, N48E, Q119H or Q146 R.

Commercially available cellulases include Celluzyme™, and Carezyme™ (Novozymes NS), Clazinase™, and Puradax HA™ (Genencor International Inc.), and KAC-500 (B)™ (Kao Corporation).

Proteases:

The additional enzyme may be another protease or protease variant. The protease may be of animal, vegetable or microbial origin, including chemically or genetically modified mutants. Microbial origin is preferred. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4, M5, M7 or M8.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family. In one aspect of the invention the protease may be a subtilase, such as a subtilisin or a variant hereof. Further the subtilases (and the serine proteases) are characterised by having two active site amino acid residues apart from the serine, namely a histidine and an aspartic acid residue.

Examples of subtilisins are those derived from Bacillus such as subtilisin lentus, Bacillus lentus, subtilisin Novo, subtilisin Carlsberg, Bacillus licheniformis, subtilisin BPN', subtilisin 309, subtilisin 147 and subtilisin 168 described in WO 89/06279 and protease PD138 (WO 93/18140). Additional serine protease examples are described in WO 98/020115, WO 01/44452, WO 01/58275, WO 01/58276, WO 03/006602 and WO 04/099401. An example of a subtilase variants may be those having mutations in any of the positions: 3, 4, 9, 15, 27, 36, 68, 76, 87, 95, 96, 97, 98, 99, 100, 101, 102, 103, 104, 106, 118, 120, 123, 128, 129, 130, 160, 167, 170, 194, 195, 199, 205, 217, 218, 222, 232, 235, 236, 245, 248, 252 and 274 using the BPN' numbering. More preferred the subtilase variants may comprise the mutations: S3T, V4I, S9R, A15T, K27R, *36D, V68A, N76D, N87S,R, *97E, A98S, S99G,D,A, S99AD, S101G, M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering). A further preferred protease is the alkaline protease from Bacillus lentus DSM 5483, as described for example in WO 95/23221, and variants thereof which are described in WO 92/21760, WO 95/23221, EP 1921147 and EP 1921148.

Examples of trypsin-like proteases are trypsin (e.g. of porcine or bovine origin) and the Fusarium protease described in WO 89/06270 and WO 94/25583. Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235, and 274.

Examples of metalloproteases are the neutral metalloprotease as described in WO 07/044993.

Preferred commercially available protease enzymes include Alcalase™, Coronase™, Duralase™, Durazym™, Esperase™, Everlase™, Kannase™, Liquanase™, Liquanase Ultra™, Ovozyme™, Polarzyme™, Primase™, Relase™, Savinase and Savinase Ultra™, (Novozymes NS), Axapem™ (Gist-Brocases N.V.), BLAP and BLAP X (Henkel AG & Co. KGaA), Excellase™, FN2™, FN3™, FN4™, Maxaca™, Maxapem™, Maxatase™, Properase™, Purafast™, Purafecem, Purafect OxP™, Purafect Prime™ and Puramax™ (Genencor int.).

Lipases and Cutinases:

Suitable lipases and cutinases include those of bacterial or fungal origin. Chemically modified or protein engineered mutant enzymes are included. Examples include lipase from Thermomyces, e.g. from T. lanuginosus (previously named Humicola lanuginosa) as described in EP258068 and EP305216, cutinase from Humicola, e.g. H. insolens (WO96/13580), lipase from strains of Pseudomonas (some of these now renamed to Burkholderia), e.g. P. alcaligenes or P. pseudoalcaligenes (EP218272), P. cepacia (EP331376), P. sp. strain SD705 (WO95/06720 & WO96/27002), P. wisconsinensis (WO96/12012), GDSL-type Streptomyces lipases (WO10/065455), cutinase from Magnaporthe grisea (WO10/107560), cutinase from Pseudomonas mendocina (U.S. Pat. No. 5,389,536), lipase from Thermobifida fusca (WO11/084412), Geobacillus stearothermophilus lipase (WO11/084417), lipase from Bacillus subtilis (WO11/084599), and lipase from Streptomyces griseus (WO11/150157) and S. pristinaespiralis (WO12/137147).

Further examples are lipases sometimes referred to as acyltransferases or perhydrolases, e.g. acyltransferases with homology to Candida antarctica lipase A (WO10/111143), acyltransferase from Mycobacterium smegmatis (WO05/56782), perhydrolases from the CE 7 family (WO09/67279), and variants of the M. smegmatis perhydrolase in particular the S54V variant used in the commercial product Gentle Power Bleach from Huntsman Textile Effects Pte Ltd (WO10/100028).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include Lipolase™, Lipex™; Lipolex™ and Lipoclean (Novozymes NS), Lumafast (originally from Genencor) and Lipomax (originally from Gist-Brocades).

Amylases

The amylase may be an alpha-amylase, a beta-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Examples of amylases are those having SEQ ID NO: 3 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444 of SEQ ID NO: 3 in WO 95/10603.

Other amylases are variants of SEQ ID NO: 1 of WO 2016/203064 having at least 75% sequence identity to SEQ ID NO: 1 thereof. Preferred variants are variants comprising a modification in one or more positions corresponding to positions 1, 54, 56, 72, 109, 113, 116, 134, 140, 159, 167, 169, 172, 173, 174, 181, 182, 183, 184, 189, 194, 195, 206, 255, 260, 262, 265, 284, 289, 304, 305, 347, 391, 395, 439, 469, 444, 473, 476, or 477 of SEQ ID NO: 1, wherein said alpha-amylase variant has a sequence identity of at least 75% but less than 100% to SEQ ID NO: 1.

Further amylases which can be used are amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylase examples are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one or more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48+T49+G107+H156+A181+N190+I201+A209+Q264.

Further amylase examples are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions G182 and H183 or positions H183 and G184.

Additional amylases are those having SEQ ID NO: 1, SEQ ID NO: 2 or SEQ ID NO: 7 of WO 96/023873 or variants thereof having 90% sequence identity to SEQ ID NO: 1, SEQ ID NO: 2 or SEQ ID NO: 7. Preferred variants of SEQ ID NO: 1, SEQ ID NO: 2 or SEQ ID NO: 7 are those having a substitution, a deletion or an insertion in one or more of the following positions: 140, 181, 182, 183, 184, 195, 206, 212, 243, 260, 269, 304 and 476. More preferred variants are those having a deletion in positions 182 and 183 or positions 183 and 184. Most preferred amylase variants of SEQ ID NO: 1, SEQ ID NO: 2 or SEQ ID NO: 7 are those having a deletion in positions 183 and 184 and a substitution in positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further amylases which can be used are amylases having SEQ ID NO: 2 of WO 09/061380 or variants thereof having 90% sequence identity to SEQ ID NO: 2. Preferred variants of SEQ ID NO: 2 are those having a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E,R, S243Q,A,E,D, Y305R, R309A, Q320R, Q359E, K444E and G475K and/or deletion in position R180 and/or S181. Most preferred amylase variants of SEQ ID NO: 2 are those having the substitutions:

N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variant optionally further comprises a substitution at position 243 and/or a deletion at position 180 and/or position 181.

Other examples of amylases are the alpha-amylase having SEQ ID NO: 12 in WO01/66712 or a variant having at least 90%, such as at least 95%, sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Commercially available amylases are Duramyl™, Termamyl™, Fungamyl™, Stainzyme™, Stainzyme Plus™, Natalase™ and BAN™ (Novozymes A/S), Rapidase™ and Purastar™ (from Genencor International Inc.).

Peroxidases/Oxidases:

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes NS).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants:

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents:

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent:

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2.2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethylamino)-s-triazin-6-ylamino) stilbene-2,2'-disulphonate and 2-(stilbyl-4"-naptho-1,2':4,5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

Soil Release Polymers:

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents:

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition may be in any convenient form, e.g., a bar, a homogenous tablet, a tablet having two or more layers, a pouch having one or more compartments, a regular or compact powder, a granule, a paste, a gel, or a regular, compact or concentrated liquid. There are a number of detergent formulation forms such as layers (same or different phases), pouches, as well as forms for machine dosing unit.

Pouches can be configured as single or multi-compartments. It can be of any form, shape and material which is suitable for hold the composition, e.g. without allowing the release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivatives thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1).

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Laundry Soap Bars

The enzymes of the invention may be added to laundry soap bars and used for hand washing laundry, fabrics and/or textiles. The term laundry soap bar includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, an enzyme, optionally one or more additional enzymes, a protease inhibitor, and a salt of a monovalent cation and an organic anion may be prepared and the mixture is then plodded. The enzyme and optional additional enzymes may be added at the same time as the protease inhibitor for example in liquid form. Besides the mixing step and the plodding step, the process may further comprise the steps of milling, extruding, cutting, stamping, cooling and/or wrapping.

Method of Producing the Composition

The present invention also relates to methods of producing the composition. The method may be relevant for the (storage) stability of the detergent composition: e.g. Soap bar premix method WO2009155557.

Uses

The present invention is also directed to methods for using the compositions thereof. The present invention may be used for example in any application which requires the degradation of xanthan gum, such as in detergents and in the oil industry. In the oil industry xanthan gum is used for increasing the viscosity of the drilling fluid, in particular the drilling mud. In all such uses there will also be the need to decrease the viscosity by degrading the xanthan gum, and for such viscosity reduction a composition of the invention comprising a xanthan lyase (e.g. variants thereof according to the present invention) having activity on xanthan gum.

Use to Degrade Xanthan Gum

Xanthan gum has been use as an ingredient in many consumer products including foods and cosmetics and has found use in the oil industry. Therefore the degradation of xanthan gum can result in improved cleaning processes, such as the easier removal of stains containing gums, such as xanthan gum, as well as the degradation of xanthan gum, which is often used in the oil and drilling industry. Thus the present invention is directed to the use of xanthan lyases of the invention (e.g. variants of the present invention) or compositions thereof to degrade xanthan gum. The present invention is also directed to the use of xanthan lyases of the invention or compositions thereof to degrade xanthan gum. An embodiment is the use of xanthan lyases of the invention (e.g. variants of the present invention) together with endoglucanase(s) or compositions thereof to degrade xanthan gum. Degradation of xanthan gum can preferably be measured using the viscosity reduction assay (e.g., ViPr assay) or alternatively as described in example 4 herein.

GH9 endoglucanase activity may alternatively be measured by assessment of reducing ends on xanthan gum pre-treated with xanthan lyase using the colorimetric assay developed by Lever (1972), *Anal. Biochem.* 47: 273-279, 1972. A preferred embodiment is the use of 0.1% xanthan gum pre-treated with xanthan lyase. Degradation of xanthan gum pre-treated with xanthan lyase may be determined by calculating difference between blank and sample wherein a difference of more than 0.5 mAU, preferably more than 0.6 mAU, more preferably more than 0.7 mAU or even more preferably more than 0.8 mAU shows degradation of xanthan gum pre-treated with xanthan lyase.

Xanthan lyase activity may alternatively be measured by assessment of reducing ends on xanthan gum using the colorimetric assay developed by Lever (1972), *Anal. Biochem.* 47: 273-279, 1972. A preferred embodiment is the use of 0.1% xanthan gum. Degradation of xanthan gum may be determined by calculating difference between blank and sample, wherein a difference of more than 0.1 mAU, preferably more than 0.15 mAU, more preferably more than 0.2 mAU or even more preferably more than 0.25 mAU, shows degradation of xanthan gum.

Xanthan lyase (e.g. variants of the present invention) and endoglucanase activity may alternatively be measured by assessment of reducing ends on xanthan gum using the colorimetric assay developed by Lever (1972), *Anal. Biochem.* 47: 273-279, 1972. A preferred embodiment is the use of 0.1% xanthan gum. Degradation of xanthan gum may be determined by calculating difference between blank and sample wherein a difference of more than 0.4 mAU, preferably more than 0.5 mAU, more preferably more than 0.6 mAU or even more preferably more than 0.8 mAU shows degradation of xanthan gum.

The invention also relates to methods for degrading xanthan gum comprising applying a composition comprising one or more xanthan lyases of the invention (e.g. variants of the present invention) to xanthan gum. The invention further relates to methods for degrading xanthan gum comprising applying a composition comprising one or more xanthan lyases to xanthan gum. An embodiment is a method for degrading xanthan gum comprising applying a composition comprising one or more xanthan lyases of the invention (e.g. variants of the present invention) together with one or more endoglucanases to xanthan gum.

Use in Detergents

The present invention inter alia relates to the use of xanthan lyases of the invention (e.g. variants of the present invention) or compositions thereof in cleaning processes such as the laundering of textiles and fabrics (e.g., household laundry washing and industrial laundry washing), as well as household and industrial hard surface cleaning, such as dish wash. The xanthan lyases of the invention (e.g. variants of the present invention) may be added to a detergent composition comprising of one or more detergent components.

In some aspects xanthan lyases of the invention (e.g. variants of the present invention) may be used together with an endoglucanase(s) or compositions thereof in cleaning processes such as the laundering of textiles and fabrics (e.g. household laundry washing and industrial laundry washing), as well as household and industrial hard surface cleaning, such as dish wash. The xanthan lyases of the invention (e.g. variants of the present invention) together with an endoglucanase(s) may be added to a detergent composition comprising of one or more detergent components.

The polypeptides of the present invention (e.g. variants of the present invention) may be added to and thus become a component of a detergent composition. The detergent composition may be formulated, for example, as a hand or machine laundry detergent composition for both household and industrial laundry cleaning, including a laundry additive composition suitable for pre-treatment of stained fabrics and a rinse added fabric softener composition, or be formulated as a detergent composition for use in general household or industrial hard surface cleaning operations, or be formulated for hand or machine (both household and industrial) dishwashing operations. In a specific aspect, the present invention relates to a detergent additive comprising a polypeptide of the present invention as described herein.

The invention also relates to methods for degrading xanthan gum on the surface of a textile or hard surface, such as dish wash, comprising applying a composition comprising one or more xanthan lyases of the invention (e.g. variants of the present invention) to xanthan gum. In some aspects the invention relates to a method for degrading xanthan gum on the surface of a textile or hard surface, such as dish wash, comprising applying a composition comprising one or more xanthan lyases of the invention (e.g. variants of the present invention) together with one or more endoglucanases to xanthan gum. In some aspects the invention relates to a composition comprising one or more detergent components as described herein. Use of xanthan lyases (e.g. variants of the present invention) having an enzyme detergency benefit.

It has been contemplated that the use of a xanthan lyase of the invention (e.g., a variant of the invention) alone gives an enzyme detergency benefit, preferably an enzyme detergency benefit on xanthan gum.

In some aspects the invention relates to the use of a detergent composition comprising one or more detergent components and an isolated xanthan lyase of the invention (e.g. a variant of the present invention) together with a GH9 endoglucanase. In some aspects the invention relates to the use of a detergent composition comprising one or more detergent components and an isolated xanthan lyase (e.g. a variant of the present invention) of the invention together with a GH9 endoglucanase.

Use in the Fracturing of a Subterranean Formation (Oil Drilling)

Hydraulic fracturing is used to create subterranean fractures that extend from the borehole into rock formation in order to increase the rate at which fluids can be produced by the formation. Generally, a high viscosity fracturing fluid is pumped into the well at sufficient pressure to fracture the subterranean formation. In order to maintain the increased exposure to the formation, a solid proppant is added to the fracturing fluid which is carried into the fracture by the high pressure applied to the fluid. Once the high viscosity fracturing fluid has carried the proppant into the formation, breakers are used to reduce the fluid's viscosity which allows the proppant to settle into the fracture and thereby increase the exposure of the formation to the well. Breakers work by reducing the molecular weight of the polymers, thus 'breaking' or degrading the polymer. The fracture then becomes a high permeability conduit for fluids and gas to be produced back to the well. Such processes are further disclosed in U.S. Pat. Nos. 7,360,593, 5,806,597, 5,562,160, 5,201,370 and 5,067,566.

Thus, the invention relates to the use of xanthan lyases of the invention (e.g. variants of the present invention) as enzyme breakers. An embodiment of the invention is the use of xanthan lyases of the invention (e.g. a variant of the present invention) together with GH9 endoglucanase as enzyme breakers.

Accordingly, the invention provides a method for breaking xanthan gum in a well bore comprising: (i) blending together a gellable fracturing fluid comprising aqueous fluid, one or more hydratable polymers, suitable cross-linking agents for cross-linking the hydratable polymer to form a polymer gel and one or more enzymes of the invention (i.e. the enzyme breaker, e.g. a variant of the present invention); (ii) pumping the cross-linked polymer gel into the well bore under sufficient pressure to fracture the surrounding formation; and (iii) allowing the enzyme breaker to degrade the cross-linked polymer to reduce the viscosity of the fluid so that the fluid can be pumped from the formation back to the well surface. As such, the xanthan lyases of the invention (e.g. variants of the present invention) can be used to control the viscosity of fracturing fluids. In an embodiment, one or more xanthan lyases of the invention (e.g. variants of the present invention) together with one or more GH9 endoglucanases can be used to control the viscosity of fracturing fluids.

The enzyme breaker of the present invention (e.g. a variant of the present invention) may be an ingredient of a fracturing fluid or a breaker-crosslinker-polymer complex which further comprises a hydratable polymer and a cross-linking agent. The fracturing fluid or complex may be a gel or may be gellable. The complex is useful in a method for using the complex in a fracturing fluid to fracture a subterranean formation that surrounds a well bore by pumping the fluid to a desired location within the well bore under sufficient pressure to fracture the surrounding subterranean formation. The complex may be maintained in a substantially non-reactive state by maintaining specific conditions of pH and temperature, until a time at which the fluid is in place in the well bore and the desired fracture is completed. Once the fracture is completed, the specific conditions at which the complex is inactive are no longer maintained. When the conditions change sufficiently, the complex becomes active and the breaker begins to catalyse polymer degradation causing the fracturing fluid to become sufficiently fluid to be pumped from the subterranean formation to the well surface.

Other Uses

The polypeptides of the present invention (e.g. variants of the present invention) may additionally be used in other application where it is beneficial to remove xanthan gum.

Methods

Method of Degrading Xanthan Gum Wherein the Xanthan Gum is Used in Fracturing of a Subterranean Formation Perpetrated by a Well Bore When a well is drilled, reservoir drilling fluid (RDF) is circulated within the drilling equipment to cool down and clean the drill bit, remove the drill cuttings out of the well bore, reduce friction between the drill string and the sides of the borehole, and form a filtercake in order to prevent fluid leak off into the formation. The driving force for the formation of the filtercake is the higher wellbore pressure applied to maintain the borehole stability. This filtercake restricts the inflow of reservoir fluids into the wellbore during the drilling process and placement of the completion. If the filtercake damage that is created during the drilling process is not removed prior to or during completion of the well, a range of issues can arise when the well is put on production, i.e., completion equipment failures and impaired reservoir productivity.

Drilling fluid (mud), also called reservoir drilling fluid (RDF), can be synthetic/oil based or water based. To minimize invasion of the drilling fluid into the formation, both oil based and water based mud filtercakes typically contain a bridging or weighting agent, usually particles of calcium carbonate, barite or a mixture of the two, that bridge at the pore throats of the formation and thereby form a relatively low permeability filtercake. Both oil based and water based mud filtercakes also contain solids called cuttings that have been picked up during drilling, as opposed to the bridging/weighting agents that are added in the formulation of the drilling fluid. These solids can be quartz (sand), silts and/or shales, depending on the reservoir formation as well as the formations traversed by the drilling path to the reservoir. In addition, oil based drilling muds contain water droplets that become trapped in the pore space of the filtercake, while water based mud filtercakes contain polymers, such as starch and xanthan gum, and other inorganic salts.

The formation of a mud filtercake is often necessary for drilling, particularly in unconsolidated formations with wellbore stability problems and typically high permeabilities. The filtercake is then treated with various chemicals, such as chelants or acids to dissolve the calcite component; and/or enzymes or oxidizers to degrade the polymer component to recover permeability.

In one aspect, the invention provides a method for degrading xanthan gum wherein xanthan gum is used in fracturing of a subterranean formation perpetrated by a well bore by applying a composition comprising one of more enzymes of the invention (e.g. variants of the present invention). The method includes the steps of: (i) pumping a treatment fluid comprising one or more enzymes of the invention (e.g. variants of the present invention) into the borehole in contact with the filtercake to be removed to establish a differential pressure between the treatment fluid and the formation adjacent the filtercake and (ii) evenly propagating treatment of the filtercake during the differential pressure period to delay breakthrough by the treatment fluid.

In one embodiment, the method includes establishing permeability through the treated filtercake between the formation and the borehole. In another embodiment, the filtercake include drilling solids and clays, and may be formed from an aqueous drilling fluid. If desired, the treatment fluid for treating the aqueous drilling fluid filtercake can also include an oxidizer and/or a chelant, or it can be substantially free of chelant and oxidizer additives. In another example, the filtercake can be formed from an oil or invert emulsion drilling fluid. If desired, the treatment fluid for treating the oil or invert emulsion drilling fluid filtercake can also include a mutual solvent, a water-wetting agent or a combination thereof to disperse hydrophobic components in the filtercake.

In one embodiment, the treatment fluid comprises one or more xanthan lyases of the invention (e.g. variants of the present invention). In a preferred embodiment, the treatment fluid comprises one or more xanthan lyases invention (e.g. variants of the present invention) and one or more GH9 endoglucanases.

Method of Degrading Xanthan Gum Wherein the Xanthan Gum is a Component in Borehole Filtercake In one aspect, the invention provides a method for cleaning borehole filtercake, comprising polymers, such as xanthan gum and drilling fluid solids once the filtercake has been pumped to the surface. Drilling mud is pumped from mud pits to the drill bit and then back out to the surface, carrying out amongst other things crushed or cut rock (cuttings) in the process. The cuttings are filtered out and the mud is returned to the mud pits where fines can settle and/or chemicals or enzymes (breakers) can be added.

The method for degrading xanthan gum wherein the xanthan gum is a component in borehole filtercake includes the steps of (i) treating the borehole filtercake with a treatment fluid comprising one or more enzymes of the invention (e.g. variants of the present invention) and (ii) separating the solids from the fluids. In one embodiment, the treatment fluid comprises one or more xanthan lyases of the invention (e.g. variants of the present invention). In a preferred embodiment, the treatment fluid comprises one or more xanthan lyases of the invention (e.g. variants of the present invention) and one or more GH9 endoglucanases.

The borehole filtercake may be treated in mud pits with one or more enzymes of the invention (e.g. variants of the present invention) and the drilling fluid can be re-circulated. Alternatively, once the filtercake has been treated with one or more enzymes of the invention (e.g. variants of the present invention), the solids and fluid are separated using solid-liquid separation processes, such as centrifugation.

The Invention is Further Defined in the Following Paragraphs:

1. A xanthan lyase variant, comprising an alteration (e.g., a substitution, deletion or insertion) at one or more positions in a region selected from the group consisting of:
   i) region 1 corresponding to amino acids 154 to 176 of SEQ ID NO: 2,
   ii) region 2 corresponding to amino acids 614 to 658 of SEQ ID NO: 2,
   iii) region 3 corresponding to amino acids 731 to 803 of SEQ ID NO: 2,
   iv) region 4 corresponding to amino acids 807 to 846 of SEQ ID NO: 2,
   v) region 5 corresponding to amino acids 872 to 885 of SEQ ID NO: 2,
   vi) region 6 corresponding to amino acids 903 to 1004 of SEQ ID NO: 2,
   wherein said variant has at least 60%, e.g., at least 65%, at least 70%, at least 75%, at least 80%, at least 85%, at least 90%, at least 95%, at least 96%, at least 97%, at least 98%, or at least 99%, and less than 100% sequence identity to SEQ ID NO: 2; preferably said xanthan lyase variant has activity on xanthan gum, further preferably said activity is a xanthan gum degrading activity.

2. The xanthan lyase variant of paragraph 1, which is a variant of a parent xanthan lyase selected from the group consisting of:
   a) a polypeptide having at least 60% sequence identity to the mature polypeptide of SEQ ID NO: 2;
   b) a polypeptide encoded by a polynucleotide that hybridizes under low stringency conditions with (i) the mature polypeptide coding sequence of SEQ ID NO: 1, or (ii) the full-length complement of (i);
   c) a polypeptide encoded by a polynucleotide having at least 60% identity to the mature polypeptide coding sequence of SEQ ID NO: 1; and
   d) a fragment of the mature polypeptide of SEQ ID NO: 2, which has xanthan lyase activity.

3. The xanthan lyase variant of paragraph 2, wherein the parent xanthan lyase has at least 60%, e.g., at least 65%, at least 70%, at least 75%, at least 80%, at least 85%, at least 90%, at least 95%, at least 96%, at least 97%, at least 98%, at least 99% or 100% sequence identity to the mature polypeptide of SEQ ID NO: 2.

4. The xanthan lyase variant of any of paragraphs 2-3, wherein the parent xanthan lyase is encoded by a polynucleotide that hybridizes under low stringency conditions, medium stringency conditions, medium-high stringency conditions, high stringency conditions, or very high stringency conditions with (i) the mature polypeptide coding sequence of SEQ ID NO: 1 or (ii) the full-length complement of (i).

5. The xanthan lyase variant of any of paragraphs 2-4, wherein the parent xanthan lyase is encoded by a polynucleotide having at least 60%, e.g., at least 65%, at least 70%, at least 75%, at least 80%, at least 85%, at least 90%, at least 95%, at least 96%, at least 97%, at least 98%, at least 99%, or 100% sequence identity to the mature polypeptide coding sequence of SEQ ID NO: 1.

6. The xanthan lyase variant of any of paragraphs 2-5, wherein the parent xanthan lyase comprises or consists of the mature polypeptide of SEQ ID NO: 2.

7. The xanthan lyase variant of any of paragraphs 2-6, wherein the parent xanthan lyase is a fragment of the mature polypeptide of SEQ ID NO: 2, wherein the fragment has xanthan lyase activity.

8. The xanthan lyase variant of any of paragraphs 2-7, which has at least 60%, e.g., at least 65%, at least 70%, at least 75%, at least 80%, at least 85%, at least 90%, at least 95% identity, at least 96%, at least 97%, at least 98%, or at least 99%, but less than 100%, sequence identity to the amino acid sequence of the parent xanthan lyase.

9. The xanthan lyase variant of any of paragraphs 1-8, wherein said region selected from the group consisting of regions 1-6 is a chelator-induced instability region;
   preferably said chelator-induced instability region (e.g., of SEQ ID NO: 2 or another parent xanthan lyase) has one or more of the following features:
   i) in the presence of a chelator it is less conformationally stable than one or more or all of its adjacent regions; and/or
   ii) in the presence of a chelator it is more exposed to said chelator than one or more or all of its adjacent regions; and/or
   iii) in the presence of a chelator it is more accessible to said chelator than one or more or all of its adjacent regions; and/or iv) in the presence of a chelator it is more conformationally dynamic than one or more or all of its adjacent regions; and/or
v) in the presence of a chelator it is more receptive to deuterium incorporation than one or more or all of its adjacent regions;
further preferably said adjacent region is selected from the group consisting of:
vi) region 7 corresponding to amino acids 1 to 153 of SEQ ID NO: 2,
vii) region 8 corresponding to amino acids 177 to 613 of SEQ ID NO: 2,
viii) region 9 corresponding to amino acids 659 to 730 of SEQ ID NO: 2,
ix) region 10 corresponding to amino acids 804 to 806 of SEQ ID NO: 2,
x) region 11 corresponding to amino acids 847 to 871 of SEQ ID NO: 2,
xi) region 12 corresponding to amino acids 886 to 902 of SEQ ID NO: 2, and
xii) region 13 corresponding to amino acids 1005 to 1037 of SEQ ID NO: 2, further most preferably said chelator is EDTA or citrate.

10. The xanthan lyase variant of any of paragraphs 1-9, wherein in an aqueous solution comprising a detergent component said region (e.g., of SEQ ID NO: 2 or another parent xanthan lyase) selected from the group consisting of regions 1-6 is less conformationally stable than one or more or all of its adjacent regions;
preferably said adjacent region is selected from the group consisting of:
i) region 7 corresponding to amino acids 1 to 153 of SEQ ID NO: 2,
ii) region 8 corresponding to amino acids 177 to 613 of SEQ ID NO: 2,
iii) region 9 corresponding to amino acids 659 to 730 of SEQ ID NO: 2,
iv) region 10 corresponding to amino acids 804 to 806 of SEQ ID NO: 2,
v) region 11 corresponding to amino acids 847 to 871 of SEQ ID NO: 2,
vi) region 12 corresponding to amino acids 886 to 902 of SEQ ID NO: 2, and
vii) region 13 corresponding to amino acids 1005 to 1037 of SEQ ID NO: 2, further preferably said detergent component is a chelator; further most preferably said chelator is EDTA or citrate.

11. The xanthan lyase variant of any of paragraphs 1-10, wherein in an aqueous solution comprising a detergent component said region (e.g., of SEQ ID NO: 2 or another parent xanthan lyase) selected from the group consisting of regions 1-6 is more exposed to said detergent component than one or more or all of its adjacent regions;
preferably said adjacent region is selected from the group consisting of:
i) region 7 corresponding to amino acids 1 to 153 of SEQ ID NO: 2,
ii) region 8 corresponding to amino acids 177 to 613 of SEQ ID NO: 2,
iii) region 9 corresponding to amino acids 659 to 730 of SEQ ID NO: 2,
iv) region 10 corresponding to amino acids 804 to 806 of SEQ ID NO: 2,
v) region 11 corresponding to amino acids 847 to 871 of SEQ ID NO: 2,
vi) region 12 corresponding to amino acids 886 to 902 of SEQ ID NO: 2, and
vii) region 13 corresponding to amino acids 1005 to 1037 of SEQ ID NO: 2, further preferably said detergent component is a chelator; further most preferably said chelator is EDTA or citrate.

12. The xanthan lyase variant of any of paragraphs 1-11, wherein in an aqueous solution comprising a detergent component said region (e.g., of SEQ ID NO: 2 or another parent xanthan lyase) selected from the group consisting of regions 1-6 is more accessible to said detergent component than one or more or all of its adjacent regions;
preferably said adjacent region is selected from the group consisting of:
i) region 7 corresponding to amino acids 1 to 153 of SEQ ID NO: 2,
ii) region 8 corresponding to amino acids 177 to 613 of SEQ ID NO: 2,
iii) region 9 corresponding to amino acids 659 to 730 of SEQ ID NO: 2,
iv) region 10 corresponding to amino acids 804 to 806 of SEQ ID NO: 2,
v) region 11 corresponding to amino acids 847 to 871 of SEQ ID NO: 2,
vi) region 12 corresponding to amino acids 886 to 902 of SEQ ID NO: 2, and
vii) region 13 corresponding to amino acids 1005 to 1037 of SEQ ID NO: 2, further preferably said detergent component is a chelator; further most preferably said chelator is EDTA or citrate.

13. The xanthan lyase variant of any of paragraphs 1-12, wherein in an aqueous solution comprising a detergent component said region (e.g., of SEQ ID NO: 2 or another parent xanthan lyase) selected from the group consisting of regions 1-6 is more conformationally dynamic than one or more or all of its adjacent regions;
preferably said adjacent region is selected from the group consisting of:
i) region 7 corresponding to amino acids 1 to 153 of SEQ ID NO: 2,
ii) region 8 corresponding to amino acids 177 to 613 of SEQ ID NO: 2,
iii) region 9 corresponding to amino acids 659 to 730 of SEQ ID NO: 2,
iv) region 10 corresponding to amino acids 804 to 806 of SEQ ID NO: 2,
v) region 11 corresponding to amino acids 847 to 871 of SEQ ID NO: 2,
vi) region 12 corresponding to amino acids 886 to 902 of SEQ ID NO: 2, and
vii) region 13 corresponding to amino acids 1005 to 1037 of SEQ ID NO: 2, further preferably said detergent component is a chelator; further most preferably said chelator EDTA or citrate.

14. The xanthan lyase variant of any of paragraphs 1-13, wherein in an aqueous solution comprising a detergent component said region (e.g., of SEQ ID NO: 2 or another parent xanthan lyase) selected from the group consisting of regions 1-6 is more receptive to deuterium incorporation than one or more or all of its adjacent regions;
preferably said adjacent region is selected from the group consisting of:
i) region 7 corresponding to amino acids 1 to 153 of SEQ ID NO: 2,
ii) region 8 corresponding to amino acids 177 to 613 of SEQ ID NO: 2,
iii) region 9 corresponding to amino acids 659 to 730 of SEQ ID NO: 2, iv) region 10 corresponding to amino acids 804 to 806 of SEQ ID NO: 2,
v) region 11 corresponding to amino acids 847 to 871 of SEQ ID NO: 2,
vi) region 12 corresponding to amino acids 886 to 902 of SEQ ID NO: 2, and
vii) region 13 corresponding to amino acids 1005 to 1037 of SEQ ID NO: 2, further preferably said detergent component is a chelator; further most preferably said chelator is EDTA or citrate.

15. The xanthan lyase variant of any of paragraphs 1-14, comprising an alteration (e.g., a substitution, deletion or insertion) at one or more positions in two or more regions selected from the group consisting of:
   i) region 1 corresponding to amino acids 154 to 176 of SEQ ID NO: 2,
   ii) region 2 corresponding to amino acids 614 to 658 of SEQ ID NO: 2,
   iii) region 3 corresponding to amino acids 731 to 803 of SEQ ID NO: 2,
   iv) region 4 corresponding to amino acids 807 to 846 of SEQ ID NO: 2,
   v) region 5 corresponding to amino acids 872 to 885 of SEQ ID NO: 2,
   vi) region 6 corresponding to amino acids 903 to 1004 of SEQ ID NO: 2,
   wherein said variant has at least 60%, e.g., at least 65%, at least 70%, at least 75%, at least 80%, at least 85%, at least 90%, at least 95%, at least 96%, at least 97%, at least 98%, or at least 99%, and less than 100% sequence identity to SEQ ID NO: 2, preferably said variant has activity on xanthan gum, further preferably said activity is a xanthan gum degrading activity.

16. The xanthan lyase variant of any of paragraphs 1-15, wherein said variant has at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 2.

17. The xanthan lyase variant of any of paragraphs 1-16, wherein said alteration (e.g., a substitution, deletion or insertion) at one or more positions is selected from the group consisting of alterations in positions: 155, 159, 620, 624, 626, 631, 635, 645, 649, 650, 656, 738, 745, 746, 748, 752, 753, 754, 757, 764, 769, 774, 775, 777, 779, 782, 785, 786, 789, 792, 796, 799, 800, 801, 819, 824, 843, 845, 875, 903, 911, 912, 915, 919, 921, 923, 925, 927, 928, 930, 932, 933, 941, 966, 967, 991 and 998. of SEQ ID NO: 2, wherein numbering is according to SEQ ID NO: 2, preferably alterations in positions: 775, 779 or 923, wherein numbering is according to SEQ ID NO: 2.

18. The xanthan lyase variant of any of paragraphs 1-17, wherein said alteration at one or more positions is selected from the group consisting of: Y155E, A159P, K620R, A624E, A626G, T631N, T631E, S635E, S635T, S635Q, A645S, T649V, T649K, T649R, Q650G, I656V, G738L, K745R, F746L, L748T, P752R, P752K, G753E, G753Q, G753S, S754E, S754L, S754Q, S754R, S757D, S757P, S757E, P764V, P764K, A769D, A769T, A769R, A769S, A769E, A769Q, A769*, A774V, L775M, L775Y, L775A, L775I, L775S, L775F, L775Q, D777K, D777R, P779V, Y782I, A785T, N786K, G789R, K792W, K792Y, K792V, K792A, N796Q, A799H, V800P, D801G, K819R, K819T, K824R, A843P, D845E, K875T, K875E, T903A, T903Q, A911V, A911M, A911S, A912T, A912I, A912Y, T915Q, T915S, T915V, T915A, T919F, T919G, T919D, T921R, T921S, T923H, T923D, T925Q, T925D, T925R, T927K, D928W, Y930H, Y930L, Y930F, A932P, D933M, G941E, G941D, A966P, A967D, N991D and V998K, wherein numbering is according to SEQ ID NO: 2.

19. The xanthan lyase variant of any of paragraphs 1-18, further comprising an alteration at one or more positions in at least one region selected from the group consisting of:
   vii) region 7 corresponding to amino acids 1 to 153 of SEQ ID NO: 2,
   viii) region 8 corresponding to amino acids 177 to 613 of SEQ ID NO: 2,
   ix) region 9 corresponding to amino acids 659 to 730 of SEQ ID NO: 2,
   x) region 10 corresponding to amino acids 804 to 806 of SEQ ID NO: 2,
   xi) region 11 corresponding to amino acids 847 to 871 of SEQ ID NO: 2,
   xii) region 12 corresponding to amino acids 886 to 902 of SEQ ID NO: 2, and
   xiii) region 13 corresponding to amino acids 1005 to 1037 of SEQ ID NO: 2.

20. The xanthan lyase variant of paragraph 19, wherein said alteration at one or more positions in at least one region selected from the group consisting of regions 7, 8, 9, 10, 11, 12 and 13 is an alteration at one or more positions selected from the group consisting of: 9, 15, 18, 46, 58, 66, 89, 95, 100, 106, 109, 183, 188, 190, 203, 204, 221, 229, 234, 238, 240, 242, 243, 257, 258, 284, 291, 293, 316, 317, 320, 324, 329, 333, 339, 341, 352, 354, 360, 372, 377, 399, 400, 419, 440, 450, 451, 454, 458, 481, 492, 505, 533, 567, 568, 576, 578, 579, 582, 664, 672, 703, 722, 726, 727, 728, 851, 855, 856, 867, 887, 892, 899, 900, 901, 902, 915, 1008 and 1016 of SEQ ID NO: 2.

21. The xanthan lyase variant of paragraph 20, wherein said alteration at one or more positions in at least one region selected from the group consisting of regions 7, 8, 9, 10, 11, 12 and 13 comprises one or more substitutions selected from the group consisting of: K9R, N15T, T18D, L46D, A58L, S66H, Q89Y, K95E, S100D, N106Y, Q109R, Q109D, Q109F, Q109K, Q109A, K183Q, K183R, V188I, A190Q, A203P, K204R, A221P, E229N, E229S, E229V, I234V, I238W, I238L, I238M, I240W, N242S, G243V, Y257W, R258E, R284G, K291R, A293G, A293P, K316R, R317K, K320R, L324Q, K329R, K333R, L339M, I341P, V352I, S354P, K360G, K360R, Q372H, F377Y, N399K, K400R, F419Y, N440K, D450P, K451E, K451R, A454V, D458S, K481R, A492H, A492L, T505I, L533I, K567R, G568A, S578K, S578N, S578R, S579R, S579K, S582K, T664K, N672D, I703L, I722F, P726Q, T727P, M728V, S851F, K855R, E856D, P867S, K887R, N892Y, N892W, N892F, G899S, I900G, D901A, T902F, N1008D and K1016T of SEQ ID NO: 2.

22. The xanthan lyase variant of any of paragraphs 1-21, comprising an alteration at one or more positions selected from the group consisting of positions 624, 631, 635, 649, 656, 738, 752, 753, 754, 757, 769, 775, 777, 800, 801, 843, 875, 911 and 915, and an alteration at one or more positions selected from the group consisting of positions 89, 100, 190, 229, 234, 352, 360, 399, 440, 458, 492, 567, 582, 664, 672, 703, 728, 892, 1008 and 1016 of SEQ ID NO: 2.

23. The xanthan lyase variant of paragraph 22, comprising one or more substitutions selected from the group consisting of Q89Y, S100D, A190Q, E229S, I234V, V352I, K360G, N399K, N440K, D458S, A492H, A492L, K567R, S582K, T664K, N672D, I703L, M728V, N892Y N1008D and K1016T, and one or more substitutions selected from the group consisting of A624E, T631N, S635E, T649K, I656V, G738L, P752K, P752R, G753E, S754E, S754R, S757D, A769D, L775A, D777P, V800P, D801G, A843P, K875T, A911V and T915A.

24. The xanthan lyase variant of any of paragraphs 1-23, wherein the total number of alterations compared to the parent xanthan lyase (e.g., SEQ ID NO: 2) is between 1 and 20, e.g. between 1 and 10 or between 1 and 5, such as 1, 2, 3, 4, 5, 6, 7, 8, 9 or 10 alterations.

25. The xanthan lyase variant of any of paragraphs 1-24, wherein said activity on xanthan gum is a xanthan gum degrading activity, preferably said xanthan lyase variant has EC 4.2.2.12 activity.

26. The xanthan lyase variant of any of paragraphs 1-25, wherein said variant has an improved stability in a detergent composition compared to a parent xanthan lyase (e.g., with SEQ ID NO: 2); preferably said detergent composition comprises a chelator; further preferably said chelator is EDTA or citrate.

27. The xanthan lyase variant of any of paragraphs 1-26, wherein said variant has a half-life improvement factor (HIF) of 1.0; preferably said variant has a half-life improvement factor (HIF) of >1.0, more preferably at least 1.2, such as at least 1.5, e.g. at least 2.0, relative to a parent xanthan lyase, e.g. a xanthan lyase with SEQ ID NO: 2.

28. The xanthan lyase variant of paragraph 27, wherein said half-life improvement factor (HIF) is determined after incubation of said xanthan lyase variant in a detergent composition at 25° C. for a time period from about 30 min to about 20 hours.

29. The xanthan lyase variant of any of paragraphs 1-28, wherein said variant is selected from the group consisting of i) the xanthan lyase variants set forth in Table 1 herein, ii) the xanthan lyase variants set forth in Table 2 herein, iii) the xanthan lyase variants set forth in Table 3 herein, iv) the xanthan lyase variants set forth in Table 4 herein, v) the xanthan lyase variants set forth in Table 5 herein, vi) the xanthan lyase variants set forth in Table 6 herein, and vii) the xanthan lyase variants set forth in any of Tables 7, 8, 9, 10, 11, 12 or 13 herein.

30. A composition comprising at least one xanthan lyase variant of any of paragraphs 1-29.

31. The composition of paragraph 30, wherein said composition is not a detergent composition, preferably said composition is a drilling fluid.

32. The composition of paragraph 30, wherein said composition is a detergent composition comprising one or more detergent components; preferably said component is a chelator; further preferably said chelator is EDTA or citrate.

33. The composition of any of paragraphs 30-32, further comprising one or more additional enzymes selected from the group consisting of: endoglucanases, proteases, amylases, lichenases, lipases, cutinases, cellulases, xanthan lyases, xyloglucanases, pectinases, pectin lyases, xanthanases, peroxidases, haloperoxygenases, catalases and mannanases, or any mixture thereof.

34. The composition of any of paragraphs 30-33, wherein said composition is in form of a bar, a homogenous tablet, a tablet having two or more layers, a pouch having one or more compartments, a regular or compact powder, a granule, a paste, a gel, or a regular, compact or concentrated liquid.

35. Use of a composition of any of paragraphs 30-34 or a xanthan lyase variant of any of paragraphs 1-29, wherein said use is selected from the group comprising or consisting of:
i) use for degrading xanthan gum, and
ii) use for controlling the viscosity of drilling fluids.

36. The use of paragraph 35, wherein said xanthan lyase variant has an enzyme detergency benefit.

37. An isolated polynucleotide encoding a xanthan lyase variant of any of paragraphs 1-29.

38. A nucleic acid construct or expression vector capable of expressing a polynucleotide of paragraph 37; preferably said nucleic acid construct or said expression vector comprising the polynucleotide of paragraph 37 operably linked to one or more control sequences that direct the production of the polypeptide in an expression host.

39. A host cell (e.g., isolated host cell, isolated recombinant host cell) comprising the polynucleotide of paragraph 37; preferably said polynucleotide is operably linked to one or more control sequences that direct the production of the polypeptide; further preferably said host cell is an isolated host cell.

40. A method for obtaining or producing a xanthan lyase variant, comprising introducing into a parent xanthan lyase (e.g., with SEQ ID NO: 2 or other parent xanthan lyase) an alteration (e.g., a substitution, deletion or insertion) at one or more positions in a region selected from the group consisting of:
i) region 1 corresponding to amino acids 154 to 176 of SEQ ID NO: 2,
ii) region 2 corresponding to amino acids 614 to 658 of SEQ ID NO: 2,
iii) region 3 corresponding to amino acids 731 to 803 of SEQ ID NO: 2,
iv) region 4 corresponding to amino acids 807 to 846 of SEQ ID NO: 2,
v) region 5 corresponding to amino acids 872 to 885 of SEQ ID NO: 2, and
vi) region 6 corresponding to amino acids 903 to 1004 of SEQ ID NO: 2,
wherein said variant has at least 60%, e.g., at least 65%, at least 70%, at least 75%, at least 80%, at least 85%, at least 90%, at least 95%, at least 96%, at least 97%, at least 98%, or at least 99%, and less than 100% sequence identity to SEQ ID NO: 2, and recovering said variant; preferably said region (e.g., of SEQ ID NO: 2 or another parent xanthan lyase) selected from the group consisting of regions 1-6 is a chelator-induced instability region; further preferably said method further comprises introducing into the parent xanthan lyase (e.g., with SEQ ID NO: 2 or another parent xanthan lyase) an alteration (e.g., a substitution, deletion or insertion) at one or more positions in one or more regions selected from the group consisting of regions 1-6.

41. The method of paragraph 40, wherein said xanthan lyase variant has at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% sequence identity to SEQ ID NO: 2.

42. The method of any of paragraphs 40-41, wherein said alteration (e.g., a substitution, deletion or insertion) at one or more positions is selected from the group consisting of alterations in positions: 155, 159, 620, 624, 626, 631, 635, 645, 649, 650, 656, 738, 745, 746, 748, 752, 753, 754, 757, 764, 769, 774, 775, 777, 779, 782, 785, 786, 789, 792, 796, 799, 800, 801, 819, 824, 843, 845, 875, 903, 911, 912, 915, 919, 921, 923, 925, 927, 928, 930, 932, 933, 941, 966, 967, 991 and 998. of the parent xanthan lyase (e.g., SEQ ID NO: 2), wherein each position corresponds to the positions of SEQ ID NO: 2, preferably alterations in positions: 775, 779 or 923, wherein numbering is according to SEQ ID NO: 2.

43. The method of any of paragraphs 40-42, wherein said alteration at one or more positions is selected from the group consisting of: Y155E, A159P, K620R, A624E, A626G, T631N, T631E, S635T, S635V, S635Q, A645S, T649V, T649K, T649R, Q650G, I656V, G738L, K745R, F746L, L748T, P752R, P752K, G753E, G753Q, G753S, S754E, S754L, S754Q, S754R, S757D, S757P, S757E, P764V, P764K, A769D, A769T, A769R, A769S, A769E, A769Q, A769*, A774V, L775M, L775Y, L775A, L775I, L775S, L775F, L775Q, D777K, D777R, P779V, Y782I, A785T, N786K, G789R, K792W, K792Y, K792V, K792A, N796Q, A799H, V800P, D801G, K819R, K819T, K824R, A843P, D845E, K875T, K875E, T903A, T903Q, A911V, A911M, A911S, A912T, A912I, A912Y, T915Q, T915S, T915V, T915A, T919F, T919G, T919D, T921R, T921S, T923H, T923D, T925Q, T925D, T925R, T927K, D928W, Y930H, Y930L, Y930F, A932P, D933M, G941E, G941D, A966P, A967D, N991D and V998K, wherein numbering is according to SEQ ID NO: 2.

44. The method of any of paragraphs 40-43, further comprising introducing into the parent xanthan lyase an alteration (e.g., a substitution, deletion or insertion) at one or more positions in at least one region selected from the group consisting of:
vii) region 7 corresponding to amino acids 1 to 153 of SEQ ID NO: 2,
viii) region 8 corresponding to amino acids 177 to 613 of SEQ ID NO: 2,
ix) region 9 corresponding to amino acids 659 to 730 of SEQ ID NO: 2,
x) region 10 corresponding to amino acids 804 to 806 of SEQ ID NO: 2,
xi) region 11 corresponding to amino acids 847 to 871 of SEQ ID NO: 2,
xii) region 12 corresponding to amino acids 886 to 902 of SEQ ID NO: 2, and
xiii) region 13 corresponding to amino acids 1005 to 1037 of SEQ ID NO: 2.

45. The method of paragraph 44, wherein said alteration at one or more positions in at least one region selected from the group consisting of regions 7, 8, 9, 10, 11, 12 and 13 is an alteration at one or more positions selected from the group consisting of: 9, 15, 18, 46, 58, 66, 89, 95, 100, 106, 109, 183, 188, 190, 203, 204, 221, 229, 234, 238, 240, 242, 243, 257, 258, 284, 291, 293, 316, 317, 320, 324, 329, 333, 339, 341, 352, 354, 360, 372, 377, 399, 400, 419, 440, 450, 451, 454, 458, 481, 492, 505, 533, 567, 568, 576, 578, 579, 582, 664, 672, 703, 722, 726, 727, 728, 851, 855, 856, 867, 887, 892, 899, 900, 901, 902, 915, 1008 and 1016 of SEQ ID NO: 2.

46. The method of paragraph 45, wherein said alteration at one or more positions in at least one region selected from the group consisting of regions 7, 8, 9, 10, 11, 12 and 13 comprises one or more substitutions selected from the group consisting of: K9R, N15T, T18D, L46D, A58L, S66H, Q89Y, K95E, S100D, N106Y, Q109R, Q109D, Q109F, Q109K, Q109A, K183Q, K183R, V188I, A190Q, A203P, K204R, A221P, E229N, E229S, E229V, I234V, I238W, I238L, I238M, I240W, N242S, G243V, Y257W, R258E, R284G, K291R, A293G, A293P, K316R, R317K, K320R, L324Q, K329R, K333R, L339M, I341P, V352I, S354P, K360G, K360R, Q372H, F377Y, N399K, K400R, F419Y, N440K, D450P, K451E, K451R, A454V, D458S, K481R, A492H, A492L, T505I, L533I, K567R, G568A, S578K, S578N, S578R, S579K, S579K, S582K, T664K, N672D, 1703L, 1722F, P726Q, T727P, M728V, S851F, K855R, E856D, P867S, K887R, N892Y, N892W, N892F, G899S, I900G, D901A, T902F, N1008D and K1016T of SEQ ID NO: 2.

47. A method of any of paragraphs 40-46, wherein said alteration (e.g., a substitution, deletion or insertion) at one or more positions provides a variant having a half-life improvement factor (HIF) of ≥1.0; preferably said variant has a half-life improvement factor (HIF) of >1.0, more preferably at least 1.2, such as at least 1.5, e.g. at least 2.0, relative to a parent xanthan lyase, e.g. a xanthan lyase with SEQ ID NO: 2.

48. A method of producing a xanthan lyase variant, comprising:
i) cultivating a host cell of paragraph 39 under conditions suitable for expression of said variant; and
ii) recovering said variant.

49. The method of paragraph 48, wherein said xanthan lyase variant is a variant according to any of paragraphs 1-29.

50. A method for degrading xanthan gum comprising: applying a composition of any of paragraphs 30-34 to a xanthan gum.

51. The method of paragraph 50, wherein said xanthan gum is on a surface or hard surface.

52. The method of paragraph 50, wherein said xanthan gum is used in fracturing of a subterranean formation perpetrated by a well bore.

53. The method of paragraph 50, wherein said xanthan gum is a component in borehole filtercake.

54. Use of deuterium for identification of chelator-induced instability region of a xanthan lyase polypeptide (e.g., having SEQ ID NO: 2 or a xanthan lyase variant according to any of paragraphs 1-29), preferably said chelator is EDTA or citrate, further preferably said deuterium is in the form of D20.

55. A method for identification of chelator-induced instability region of a xanthan lyase polypeptide (e.g., having SEQ ID NO: 2 or a xanthan lyase variant according to any of paragraphs 1-29), said method comprising:
i) providing in the presence of a chelator, preferably said chelator is EDTA or citrate:
  a) a xanthan lyase polypeptide (e.g., having SEQ ID NO: 2 or a xanthan lyase variant according to any of paragraphs 1-29),
ii) providing in the absence of a chelator:
  b) the xanthan lyase polypeptide according to a),
iii) providing deuterium to i) and ii) for hydrogen-deuterium exchange, preferably said deuterium is in the form of D20 iv) digesting deuterated polypeptides from step iii) with pepsin,
v) identifying peptic peptides produced in step iv),
vi) quantifying and comparing deuterium incorporation into individual peptides from step v) in the presence and absence of said chelator.

The present invention is further described by the following examples that should not be construed as limiting the scope of the invention.

EXAMPLES

Example 1: Hydrogen Exchange—HDX

Continuous amide Hydrogen/Deuterium (H/D) exchange of the parent xanthan lyase of SEQ ID NO: 2 was initiated by addition of 99.9% deuterated 20 mM Tris, 1 mM CaCl2, pH 8 in the absence or presence of 5 mM EDTA to a final deuterium concentration of 85%. H/D exchange was performed in triplicates at 22° C. at a concentration of 1 µM. At five time points ranging from 15 seconds to 1 hour the samples were quenched by addition of 1:1 (v/v) ice-cold 6M guanidinium hydrochloride, 300 mM phosphate, pH 2.05 to a final pH of 2.6. The quenched samples were immediately frozen and stored at −80° C. until LC-MS analysis. Non-deuterated samples were prepared following the same procedure, but using protiated buffers. Fully deuterated samples (85% D20 for the parent xanthan lyase of SEQ ID NO: 2) were prepared by over-night incubation in 99.9% deuterated 6M guanidinium hydrochloride and quenched in 300 mM phosphate, pH 2.3 to a final pH of 2.6. To study the reversibility of the effects of EDTA on xanthan lyase H/D exchange was done for 10 minutes on three states of xanthan lyase (XL): (1) XL; (2) XL+5 mM EDTA; (3) XL XL preincubated with first 5 mM EDTA for 30 minutes and second with 10 mM CaCl2 for 30 minutes. The samples were quenched as described above.

The quenched samples were loaded into a cooled HDX-UPLC system for online pepsin digestion using an immobilized pepsin column (Pierce, Rockford, USA). The peptides were desalted using a trap column (Waters VanGuard C18, 1.7 µM, 2.1×5 mm) at a flow of 200 µl/min 0.23% formic acid for 3 min and peptides were separated by reverse phase chromatography (Waters Acquity BEH C18, 1.7 µm, 1×100 mm) using a two-step gradient from 8-18% in 2 min and 18-40% in 10 min 0.23% formic acid in acetonitrile at a flow of 40 µl/min. Positive electrospray ionization mass spectrometry with ion mobility was performed on the peptides using a Synapt G2 mass spectrometer (Waters, Milford, USA).

The peptic peptides of the mature parent xanthan lyase of SEQ ID NO: 2 were identified by tandem mass spectrometry of non-deuterated samples using a combination of data independent (MSe) and data dependent acquisition schemes (DDA) and data-analysis in Protein Lynx Global Server v. 2.5. Deuterium incorporation of individual peptides were determined in DynamX v. 3.0 or in HXexpress (M. Guttman, D. Weis, J. Engen, K. Lee, *J. Am. Soc. Mass. Spectrom.* 2013, 24, 1906-1912). Statistical analysis (F-tests and student T-tests) were employed to determine statistically significant changes in H/D exchange (ΔDX) between the analyzed protein states.

Peptides with significant changes in H/D exchange (ΔDX>0.5) were selected as identifying chelator-induced instability regions within SEQ ID NO: 2. The following chelator-induced instability regions were identified within xanthan lyase of SEQ ID NO: 2: region 1 corresponding to amino acids 154 to 176 of SEQ ID NO: 2, region 2 corresponding to amino acids 614 to 658 of SEQ ID NO: 2, region 3 corresponding to amino acids 731 to 803 of SEQ ID NO: 2, region 4 corresponding to amino acids 807 to 846 of SEQ ID NO: 2, region 5 corresponding to amino acids 872 to 885 of SEQ ID NO: 2, and region 6 corresponding to amino acids 903 to 1004 of SEQ ID NO: 2.

Example 2: Construction and Expression of Xanthan Lyase Variants

Xanthan lyase parent gene (i.e., SEQ ID NO: 1) was PCR assembled into a linear cassette containing the promoter system on the upstream and cat selection maker on the downstream. To enable chromosomal integration of the cassette at the Pel locus of *B. subtilis* host by homologous recombination, >2 kb DNA sequence identical to the site of integration was included on both the sides of the cassette. Genomic DNA prepared from the strain containing xanthan lyase parent gene (SEQ ID NO: 1) was used as template for generating the site-directed mutants. Mutagenic forward and reverse primers were used to generate an approximately 6 kb PCR fragment. This fragment was used as a megaprimer along with another forward primer to amplify >8 kb DNA fragment. This fragment contained the complete cassette (promoter system, xanthan lyase and cat gene along with homologous DNA sequence required for recombination at Pel locus) was used for transformation.

The triple promoter system used in the cassette has been described in WO 99/43835 and it consists of promoters from *Bacillus licheniformis* alpha-amylase gene (amyL), *Bacillus amyloliquefaciens* alpha-amylase gene (amyQ), and the *Bacillus thuringiensis* cryIIIA promoter including the stabilizing sequence. Protease signal sequence from *Bacillus clausii* was included to export the protein out of the cells.

Generated variants of the mature parent xanthan lyase of SEQ ID NO: 2 are shown in Tables 1 and 2 below. The presence of the alteration was confirmed by sequencing.

TABLE 1

Generated variants of the mature parent xanthan lyase of SEQ ID NO: 2

| Regions | Alteration |
| --- | --- |
| Region 1 (amino acids 154 to 176 of SEQ ID NO: 2): | Y155E |
| | A159P |
| Region 2 (amino acids 614 to 658 of SEQ ID NO: 2): | A624E |
| | A626G |
| | T631N |
| | T631E |
| | S635E |
| | S635T |
| | S635Q |
| | A645S |
| | T649V |
| | T649K |
| | T649R |
| | Q650G |
| | I656V |
| Region 3 (amino acids 731 to 803 of SEQ ID NO: 2): | G738L |
| | K745R |
| | F746L |
| | L748T |
| | P752R |
| | P752K |
| | G753E |
| | G753Q |
| | G753S |
| | S754E |
| | S754L |
| | S754Q |
| | S754R |
| | S757D |

TABLE 1-continued

Generated variants of the mature parent xanthan lyase of SEQ ID NO: 2

| Regions | Alteration |
|---|---|
| | S757P |
| | S757E |
| | P764V |
| | P764K |
| | A769D |
| | A769T |
| | A769R |
| | A769S |
| | A769E |
| | A769Q |
| | A769* |
| | A774V |
| | L775M |
| | L775Y |
| | L775A |
| | L775I |
| | L775S |
| | L775F |
| | L775Q |
| | D777K |
| | D777R |
| | P779V |
| | Y782I |
| | A785T |
| | N786K |
| | G789R |
| | K792W |
| | K792Y |
| | K792V |
| | K792A |
| | N796Q |
| | A799H |
| | V800P |
| | D801G |
| Region 4 (amino acids 807 to 846 of SEQ ID NO: 2): | K819R |
| | K819T |
| | K824R |
| | A843P |
| | D845E |
| Region 6 (amino acids 903 to 1004 of SEQ ID NO: 2): | T903A |
| | T903Q |
| | A911V |
| | A911M |
| | A911S |
| | A912T |
| | A912I |
| | A912Y |
| | T915Q |
| | T915S |
| | T915V |
| | T915A |
| | T919F |
| | T919G |
| | T919D |
| | T921R |
| | T921S |
| | T923H |
| | T923D |
| | T925Q |
| | T925D |
| | T925R |
| | T927K |
| | D928W |
| | Y930H |
| | Y930L |
| | Y930F |
| | A932P |
| | D933M |
| | G941E |
| | G941D |
| | A966P |
| | A967D |
| | N991D |
| | V998K |

TABLE 2

Generated variants of the mature parent xanthan lyase of SEQ ID NO: 2

| Regions | Alteration |
|---|---|
| Region 2 (amino acids 614 to 658 of SEQ ID NO: 2): | T631N |
| Region 3 (amino acids 731 to 803 of SEQ ID NO: 2): | A769D |
| | A769T |
| | L775A |
| | L775F |
| | L775I |
| | L775M |
| | L775Q |
| | L775S |
| | L775Y |
| | P779V |
| | K792A |
| | K792V |
| | K792Y |
| | N796Q |
| | A799H |
| | D801G |
| Region 5 (amino acids 872 to 885 of SEQ ID NO: 2): | K875T |
| Region 6 (amino acids 903 to 1004 of SEQ ID NO: 2): | T903A |
| | T903Q |
| | A911M |
| | A911V |
| | A912I |
| | A912T |
| | A912Y |
| | T915S |
| | T915V |
| | T919D |
| | T919G |
| | T921R |
| | T921S |
| | T923D |
| | T923H |
| | T925D |
| | T925Q |
| | T925R |
| | T927K |
| | D928W |
| | Y930F |
| | Y930H |
| | Y930L |
| | D933M |
| | G941D |
| | V998K |

*Bacillus* organism containing a variant was inoculated in LB broth containing chloramphenicol (6 µg/ml) and grown overnight at 37° C. For expression of xanthan lyase variants, 2% of overnight culture was added to 300 ml of 10-R medium in 1000 ml baffled flask and grown at 30° C. for 96 hrs. at 180 rpm.

10-R medium contained 33 g/L Soluble starch, 6 g/L (NH4)2HPO4, 5 g/L Potato peptone, 1.2 g/L (MgSO4× 7H2O), 12 g/L KH2PO4, 5 g/L (Na2HPO4×2H2O), 18 mL/L of Trace metal solution, 1.8 g/L K2SO4 and 0.1 g/L (CaCl2)×2H2O) and 0.5 mL/L SB2121 (anti-foam agent). Trace metal solution was made by mixing 0.49 g/L (MnSO4×H2O), 1.97 g/L (FeSO4×7H2O), 0.1 g/L (CuSO4× 5H2O), 0.3 g/L ZnCl2 and 19.6 g/L citric acid.

Example 3: Purification of Xanthan Lyase Variants

Prior to purification, *Bacillus subtilis* broth was clarified by centrifuging at 8000×g for 30 minutes at 10° C. followed by vacuum filtration using a combination of Seitz filter (K250) and WHATMAN glass filter GF/F grade in a Buchner funnel. Finally, the supernatant was filtered through 0.22µ Tangential flow filtration unit.

Xanthan lyase variants were purified using three-step automated tandem column chromatography. Macro-Prep Methyl HIC column was pre-equilibrated with 50 mM Tris, pH 8.0 containing 1 M (NH4)2SO4 and 1 mM CaCl2 buffer. During sample loading onto the column the clarified culture supernatant (250 mL) was diluted 1:1 in-line with 50 mM Tris, pH 8.0 containing 2 M (NH4)2SO4 and 1 mM CaCl2 buffer to make the final concentration to 1 M. The unbound or weakly bound protein was washed with the equilibration buffer until the Absorbance at 280 nm comes below 0.1 AU. Elution was carried out using 50 mM Tris pH 8 containing 0.5 M (NH4)2SO4 and 1 mM CaCl2. Eluted protein peak was automatically loaded on MEP-Hypercel column pre-equilibrated with 50 mM Tris, pH 8 containing 0.5 M (NH4)2SO4 and 1 mM CaCl2. The unbound or weakly bound protein was washed with the equilibration buffer until the Absorbance at 280 nm comes below 0.1 AU. The column was washed again with 50 mM Tris, pH 8 containing 1 mM CaCl2 to remove impurities. The Purified protein was eluted with 50 mM Na-acetate, pH 5 containing 1 mM CaCl2. The eluted purified protein was automatically transferred to Sephadex G-25 column pre-equilibrated with 50 mM MOPS, pH 8 containing 1 mM CaCl2 for desalting.

Example 4: Detergent Stability Assay

Reagents for the detergent stability assay were prepared as follows:

A stock of 1.0 M MOPS buffer was prepared by dissolving 209.26 g of 3-Morpholinopropanesulfonic acid in Milli Q water. pH was adjusted to 7.5 using NaOH and the final volume of buffer was made up to 1000 ml. This buffer stock was stored at 4° C. until use. A 50 mM working solution of MOPS buffer was prepared by adding 50 ml of 1.0 M stock to 950 ml of Milli Q water.

A substrate solution of 0.4% w/v xanthan gum was freshly prepared by dissolving 400 mg of xanthan gum in 100 ml of Milli Q water.

A stock solution mix containing 1.0 M Na2CO3, 0.17 M potassium sodium tartrate and 5 mM (Bi(NO3)3×5H2O) was prepared by dissolving 106.99 g of Na2CO3, 47.98 g of potassium sodium tartrate and 2.42 mg of (Bi(NO3)3× 5H2O) in Milli Q water for a final volume of 1000 ml. This stock solution mix was filtered and stored at room temperature.

A PAHBAH reagent (1.5% PAHBAH) was freshly prepared by dissolving 1.5 g of p-hydroxybenzoic acid hydrazide (PAHBAH) in the stock solution mix.

Detergent Stability Assay:

A. Screening of Culture Supernatant

The in-detergent stability was determined by measuring the enzymatic activity present in culture supernatants of variants or wild-type controls after incubation with detergent (70%, final concentration) at 30° C.

Detergent stress was carried out by addition of 30 µl of culture supernatant and 70 µl of a Persil Universal Gel detergent (100%) into wells of 96-well microtitre plates which were shaken for 15 min at 1000 rpm. Two identical plates were produced whereof one plate was incubated at 4° C. (unstressed plate) and the other plate was incubated at 30° C. (stressed plate) for 1 hour. After incubation, samples from unstressed and stressed plates were diluted 50× with dilution buffer (50 mM MOPS, 5 mM CaCl2, pH 7.5).

To measure the enzyme activity of diluted enzyme-detergent samples, reaction mixtures were prepared in 96-well PCR plates. 50 µl of diluted samples were mixed with 50 µl of freshly prepared substrate solution and incubated at 40° C. for 1 hour.

After incubation, 75 µl of PAHBAH reagent was added to reaction mixture in the same PCR plate and incubated in a programmable thermal cycler (T-ROBOT) for 10 min at 90° C. followed by subsequent cooling at 10° C. Samples (25 µl) were transferred to a 384 well microtitre plate and the absorbance was measured at 405 nm using an Infinite M1000 reader (TECAN, Switzerland).

The residual activity (RA) for variants and wild-type controls was calculated as the percentage of enzymatic activity remaining after incubation at 30° C. relative to enzymatic activity remaining after incubation at 4° C., i.e., according to the following formula after subtracting relevant background absorbance contributions:

Residual activity (RA)=100%*$A405$ (sample incubated at 30° C.)/$A405$ (sample incubated at 4° C.).

The variants with higher detergent stability were picked with respect to the wild-types grown in the plates.

B. Screening of Purified Variants

The detergent stability of purified variants was determined by measuring the enzyme activity of the purified protein after incubation with detergent (90%, final concentration) at 30° C.

Purified variants were diluted to a concentration of 200 ppm using 50 mM MOPS buffer. For detergent treatment, 10 µl of diluted purified samples were mixed with 90 µl of Persil Universal Gel detergent (100%) into wells of 96-well microtitre plates which were shaken for 20 min at 1000 rpm. Two identical plates were produced whereof one plate was incubated at 4° C. (unstressed plate) and the other plate was incubated at 30° C. (stressed plate) for 1 hour. After incubation, samples from unstressed and stressed plates were diluted 50× with dilution buffer (50 mM MOPS, 1 mM CaCl2, pH 7.5).

Enzymatic activity analysis of unstressed and stressed samples was done as described in section A.

C. Calculating Half-Lives and Half-Life Improvement Factors (HIF)

Half-life (T½ (in hours)) was calculated at a given detergent concentration and storage temperature for the wild-type controls and/or variants, as the degradation follows an exponential decay and the incubation time (hours) is known, i.e., according to the following formulas:

$T½(\text{variant})=(Ln(0.5)/Ln(RA\text{-variant}/100))*\text{Time}$ $T½(\text{Wild-type})=(Ln(0.5)/Ln(RA\text{-Wild-type}/100))*\text{Time}$ Wherein "RA" is the residual activity in percent and "Time" is the incubation time.

A half-life improvement factor (HIF) under a given set of storage conditions (detergent concentration and temperature) is calculated as HIF=T½(variant)/T½ (Wild-type), where the Wild-type is incubated under the same storage conditions as the variant.

The obtained HIF values for the purified variants are shown in Table 3 below.

TABLE 3

Half-life improvement factors of purified variants:

| Regions | Alteration | HIF |
|---|---|---|
| — | Wild-type | 1 |
| Region 1 (amino acids 154 to 176 of SEQ ID NO: 2) | Y155E | 1.4 |
| Region 2 (amino acids 614 to 658 of SEQ ID NO: 2): | K620R | 1.5 |
| | Q650G | 4.8 |
| | T631N | 1.4 |
| | T649V | 1.2 |

TABLE 3-continued

Half-life improvement factors of purified variants:

| Regions | Alteration | HIF |
|---|---|---|
| Region 3 (amino acids 731 to 803 of SEQ ID NO: 2): | K745R | 2.4 |
|  | S757D | 3.4 |
|  | G753E | 4.4 |
|  | G753Q | 3.8 |
|  | G753S | 2.5 |
|  | S754E | 2 |
|  | P752R | 1.4 |
|  | S754L | 1.3 |
|  | K792W | >5 |
| Region 4 (amino acids 807 to 846 of SEQ ID NO: 2) | K819R | 1.2 |
|  | K824R | 1.2 |
| Region 6 (amino acids 903 to 1004 of SEQ ID NO: 2) | A966P | 1.5 |
|  | N991D | 1.7 |

The obtained HIF values for culture supernatants of variants are shown in Table 4 below.

TABLE 4

Half-life improvement factors of culture supernatants of variants:

| Regions | Alteration | HIF |
|---|---|---|
|  | Wild-type | 1 |
| Region 2 (amino acids 614 to 658 of SEQ ID NO: 2) | T631N | 1.2 |
| Region 3 (amino acids 731 to 803 of SEQ ID NO: 2) | A769D | 3.2 |
|  | A769T | 1.5 |
|  | L775A | >5.0 |
|  | L775F | 2.3 |
|  | L775I | >5.0 |
|  | L775M | >5.0 |
|  | L775Q | 1.3 |
|  | L775S | >5.0 |
|  | L775Y | >5.0 |
|  | P779V | >5.0 |
|  | K792A | 1.9 |
|  | K792V | 3.3 |
|  | K792Y | >5.0 |
|  | N796Q | 1.2 |
|  | A799H | 1.3 |
|  | D801G | 2.5 |
| Region 5 (amino acids 872 to 885 of SEQ ID NO: 2) | K875T | >5.0 |
| Region 6 (amino acids 903 to 1004 of SEQ ID NO: 2) | T903A | 1.3 |
|  | T903Q | 1.2 |
|  | A911M | 1.5 |
|  | A911V | 2.1 |
|  | A912I | 1.5 |
|  | A912T | 1.6 |
|  | A912Y | 1.4 |
|  | T915S | 1.3 |
|  | T915V | 1.2 |
|  | T919D | 1.2 |
|  | T919G | 1.3 |
|  | T921R | 1.3 |
|  | T921S | 1.2 |
|  | T923D | 1.3 |
|  | T923H | 2.3 |
|  | T925D | 1.2 |
|  | T925Q | 1.2 |
|  | T925R | 1.2 |
|  | T927K | 1.2 |
|  | D928W | 2.3 |
|  | Y930F | 1.2 |
|  | Y930H | 1.2 |
|  | Y930L | 1.2 |
|  | D933M | 1.5 |
|  | G941D | 1.2 |
|  | V998K | 1.3 |

Example 5: Half-Life of Xanthan Lyase Variants

Variants of the mature parent xanthan lyase of SEQ ID NO: 2 were prepared and purified as described above in Examples 2 and 3. The in-detergent stability of the variants was determined as described in Example 4 by measuring the enzymatic activity present in either culture supernatants or purified samples of the variants after incubation with detergent. Incubation was performed using a 70% concentration of Persil Universal Gel detergent (PUG) at 30° C. for the culture supernatants, and a 70% or 90% concentration of PUG detergent at 30° C. for the purified variants, with a variant incubation time of one hour for the culture supernatants and one hour or three hours for the purified variants.

The half-lives and calculated half-life improvement factor (HIF) values for culture supernatants are provided in Table 5 below. Table 6 shows the half-life and half-life improvement factors (HIF) for purified variants, where HIF for variants incubated with a 70% detergent concentration are calculated based on a wild-type half-life of 0.22 h and variants incubated with a 90% detergent concentration are calculated based on a wild-type half-life of 0.20 h.

TABLE 5

Half-life and half-life improvement factor (HIF) of culture supernatants of variants

| Region | Mutation | Half-life (h) | HIF |
|---|---|---|---|
| — | Wild-type | 0.42 | 1 |
| Region 1 (amino acids 154 to 176 of SEQ ID NO: 2) | A159P | 0.5 | 1.2 |
| Region 2 (amino acids 614 to 658 of SEQ ID NO: 2) | S635T | 0.6 | 1.4 |
| Region 3 (amino acids 731 to 803 of SEQ ID NO: 2) | S754Q | 0.5 | 1.2 |
|  | S757E | 0.6 | 1.4 |
|  | S757P | 0.6 | 1.4 |
|  | A769R | 0.6 | 1.4 |
|  | A769T | 1.1 | 2.6 |
|  | L775F | 1.0 | 2.4 |
|  | L775I | 1.1 | 2.6 |
|  | L775Q | 0.5 | 1.2 |
|  | L775S | 1.1 | 2.6 |
|  | T778T | 0.6 | 1.4 |
|  | Y782I | 0.7 | 1.6 |
|  | N786K | 0.5 | 1.2 |
|  | G789R | 0.5 | 1.2 |
|  | K792A | 0.8 | 1.9 |
|  | K792V | 1.1 | 2.6 |
|  | K792Y | 1.1 | 2.6 |
|  | N796Q | 0.5 | 1.2 |
|  | A799H | 0.5 | 1.2 |
| Region 5 (amino acids 872 to 885 of SEQ ID NO: 2) | K875E | 0.6 | 1.4 |
| Region 6 (amino acids 903 to 1004 of SEQ ID NO: 2) | T903A | 0.5 | 1.2 |
|  | T903Q | 0.5 | 1.2 |
|  | A911M | 0.6 | 1.4 |
|  | A911S | 0.6 | 1.4 |
|  | A911V | 0.9 | 2.1 |
|  | A912Y | 0.6 | 1.4 |
|  | A912T | 0.7 | 1.6 |
|  | T915Q | 0.6 | 1.4 |
|  | T915S | 0.5 | 1.2 |
|  | T919D | 0.5 | 1.2 |
|  | T919F | 0.5 | 1.2 |
|  | T921R | 0.6 | 1.4 |
|  | T921S | 0.5 | 1.2 |
|  | T923D | 0.5 | 1.2 |
|  | T923H | 1.0 | 2.4 |
|  | T925D | 0.5 | 1.2 |
|  | T925Q | 0.5 | 1.2 |
|  | T925R | 0.5 | 1.2 |
|  | T927K | 0.5 | 1.2 |
|  | D928W | 1.0 | 2.4 |
|  | Y930F | 0.5 | 1.2 |

TABLE 5-continued

Half-life and half-life improvement factor
(HIF) of culture supernatants of variants

| Region | Mutation | Half-life (h) | HIF |
|---|---|---|---|
| | Y930H | 0.5 | 1.2 |
| | Y930L | 0.5 | 1.2 |
| | D933M | 0.6 | 1.4 |
| | G941E | 0.5 | 1.2 |

TABLE 6

Half-life and half-life improvement
factor (HIF) of purified variants

| Mutations | Detergent (%) | Incubation time (h) | Half-life (h) | HIF |
|---|---|---|---|---|
| Wild-type | 70 | 1 | 0.22 | 1 |
| Wild-type | 90 | 1 | 0.2 | 1 |
| K620R | 70 | 1 | 0.6 | 2.6 |
| T631N | 70 | 1 | 0.6 | 2.5 |
| S635E | 90 | 1 | 0.7 | 3.3 |
| S757D | 70 | 1 | 0.6 | 2.9 |
| L775A | 90 | 3 | 1.6 | 8.1 |
| L775Y | 90 | 1 | 2.2 | 11 |
| L775M | 90 | 1 | 3.7 | 19 |
| P779V | 90 | 1 | 0.8 | 4.2 |
| D801G | 90 | 1 | 0.6 | 3.1 |
| A843P | 90 | 1 | 0.6 | 2.9 |
| K875T | 90 | 1 | 0.7 | 3.5 |
| T631N, K875T | 90 | 1 | 1.0 | 5.1 |
| S757D, D801G | 90 | 1 | 4.1 | 20 |
| S757D, K875T | 90 | 3 | 1.1 | 5.7 |
| K875T, N991D | 90 | 3 | 2.1 | 11 |

Example 6: Half-Life of Xanthan Lyase Variants with Mutations in Chelator-Induced Instability Regions and Adjacent Regions Variants of the mature parent xanthan lyase of SEQ ID NO: 2 were prepared and purified as described above in Examples 2 and 3. For the purposes of this example, variants were produced having mutations in at least one chelator-induced instability region (regions 1, 2, 3, 4, 5, 6) and in at least one adjacent region (regions 7, 8, 9, 10, 11, 12, 13). The in-detergent stability of the variants was determined as described in Example 4 by measuring the enzymatic activity present in purified samples of the variants after incubation with detergent. Incubation was performed using a 70%, 90% or 95% concentration of Persil Universal Gel detergent (PUG), with incubation at a temperature of 30, 32, 35 or 37° C. and a variant incubation time ranging from one hour to up to 840 hours.

Half-lives were calculated as described above in Example 4. In cases where the difference in stability between wild-type and variants was too large to accurately assess half-life for both wild-type and variant using the same incubation time, the incubation time for wild-type and variant is different, e.g. 1 h for wild-type and up to 840 h for the most stable variants.

Further, in order to determine the stability (half-life) within a shorter duration of incubation time for the more stable variants, e.g. <168 h, the incubation temperature for some variants was increased by 2-7° C. For variants tested at a higher temperature (i.e. >30° C.), HIF values based on the wild-type could not be calculated as the half-life of the wild-type (order of magnitude of minutes) could not be determined accurately at these temperatures. Stability of the variants in the tables below is therefore reported in terms of half-life (in hours).

Tables 7-13 below show the half-life for the purified variants along with information on the test conditions (temperature, detergent concentration, incubation time) for each variant.

TABLE 7

Half-life of purified variants: Temperature
(T) 30° C., detergent concentration 70%

| Mutations | T (° C.) | Detergent (%) | Incubation time (h) | Half-life (h) |
|---|---|---|---|---|
| No mutations (Wild-type) | 30 | 70 | 1 | 0.22 |
| K620R, K855R | 30 | 70 | 1 | 1.0 |
| K329R, K745R | 30 | 70 | 1 | 0.8 |
| K360R, K745R | 30 | 70 | 1 | 0.7 |
| A293G, K567R, S579R, K620R | 30 | 70 | 1 | 1.5 |
| S100D, N991D | 30 | 70 | 1 | 0.5 |

TABLE 8

Half-life of purified variants: Temperature (T) 30° C.,
detergent concentration 90%

| Mutations | T (° C.) | Detergent (%) | Incubation time (h) | Half-life (h) |
|---|---|---|---|---|
| No mutations (Wild-type) | 30 | 90 | 1 | 0.20 |
| L339M, K451R, S579R, N672D, K745R, G899S | 30 | 90 | 1 | 0.4 |
| V188I, L339M, S579R, N672D, K745R, G899S | 30 | 90 | 1 | 0.5 |
| K291R, L339M, S579R, N672D, K745R, G899S | 30 | 90 | 1 | 0.5 |
| L339M, S579R, T631N, N672D, K745R, G899S | 30 | 90 | 1 | 0.5 |
| N242S, L339M, F377Y, S579R, T631N, N672D | 30 | 90 | 1 | 0.5 |
| L339M, F377Y, S579R, N672D, K745R, G899S | 30 | 90 | 1 | 0.5 |
| F377Y, T631N, K819R, N892Y | 30 | 90 | 1 | 0.5 |
| A221P, L339M, S579R, N672D, K745R, G899S | 30 | 90 | 1 | 0.6 |
| K316R, L339M, S579R, N672D, K745R, G899S | 30 | 90 | 1 | 0.6 |
| I238M, L339M, S579R, N672D, K745R, G899S | 30 | 90 | 1 | 0.6 |
| S579R, N991D | 30 | 90 | 1 | 0.6 |
| K9R, T631N, K819R, N892Y | 30 | 90 | 1 | 0.6 |
| S578R, K819R | 30 | 90 | 1 | 0.6 |
| S579R, K819R | 30 | 90 | 1 | 0.6 |
| N242S, L339M, F377Y, S579R, N672D, T727P, N991D | 30 | 90 | 1 | 0.6 |
| N242S, L339M, F377Y, S579R, N672D, S757D | 30 | 90 | 1 | 0.7 |
| S578R, N991D | 30 | 90 | 1 | 0.8 |
| A293G, K567R, S579R, K620R | 30 | 90 | 1 | 0.8 |
| Q109R, L339M, S579R, N672D, K745R, G899S | 30 | 90 | 1 | 0.9 |
| S579R, I722F, T727P, K819R, N892Y | 30 | 90 | 1 | 0.9 |
| N892Y, N991D | 30 | 90 | 1 | 0.9 |
| N15T, N892Y, N991D | 30 | 90 | 1 | 1.0 |
| T631N, K819R, N892Y | 30 | 90 | 1 | 1.1 |
| K451R, K620R, N892Y | 30 | 90 | 1 | 1.1 |
| N672D, K819R, N892Y | 30 | 90 | 3 | 1.2 |
| S579R, T631N, A645S, N892Y | 30 | 90 | 1 | 1.3 |
| K819R, N892Y | 30 | 90 | 1 | 1.3 |
| S579R, K620R, N892Y | 30 | 90 | 1 | 1.3 |
| N672D, K875T | 30 | 90 | 3 | 1.3 |

TABLE 8-continued

Half-life of purified variants: Temperature (T) 30° C., detergent concentration 90%

| Mutations | T (° C.) | Detergent (%) | Incubation time (h) | Half-life (h) |
|---|---|---|---|---|
| K316R, S578R, K819R | 30 | 90 | 3 | 1.4 |
| N15T, T631N, K819R, N892Y | 30 | 90 | 3 | 1.4 |
| K183R, T631N, K819R, N892Y | 30 | 90 | 3 | 1.4 |
| S579R, A843P | 30 | 90 | 3 | 1.6 |
| S579R, T631N, K819R, N892Y | 30 | 90 | 3 | 1.6 |
| E229S, S757D | 30 | 90 | 3 | 1.7 |
| R258E, S578R, K819R | 30 | 90 | 3 | 1.7 |
| S579R, S635T | 30 | 90 | 3 | 1.8 |
| E229S, K620R | 30 | 90 | 3 | 1.8 |
| S579R, K875T | 30 | 90 | 3 | 1.8 |
| S578R, N672D, K819R | 30 | 90 | 3 | 1.8 |
| S579R, D801G | 30 | 90 | 3 | 1.8 |
| S579R, T727P, N892Y, N991D | 30 | 90 | 1 | 1.9 |
| S579R, N892Y, N991D | 30 | 90 | 3 | 1.9 |
| A221P, S578R, K819R | 30 | 90 | 3 | 1.9 |
| K451R, T631N, N892Y | 30 | 90 | 1 | 1.9 |
| N672D, D801G | 30 | 90 | 1 | 2.0 |
| K291R, S578R, D801G | 30 | 90 | 3 | 2.0 |
| I238M, S578R, K819R | 30 | 90 | 3 | 2.1 |
| S578R, D801G, K819R | 30 | 90 | 3 | 2.1 |
| S578R, D801G | 30 | 90 | 3 | 2.1 |
| S578R, S757D, K819R | 30 | 90 | 3 | 2.2 |
| Q109R, K819R, N892Y | 30 | 90 | 3 | 2.2 |
| V188I, S578R, K819R | 30 | 90 | 3 | 2.2 |
| K9R, S578R, K819R | 30 | 90 | 3 | 2.2 |
| L324Q, S578R, K819R | 30 | 90 | 3 | 2.3 |
| K95E, S578R, K819R | 30 | 90 | 3 | 2.3 |
| S578R, K819R, N892Y, N991D | 30 | 90 | 3 | 2.3 |
| S578R, T631N, K819R, N892Y | 30 | 90 | 3 | 2.3 |
| S100D, S578R, N892Y, A967D | 30 | 90 | 3 | 2.3 |
| V188I, S578R, N892Y, A967D | 30 | 90 | 3 | 2.3 |
| K291R, S578R, K875T | 30 | 90 | 3 | 2.3 |
| K567R, S578R, K819R | 30 | 90 | 3 | 2.4 |
| K316R, S578R, K819R | 30 | 90 | 3 | 2.4 |
| Q109R, T631N, K819R, N892Y | 30 | 90 | 3 | 2.4 |
| Q109R, A843P | 30 | 90 | 3 | 2.4 |
| K204R, S578R, K819R | 30 | 90 | 3 | 2.4 |
| S578R, K875T | 30 | 90 | 3 | 2.4 |
| Q109R, D801G | 30 | 90 | 3 | 2.4 |
| K291R, S578R, N991D | 30 | 90 | 3 | 2.4 |
| N106Y, S578R, K819R | 30 | 90 | 3 | 2.5 |
| Q109R, S635T | 30 | 90 | 3 | 2.5 |
| K291R, S578R, D801G | 30 | 90 | 3 | 2.5 |
| S578R, K819R, N892Y | 30 | 90 | 3 | 2.5 |
| K183R, S578R, K819R | 30 | 90 | 3 | 2.5 |
| S578R, K620R, K819R | 30 | 90 | 3 | 2.6 |
| K291R, S578R, K620R | 30 | 90 | 3 | 2.6 |
| S578R, S635T | 30 | 90 | 3 | 2.6 |
| S578R, A843P | 30 | 90 | 3 | 2.7 |
| K291R, S578R, T631N | 30 | 90 | 3 | 2.7 |
| S578R, K819R, K875T | 30 | 90 | 3 | 2.7 |
| N15T, S578R, K819R | 30 | 90 | 3 | 2.8 |
| L339M, S578R, K819R | 30 | 90 | 3 | 2.9 |
| K291R, S578R, S757D | 30 | 90 | 3 | 2.9 |
| Q109R, K875T | 30 | 90 | 3 | 2.9 |
| F377Y, S579R, K745R | 30 | 90 | 3 | 2.9 |
| Q109R, S578R, K819R | 30 | 90 | 3 | 3.7 |
| L339M, S579R, N672D, P726Q, T727P, K745R, A785T, N892Y, G899S | 30 | 90 | 1 | 4.2 |
| S100D, R317K, S578R, K620R | 30 | 90 | 1 | 4.5 |
| S579R, S757D, N892Y | 30 | 90 | 1 | 4.7 |
| K875T, N892Y | 30 | 90 | 3 | 9.3 |
| N106Y, S578R, K819R, K875T | 30 | 90 | 16 | 9.7 |
| N15T, S578R, L775A, K819R | 30 | 90 | 16 | 11 |
| Q109R, N672D, K875T | 30 | 90 | 16 | 11 |
| Q109R, S757D, K875T | 30 | 90 | 16 | 11 |
| K183R, S578R, L775A, K819R | 30 | 90 | 16 | 11 |
| N106Y, S578R, L775A, K819R | 30 | 90 | 16 | 11 |
| N15T, F377Y, S578R, K819R | 30 | 90 | 16 | 12 |
| Q109R, D801G, K819R, N892Y | 30 | 90 | 16 | 12 |
| K183R, S578R, K819R, K875T | 30 | 90 | 16 | 12 |
| Q109R, D801G, K875T | 30 | 90 | 16 | 12 |
| Q109R, K819R, K875T, N892Y | 30 | 90 | 16 | 12 |
| Q109R, P779V, K819R, N892Y | 30 | 90 | 16 | 12 |
| Q109R, P779V, K875T | 30 | 90 | 16 | 13 |
| V188I, K291R, S578R, L775A | 30 | 90 | 20 | 13 |
| I341P, S578R, L775A | 30 | 90 | 16 | 13 |
| Q109R, F377Y, K875T | 30 | 90 | 16 | 13 |
| Q109R, S578R, K875T | 30 | 90 | 16 | 13 |
| Q109R, S579R, K819R, N892Y | 30 | 90 | 16 | 13 |
| K291R, L324Q, S578R, K620R | 30 | 90 | 20 | 13 |
| Q109R, T631N, K875T | 30 | 90 | 16 | 13 |
| Q109R, S578R, L775A, K819R | 30 | 90 | 16 | 13 |
| I341P, S578R, L775M | 30 | 90 | 16 | 13 |
| I341P, S578R, T631N | 30 | 90 | 16 | 14 |
| Q109R, K875T, N991D | 30 | 90 | 16 | 14 |
| Q109R, K620R, K875T | 30 | 90 | 16 | 14 |
| K320R, S578R, L775A, K819R | 30 | 90 | 16 | 14 |
| Q109R, L775M, K875T | 30 | 90 | 16 | 14 |
| Q109R, K875T, N892Y | 30 | 90 | 16 | 15 |
| E229S, S578R, D801G | 30 | 90 | 16 | 15 |
| Q109R, S578R, L775A, K875T | 30 | 90 | 20 | 15 |
| Q109R, L775M, K819R, N892Y | 30 | 90 | 16 | 15 |
| I341P, S578R, K875T | 30 | 90 | 16 | 16 |
| Q109R, L775A, K819R, N892Y | 30 | 90 | 16 | 16 |
| Q109R, S579R, D801G, K875T | 30 | 90 | 20 | 16 |
| E229S, S578R, P779V | 30 | 90 | 16 | 16 |
| Q109R, L775A, K875T | 30 | 90 | 16 | 16 |
| Q109R, S578K, K819R, K875T, N892Y | 30 | 90 | 20 | 17 |
| E229S, S578R, K875T | 30 | 90 | 16 | 17 |
| Q109R, L775A, P779V, K792Y, K819R, N892Y | 30 | 90 | 20 | 18 |
| E229S, S579R, L775A | 30 | 90 | 20 | 18 |
| E229S, S579R, D928W | 30 | 90 | 20 | 18 |
| E229S, S578R, L775A | 30 | 90 | 16 | 18 |
| E229S, S578R, K819R | 30 | 90 | 16 | 18 |
| V188I, S578R, L775A, N892Y, A967D | 30 | 90 | 16 | 19 |
| Q109R, E229S, K819R, K875T, N892Y | 30 | 90 | 20 | 20 |
| Q109R, L775A, P779V, K875T, N892Y | 30 | 90 | 20 | 20 |
| Q109R, D801G, K819R, K875T, N892Y | 30 | 90 | 20 | 20 |
| E229S, S578R, N991D | 30 | 90 | 16 | 20 |
| L339M, S578R, K819R | 30 | 90 | 20 | 21 |
| E229S, S579R, K875T | 30 | 90 | 20 | 21 |
| Q109R, N892Y, N991D | 30 | 90 | 20 | 10 |
| K320R, S578R, K819R, K875T | 30 | 90 | 20 | 9 |
| K183R, S578R, K819R, N892Y | 30 | 90 | 20 | 9 |
| Q109R, S578R, K819R, K875T | 30 | 90 | 20 | 14 |
| E229S, S579R, A843P | 30 | 90 | 20 | 17 |
| Q109R, S579R, A843P | 30 | 90 | 20 | 12 |
| S578R, D801G, A843P | 30 | 90 | 20 | 10 |
| Q109R, S578R, K875T, N892Y | 30 | 90 | 20 | 22 |
| Q109R, L775A, P779V, K792Y, K819R, K875T, N892Y | 30 | 90 | 20 | 22 |
| E229S, S578R, K620R | 30 | 90 | 16 | 26 |
| S578R, K620R, A769# | 30 | 90 | 3 | 26 |
| Q109R, L775A, D801G, K875T | 30 | 90 | 20 | 26 |
| E229S, S578R, T923H | 30 | 90 | 16 | 26 |
| Q109R, L775A, K792Y, K819R, N892Y | 30 | 90 | 20 | 27 |
| Q109R, L775M, K875T, N892Y | 30 | 90 | 20 | 27 |
| Q109R, S578K, L775A, K819R, N892Y | 30 | 90 | 20 | 27 |
| Q109R, A769I, L775A, K792Y, K819R, N892Y | 30 | 90 | 20 | 29 |
| Q109R, P779V, K792Y, K875T, N892Y | 30 | 90 | 20 | 29 |
| L775A, K875T, N892Y | 30 | 90 | 88 | 33 |
| Q109R, L775A, P779V, K792Y, K875T, N892Y | 30 | 90 | 20 | 33 |
| S578K, L775A, K875T, N892Y, A911V | 30 | 90 | 90 | 38 |
| Q109R, L775A, K792Y, K875T | 30 | 90 | 20 | 43 |
| S578K, P752K, G753E, L775A, K875T, N892Y | 30 | 90 | 90 | 46 |
| Q109R, L775A, K792Y, K875T, N892Y | 30 | 90 | 20 | 47 |
| S578K, L775A, K875T, N892Y, A912T | 30 | 90 | 90 | 49 |
| S578K, P752R, G753E, L775A, K875T, N892Y | 30 | 90 | 90 | 49 |
| S578K, P752R, G753E, S754E, L775A, K875T, N892Y | 30 | 90 | 90 | 51 |

TABLE 8-continued

Half-life of purified variants: Temperature (T) 30° C., detergent concentration 90%

| Mutations | T (° C.) | Detergent (%) | Incubation time (h) | Half-life (h) |
|---|---|---|---|---|
| Q109R, L775A, K875T, N892Y | 30 | 90 | 88 | 54 |
| S578K, G753E, S754E, L775A, K875T, N892Y | 30 | 90 | 167 | 61 |
| S578K, P752K, G753E, S754E, L775A, K875T, N892Y | 30 | 90 | 167 | 62 |
| Q109R, E229V, L775A, D801G, K875T | 30 | 90 | 88 | 67 |
| S578K, P752R, S754E, L775A, K875T, N892Y | 30 | 90 | 167 | 67 |
| S578K, A769D, L775A, K875T, N892Y | 30 | 90 | 90 | 68 |
| S578K, L775A, D801G, K875T, N892Y | 30 | 90 | 90 | 69 |
| Q109R, A769T, L775A, K875T, N892Y | 30 | 90 | 168 | 71 |
| Q109R, S754E, A769T, L775A, K875T, N892Y | 30 | 90 | 88 | 72 |
| S578K, G753E, L775A, K875T, N892Y | 30 | 90 | 167 | 73 |
| Q109R, L775A, K875T, N892Y | 30 | 90 | 168 | 75 |
| Q109R, A769T, L775A, K792Y, K875T, N892Y | 30 | 90 | 168 | 78 |
| E229S, G753E, S754E, L775A, K875T, N892Y | 30 | 90 | 167 | 79 |
| E229S, P752R, G753E, L775A, K875T, N892Y | 30 | 90 | 167 | 80 |
| E229S, P752K, G753E, L775A, K875T, N892Y | 30 | 90 | 167 | 81 |
| S100D, L775A, D801G, K875T, N892Y | 30 | 90 | 167 | 81 |
| Q109R, A769T, L775A, K875T, N892Y | 30 | 90 | 168 | 82 |
| E229S, P752K, G753E, S754E, L775A, K875T, N892Y | 30 | 90 | 167 | 82 |
| S754E, L775A, D801G, K875T, N892Y | 30 | 90 | 167 | 86 |
| E229S, S578R, G753E, N892Y | 30 | 90 | 88 | 86 |
| L775A, D801G, K875T, N892Y | 30 | 90 | 168 | 86 |
| Q109R, S578K, L775A, D801G, K875T | 30 | 90 | 88 | 86 |
| E229S, S578R, L775A, N892Y | 30 | 90 | 88 | 87 |
| E229S, G753E, L775A, K875T, N892Y | 30 | 90 | 167 | 89 |
| Q109R, E229S, A769T, L775A, K875T, N892Y | 30 | 90 | 88 | 95 |
| Q109R, L775A, P779V, K792Y, D801G, K819R, K875T, N892Y | 30 | 90 | 88 | 96 |
| Q109R, G753E, S754E, A769T, L775A, K875T, N892Y | 30 | 90 | 168 | 102 |
| Q109R, P752R, G753E, S754E, A769T, L775A, K875T, N892Y | 30 | 90 | 168 | 102 |
| E229S, P752K, G753E, S754E, L775A, K875T, N892Y | 30 | 90 | 167 | 103 |
| E229S, S578R, G753E, A769D, K792Y, N892Y | 30 | 90 | 168 | 106 |
| P752S, S754E, L775A, D801G, K875T, N892Y | 30 | 90 | 167 | 109 |
| S100D, E229S, S578R, N892Y, A912T | 30 | 90 | 168 | 109 |
| E229S, S578R, L775A, P779V, K792Y, N892Y | 30 | 90 | 168 | 110 |
| E229S, S578R, P752K, S754E, K792Y, N892Y, A912T | 30 | 90 | 168 | 112 |
| E229S, S578R, P752R, G753E, K792Y, N892Y, A912T | 30 | 90 | 168 | 116 |
| E229S, L775A, D801G, K875T, N892Y | 30 | 90 | 167 | 116 |
| Q109R, P752K, G753E, A769T, L775A, K875T, N892Y | 30 | 90 | 88 | 117 |
| E229S, S578K, A769D, K792Y | 30 | 90 | 88 | 119 |
| Q109R, P752K, G753E, L775A, D801G, K875T | 30 | 90 | 88 | 120 |
| Q109R, G753E, A769T, L775A, K875T, N892Y | 30 | 90 | 88 | 120 |
| E229S, S578K, K792Y, D801G, N892Y | 30 | 90 | 168 | 120 |
| E229S, S578R, L775A, P779V, K792Y | 30 | 90 | 88 | 122 |
| E229S, S578R, A769D, P779V, K792Y, N892Y | 30 | 90 | 168 | 122 |
| E229S, A492L, S578R, N892Y, A912T | 30 | 90 | 168 | 122 |
| E229S, S578R, A769S, K792Y, N892Y | 30 | 90 | 168 | 123 |
| E229S, A769D, L775A, K875T, N892Y | 30 | 90 | 167 | 125 |
| Q109R, E229S, A769T, L775A, K792Y, K875T, N892Y | 30 | 90 | 168 | 125 |
| G753E, L775A, D801G, K875T, N892Y | 30 | 90 | 168 | 127 |
| E229S, F419Y, S578K, G753E | 30 | 90 | 168 | 127 |
| E229S, S578R, A769D, L775A, K792Y, N892Y, A912T | 30 | 90 | 168 | 127 |
| Q109R, E229S, P752G, G753E, A769T, L775A, K875T, N892Y | 30 | 90 | 168 | 128 |
| Q109R, E229S, P752K, S754E, A769T, L775A, K875T, N892Y | 30 | 90 | 168 | 130 |
| Q109R, E229S, G753E, A769T, L775A, K875T, N892Y | 30 | 90 | 168 | 130 |
| Q109R, E229S, P752R, G753E, S754E, A769T, L775A, K875T, N892Y | 30 | 90 | 168 | 131 |
| E229S, S578K, D801G | 30 | 90 | 88 | 133 |
| Q109R, P752K, G753E, S754E, A769T, L775A, K875T, N892Y | 30 | 90 | 88 | 133 |
| E229S, S578K, G753E, A843P | 30 | 90 | 168 | 134 |
| E229S, S578R, L775A, K792Y, N892Y, A912T | 30 | 90 | 168 | 137 |
| E229S, S578K, T631N, G753E | 30 | 90 | 168 | 137 |
| E229S, S578K, P752R, G753E | 30 | 90 | 88 | 139 |
| Q109R, P752K, G753E, A769T, L775A, K875T, N892Y | 30 | 90 | 88 | 139 |
| E229S, A492L, S578K, G753E, D801G | 30 | 90 | 168 | 140 |
| Q109R, E229S, G753E, S754E, A769T, L775A, K875T, N892Y | 30 | 90 | 168 | 141 |
| E229S, S578K, K875T | 30 | 90 | 88 | 143 |
| E229S, S578R, G753E, A769D, L775A, N892Y | 30 | 90 | 167 | 143 |
| G753E, L775A, D801G, K875T, N892Y | 30 | 90 | 167 | 144 |
| E229S, S578K, G753E, N892Y | 30 | 90 | 168 | 144 |
| E229N, S578K, A769D, L775A, K875T, N892Y | 30 | 90 | 168 | 145 |
| E229S, S578K, G753E, L775A, P779V | 30 | 90 | 168 | 145 |
| Q109R, E229S, S578K, A769T, L775A, K875T, N892Y | 30 | 90 | 168 | 146 |
| E229S, S578R, P752K, K792Y, N892Y, A912T | 30 | 90 | 168 | 149 |
| E229S, K360R, S578K, P752K, G753E, S754E | 30 | 90 | 168 | 149 |
| E229S, A492L, S578K, G753E | 30 | 90 | 168 | 150 |
| E229S, S578K, K792Y, N892Y | 30 | 90 | 168 | 151 |
| E229S, S578K, P779V | 30 | 90 | 88 | 151 |
| E229S, S578K, G753E | 30 | 90 | 88 | 153 |
| E229S, K360R, S578K, A769D, L775A, K792Y | 30 | 90 | 168 | 154 |
| Q109R, E229S, T631N, G753E, S754E, A769T, L775A, K875T, N892Y | 30 | 90 | 168 | 156 |
| Q109R, E229S, A769D, L775A, K875T, N892Y | 30 | 90 | 168 | 156 |
| G753E, L775A, D801G, K875T, N892Y, A912T | 30 | 90 | 168 | 157 |
| Q109R, E229S, K567R, G753E, S754E, A769T, L775A, K875T, N892Y | 30 | 90 | 168 | 158 |
| P752R, G753E, L775A, D801G, K875T, N892Y | 30 | 90 | 167 | 158 |
| E229S, S578K, T631N, P752K, G753E, S754E | 30 | 90 | 168 | 159 |
| E229S, A492L, S578K, G753E, K1016T | 30 | 90 | 168 | 159 |
| E229S, S578K, T631N, G753E, S754E | 30 | 90 | 168 | 159 |
| E229S, S578K, P752R | 30 | 90 | 88 | 160 |
| E229S, S578R, G753E, A769D, P779V, N892Y | 30 | 90 | 168 | 160 |
| E229S, S578K, G753E, N1008D | 30 | 90 | 168 | 162 |
| P752K, G753E, L775A, D801G, K875T, N892Y | 30 | 90 | 167 | 162 |
| E229S, S578K, G753E, A912T | 30 | 90 | 168 | 163 |
| E229S, S578K, G753E, S754E | 30 | 90 | 88 | 165 |
| E229S, S578K, P752K, S754E | 30 | 90 | 88 | 165 |
| E229S, A492L, S578K, G753E, S754E | 30 | 90 | 168 | 167 |
| E229S, S578K, A769D, P779V | 30 | 90 | 88 | 168 |
| A769D, L775A, D801G, K875T, N892Y | 30 | 90 | 167 | 172 |
| Q109R, E229S, G753E, S754E, A769T, L775A, A843P, K875T, N892Y | 30 | 90 | 168 | 172 |
| Q109R, E229S, S635T, G753E, S754E, A769T, L775A, K875T, N892Y | 30 | 90 | 168 | 175 |

TABLE 8-continued

Half-life of purified variants: Temperature (T) 30° C., detergent concentration 90%

| Mutations | T (° C.) | Detergent (%) | Incubation time (h) | Half-life (h) |
|---|---|---|---|---|
| E229S, S578K, T631N, G753E, D801G | 30 | 90 | 168 | 176 |
| E229S, K360R, S578K, P752R, S754E, A769T, L775A, K875T, N892Y | 30 | 90 | 168 | 178 |
| E229S, S578K, T923H | 30 | 90 | 88 | 178 |
| Q109R, E229S, G753E, S754E, A769T, L775A, K875T, N892Y, K1016T | 30 | 90 | 168 | 180 |
| G753E, L775A, D801G, K875T, N892Y, V998K | 30 | 90 | 168 | 180 |
| E229S, S578K, T631N, G753E, K1016T | 30 | 90 | 168 | 180 |
| Q109R, E229S, S578K, G753E, S754E, A769T, L775A, K875T, N892Y | 30 | 90 | 168 | 182 |
| E229S, S578K, L775A, K792Y | 30 | 90 | 88 | 184 |
| E229S, S578K, P752K, S754E | 30 | 90 | 88 | 184 |
| E229S, S578K, A911V, A912T, T923H | 30 | 90 | 88 | 186 |
| E229S, S578K, T631N, G753E, A769T, L775A | 30 | 90 | 168 | 187 |
| E229S, S578K, T631N, G753E, A769D, K792Y | 30 | 90 | 168 | 188 |
| E229S, S578K, P752K | 30 | 90 | 88 | 188 |
| P752K, G753E, S754E, L775A, D801G, K875T, N892Y | 30 | 90 | 168 | 190 |
| Q109R, E229S, G753E, S754E, A769T, L775A, K875T, N892Y, A932P | 30 | 90 | 168 | 191 |
| E229S, A492L, S578K, G753E, L775A | 30 | 90 | 168 | 195 |
| P752K, G753E, S754E, L775A, D801G, K875T, N892Y | 30 | 90 | 167 | 195 |
| E229S, S578K, T631N, G753E, D901A | 30 | 90 | 168 | 197 |
| E229S, K360R, S578K, P752R, A769D, L775A, K875T, N892Y | 30 | 90 | 167 | 209 |
| E229S, S578K, A911V | 30 | 90 | 88 | 210 |
| Q109R, E229S, A769T, L775A, D801G, K875T, N892Y | 30 | 90 | 168 | 221 |
| E229S, A492L, S578K, G753E, N1008D | 30 | 90 | 168 | 226 |
| E229S, A492L, S578K, G753E, L775A, P779V | 30 | 90 | 168 | 227 |
| E229S, A492L, S578K, G753E, A769D | 30 | 90 | 168 | 230 |
| E229S, S578K, T631N, G753E, A769D, A774V, L775A, P779V, K792Y | 30 | 90 | 168 | 234 |
| A769D, L775A, D801G, K875T, N892Y, V998K | 30 | 90 | 168 | 238 |
| E229S, K360R, S578K, S754E, A769D, L775A, K875T, N892Y | 30 | 90 | 168 | 238 |
| E229S, S578K, A769D, L775A, K875T, N892Y | 30 | 90 | 168 | 239 |
| S635T, A769D, L775A, D801G, K875T, N892Y | 30 | 90 | 168 | 243 |
| E229S, S578K, S754E | 30 | 90 | 88 | 243 |
| Q109R, E229S, G753E, S754E, A769E, L775A, K875T, N892Y | 30 | 90 | 168 | 249 |
| E229S, A492L, S578K, G753E, L775A, K792Y | 30 | 90 | 168 | 259 |
| A769D, L775A, D801G, A843P, K875T, N892Y | 30 | 90 | 168 | 270 |
| G753E, S754E, L775A, D801G, K875T, N892Y | 30 | 90 | 168 | 276 |
| G753E, S754E, A769D, L775A, D801G, K875T, N892Y | 30 | 90 | 168 | 277 |
| E229S, K360R, S578K, P752K, A769D, L775A, K875T, N892Y | 30 | 90 | 168 | 280 |
| E229S, S578K, T631N, G753E, A912T | 30 | 90 | 168 | 281 |
| Q109R, E229S, N672D, G753E, S754E, A769T, L775A, K875T, N892Y | 30 | 90 | 168 | 297 |
| A190Q, A769D, L775A, D801G, K875T, N892Y | 30 | 90 | 168 | 297 |
| P752R, G753E, A769D, L775A, D801G, K875T, N892Y | 30 | 90 | 168 | 300 |
| P752R, G753E, S754E, L775A, D801G, K875T, N892Y | 30 | 90 | 168 | 341 |
| A769D, L775A, D801G, K875T, N892Y, N1008D | 30 | 90 | 168 | 343 |
| G753E, A769D, L775A, D801G, K875T, N892Y | 30 | 90 | 168 | 344 |
| E229S, K360R, S578K, P752R, G753E, A769D, L775A, K875T, N892Y | 30 | 90 | 168 | 375 |
| N672D, A769D, L775A, D801G, K875T, N892Y | 30 | 90 | 168 | 380 |
| N672D, G753E, L775A, D801G, K875T, N892Y | 30 | 90 | 168 | >385 |
| Q109R, G753E, S754E, A769T, L775A, D801G, K875T, N892Y | 30 | 90 | 168 | >385 |
| E229S, G753E, L775A, D801G, K875T, N892Y | 30 | 90 | 168 | >385 |
| E229N, G753E, L775A, D801G, K875T, N892Y | 30 | 90 | 168 | >385 |
| P752K, G753E, S754E, A769D, L775A, D801G, K875T, N892Y | 30 | 90 | 168 | >385 |
| E229N, A769D, L775A, D801G, K875T, N892Y | 30 | 90 | 168 | >385 |
| E229S, K360R, S578K, P752K, G753E, A769D, L775A, K875T, N892Y | 30 | 90 | 168 | >385 |
| E229S, A769D, L775A, D801G, K875T, N892Y | 30 | 90 | 168 | >385 |
| E229S, K360R, S578K, G753E, S754E, A769D, L775A, K875T, N892Y | 30 | 90 | 168 | >385 |
| Q109R, N672D, G753E, S754E, A769T, L775A, K875T, N892Y | 30 | 90 | 168 | >385 |
| T631N, A769D, L775A, D801G, K875T, N892Y | 30 | 90 | 168 | >385 |
| Q109R, E229S, G753E, S754E, A769T, L775A, D801G, K875T, N892Y | 30 | 90 | 168 | >385 |

TABLE 9

Half-life of purified variants: Temperature (T) 30° C., detergent concentration 95%

| Mutations | T (° C.) | Detergent (%) | Incubation time (h) | Half-life (h) |
|---|---|---|---|---|
| No mutations (Wild-type) | 30 | 95 | 1 | <0.2 |
| E229N, N672D, P752K, G753E, A769D, L775A, D801G, K875T, N892Y | 30 | 95 | 672 | 281 |
| Q109R, E229S, N672D, P752R, G753E, S754E, A769T, L775A, D801G, K875T, N892Y | 30 | 95 | 672 | 310 |
| Q109R, E229S, N672D, P752R, G753E, S754E, A769T, L775A, D801G, K875T, N892Y, D901A | 30 | 95 | 672 | 316 |
| Q109R, A159P, E229S, N672D, P752R, G753E, S754E, A769T, L775A, D801G, K875T, N892Y | 30 | 95 | 672 | 355 |
| E229N, N672D, P752R, G753E, A769D, L775A, D801G, K875T, N892Y | 30 | 95 | 672 | 355 |
| E229N, N672D, G753E, S754E, A769D, L775A, D801G, K875T, N892Y, N1008D | 30 | 95 | 672 | 356 |
| Q109R, E229S, G753E, S754E, A769D, L775A, D801G, K875T, N892Y, N1008D | 30 | 95 | 672 | 357 |
| Q109R, E229S, G753E, S754E, A769D, L775A, D801G, K875T, N892Y | 30 | 95 | 672 | 358 |
| Q109R, E229S, N672D, G753E, S754E, A769T, L775A, D801G, K875T, N892Y, T923H | 30 | 95 | 672 | 359 |
| Q109R, A159P, E229S, G753E, S754E, A769D, L775A, D801G, A843P, K875T, N892Y | 30 | 95 | 672 | 366 |
| Q109R, A159P, E229S, S635E, T649K, G753E, S754E, A769D, L775A, D801G, K875T, N892Y | 30 | 95 | 672 | 373 |
| Q109R, A190Q, E229S, N672D, G753E, S754E, A769T, L775A, D801G, K875T, N892Y | 30 | 95 | 672 | 383 |

TABLE 9-continued

Half-life of purified variants: Temperature (T) 30° C., detergent concentration 95%

| Mutations | T (° C.) | Detergent (%) | Incubation time (h) | Half-life (h) |
|---|---|---|---|---|
| Q109R, E229S, T631N, N672D, P752R, G753E, S754E, A769T, L775A, D801G, K875T, N892Y | 30 | 95 | 672 | 383 |
| E229N, N672D, G753E, S754E, A769D, L775A, D801G, K875T, N892Y | 30 | 95 | 672 | 384 |
| Q109R, E229S, N672D, I703L, G753E, S754E, A769T, L775A, D801G, K875T, N892Y | 30 | 95 | 672 | 399 |
| E229N, P752K, G753E, A769D, L775A, D801G, A843P, K875T, N892Y | 30 | 95 | 672 | 404 |
| Q109R, E229S, N672D, G753E, S754E, A769E, L775A, D801G, K875T, N892Y | 30 | 95 | 672 | 405 |
| Q109R, A159P, E229S, N672D, G753E, S754E, A769T, L775A, D801G, A843P, K875T, N892Y | 30 | 95 | 672 | 421 |
| Q109R, A159P, E229S, G753E, S754E, A769D, L775A, D801G, K875T, N892Y | 30 | 95 | 672 | 428 |
| Q109R, A159P, E229S, I703L, G753E, S754E, A769D, L775A, D801G, K875T, N892Y | 30 | 95 | 672 | 433 |
| Q109R, A159P, E229S, K567R, N672D, G753E, S754E, A769T, L775A, D801G, K875T, N892Y | 30 | 95 | 672 | 452 |
| Q109R, A159P, E229S, N672D, G753E, S754E, A769T, L775A, D801G, K875T, N892Y | 30 | 95 | 672 | 454 |
| Q109R, E229S, T631N, N672D, P752R, G753E, S754E, A769D, L775A, D801G, A843P, K875T, N892Y | 30 | 95 | 672 | 477 |
| Q109R, A159P, E229S, T631N, G753E, S754E, A769D, L775A, D801G, K875T, N892Y | 30 | 95 | 672 | 481 |
| Q109R, E229S, N672D, G753E, S754E, A769T, L775A, D801G, A843P, K875T, N892Y | 30 | 95 | 672 | 485 |
| Q109R, E229S, N672D, I703L, P752R, G753E, S754E, A769T, L775A, D801G, K875T, N892Y | 30 | 95 | 672 | 499 |
| Q109R, E229S, T631N, S635E, T649K, N672D, P752R, G753E, S754E, A769D, L775A, D801G, K875T, N892Y | 30 | 95 | 672 | 513 |
| Q109R, A159P, E229S, A624E, A626G, S635E, T649K, N672D, G753E, S754E, S757D, A769T, L775A, D801G, K875T, N892Y | 30 | 95 | 672 | 519 |
| Q109R, A159P, E229S, S635E, T649K, N672D, I703L, G753E, S754E, S757D, A769T, L775A, D801G, K875T, N892Y | 30 | 95 | 672 | 529 |
| Q109R, E229S, T631N, N672D, P752R, G753E, S754E, S757D, A769T, L775A, D801G, K875T, N892Y | 30 | 95 | 672 | 562 |
| Q109R, E229S, T631N, N672D, P752R, G753E, S754E, S757D, A769D, L775A, D801G, K875T, N892Y | 30 | 95 | 672 | 565 |
| E229S, I234V, S635E, T649K, I656V, N672D, G753E, A769D, L775A, D801G, K875T, N892Y | 30 | 95 | 672 | 611 |
| Q109R, E229S, T631N, N672D, P752R, G753E, S754E, S757D, A769D, L775A, D801G, K875T, N892Y, K1016T | 30 | 95 | 672 | 637 |
| E229S, S635E, T649K, I656V, N672D, S754E, A769D, L775A, D801G, K875T, N892Y | 30 | 95 | 672 | 662 |
| E229S, A624E, S635E, T649K, I656V, N672D, I703L, G753E, S754E, A769D, L775A, D801G, K875T, N892Y, N1008D | 30 | 95 | 672 | 663 |
| E229S, N440K, S582K, N672D, G753E, S754E, A769D, L775A, D801G, K875T, N892Y, N1008D | 30 | 95 | 672 | 691 |
| T18D, Q109R, E229S, T631N, N672D, P752R, G753E, S754E, S757D, A769D, L775A, D801G, K875T, N892Y | 30 | 95 | 840 | 694 |
| E229S, N440K, S582K, T631N, N672D, G753E, S754E, A769D, L775A, D801G, K875T, N892Y, N1008D | 30 | 95 | 840 | 713 |
| L46D, E229S, K360G, D458S, S582K, N672D, G753E, S754E, A769D, L775A, D801G, K875T, N892Y, N1008D | 30 | 95 | 840 | 714 |
| Q109R, E229S, K567R, T631N, N672D, P752R, G753E, S754E, S757D, A769D, L775A, D801G, K875T, N892Y | 30 | 95 | 840 | 732 |
| S100D, E229S, S635E, T649K, I656V, N672D, I703L, G753E, A769D, L775A, D801G, A843P, K875T, N892Y, N1008D | 30 | 95 | 672 | 754 |
| E229S, D458S, K567R, T631N, N672D, G753E, S754E, A769D, L775A, D801G, K875T, N892Y | 30 | 95 | 672 | 780 |
| E229S, D458S, S582K, N672D, G753E, S754E, A769D, L775A, D801G, K875T, N892Y | 30 | 95 | 672 | 783 |
| E229S, S635E, T649K, I656V, N672D, G753E, S754E, A769D, L775A, D801G, K875T, N892Y | 30 | 95 | 672 | 796 |
| E229S, N672D, G753E, S754E, A769D, L775A, D801G, K875T, N892Y | 30 | 95 | 672 | 827 |
| Q109R, E229S, K360G, T631N, N672D, P752R, G753E, S754E, S757D, A769D, L775A, D801G, K875T, N892Y | 30 | 95 | 840 | 831 |
| E229N, T631N, N672D, G753E, S754E, A769D, L775A, D801G, K875T, N892Y, N1008D | 30 | 95 | 672 | 834 |
| E229S, S635E, T649K, I656V, N672D, P752R, G753E, S754E, A769D, L775A, D801G, K875T, N892Y | 30 | 95 | 672 | 836 |
| E229S, I234V, N672D, G753E, S754E, A769D, L775A, D801G, K875T, N892Y | 30 | 95 | 840 | 844 |
| E229S, S635E, T649K, I656V, N672D, G753E, A769D, L775A, D801G, K875T, N892Y | 30 | 95 | 672 | 857 |
| E229S, I234V, A492L, S582K, N672D, M728V, G753E, S754E, A769D, L775A, D801G, K875T, N892Y | 30 | 95 | 840 | 857 |
| E229S, S635E, T649K, I656V, N672D, G753E, S754E, A769D, L775A, D801G, K875T, N892Y | 30 | 95 | 840 | 868 |
| E229S, S635E, T649K, I656V, N672D, G753E, A769D, L775A, D801G, K875T, N892Y | 30 | 95 | 672 | 943 |
| A159P, E229S, N440K, N672D, G753E, S754E, A769D, L775A, D801G, K875T, N892Y | 30 | 95 | 672 | 946 |
| E229S, D458S, N672D, G753E, S754E, A769D, L775A, D801G, K875T, N892Y | 30 | 95 | 840 | 950 |
| E229S, D458S, T631N, N672D, G753E, S754E, S757D, A769D, L775A, D801G, K875T, N892Y | 30 | 95 | 672 | 956 |
| S100D, E229S, S635E, T649K, I656V, N672D, P752K, G753E, S754E, A769D, L775A, D801G, K875T, N892Y | 30 | 95 | 672 | 956 |
| E229S, D458S, T631N, N672D, G753E, S754E, A769D, L775A, D801G, K875T, N892Y | 30 | 95 | 840 | 961 |
| E229S, S582K, N672D, G753E, S754E, A769D, L775A, D801G, K875T, N892Y | 30 | 95 | 672 | 966 |
| E229S, S635E, T649K, I656V, N672D, P752K, G753E, S754E, A769D, L775A, D801G, K875T, N892Y | 30 | 95 | 672 | 978 |
| E229S, D458S, S582K, T631E, N672D, G753E, S754E, A769D, L775A, D801G, K875T, N892Y | 30 | 95 | 840 | 993 |
| A190Q, E229S, S635E, T649K, I656V, N672D, I703L, G753E, S754E, S757D, A769D, L775A, D801G, K875T, N892Y, N1008D | 30 | 95 | 672 | 1004 |

TABLE 9-continued

Half-life of purified variants: Temperature (T) 30° C., detergent concentration 95%

| Mutations | T (° C.) | Detergent (%) | Incubation time (h) | Half-life (h) |
|---|---|---|---|---|
| A190Q, E229S, S635E, T649K, I656V, N672D, I703L, G753E, S754E, A769D, L775A, V800P, D801G, K875T, N892Y, N1008D | 30 | 95 | 672 | 1015 |
| A190Q, E229S, I234V, S582K, N672D, G753E, S754E, A769D, L775A, D801G, K875T, N892Y | 30 | 95 | 672 | 1019 |
| T18D, E229S, S582K, N672D, G753E, S754E, A769D, L775A, D801G, K875T, N892Y | 30 | 95 | 840 | 1023 |
| E229S, D458S, T631E, N672D, G753E, S754E, S757D, A769D, L775A, D801G, K875T, N892Y | 30 | 95 | 840 | 1030 |
| Q89Y, E229S, N672D, G753E, S754E, A769D, L775A, D801G, K875T, N892Y | 30 | 95 | 840 | 1038 |
| S100D, E229S, D458S, K567R, S635E, N672D, G753E, S754E, A769D, L775A, D801G, K875T, N892Y | 30 | 95 | 672 | 1041 |
| E229S, S635E, T649K, I656V, N672D, I703L, G753E, S754E, A769D, L775A, D801G, K875T, N892Y, N1008D | 30 | 95 | 840 | 1045 |
| E229S, V352I, S635E, T649K, I656V, N672D, G753E, S754E, A769D, L775A, V800P, D801G, K875T, N892Y | 30 | 95 | 840 | 1065 |
| E229S, N672D, P752R, G753E, S754E, A769D, L775A, D801G, K875T, N892Y | 30 | 95 | 672 | 1066 |
| E229S, K360G, D458S, S582K, N672D, G753E, S754E, A769D, L775A, D801G, K875T, N892Y, N1008D | 30 | 95 | 840 | 1067 |
| E229S, I234V, A492L, N672D, G753E, S754E, A769D, L775A, D777D, D801G, K875T, N892Y | 30 | 95 | 840 | 1070 |
| E229S, S635E, T649K, N672D, G753E, S754E, A769D, L775A, D801G, K875T, N892Y, N1008D | 30 | 95 | 840 | 1081 |
| E229S, N440K, S582K, A624E, N672D, P752R, G753E, S754E, A769D, L775A, D801G, K875T, N892Y, N1008D | 30 | 95 | 624 | 1087 |
| E229S, I234V, S582K, N672D, G753E, S754E, A769D, L775A, V800P, D801G, K875T, N892Y | 30 | 95 | 792 | 1094 |
| T18D, E229S, S582K, N672D, G753E, S754E, A769D, L775A, D801G, K875T, N892Y, T902F | 30 | 95 | 672 | 1101 |
| Q89Y, E229S, N440K, S582K, A624E, N672D, G753E, S754E, A769D, L775A, D801G, K875T, N892Y | 30 | 95 | 672 | 1117 |
| E229S, D458S, T631E, N672D, G753E, S754E, A769D, L775A, D777K, D801G, K875T, N892Y | 30 | 95 | 840 | 1121 |
| E229S, S635E, T649K, I656V, N672D, P752K, G753E, A769D, L775A, D801G, A843P, K875T, N892Y | 30 | 95 | 672 | 1141 |
| E229S, S635E, T649K, I656V, N672D, G753E, S754E, S757D, A769D, L775A, D801G, K875T, N892Y | 30 | 95 | 672 | 1145 |
| E229S, N440K, S582K, N672D, G753E, S754E, A769D, L775A, D801G, A843P, K875T, N892Y, N1008D | 30 | 95 | 672 | 1146 |
| S100D, E229S, S635E, T649K, I656V, N672D, G753E, S754E, A769D, L775A, D801G, K875T, N892Y | 30 | 95 | 672 | 1153 |
| L46D, E229S, K360R, S578K, N672D, G753E, S754E, A769D, L775A, D801G, K875T, N892Y | 30 | 95 | 840 | 1172 |
| E229S, T631N, N672D, I703L, P752K, G753E, A769D, L775A, D801G, A843P, K875T, N892Y | 30 | 95 | 840 | 1183 |
| E229S, A624E, S635E, T649K, I656V, N672D, G738L, G753E, S754E, S757D, A769D, L775A, D777D, D801G, K875T, N892Y | 30 | 95 | 792 | 1192 |
| E229S, N440K, S582K, A624E, N672D, G753E, S754E, A769D, L775A, V800P, D801G, K875T, N892Y | 30 | 95 | 624 | 1214 |
| E229S, D458S, K567R, S635E, N672D, G753E, S754E, A769D, L775A, D801G, K875T, N892Y | 30 | 95 | 624 | 1226 |
| A190Q, E229S, S635E, T649K, I656V, N672D, I703L, P752K, G753E, S754E, A769D, L775A, D801G, K875T, N892Y, N1008D | 30 | 95 | 672 | 1238 |
| E229S, T631N, N672D, I703L, P752K, G753E, S754E, A769D, L775A, D801G, K875T, N892Y | 30 | 95 | 840 | 1259 |
| A190Q, E229S, T631N, N672D, I703L, P752K, G753E, A769D, L775A, D801G, K875T, N892Y | 30 | 95 | 840 | 1269 |
| A190Q, E229S, S635E, T649K, I656V, N672D, P752K, G753E, A769D, L775A, D801G, A843P, K875T, N892Y | 30 | 95 | 672 | 1282 |
| A159P, A190Q, E229S, I234V, S582K, N672D, G753E, S754E, A769D, L775A, D801G, K875T, N892Y | 30 | 95 | 672 | 1289 |
| E229S, A492L, S635E, T649K, I656V, N672D, P752K, G753E, S754E, A769D, L775A, D801G, K875T, N892Y, N1008D | 30 | 95 | 672 | 1298 |
| A190Q, E229S, S582K, N672D, G753E, S754E, A769D, L775A, D801G, K875T, N892Y | 30 | 95 | 792 | 1299 |
| T18D, E229S, S582K, N672D, G753E, S754E, P764K, A769D, L775A, D801G, K875T, N892Y | 30 | 95 | 624 | 1299 |
| E229S, N440K, S582K, N672D, P752R, G753E, S754E, S757D, A769D, L775A, D801G, K875T, N892Y, N1008D | 30 | 95 | 624 | 1328 |
| E229S, A492L, S635E, T649K, I656V, N672D, G753E, A769D, L775A, D801G, K875T, N892Y | 30 | 95 | 840 | 1329 |
| E229S, S582K, S635E, N672D, P752R, G753E, S754E, A769D, L775A, D801G, K875T, N892Y, N1008D | 30 | 95 | 792 | 1352 |
| A190Q, E229S, N440K, S582K, A624E, S635E, N672D, G753E, S754E, A769D, L775A, D801G, K875T, N892Y | 30 | 95 | 672 | 1358 |
| A190Q, E229S, D458S, T631N, N672D, G753E, S754E, A769D, L775A, D801G, K875T, N892Y | 30 | 95 | 624 | 1398 |
| E229S, I234V, A492L, S582K, N672D, G753E, S754E, A769D, L775A, D801G, K875T, N892Y | 30 | 95 | 840 | 1426 |
| E229S, N440K, S582K, S635E, N672D, G753E, S754E, A769D, L775A, D801G, A843P, K875T, N892Y, N1008D | 30 | 95 | 840 | 1456 |
| S100D, A190Q, E229S, I234V, S582K, N672D, G753E, S754E, A769D, L775A, D801G, K875T, N892Y | 30 | 95 | 672 | 1460 |
| A190Q, E229S, K360G, D458S, S582K, T664K, N672D, G753E, S754E, A769D, L775A, D801G, K875T, N892Y, N1008D | 30 | 95 | 792 | 1481 |
| S100D, E229S, N440K, S582K, N672D, P752R, G753E, S754E, A769D, L775A, D801G, K875T, N892Y, N1008D | 30 | 95 | 840 | 1489 |
| E229S, S635E, T649K, I656V, N672D, P752K, G753E, S757D, A769D, L775A, D801G, A843P, K875T, N892Y | 30 | 95 | 672 | 1519 |
| S100D, E229S, K360G, D458S, S582K, N672D, G753E, S754E, S757D, A769D, L775A, D801G, A843P, K875T, N892Y, T915A, N1008D | 30 | 95 | 792 | 1530 |
| E229S, N440K, S582K, A624E, S635E, N672D, G738L, G753E, S754E, S757D, A769D, L775A, D801G, K875T, N892Y | 30 | 95 | 792 | 1535 |

TABLE 9-continued

Half-life of purified variants: Temperature (T) 30° C., detergent concentration 95%

| Mutations | T (° C.) | Detergent (%) | Incubation time (h) | Half-life (h) |
|---|---|---|---|---|
| S100D, E229S, K360G, D458S, S582K, N672D, G753E, S754E, A769D, L775A, D801G, K875T, N892Y, N1008D | 30 | 95 | 840 | 1538 |
| A190Q, E229S, D458S, T631N, N672D, G753E, S754E, A769D, L775A, D801G, A843P, K875T, N892Y | 30 | 95 | 672 | 1551 |
| A190Q, E229S, K360G, D458S, S582K, N672D, G753E, S754E, A769D, L775A, D801G, K875T, N892Y, N1008D | 30 | 95 | 840 | 1556 |
| E229S, S582K, S635E, T649K, I656V, N672D, M728V, G753E, S754R, S757D, A769D, L775A, D801G, K875T, N892Y | 30 | 95 | 672 | 1594 |
| A190Q, E229S, N440K, S582K, A624E, S635E, N672D, G753E, S754E, S757D, A769D, L775A, D801G, K875T, N892Y | 30 | 95 | 792 | 1601 |
| S100D, A190Q, E229S, S635E, T649K, I656V, N672D, I703L, G753E, S754E, A769D, L775A, D801G, K875T, N892Y, N1008D | 30 | 95 | 624 | 1606 |
| S100D, E229S, D458S, K567R, S582K, S635E, N672D, G753E, S754E, A769D, L775A, D801G, K875T, N892Y | 30 | 95 | 792 | 1612 |
| E229S, S582K, S635E, T649K, I656V, N672D, P752K, G753E, S757D, A769D, L775A, D801G, A843P, K875T, N892Y | 30 | 95 | 624 | 1619 |
| E229S, S635E, T649K, I656V, N672D, G753E, S754R, S757D, A769D, L775A, D801G, A843P, K875T, N892Y | 30 | 95 | 672 | 1664 |
| T18D, E229S, D458S, T631N, N672D, M728V, G753E, S754E, S757D, A769D, L775A, D801G, K875T, N892Y | 30 | 95 | 792 | 1700 |
| E229S, D458S, S582K, T631N, S635E, N672D, M728V, G753E, S754E, S757D, A769D, L775A, D801G, K875T, N892Y | 30 | 95 | 792 | 1704 |
| A190Q, E229S, K360G, D458S, S582K, N672D, G753E, S754E, S757D, A769D, L775A, D801G, K875T, N892Y, N1008D | 30 | 95 | 792 | 1714 |
| S100D, E229S, K360G, D458S, S582K, N672D, G753E, S754E, S757D, A769D, L775A, D801G, A843P, K875T, N892Y, N1008D | 30 | 95 | 792 | 1741 |
| E229S, S635E, N672D, P752R, G753E, S754E, A769D, L775A, D777K, D801G, K875T, N892Y | 30 | 95 | 792 | 1745 |
| A159P, E229S, D458S, T631N, N672D, M728V, G753E, S754E, S757D, A769D, L775A, D801G, K875T, N892Y | 30 | 95 | 792 | 1783 |
| E229S, A492L, S635E, T649K, I656V, N672D, G753E, S757D, A769D, L775A, D801G, K875T, N892Y | 30 | 95 | 792 | 1826 |
| S100D, A190Q, E229S, K360G, D458S, S582K, N672D, G753E, S754E, A769D, L775A, D801G, K875T, N892Y, N1008D | 30 | 95 | 792 | 1844 |
| S100D, E229S, N440K, S582K, T631N, N672D, G753E, S754E, A769D, L775A, D801G, K875T, N892Y, N1008D | 30 | 95 | 624 | 1907 |
| E229S, I234V, A492L, N672D, G753E, S754E, A769D, L775A, D777K, D801G, K875T, N892Y | 30 | 95 | 624 | 1924 |
| A190Q, E229S, I234V, S582K, N672D, G753E, S754E, S757D, A769D, L775A, D801G, K875T, N892Y | 30 | 95 | 672 | 1993 |
| E229S, D458S, A492L, T631N, N672D, G753E, S754E, S757D, A769D, L775A, D801G, K875T, N892Y | 30 | 95 | 624 | 2378 |
| E229S, A624E, S635E, T649K, I656V, N672D, G753E, S754E, S757D, A769D, L775A, D777K, D801G, K875T, N892Y | 30 | 95 | 624 | 2380 |
| S100D, E229S, K360G, D458S, S582K, N672D, G753E, S754E, S757D, A769D, L775A, D801G, A843P, K875T, N892Y, N1008D | 30 | 95 | 792 | 3039 |
| E229S, D458S, K567R, S582K, S653E, T649K, N672D, G753E, S754E, A769D, L775A, D777D, D801G, K875T, N892Y | 30 | 95 | 840 | 674 |
| S100D, E229S, K360G, D458S, S582K, T664K, N672D, G753E, S754R, S757D, A769D, L775A, D801G, A843P, K875T, N892Y, N1008D, K1016T | 30 | 95 | 840 | 1023 |
| S100D, E229S, K360G, D458S, S582K, T664K, N672D, G753E, S754E, S757D, A769D, L775A, D801G, A843P, K875T, N892Y, N1008D, K1016T | 30 | 95 | 840 | 963 |
| S100D, E229S, K360G, D458S, S582K, N672D, G753E, S754E, S757D, A769D, L775A, D801G, A843P, K875T, N892Y, A911V, N1008D | 30 | 95 | 840 | 982 |
| S100D, E229S, K360G, D458S, S582K, N672D, G753E, S754E, S757D, A769D, L775A, D801G, A843P, K875T, N892Y, A911V, N1008D, K1016T | 30 | 95 | 840 | 906 |
| S100D, E229S, K360G, D458S, S582K, S635E, N672D, G753E, S754E, S757D, A769D, L775A, D801G, A843P, K875T, N892Y, N1008D | 30 | 95 | 840 | 918 |
| S100D, E229S, K360G, D458S, S582K, T664K, N672D, G753E, S754E, S757D, A769D, L775A, D801G, A843P, K875T, N892Y, A911V, N1008D, K1016T | 30 | 95 | 840 | 962 |
| S100D, E229S, K360G, D458S, S582K, N672D, G753E, S754E, S757D, A769D, L775A, D801G, A843P, K875T, N892Y, N1008D, K1016T | 30 | 95 | 840 | 888 |
| S100D, E229S, K360G, D458S, S582K, T664K, N672D, G753E, S754E, S757D, A769D, L775A, D801G, A843P, K875T, N892Y, A911V, N1008D, K1016T | 30 | 95 | 840 | 1091 |
| S100D, E229S, K360G, D458S, S582K, N672D, G753E, S754E, S757D, A769D, L775A, D801G, A843P, K875T, N892Y, N1008D, K1016T | 30 | 95 | 840 | 796 |
| S100D, E229S, K360G, D458S, S582K, S635E, T649K, N672D, G753E, S754E, S757D, A769D, L775A, D801G, A843P, K875T, N892Y, N1008D | 30 | 95 | 840 | 984 |
| S100D, E229S, K360G, D458S, S582K, N672D, G753E, S754E, S757D, A769D, L775A, D801G, A843P, K875T, N892Y, N1008D | 30 | 95 | 840 | 867 |
| S100D, E229S, K360G, D458S, S582K, N672D, G753E, S754E, S757D, A769D, L775A, D801G, A843P, K875T, N892Y | 30 | 95 | 840 | 876 |
| E229S, N440K, S582K, A624E, S635E, N672D, G738L, G753E, S754E, S757D, A769D, L775A, D801G, K875T, N892Y | 30 | 95 | 840 | 689 |
| E229S, N399K, D458S, A492H, K567R, S582K, S635E, T649K, N672D, G753E, S754E, A769D, L775A, D777R, D801G, K875T, N892Y | 30 | 95 | 840 | 2256 |
| A190Q, E229S, I234V, T505I, S582K, N672D, G753E, S754E, S757D, A769D, L775A, D801G, K875T, N892Y | 30 | 95 | 840 | 698 |
| E229S, D458S, A492H, K567R, S582K, S635E, T649K, N672D, G753E, S754E, A769D, L775A, D777R, D801G, K875T, N892Y | 30 | 95 | 840 | 492 |
| E229S, N399K, D458S, K567R, S582K, S635E, N672D, G753E, S754E, A769D, L775A, D777R, D801G, K875T, N892Y | 30 | 95 | 840 | 3540 |
| E229S, D458S, A492H, K567R, S582K, S635E, N672D, G753E, S754E, A769D, L775A, D777R, D801G, K875T, N892Y | 30 | 95 | 840 | 2837 |

TABLE 9-continued

Half-life of purified variants: Temperature (T) 30° C., detergent concentration 95%

| Mutations | T (° C.) | Detergent (%) | Incubation time (h) | Half-life (h) |
|---|---|---|---|---|
| E229S, N399K, D458S, A492H, K567R, S582K, S635E, N672D, G753E, S754E, A769D, L775A, D777R, D801G, K875T, N892Y | 30 | 95 | 840 | 536 |
| E229S, N399K, D458S, K567R, S582K, S635E, T649K, N672D, G753E, S754E, A769D, L775A, D777R, D801G, K875T, N892Y | 30 | 95 | 840 | 2830 |
| A190Q, E229S, I234V, S582K, N672D, G753E, S754E, S757D, A769D, L775A, D801G, K875T, N892Y | 30 | 95 | 840 | 874 |
| E229S, N440K, S582K, A624E, S635E, N672D, G738L, G753E, S754E, S757D, A769D, L775A, D801G, K875T, N892Y | 30 | 95 | 840 | 768 |
| S100D, E229S, K360G, D458S, S582K, N672D, G753E, S754E, S757D, A769D, L775A, D801G, A843P, K875T, N892Y, N1008D | 30 | 95 | 840 | 883 |
| E229S, N399K, D458S, A492H, K567R, S582K, S635E, T649K, N672D, G753E, S754E, A769D, L775A, D777R, D801G, K875T, N892Y | 30 | 95 | 840 | 1836 |

TABLE 10

Half-life of purified variants: Temperature (T) 32° C., detergent concentration 90%

| Mutations | T (° C.) | Detergent (%) | Incubation time (h) | Half-life (h) |
|---|---|---|---|---|
| No mutations (Wild-type) | 32 | 90 | 1 | <0.2 |
| Q109R, A769T, L775A, K792Y, K875T | 32 | 90 | 20 | 12 |
| L775A, K875T, N892Y, A911V, D933M | 32 | 90 | 20 | 13 |
| Q109R, L775A, K792Y, K875T | 32 | 90 | 20 | 13 |
| L775A, K875T, N892Y | 32 | 90 | 20 | 14 |
| L775A, S851F, K875T, N892Y, A911V | 32 | 90 | 20 | 14 |
| L775A, K875T, N892Y, A911V, A912T, T923H | 32 | 90 | 20 | 14 |
| L775A, K875T, N892Y, D933M | 32 | 90 | 20 | 15 |
| E229S, S578R, A769D, L775A, K819R | 32 | 90 | 20 | 16 |
| E229S, K291R, S578R, P752R, G753E | 32 | 90 | 20 | 17 |
| E229S, L775A, K875T, N892Y | 32 | 90 | 20 | 17 |
| E229S, K291R, S578R, G753E | 32 | 90 | 20 | 17 |
| Q109R, S578K, D801G, K875T | 32 | 90 | 20 | 17 |
| E229S, S578R, L775A, K819R | 32 | 90 | 20 | 18 |
| E229S, S578R, D801G, K819R | 32 | 90 | 20 | 18 |
| E229S, S578R, K792Y, K819R | 32 | 90 | 20 | 18 |
| Q109R, L775A, K792Y, K875T, N892Y | 32 | 90 | 20 | 19 |
| E229S, S578R, A769D, K792Y, K819R | 32 | 90 | 20 | 19 |
| S578L, L775A, K875T, N892Y | 32 | 90 | 20 | 20 |
| E229S, S578R, P752R, K875T, N892Y | 32 | 90 | 20 | 20 |
| E229S, S578R, S754E, N892Y | 32 | 90 | 20 | 20 |
| E229S, S578R, L775A, N892Y | 32 | 90 | 20 | 21 |
| E229S, S578R, L775A, K792Y, K819R | 32 | 90 | 20 | 21 |
| E229S, S578R, G753E, N892Y | 32 | 90 | 20 | 21 |
| Q109R, L775A, K875T, N892Y | 32 | 90 | 20 | 21 |
| E229S, K291R, S578R, P752R, G753E | 32 | 90 | 20 | 21 |
| E229S, K291R, S578R, P752R | 32 | 90 | 20 | 21 |
| E229S, S578R, K819R | 32 | 90 | 20 | 22 |
| E229S, S578R, P779V, K819R | 32 | 90 | 20 | 22 |
| E229S, S578R, K819R | 32 | 90 | 20 | 23 |
| Q109R, A769T, L775A, K792Y, D801G, K819R, N892Y | 32 | 90 | 20 | 23 |
| Q109R, A769T, L775A, D801G, K819R, N892Y | 32 | 90 | 20 | 25 |
| E229S, S578R, P752K, G753E, N892Y | 32 | 90 | 20 | 25 |
| E229S, S578R, A769Q, K819R | 32 | 90 | 20 | 25 |
| E229S, S578R, P752K, S754E, N892Y | 32 | 90 | 20 | 27 |

TABLE 10-continued

Half-life of purified variants: Temperature (T) 32° C., detergent concentration 90%

| Mutations | T (° C.) | Detergent (%) | Incubation time (h) | Half-life (h) |
|---|---|---|---|---|
| Q109R, L775A, K875T, N892Y | 32 | 90 | 20 | 28 |
| Q109R, A769T, L775A, K792Y, K875T, N892Y | 32 | 90 | 20 | 31 |
| Q109R, A769T, L775A, K875T, N892Y | 32 | 90 | 20 | 33 |
| L775A, D801G, K875T, N892Y | 32 | 90 | 20 | 36 |
| Q109R, L775A, P779V, K792Y, D801G, K819R, K875T, N892Y | 32 | 90 | 20 | 37 |
| Q109R, A769T, L775A, K875T, N892Y | 32 | 90 | 20 | 38 |
| Q109R, E229S, A769T, L775A, K875T, N892Y | 32 | 90 | 20 | 45 |
| Q109R, P752R, G753E, A769T, L775A, K875T, N892Y | 32 | 90 | 20 | 55 |
| Q109R, P752K, G753E, S754E, A769T, L775A, K875T, N892Y | 32 | 90 | 20 | 56 |
| Q109R, S754E, A769T, L775A, K875T, N892Y | 32 | 90 | 20 | 58 |
| Q109R, P752R, G753E, S754E, A769T, L775A, K875T, N892Y | 32 | 90 | 20 | 58 |
| Q109R, P752K, G753E, A769T, L775A, K875T, N892Y | 32 | 90 | 20 | 60 |
| Q109R, G753E, A769T, L775A, K875T, N892Y | 32 | 90 | 20 | 61 |
| Q109R, G753E, S754E, A769T, L775A, K875T, N892Y | 32 | 90 | 20 | 62 |
| Q109R, N672D, G753E, S754E, A769T, L775A, K875T, N892Y | 32 | 90 | 167 | 95 |
| E229S, K360K, S578K, P752R, A769D, L775A, K875T, N892Y, A911V | 32 | 90 | 167 | 98 |
| E229S, K360R, S578R, N672D, P752R, A769D, L775A, K875T, N892Y | 32 | 90 | 167 | 98 |
| N672D, G753E, L775A, D801G, K875T, N892Y, A911V | 32 | 90 | 167 | 108 |
| E229S, K360R, S578K, N672D, P752R, A769D, L775A, K875T, N892Y | 32 | 90 | 167 | 116 |
| N672D, A769D, L775A, D801G, K875T, N892Y | 32 | 90 | 167 | 120 |
| T631N, N672D, A769D, L775A, D801G, K875T, N892Y | 32 | 90 | 167 | 122 |
| N672D, G753E, L775A, D801G, K875T, N892Y, N1008D | 32 | 90 | 167 | 123 |
| A190Q, N672D, A769D, L775A, D801G, K875T, N892Y | 32 | 90 | 167 | 124 |
| Q109R, G753E, S754E, A769T, L775A, D801G, K875T, N892Y | 32 | 90 | 167 | 126 |
| Q89Y, N672D, A769D, L775A, D801G, K875T, N892Y | 32 | 90 | 167 | 129 |
| N672D, G753E, L775A, D801G, A843P, K875T, N892Y | 32 | 90 | 167 | 131 |
| L46D, E229S, K360R, S578K, N672D, P752R, A769D, L775A, K875T, N892Y | 32 | 90 | 167 | 131 |
| E229S, K360R, S578K, N672D, P752R, A769D, L775A, K875T, N892Y | 32 | 90 | 167 | 133 |
| E229S, K360R, S578K, N672D, P752R, A769D, L775A, K875T, N892Y, A912T | 32 | 90 | 167 | 135 |
| E229S, K360R, S578K, P752R, G753E, S754E, A769D, L775A, K875T, N892Y | 32 | 90 | 167 | 136 |
| E229S, S578R, A769D, L775A, K875T, N892Y | 32 | 90 | 167 | 138 |
| E229S, S578K, P752K, S754E, K875T, N892Y | 32 | 90 | 167 | 140 |
| E229S, K567R, S578R, A769D, L775A, K875T, N892Y | 32 | 90 | 167 | 141 |
| E229S, K360R, S578K, P752R, A769D, L775A, D801G, K875T, N892Y | 32 | 90 | 167 | 155 |
| N672D, G753E, L775A, D801G, K875T, N892Y | 32 | 90 | 167 | 160 |
| E229S, S578K, A769D, L775A, P779V, K792Y, K875T, N892Y | 32 | 90 | 167 | 167 |
| E229S, K360R, S578K, T631N, N672D, P752R, A769D, L775A, K875T, N892Y | 32 | 90 | 167 | 168 |
| N672D, A769D, L775A, D801G, A843P, K875T, N892Y | 32 | 90 | 167 | 171 |

TABLE 10-continued

Half-life of purified variants: Temperature (T) 32° C., detergent concentration 90%

| Mutations | T (° C.) | Detergent (%) | Incubation time (h) | Half-life (h) |
|---|---|---|---|---|
| E229S, K360R, S578K, N672D, P752R, A769D, L775A, K875T, N892Y, A932P | 32 | 90 | 167 | 175 |
| E229S, A492L, S578K, T631N, G753E | 32 | 90 | 167 | 176 |
| E229S, S578K, P752K, G753E, A769D, L775A, K875T, N892Y | 32 | 90 | 167 | 182 |
| E229S, K360R, S578K, N672D, P752R, G753E, A769D, L775A, K875T, N892Y | 32 | 90 | 167 | 185 |
| N672D, G753E, S754E, A769D, L775A, D801G, K875T, N892Y | 32 | 90 | 167 | 187 |
| E229S, S578K, P752K, G753E, S754E, A769D, L775A, K875T, N892Y | 32 | 90 | 167 | 196 |
| E229S, K360R, S578K, N672D, P752R, G753E, S754E, A769D, L775A, K875T, N892Y | 32 | 90 | 167 | 205 |
| E229S, K360R, S578K, N672D, P752K, G753E, S754E, A769D, L775A, K875T, N892Y | 32 | 90 | 167 | 216 |
| E229S, S578K, G753E, A769D, L775A, K875T, N892Y | 32 | 90 | 167 | 218 |
| E229S, K360R, S578K, N672D, G753E, S754E, A769D, L775A, D845E, K875T, N892Y | 32 | 90 | 167 | 221 |
| Q109R, E229S, S578K, P752K | 32 | 90 | 167 | 225 |
| E229S, S578K, G753E, S754E, A769D, L775A, K875T, N892Y | 32 | 90 | 167 | 234 |
| E229S, K360R, S578K, N672D, P752K, G753E, A769D, L775A, K875T, N892Y | 32 | 90 | 167 | 234 |
| E229S, S578K, N672D, A769D, L775A, K875T, N892Y | 32 | 90 | 167 | 239 |
| E229S, S578K, P752R, G753E, S754E, A769D, L775A, K875T, N892Y | 32 | 90 | 167 | 278 |
| Q109R, E229S, G753E, S754E, A769T, L775A, D801G, K875T, N892Y | 32 | 90 | 167 | 308 |
| E229S, S578K, A769D, L775A, D801G, K875T, N892Y | 32 | 90 | 167 | 337 |
| E229S, N672D, G753E, L775A, D801G, K875T, N892Y | 32 | 90 | 167 | 367 |
| E229N, N672D, A769D, L775A, D801G, K875T, N892Y | 32 | 90 | 167 | >385 |
| E229S, N672D, A769D, L775A, D801G, K875T, N892Y | 32 | 90 | 167 | >385 |

TABLE 11

Half-life of purified variants: Temperature (T) 35° C., detergent concentration 90%

| Mutations | T (° C.) | Detergent (%) | Incubation time (h) | Half-life (h) |
|---|---|---|---|---|
| No mutations (Wild-type) | 35 | 90 | 1 | <0.2 |
| E229N, P752R, G753E, S754E, L775A, D801G, K875T, N892Y | 35 | 90 | 71 | 27 |
| E229N, G753E, L775A, D801G, K875T, N892Y | 35 | 90 | 71 | 27 |
| Q109R, E229S, K451R, A769T, L775A, D801G, K875T, N892Y | 35 | 90 | 70 | 28 |
| E229S, S578K, G753E, A912T | 35 | 90 | 70 | 28 |
| T631N, P752R, G753E, S754E, A769D, L775A, D801G, E845D, K875T, N892Y | 35 | 90 | 71 | 30 |
| E229S, K360R, S578K, P752K, S754E, A769D, L775A, K875T, N892Y | 35 | 90 | 71 | 30 |
| Q89Y, Q109R, E229S, A769T, L775A, D801G, K875T, N892Y | 35 | 90 | 70 | 30 |
| N672D, A769D, L775A, D801G, K875T, N892Y | 35 | 90 | 70 | 33 |
| E229N, A769D, L775A, D801G, K875T, N892Y | 35 | 90 | 71 | 33 |
| Q109R, N672D, G753E, S754E, A769T, L775A, K875T, N892Y | 35 | 90 | 70 | 33 |
| Q109R, E229S, S578K, P779V | 35 | 90 | 70 | 34 |
| N672D, G753E, L775A, D801G, K875T, N892Y, A911V | 35 | 90 | 70 | 34 |
| E229S, S578K, G753E, A912T | 35 | 90 | 70 | 34 |
| S100D, Q109R, N672D, G753E, S754E, A769T, L775A, K875T, N892Y | 35 | 90 | 70 | 35 |
| E229S, K360R, S578K, S635E, T649K, P752R, A769D, L775A, D801G, K875T, N892Y | 35 | 90 | 71 | 38 |
| Q109R, G753E, S754E, A769E, L775A, D801G, K875T, N892Y | 35 | 90 | 71 | 38 |
| E229S, K360R, S578K, N672D, P752R, S754E, A769D, L775A, K875T, N892Y | 35 | 90 | 71 | 40 |
| Q109R, E229S, S578K, A912T | 35 | 90 | 70 | 40 |
| E229S, K360R, S578K, P752R, A769D, L775A, D801G, K875T, N892Y | 35 | 90 | 71 | 42 |
| Q109R, A159P, E229S, N672D, F746L, G753E, S754E, A769T, L775A, D801G, A843P, K875T, N892Y | 35 | 90 | 168 | 42 |
| E229S, S578K, G753E, P779V, K792Y, D801G, A912T | 35 | 90 | 70 | 42 |
| E229S, K360R, S578K, P752K, S754E, A769D, L775A, D801G, K875T, N892Y | 35 | 90 | 71 | 44 |
| E229S, T631N, A769D, L775A, D801G, K875T, N892Y | 35 | 90 | 166 | 44 |
| E229S, S578K, P752K, G753E, S754E, D801G, A912T | 35 | 90 | 70 | 46 |
| E229N, S754E, A769D, L775A, D801G, K875T, N892Y | 35 | 90 | 71 | 47 |
| E229N, N672D, P752R, G753E, A769D, L775A, D801G, K875T, N892Y, N991D | 35 | 90 | 119 | 48 |
| E229N, P752K, G753E, A769D, L775A, D801G, K875T, N892Y | 35 | 90 | 120 | 48 |
| S100D, E229S, K360R, S578K, T631N, P752R, G753E, S754E, A769D, L775A, D801G, K875T, N892Y | 35 | 90 | 119 | 50 |
| E229S, K360R, S578K, T631N, P752R, G753E, S754E, A769D, L775A, D801G, K875T, N892Y, N991D | 35 | 90 | 119 | 51 |
| E229N, T631N, N672D, A769D, L775A, D801G, K875T, N892Y | 35 | 90 | 70 | 52 |
| A58L, E229S, K360R, S578K, N672D, G753E, S754E, A769D, L775A, K875T, N892Y | 35 | 90 | 70 | 52 |
| E229S, K360R, S578K, N672D, G753E, S754E, A769D, L775A, D845E, K875T, N892Y | 35 | 90 | 70 | 56 |
| Q109R, N672D, G753E, S754E, A769E, L775A, D801G, K875T, N892Y | 35 | 90 | 71 | 56 |
| E229S, K360R, S578K, T631N, N672D, P752R, G753E, S754E, A769D, L775A, D801G, K875T, N892Y | 35 | 90 | 119 | 57 |
| E229S, S578K, N672D, A769D, L775A, K875T, N892Y | 35 | 90 | 120 | 58 |
| L46D, E229S, K360R, S578K, N672D, G753E, S754E, A769D, L775A, A843P, K875T, N892Y | 35 | 90 | 70 | 58 |
| E229N, S635E, T649K, I656V, N672D, A769D, L775A, D801G, K875T, N892Y | 35 | 90 | 166 | 59 |
| L46D, E229S, K360R, S578K, T631N, N672D, G753E, S754E, A769D, L775A, K875T, N892Y | 35 | 90 | 70 | 59 |
| E229S, S578K, P752K, G753E, S754E, A912T | 35 | 90 | 166 | 61 |
| Q109R, E229S, G753E, S754E, A769T, L775A, D801G, K875T, N892Y, A911V | 35 | 90 | 166 | 61 |
| E229S, K360R, S578K, P752K, G753E, S754E, A769D, L775A, D801G, K875T, N892Y | 35 | 90 | 166 | 62 |

TABLE 11-continued

Half-life of purified variants: Temperature (T) 35° C., detergent concentration 90%

| Mutations | T (° C.) | Detergent (%) | Incubation time (h) | Half-life (h) |
|---|---|---|---|---|
| Q109R, E229S, S578K, P752R, G753E | 35 | 90 | 166 | 62 |
| Q109R, E229S, A769T, L775A, D801G, K875T, N892Y | 35 | 90 | 166 | 62 |
| L46D, E229S, S578K, G753E, S754E, A769D, L775A, D801G, K875T, N892Y | 35 | 90 | 167 | 63 |
| Q109R, E229S, T631N, G753E, S754E, A769T, L775A, D801G, K875T, N892Y | 35 | 90 | 166 | 63 |
| Q109R, E229S, D458S, G753E, S754E, A769T, L775A, D801G, K875T, N892Y | 35 | 90 | 166 | 64 |
| Q109R, E229S, G753E, S754E, A769T, L775A, D801G, K875T, N892Y | 35 | 90 | 166 | 64 |
| S100D, E229S, S578K, G753E, A912T | 35 | 90 | 166 | 64 |
| E229S, K360R, S578K, P752R, G753E, S754E, A769D, L775A, D801G, K875T, N892Y | 35 | 90 | 71 | 64 |
| E229N, P752K, G753E, S754E, A769D, L775A, D801G, K875T, N892Y | 35 | 90 | 166 | 64 |
| E229N, S635E, T649K, I656V, N672D, G753E, A769D, L775A, D801G, K875T, N892Y, N991D | 35 | 90 | 168 | 64 |
| Q109R, E229S, S635E, G753E, S754E, A769T, L775A, D801G, K875T, N892Y | 35 | 90 | 166 | 65 |
| E229N, S635E, T649K, I656V, N672D, S757D, A769D, L775A, D801G, A843P, K875T, N892Y | 35 | 90 | 168 | 65 |
| E229N, N672D, P752R, S754E, A769D, L775A, D801G, K875T, N892Y | 35 | 90 | 70 | 66 |
| E229N, K567R, S635E, T649K, I656V, N672D, G753E, A769D, L775A, D801G, K875T, N892Y | 35 | 90 | 168 | 66 |
| E229S, S578K, G753E, D801G, A912T | 35 | 90 | 166 | 66 |
| Q109R, E229S, G753E, S754E, A769T, L775A, D801G, K875T, N892Y, D901A | 35 | 90 | 166 | 66 |
| Q109R, A190Q, E229S, G753E, S754E, A769T, L775A, D801G, K875T, N892Y | 35 | 90 | 166 | 66 |
| Q109R, E229S, A769T, L775A, D801G, A843P, K875T, N892Y | 35 | 90 | 166 | 66 |
| E229N, I234V, S635E, T649K, I656V, N672D, A769D, L775A, D801G, A843P, K875T, N892Y | 35 | 90 | 120 | 66 |
| E229N, S635E, T649K, I656V, N672D, A769D, L775A, D801G, A843P, K875T, N892Y | 35 | 90 | 168 | 66 |
| Q109R, E229S, G753E, S754E, A769T, L775A, D801G, K875T, N892Y, N1008D | 35 | 90 | 166 | 67 |
| T631N, A769D, L775A, D801G, K875T, N892Y | 35 | 90 | 166 | 67 |
| Q109R, E229S, A492L, A769T, L775A, D801G, K875T, N892Y | 35 | 90 | 166 | 67 |
| E229N, P752K, G753E, A769D, L775A, D801G, A843P, K875T, N892Y | 35 | 90 | 168 | 68 |
| E229S, S578N, N672D, A769D, L775A, D801G, K875T, N892Y | 35 | 90 | 168 | 68 |
| 727\, E229S, K360R, S578K, N672D, G753E, S754E, A769D, L775A, D801G, K875T, N892Y | 35 | 90 | 166 | 69 |
| E229S, P752K, G753E, A769D, L775A, D801G, K875T, N892Y | 35 | 90 | 168 | 69 |
| E229N, S635E, T649K, I656V, N672D, S754E, A769D, L775A, D801G, K875T, N892Y | 35 | 90 | 166 | 69 |
| L46D, E229S, I234V, K360R, S578K, N672D, G753E, S754E, A769D, L775A, D801G, K875T, N892Y | 35 | 90 | 168 | 69 |
| E229N, I234V, N672D, G753E, S754E, A769D, L775A, D801G, K875T, N892Y, N1008D | 35 | 90 | 168 | 70 |
| L46D, E229S, K360R, S578K, N672D, G753E, S754E, A769D, L775A, D801G, K875T, N892Y | 35 | 90 | 168 | 70 |
| E229N, N672D, P752K, A769D, L775A, D801G, K875T, N892Y | 35 | 90 | 166 | 70 |
| Q109R, E229S, P752K, G753E, S754E, A769T, L775A, D801G, K875T, N892Y | 35 | 90 | 166 | 70 |
| E229N, N672D, A769D, L775A, D801G, K875T, N892Y | 35 | 90 | 70 | 70 |
| Q109R, E229S, T631N, S635E, T649K, N672D, P752K, G753E, S754E, A769T, L775A, D801G, K875T, N892Y | 35 | 90 | 167 | 71 |
| Q109R, E229S, G753E, S754E, A769D, L775A, P779V, D801G, K875T, N892Y | 35 | 90 | 166 | 71 |
| E229N, D458S, N672D, G753E, S754E, A769D, L775A, D801G, K875T, N892Y | 35 | 90 | 166 | 72 |
| L46D, E229S, K360R, S578K, N672D, G753E, S754E, A769D, L775A, D801G, K875T, N892Y | 35 | 90 | 168 | 72 |
| A58L, E229N, N672D, G753E, S754E, A769D, L775A, D801G, K875T, N892Y | 35 | 90 | 166 | 73 |
| A159P, E229N, N672D, G753E, S754E, A769D, L775A, D801G, K875T, N892Y | 35 | 90 | 166 | 73 |
| E229N, S635E, T649K, I656V, N672D, G753E, S754E, A769D, L775A, D801G, K875T, N892Y | 35 | 90 | 166 | 74 |
| E229N, N672D, G753E, S754E, A769D, L775A, D801G, K875T, N892Y, N1008D | 35 | 90 | 168 | 75 |
| E229S, K360R, S578K, N672D, P752R, A769D, L775A, D801G, K875T, N892Y | 35 | 90 | 71 | 75 |
| Q109R, A159P, E229S, S635E, G753E, S754E, A769D, L775A, D801G, K875T, N892Y | 35 | 90 | 167 | 75 |
| E229S, S578K, N672D, G753E, S754E, A769D, L775A, K875T, N892Y | 35 | 90 | 168 | 75 |
| E229N, S635E, T649K, I656V, N672D, G753E, A769D, L775A, D801G, K875T, N892Y, T923H | 35 | 90 | 168 | 76 |
| E229S, T631N, P752K, G753E, A769D, L775A, D801G, K875T, N892Y | 35 | 90 | 167 | 76 |
| E229N, S635E, T649K, I656V, N672D, P752R, G753E, S754E, A769D, L775A, D801G, K875T, N892Y | 35 | 90 | 166 | 77 |
| E229N, S635E, T649K, I656V, N672D, P752K, G753E, A769D, L775A, D801G, A843P, K875T, N892Y | 35 | 90 | 168 | 77 |
| A190Q, E229S, K360R, S578K, P752R, G753E, S754E, A769D, L775A, D801G, K875T, N892Y | 35 | 90 | 168 | 77 |
| A58L, E229S, I234V, N672D, G753E, S754E, A769D, L775A, D801G, K875T, N892Y | 35 | 90 | 168 | 78 |
| L46D, E229S, K360R, S578K, N672D, G753E, S754E, A769D, L775A, K875T, N892Y, A912T | 35 | 90 | 70 | 78 |
| L46D, E229S, K360R, S578K, N672D, P752K, G753E, S754E, A769D, L775A, K875T, N892Y | 35 | 90 | 70 | 78 |
| E229S, N672D, G753E, L775A, D801G, K875T, N892Y, A911V | 35 | 90 | 166 | 78 |
| A159P, E229N, N672D, G753E, S754E, A769D, L775A, D801G, K875T, N892Y, N1008D | 35 | 90 | 166 | 79 |
| E229N, S635E, N672D, G753E, S754E, A769D, L775A, D801G, K875T, N892Y, N1008D | 35 | 90 | 168 | 80 |
| E229N, S635E, T649K, I656V, N672D, A769D, L775A, D801G, A843P, K875T, N892Y, N991D | 35 | 90 | 120 | 80 |
| E229N, T631N, N672D, G753E, S754E, A769D, L775A, D801G, K875T, N892Y | 35 | 90 | 166 | 80 |
| E229N, N672D, P752K, G753E, S754E, A769D, L775A, D801G, K875T, N892Y, N1008D | 35 | 90 | 168 | 80 |
| E229N, N672D, G753E, S754E, A769D, L775A, D801G, K875T, N892Y, V998K | 35 | 90 | 166 | 80 |

TABLE 11-continued

Half-life of purified variants: Temperature (T) 35° C., detergent concentration 90%

| Mutations | T (° C.) | Detergent (%) | Incubation time (h) | Half-life (h) |
|---|---|---|---|---|
| Q109R, E229S, K567R, A769T, L775A, D801G, K875T, N892Y | 35 | 90 | 166 | 81 |
| E229N, S635T, N672D, G753E, S754E, A769D, L775A, D801G, K875T, N892Y | 35 | 90 | 166 | 82 |
| Q109R, A159P, E229S, S635E, T649K, G753E, S754E, A769D, L775A, D801G, K875T, N892Y, N1008D | 35 | 90 | 167 | 82 |
| E229N, N672D, G753E, S754E, A769D, L775A, D801G, A843P, K875T, N892Y | 35 | 90 | 166 | 82 |
| E229N, N672D, I703L, A769D, L775A, D801G, K875T, N892Y | 35 | 90 | 166 | 82 |
| E229S, K360R, S578K, T631N, P752R, G753E, S754E, A769D, L775A, D801G, K875T, N892Y | 35 | 90 | 120 | 82 |
| E229N, N672D, I703L, G753E, S754E, A769D, L775A, D801G, K875T, N892Y | 35 | 90 | 166 | 82 |
| E229S, S635E, T649K, I656V, N672D, A769D, L775A, D801G, K875T, N892Y | 35 | 90 | 168 | 83 |
| Q109R, E229S, N672D, P752R, G753E, S754E, A769S, L775A, D801G, K875T, N892Y | 35 | 90 | 168 | 83 |
| Q109R, A159P, E229S, L533I, S582K, N672D, M728V, G753E, S754E, A769T, L775A, D801G, A843P, K875T, N892Y | 35 | 90 | 168 | 84 |
| Q109R, A159P, E229S, N672D, G753E, S754E, A769T, L775A, D801G, K875T, N892Y, A911V | 35 | 90 | 168 | 84 |
| E229N, S635E, T649K, I656V, N672D, P752K, G753E, A769D, L775A, D801G, K875T, N892Y | 35 | 90 | 166 | 84 |
| Q109R, A159P, E229S, G753E, S754E, A769T, L775A, D801G, K875T, N892Y | 35 | 90 | 166 | 85 |
| E229N, S635E, T649K, I656V, N672D, G753E, A769D, L775A, D801G, K875T, N892Y | 35 | 90 | 168 | 86 |
| E229S, K567R, P752K, G753E, A769D, L775A, D801G, K875T, N892Y | 35 | 90 | 167 | 86 |
| E229N, N672D, G753E, A769D, L775A, D801G, K875T, N892Y | 35 | 90 | 166 | 87 |
| Q109R, E229S, T631N, G753E, S754E, A769D, L775A, D801G, K875T, N892Y | 35 | 90 | 166 | 87 |
| L46D, E229S, K360R, S578K, A624E, N672D, G753E, S754E, A769D, L775A, D801G, K875T, N892Y | 35 | 90 | 168 | 87 |
| Q109R, A159P, E229S, S635E, T649K, G753E, S754E, A769D, L775A, D801G, K875T, N892Y, A912T | 35 | 90 | 167 | 87 |
| E229N, T631N, S635E, T649K, I656V, N672D, A769D, L775A, D801G, K875T, N892Y | 35 | 90 | 70 | 88 |
| Q109R, E229S, K451R, N672D, G753E, S754E, A769T, L775A, D801G, K875T, N892Y | 35 | 90 | 166 | 88 |
| E229N, S635E, T649K, I656V, N672D, P752K, G753E, S754E, A769D, L775A, D801G, K875T, N892Y | 35 | 90 | 166 | 89 |
| S100D, Q109R, A159P, E229S, S635E, T649K, G753E, S754E, A769D, L775A, D801G, K875T, N892Y | 35 | 90 | 167 | 89 |
| E229N, S635E, T649K, I656V, N672D, P752R, G753E, A769D, L775A, D801G, A843P, K875T, N892Y | 35 | 90 | 168 | 89 |
| Q109R, E229S, N672D, P752R, G753E, S754E, A769T, L775A, D801G, K875T, N892Y, A911V | 35 | 90 | 168 | 90 |
| E229N, K567R, S635E, T649K, I656V, N672D, A769D, L775A, D801G, K875T, N892Y | 35 | 90 | 70 | 90 |
| Q109R, A159P, E229S, N672D, G753E, S754E, A769T, L775A, D801G, K875T, N892Y | 35 | 90 | 168 | 90 |
| E229N, N672D, P752R, G753E, S754E, A769D, L775A, D801G, K875T, N892Y | 35 | 90 | 166 | 90 |
| E229S, S635E, T649K, I656V, N672D, G753E, S754E, A769D, L775A, V800P, D801G, K875T, N892Y | 35 | 90 | 149 | 90 |
| Q109R, E229S, S635E, T649K, G753E, S754E, A769D, L775A, D801G, K875T, N892Y | 35 | 90 | 166 | 91 |
| Q109R, A159P, E229S, G753E, S754E, A769D, L775A, D801G, K875T, N892Y | 35 | 90 | 168 | 91 |
| Q109R, E229S, N672D, P752R, G753E, S754E, A769T, L775A, D801G, K875T, N892Y, A912T | 35 | 90 | 168 | 91 |
| Q109R, A190Q, E229S, G753E, S754E, A769D, L775A, D801G, K875T, N892Y | 35 | 90 | 166 | 91 |
| Q109R, A159P, A190Q, E229S, G753E, S754E, A769D, L775A, D801G, K875T, N892Y | 35 | 90 | 168 | 92 |
| E229S, P752K, G753E, A769D, L775A, D801G, A843P, K875T, N892Y | 35 | 90 | 168 | 92 |
| Q109R, A159P, E229S, S635E, T649K, P752R, G753E, S754E, A769D, L775A, D801G, K875T, N892Y | 35 | 90 | 167 | 92 |
| E229N, N672D, G753E, S754E, A769D, L775A, D801G, K875T, N892Y, N1008D | 35 | 90 | 168 | 93 |
| Q109R, E229S, S635E, G753E, S754E, A769D, L775A, D801G, K875T, N892Y | 35 | 90 | 166 | 95 |
| Q109R, A159P, E229S, D458S, G753E, S754E, A769D, L775A, D801G, K875T, N892Y | 35 | 90 | 168 | 95 |
| E229N, N672D, P752K, G753E, A769D, L775A, D801G, A843P, K875T, N892Y | 35 | 90 | 168 | 96 |
| E229N, N672D, P752R, G753E, A769D, L775A, D801G, K875T, N892Y | 35 | 90 | 166 | 96 |
| E229N, N672D, G753E, S754E, A769D, L775A, D801G, K875T, N892Y | 35 | 90 | 166 | 97 |
| E229S, S582K, S635E, T649K, I656V, N672D, G738L, G753E, S754E, A769D, L775A, D801G, K875T, N892Y | 35 | 90 | 168 | 97 |
| Q109R, A159P, E229S, S635E, T649K, N672D, P752K, G753E, S754E, A769T, L775A, D801G, K875T, N892Y | 35 | 90 | 167 | 97 |
| Q109R, E229S, T631N, N672D, P752K, G753E, S754E, A769T, L775A, D801G, K875T, N892Y | 35 | 90 | 167 | 98 |
| E229N, T631N, N672D, P752K, G753E, A769D, L775A, D801G, K875T, N892Y | 35 | 90 | 167 | 98 |
| E229N, S635E, T649K, I656V, N672D, P752R, G753E, S754E, A769D, L775A, D801G, A843P, K875T, N892Y | 35 | 90 | 167 | 100 |
| E229N, T631N, N672D, G753E, S754E, A769D, L775A, D801G, K875T, N892Y, N1008D | 35 | 90 | 168 | 100 |
| E229N, N672D, P752K, G753E, A769D, L775A, D801G, K875T, N892Y, T923H | 35 | 90 | 167 | 101 |
| Q89Y, Q109R, A159P, E229S, S635E, T649K, N672D, G753E, S754E, A769T, L775A, D801G, K875T, N892Y | 35 | 90 | 167 | 101 |
| A190Q, E229S, S635E, T649K, I656V, N672D, I703L, G753E, S754E, A769D, L775A, D801G, K875T, N892Y, N1008D | 35 | 90 | 168 | 102 |
| Q109R, E229S, N672D, P752R, G753E, S754E, A769T, L775A, D801G, K875T, N892Y | 35 | 90 | 168 | 103 |
| Q109R, E229S, N672D, G753E, S754E, A769T, L775A, D801G, K875T, N892Y | 35 | 90 | 166 | 103 |
| Q109R, E229S, G753E, S754E, A769D, L775A, D801G, K875T, N892Y | 35 | 90 | 166 | 103 |
| Q109R, A159P, E229S, K567R, G753E, S754E, A769D, L775A, D801G, K875T, N892Y | 35 | 90 | 168 | 103 |

TABLE 11-continued

Half-life of purified variants: Temperature (T) 35° C., detergent concentration 90%

| Mutations | T (° C.) | Detergent (%) | Incubation time (h) | Half-life (h) |
|---|---|---|---|---|
| E229S, D458S, K567R, N672D, G753E, S754E, A769D, L775A, D801G, K875T, N892Y | 35 | 90 | 168 | 103 |
| E229S, K360R, S578K, P752R, G753E, S754E, A769D, L775A, D801G, K875T, N892Y | 35 | 90 | 120 | 104 |
| A159P, E229N, S635E, T649K, I656V, N672D, A769D, L775A, D801G, K875T, N892Y | 35 | 90 | 70 | 104 |
| L46D, Q109R, A159P, E229S, N672D, G753E, S754E, A769T, L775A, D801G, A843P, K875T, N892Y | 35 | 90 | 168 | 104 |
| Q109R, A159P, E229S, D458S, N672D, G753E, S754E, A769T, L775A, D801G, K875T, N892Y | 35 | 90 | 168 | 104 |
| Q109R, A159P, E229S, S635E, T649K, G753E, S754E, A769T, L775A, D801G, K875T, N892Y, K1016T | 35 | 90 | 167 | 104 |
| Q109R, E229S, N672D, P752R, G753E, S754E, A769T, L775A, D801G, K875T, N892Y | 35 | 90 | 168 | 107 |
| L46D, A58L, E229S, K360R, S578K, N672D, G753E, S754E, A769D, L775A, K875T, N892Y | 35 | 90 | 70 | 108 |
| E229S, S635E, T649K, I656V, N672D, G753E, A769D, L775A, D801G, K875T, N892Y | 35 | 90 | 168 | 109 |
| Q109R, E229S, N672D, G753E, S754E, A769T, L775A, D801G, K875T, N892Y, N991D | 35 | 90 | 166 | 109 |
| Q109R, A159P, E229S, S635E, T649K, N672D, G753E, S754E, A769T, L775A, D801G, K875T, N892Y | 35 | 90 | 168 | 109 |
| Q109R, A159P, E229S, S635E, T649K, G753E, S754E, A769D, L775A, D801G, K875T, N892Y | 35 | 90 | 168 | 110 |
| Q109R, E229S, N672D, G753E, S754E, A769T, L775A, D801G, K875T, N892Y, T923H | 35 | 90 | 166 | 110 |
| L46D, E229S, P752K, G753E, S757D, A769D, L775A, D801G, K875T, N892Y | 35 | 90 | 149 | 110 |
| A190Q, E229N, N672D, G753E, S754E, A769D, L775A, D801G, K875T, N892Y | 35 | 90 | 166 | 112 |
| E229S, S635E, T649K, I656V, N672D, S754E, A769D, L775A, D801G, K875T, N892Y | 35 | 90 | 168 | 112 |
| Q109R, E229S, G753E, S754E, A769D, L775A, D801G, K875T, N892Y, N1008D | 35 | 90 | 166 | 112 |
| E229N, N672D, I703L, P752K, G753E, A769D, L775A, D801G, K875T, N892Y | 35 | 90 | 167 | 113 |
| E229S, T631N, S635E, T649K, I656V, N672D, I703L, G753E, S754E, A769D, L775A, D801G, K875T, N892Y, N1008D | 35 | 90 | 168 | 113 |
| E229S, S635E, T649K, I656V, N672D, I703L, M728V, G753E, S754E, A769D, L775A, D801G, K875T, N892Y, N1008D | 35 | 90 | 168 | 114 |
| Q109R, A159P, E229S, G753E, S754E, A769D, L775A, D801G, K875T, N892Y, A912T | 35 | 90 | 168 | 114 |
| E229N, N672D, P752K, G753E, A769D, L775A, D801G, K875T, N892Y | 35 | 90 | 168 | 114 |
| E229S, S635E, T649K, I656V, N672D, I703L, G753E, S754E, A769D, L775A, D801G, K875T, N892Y, N1008D | 35 | 90 | 168 | 114 |
| E229S, K360G, N672D, G753E, S754E, A769D, L775A, D801G, K875T, N892Y | 35 | 90 | 168 | 114 |
| Q109R, A159P, E229S, K567R, N672D, G753E, S754E, A769T, L775A, D801G, K875T, N892Y | 35 | 90 | 168 | 114 |
| Q109R, E229S, N672D, G753E, S754E, A769T, L775A, D801G, K875T, N892Y, K1016T | 35 | 90 | 166 | 115 |
| L46D, E229S, N672D, G753E, S754E, A769D, L775A, D801G, K875T, N892Y | 35 | 90 | 168 | 115 |
| Q109R, A159P, E229S, G753E, S754E, A769D, L775A, D801G, K875T, N892Y, N1008D | 35 | 90 | 168 | 115 |
| Q109R, A159P, E229S, N672D, G753E, S754E, A769T, L775A, V800P, D801G, A843P, K875T, N892Y | 35 | 90 | 168 | 116 |
| Q109R, A159P, E229S, G753E, S754E, A769D, L775A, D801G, A843P, K875T, N892Y | 35 | 90 | 168 | 116 |
| Q109R, E229S, G753E, S754E, A769D, L775A, D801G, K875T, N892Y | 35 | 90 | 166 | 117 |
| Q109R, A159P, E229S, I703L, G753E, S754E, A769D, L775A, D801G, K875T, N892Y | 35 | 90 | 168 | 117 |
| Q109R, E229S, S582K, N672D, G753E, S754E, A769D, L775A, D801G, A843P, K875T, N892Y | 35 | 90 | 149 | 117 |
| Q109R, E229S, S635E, T649K, I656V, N672D, I703L, G753E, S754E, A769D, L775A, D801G, K875T, N892Y, N1008D | 35 | 90 | 168 | 117 |
| Q109R, A159P, E229S, S635E, T649K, N672D, G753E, S754E, A769T, L775A, D801G, K875T, N892Y | 35 | 90 | 167 | 117 |
| E229S, S635E, T649K, I656V, N672D, P752K, G753E, A769D, L775A, D801G, K875T, N892Y, A912T | 35 | 90 | 168 | 117 |
| Q109R, E229S, K567R, T631N, N672D, P752R, G753E, S754E, A769D, L775A, D801G, K875T, N892Y | 35 | 90 | 149 | 117 |
| Q109R, A190Q, E229S, N672D, G753E, S754E, A769T, L775A, D801G, K875T, N892Y | 35 | 90 | 166 | 118 |
| Q109R, A159P, E229S, T631N, G753E, S754E, A769D, L775A, D801G, K875T, N892Y | 35 | 90 | 168 | 118 |
| E229S, N440K, S582K, A624E, N672D, G753E, S754E, A769D, L775A, D801G, K875T, N892Y | 35 | 90 | 168 | 120 |
| Q109R, E229S, N672D, I703L, P752R, G753E, S754E, A769T, L775A, D801G, K875T, N892Y | 35 | 90 | 168 | 120 |
| A190Q, E229S, D458S, N672D, G753E, S754E, A769D, L775A, D801G, K875T, N892Y | 35 | 90 | 168 | 120 |
| E229S, S635E, T649K, I656V, N672D, G753E, A769D, L775A, D801G, K875T, N892Y | 35 | 90 | 168 | 121 |
| Q109R, E229S, A624E, N672D, G753E, S754E, A769T, L775A, D801G, A843P, K875T, N892Y | 35 | 90 | 149 | 121 |
| E229S, S635E, T649K, I656V, N672D, P752R, S754E, A769D, L775A, D801G, K875T, N892Y | 35 | 90 | 168 | 121 |
| E229S, S635E, T649K, I656V, N672D, G753E, A769D, L775A, D801G, K875T, N892Y, K1016T | 35 | 90 | 168 | 122 |
| Q109R, E229S, N672D, G753E, S754E, A769T, L775A, D801G, K875T, N892Y, V998K | 35 | 90 | 166 | 122 |
| E229N, S635E, T649K, I656V, N672D, P752R, S754E, A769D, L775A, D801G, K875T, N892Y | 35 | 90 | 70 | 122 |
| E229S, D458S, T631N, N672D, G753E, S754E, A769D, L775A, D801G, K875T, N892Y | 35 | 90 | 168 | 122 |
| E229S, D458S, S635E, N672D, G753E, S754E, A769D, L775A, D801G, K875T, N892Y, N1008D | 35 | 90 | 168 | 126 |

TABLE 11-continued

Half-life of purified variants: Temperature (T) 35° C., detergent concentration 90%

| Mutations | T (° C.) | Detergent (%) | Incubation time (h) | Half-life (h) |
|---|---|---|---|---|
| Q109R, E229S, T631N, N672D, P752R, G753E, S754E, A769T, L775A, D801G, K875T, N892Y | 35 | 90 | 168 | 126 |
| E229S, K360G, S635E, T649K, I656V, N672D, G753E, A769D, L775A, D801G, K875T, N892Y | 35 | 90 | 168 | 126 |
| E229N, T631N, N672D, G753E, S754E, A769D, L775A, D801G, K875T, N892Y, N1008D | 35 | 90 | 167 | 126 |
| Q109R, A159P, E229S, S635E, T649K, G753E, S754E, A769D, L775A, D801G, A843P, K875T, N892Y | 35 | 90 | 167 | 127 |
| A159P, E229S, N672D, G753E, S754E, A769D, L775A, D801G, K875T, N892Y | 35 | 90 | 168 | 127 |
| E229S, S635E, T649K, I656V, N672D, S757D, A769D, L775A, D801G, K875T, N892Y | 35 | 90 | 168 | 128 |
| E229N, S635E, T649K, I656V, N672D, P752R, A769D, L775A, D801G, K875T, N892Y | 35 | 90 | 70 | 128 |
| A159P, E229S, I234V, N672D, G753E, S754E, A769D, L775A, D801G, K875T, N892Y | 35 | 90 | 168 | 128 |
| Q109R, E229S, N672D, P752R, G753E, S754E, A769T, L775A, D801G, K875T, N892Y, D901A | 35 | 90 | 168 | 129 |
| E229S, S635E, T649K, I656V, N672D, G753E, A769D, L775A, V800P, D801G, K875T, N892Y | 35 | 90 | 168 | 130 |
| L46D, E229S, K360G, S578K, N672D, G753E, S754E, A769D, L775A, D801G, K875T, N892Y | 35 | 90 | 168 | 130 |
| Q109R, A159P, E229S, T631E, S635E, T649K, P752R, G753E, S754E, A769D, L775A, D801G, K875T, N892Y | 35 | 90 | 149 | 133 |
| E229S, N672D, G753E, S754E, A769D, L775A, D801G, K875T, N892Y | 35 | 90 | 168 | 135 |
| E229S, I234V, N672D, G753E, S754E, A769D, L775A, D801G, K875T, N892Y | 35 | 90 | 168 | 135 |
| L46D, E229S, S635E, T649K, I656V, N672D, G753E, S754E, A769D, L775A, D801G, K875T, N892Y | 35 | 90 | 149 | 136 |
| Q109R, E229S, T631N, N672D, P752R, G753E, S754E, A769D, L775A, D801G, K875T, N892Y | 35 | 90 | 167 | 136 |
| S100D, A190Q, E229S, I234V, N672D, G753E, S754E, A769D, L775A, D801G, K875T, N892Y | 35 | 90 | 168 | 137 |
| E229S, S635E, T649K, I656V, N672D, G753E, S754E, A769D, L775A, D801G, K875T, N892Y | 35 | 90 | 168 | 138 |
| E229N, N672D, P752R, G753E, A769D, L775A, D801G, K875T, N892Y | 35 | 90 | 166 | 138 |
| E229S, P752K, G753E, S757D, A769D, L775A, D801G, K875T, N892Y | 35 | 90 | 167 | 139 |
| E229S, A624E, N672D, G753E, S754E, A769D, L775A, D801G, K875T, N892Y | 35 | 90 | 168 | 139 |
| E229S, S635E, T649K, I656V, N672D, I703L, G753E, S754E, A769D, L775A, D801G, K875T, N892Y, N1008D | 35 | 90 | 168 | 139 |
| Q109R, E229S, D458S, N672D, G753E, S754E, A769T, L775A, D801G, K875T, N892Y | 35 | 90 | 166 | 140 |
| A190Q, E229S, I234V, N672D, G753E, S754E, A769D, L775A, D801G, K875T, N892Y | 35 | 90 | 168 | 140 |
| E229S, S635E, T649K, I656V, N672D, P752R, G753E, S754E, A769D, L775A, D801G, K875T, N892Y | 35 | 90 | 167 | 141 |
| Q109R, A159P, E229S, S635E, T649K, N672D, G753E, S754E, S757D, A769T, L775A, D801G, K875T, N892Y | 35 | 90 | 167 | 141 |
| Q109R, E229S, N672D, I703L, G753E, S754E, A769T, L775A, D801G, K875T, N892Y | 35 | 90 | 166 | 141 |
| Q109R, E229S, T631N, N672D, G753E, S754E, A769T, L775A, D801G, K875T, N892Y | 35 | 90 | 166 | 141 |
| E229S, T631E, P752K, G753E, S757D, A769D, L775A, D801G, K875T, N892Y | 35 | 90 | 168 | 141 |
| E229S, N440K, S582K, N672D, G753E, S754E, S757D, A769D, L775A, D801G, K875T, N892Y, N1008D | 35 | 90 | 168 | 141 |
| E229S, K567R, S635E, T649K, I656V, N672D, G753E, A769D, L775A, D801G, K875T, N892Y | 35 | 90 | 168 | 142 |
| E229S, S635E, T649K, I656V, N672D, P752K, G753E, A769D, L775A, D801G, K875T, N892Y, T923H, N1008D | 35 | 90 | 168 | 142 |
| Q109R, A159P, E229S, N672D, G753E, S754E, A769T, L775A, D801G, K875T, N892Y | 35 | 90 | 168 | 142 |
| E229S, A624E, S635E, T649K, I656V, N672D, I703L, G753E, S754E, A769D, L775A, D801G, K875T, N892Y, N1008D | 35 | 90 | 168 | 143 |
| A159P, E229S, S635E, T649K, I656V, N672D, G753E, A769D, L775A, D801G, K875T, N892Y | 35 | 90 | 168 | 145 |
| E229S, S635E, T649K, I656V, N672D, P752K, G753E, S754E, A769D, L775A, D801G, K875T, N892Y | 35 | 90 | 168 | 145 |
| Q109R, E229S, A624E, T631N, N672D, P752R, G753E, S754E, A769D, L775A, D801G, K875T, N892Y | 35 | 90 | 149 | 146 |
| Q109R, A159P, E229S, S635E, T649K, N672D, G753E, S754E, S757D, A769T, L775A, D801G, K875T, N892Y, N1008D | 35 | 90 | 168 | 146 |
| E229S, S582K, S635E, T649K, I656V, N672D, G753E, A769D, L775A, D801G, K875T, N892Y | 35 | 90 | 168 | 146 |
| E229S, I234V, V352I, N672D, G753E, S754E, A769D, L775A, D801G, K875T, N892Y | 35 | 90 | 168 | 147 |
| T18D, E229S, N672D, G753E, S754E, A769D, L775A, D801G, K875T, N892Y, N1008D | 35 | 90 | 168 | 149 |
| A159P, E229S, I234V, N672D, G753E, S754E, A769D, L775A, D801G, K875T, N892Y, N1008D | 35 | 90 | 168 | 149 |
| E229S, D458S, T631N, N672D, G753E, S754E, A769D, L775A, D801G, K875T, N892Y | 35 | 90 | 168 | 149 |
| Q109R, E229S, T631N, N672D, P752R, G753E, S754E, A769D, L775A, D801G, K875T, N892Y, T923H | 35 | 90 | 149 | 150 |
| E229S, S635E, T649K, I656V, N672D, I703L, G753E, S754E, A769D, L775A, D801G, K875T, N892Y | 35 | 90 | 168 | 150 |
| Q109R, E229S, N672D, G753E, S754E, A769E, L775A, D801G, K875T, N892Y | 35 | 90 | 166 | 152 |
| Q109R, A159P, E229S, N672D, P752R, G753E, S754E, A769D, L775A, D801G, K875T, N892Y | 35 | 90 | 168 | 152 |
| E229S, N672D, P752R, G753E, A769D, L775A, D801G, K875T, N892Y | 35 | 90 | 167 | 154 |
| E229S, S635E, T649K, I656V, N672D, G753E, A769D, L775A, D801G, K875T, N892Y, A911V | 35 | 90 | 168 | 155 |
| E229S, D458S, K567R, T631E, N672D, G753E, S754E, A769D, L775A, D801G, K875T, N892Y | 35 | 90 | 168 | 155 |
| E229S, S635E, T649K, I656V, N672D, I703L, G753E, S754E, A769D, L775A, D801G, K875T, N892Y, N1008D | 35 | 90 | 168 | 158 |

TABLE 11-continued

Half-life of purified variants: Temperature (T) 35° C., detergent concentration 90%

| Mutations | T (° C.) | Detergent (%) | Incubation time (h) | Half-life (h) |
|---|---|---|---|---|
| E229S, N440K, S582K, N672D, G753E, S754E, A769D, L775A, D801G, K875T, N892Y, N1008D | 35 | 90 | 168 | 158 |
| Q109R, A159P, E229S, N672D, G753E, S754E, A769T, L775A, D801G, A843P, K875T, N892Y | 35 | 90 | 168 | 159 |
| E229S, S635E, T649K, I656V, N672D, G753E, S754E, A769D, L775A, D801G, K875T, N892Y, K1016T | 35 | 90 | 168 | 160 |
| E229S, S635E, N672D, G753E, S754E, A769D, L775A, D801G, K875T, N892Y | 35 | 90 | 168 | 160 |
| E229S, N672D, P752R, G753E, S754E, A769D, L775A, D801G, K875T, N892Y | 35 | 90 | 167 | 160 |
| E229S, N672D, G753E, S754E, A769D, L775A, D801G, K875T, N892Y | 35 | 90 | 168 | 161 |
| E229S, D458S, N672D, G753E, S754E, A769D, L775A, V800P, D801G, K875T, N892Y, N1008D | 35 | 90 | 149 | 162 |
| E229S, I234V, N672D, G753E, S754E, A769D, L775A, D801G, K875T, N892Y | 35 | 90 | 168 | 162 |
| E229S, N672D, G753E, S754E, A769D, L775A, D801G, K875T, N892Y | 35 | 90 | 168 | 166 |
| E229N, S635E, T649K, I656V, N672D, A769D, L775A, D801G, K875T, N892Y, N991D | 35 | 90 | 70 | 166 |
| Q109R, A159P, E229S, N672D, P752K, G753E, S754E, A769T, L775A, D801G, K875T, N892Y | 35 | 90 | 168 | 167 |
| E229S, S635E, T649K, N672D, G753E, S754E, A769D, L775A, D801G, K875T, N892Y, N1008D | 35 | 90 | 168 | 167 |
| E229S, S635E, T649K, I656V, N672D, P752E, G753E, S757D, A769D, L775A, D801G, K875T, N892Y, N1008D | 35 | 90 | 168 | 167 |
| Q109R, E229S, N672D, G753E, S754E, A769T, L775A, D801G, A843P, K875T, N892Y | 35 | 90 | 166 | 167 |
| E229S, V352I, S635E, T649K, I656V, N672D, I703L, G753E, A769D, L775A, D801G, K875T, N892Y, N1008D | 35 | 90 | 168 | 168 |
| Q109R, A159P, E229S, S635E, T649K, N672D, G738L, G753E, S754E, S757D, A769T, L775A, D801G, K875T, N892Y | 35 | 90 | 168 | 168 |
| E229S, N440K, S582K, A624E, N672D, G753E, S754E, A769D, L775A, D801G, K875T, N892Y | 35 | 90 | 168 | 169 |
| T18D, A159P, E229S, I234V, N672D, G753E, S754E, A769D, L775A, D801G, K875T, N892Y | 35 | 90 | 168 | 173 |
| E229S, D458S, N672D, G753E, S754E, A769D, L775A, D801G, K875T, N892Y | 35 | 90 | 168 | 174 |
| A190Q, E229S, P752K, G753E, S757D, A769D, L775A, D801G, K875T, N892Y | 35 | 90 | 168 | 175 |
| E229S, N440K, S582K, A624E, T631N, N672D, G753E, S754E, A769D, L775A, D801G, K875T, N892Y | 35 | 90 | 168 | 175 |
| E229S, D458S, A492L, T631N, N672D, G753E, S754E, A769D, L775A, D801G, K875T, N892Y | 35 | 90 | 168 | 176 |
| E229S, N672D, G753E, S754E, A769D, L775A, D801G, K875T, N892Y | 35 | 90 | 168 | 176 |
| Q109R, A159P, E229S, A624E, A626G, S635E, T649K, N672D, G753E, S754E, S757D, A769T, L775A, D801G, K875T, N892Y | 35 | 90 | 168 | 176 |
| E229S, N440K, S582K, N672D, P752R, G753E, S754E, A769D, L775A, D801G, K875T, N892Y, N1008D | 35 | 90 | 168 | 178 |
| E229S, D458S, T631N, S635E, T649K, N672D, G753E, S754E, A769D, L775A, D801G, K875T, N892Y | 35 | 90 | 168 | 178 |
| E229S, S582K, N672D, G753E, S754E, A769D, L775A, D801G, K875T, N892Y | 35 | 90 | 168 | 179 |
| E229S, I234V, A492L, N672D, G753E, S754E, A769D, L775A, D801G, K875T, N892Y | 35 | 90 | 168 | 181 |
| Q109R, E229S, T631N, N672D, P752R, G753E, S754E, S757D, A769T, L775A, D801G, K875T, N892Y | 35 | 90 | 167 | 182 |
| E229S, D458S, S582K, N672D, G753E, S754E, A769D, L775A, D801G, K875T, N892Y, N1008D | 35 | 90 | 168 | 183 |
| A159P, E229S, S635E, T649K, I656V, N672D, I703L, G753E, S754E, A769D, L775A, D801G, K875T, N892Y, N1008D | 35 | 90 | 168 | 183 |
| Q109R, E229S, T631N, N672D, P752R, G753E, S754E, A769D, L775A, D801G, A843P, K875T, N892Y | 35 | 90 | 168 | 188 |
| Q109R, E229S, T631N, N672D, P752R, G753E, S754E, S757D, A769T, L775A, D801G, K875T, N892Y | 35 | 90 | 149 | 188 |
| Q109R, A159P, E229S, S635E, T649K, N672D, I703L, G753E, S754E, S757D, A769T, L775A, D801G, K875T, N892Y | 35 | 90 | 149 | 188 |
| Q89Y, E229S, N672D, G753E, S754E, A769D, L775A, D801G, K875T, N892Y | 35 | 90 | 168 | 188 |
| E229S, S635E, T649K, I656V, N672D, P752K, G753E, A769D, L775A, D801G, A843P, K875T, N892Y | 35 | 90 | 168 | 188 |
| E229S, A492L, S635E, T649K, I656V, N672D, G753E, A769D, L775A, D801G, K875T, N892Y | 35 | 90 | 168 | 189 |
| E229S, D458S, S582K, A624E, N672D, G753E, S754E, A769D, L775A, D801G, K875T, N892Y | 35 | 90 | 168 | 189 |
| E229S, D458S, T631N, S635E, N672D, G753E, S754E, A769D, L775A, D801G, K875T, N892Y | 35 | 90 | 168 | 189 |
| E229S, S635E, T649K, I656V, N672D, P752K, G753E, A769D, L775A, V800P, D801G, K875T, N892Y, N1008D | 35 | 90 | 168 | 193 |
| E229S, D458S, N672D, G753E, S754E, A769D, L775A, D801G, K875T, N892Y, N1008D | 35 | 90 | 149 | 193 |
| T18D, E229S, N440K, N672D, G753E, S754E, A769D, L775A, D801G, K875T, N892Y | 35 | 90 | 168 | 194 |
| A159P, E229S, N440K, N672D, G753E, S754E, A769D, L775A, D801G, K875T, N892Y | 35 | 90 | 168 | 196 |
| Q109R, A159P, E229S, S635E, T649K, N672D, P752G, G753E, S754E, A769D, L775A, D801G, K875T, N892Y | 35 | 90 | 168 | 197 |
| E229S, I234V, S635E, T649K, I656V, N672D, G753E, A769D, L775A, D801G, K875T, N892Y | 35 | 90 | 168 | 197 |
| Q109R, E229S, T631N, N672D, P752R, G753E, S754E, A769D, L775A, D801G, K875T, N892Y, N1008D | 35 | 90 | 149 | 197 |
| E229S, D458S, T631E, N672D, G753E, S754E, A769D, L775A, D801G, K875T, N892Y | 35 | 90 | 168 | 200 |
| A190Q, E229S, S635E, T649K, I656V, N672D, I703L, G753E, S754E, A769D, L775A, V800P, D801G, K875T, N892Y, N1008D | 35 | 90 | 168 | 200 |
| E229S, D458S, N672D, P752R, G753E, S754E, A769D, L775A, D801G, K875T, N892Y | 35 | 90 | 168 | 200 |
| A190Q, E229S, T631E, S635E, T649K, I656V, N672D, I703L, G753E, S754E, A769D, L775A, D801G, K875T, N892Y, N1008D | 35 | 90 | 168 | 203 |

TABLE 11-continued

Half-life of purified variants: Temperature (T) 35° C., detergent concentration 90%

| Mutations | T (° C.) | Detergent (%) | Incubation time (h) | Half-life (h) |
|---|---|---|---|---|
| E229S, N440K, A492L, S582K, A624E, N672D, G753E, S754E, A769D, L775A, D801G, K875T, N892Y | 35 | 90 | 168 | 203 |
| E229S, D458S, K567R, T631N, N672D, G753E, S754E, A769D, L775A, D801G, K875T, N892Y | 35 | 90 | 168 | 203 |
| L46D, E229S, K360R, S578K, N672D, G753E, S754E, A769D, L775A, D801G, K875T, N892Y | 35 | 90 | 168 | 203 |
| E229S, S582K, S635E, T649K, I656V, N672D, I703L, G753E, S754E, A769D, L775A, D801G, K875T, N892Y, N1008D | 35 | 90 | 168 | 204 |
| Q109R, A159P, E229S, S635E, T649K, G753E, S754E, S757D, A769D, L775A, D801G, K875T, N892Y | 35 | 90 | 167 | 204 |
| T18D, E229S, S635E, T649K, I656V, N672D, G753E, S754E, A769D, L775A, D801G, K875T, N892Y | 35 | 90 | 149 | 205 |
| Q109R, A159P, E229S, G753E, S754E, S757D, A769D, L775A, D801G, K875T, N892Y | 35 | 90 | 168 | 206 |
| E229S, N672D, G753E, S754E, A769D, L775A, D801G, K875T, N892Y | 35 | 90 | 168 | 206 |
| E229N, T631N, N672D, P752R, G753E, A769D, L775A, D801G, K875T, N892Y, A911V | 35 | 90 | 149 | 207 |
| Q109R, E229S, T631N, S635E, T649K, N672D, P752R, G753E, S754E, A769D, L775A, D801G, K875T, N892Y | 35 | 90 | 149 | 209 |
| E229S, D458S, K567R, N672D, M728V, G753E, S754E, A769D, L775A, D801G, K875T, N892Y | 35 | 90 | 168 | 209 |
| E229S, I234V, S582K, N672D, G753E, S754E, A769D, L775A, D801G, K875T, N892Y | 35 | 90 | 168 | 212 |
| E229S, N440K, S582K, T631N, N672D, G753E, S754E, A769D, L775A, D801G, K875T, N892Y, N1008D | 35 | 90 | 168 | 213 |
| A190Q, E229S, I234V, S582K, N672D, G753E, S754E, A769D, L775A, D801G, K875T, N892Y | 35 | 90 | 168 | 215 |
| A190Q, E229S, I234V, A624E, N672D, G753E, S754E, A769D, L775A, D801G, K875T, N892Y | 35 | 90 | 168 | 216 |
| E229S, N440K, S582K, A624E, S635E, N672D, G753E, S754E, A769D, L775A, D801G, K875T, N892Y | 35 | 90 | 168 | 216 |
| E229S, S635E, T649K, I656V, N672D, G753E, S754E, A769D, L775A, D801G, K875T, N892Y | 35 | 90 | 168 | 218 |
| S100D, E229S, S635E, T649K, I656V, N672D, I703L, G753E, A769D, L775A, D801G, A843P, K875T, N892Y, N1008D | 35 | 90 | 168 | 219 |
| A190Q, E229S, S635E, T649K, I656V, N672D, I703L, P752R, G753E, S754E, A769D, L775A, D801G, K875T, N892Y, N1008D | 35 | 90 | 168 | 224 |
| Q89Y, E229S, N440K, S582K, A624E, N672D, G753E, S754E, A769D, L775A, D801G, K875T, N892Y | 35 | 90 | 168 | 225 |
| A190Q, E229S, S635E, T649K, I656V, N672D, I703L, G753E, S754E, S757D, A769D, L775A, D801G, K875T, N892Y, N1008D | 35 | 90 | 168 | 231 |
| E229S, I234V, N672D, G753E, S754E, A769D, L775A, D801G, A843P, K875T, N892Y | 35 | 90 | 149 | 235 |
| E229S, S635E, T649K, I656V, N672D, G753E, S754E, S757D, A769D, L775A, D801G, K875T, N892Y | 35 | 90 | 168 | 236 |
| T18D, E229S, S582K, N672D, G753E, S754E, A769D, L775A, D801G, K875T, N892Y | 35 | 90 | 168 | 239 |
| E229S, D458S, T631N, N672D, G753E, S754E, S757D, A769D, L775A, D801G, K875T, N892Y | 35 | 90 | 168 | 239 |
| E229S, S635E, T649K, I656V, N672D, P752R, G753E, S754E, A769D, L775A, D801G, K875T, N892Y, N1008D | 35 | 90 | 168 | 239 |
| E229S, N440K, S582K, A624E, N672D, G753E, S754E, A769D, L775A, V800P, D801G, K875T, N892Y | 35 | 90 | 168 | 242 |
| A190Q, E229S, D458S, T631N, N672D, G753E, S754E, A769D, L775A, D801G, K875T, N892Y | 35 | 90 | 168 | 245 |
| E229S, K360G, D458S, S582K, N672D, G753E, S754E, A769D, L775A, D801G, K875T, N892Y, N1008D | 35 | 90 | 168 | 251 |
| S100D, E229S, S635E, T649K, I656V, N672D, G753E, S754E, A769D, L775A, D801G, K875T, N892Y | 35 | 90 | 149 | 253 |
| A190Q, E229S, S635E, T649K, I656V, N672D, G753E, S754E, A769D, L775A, D801G, K875T, N892Y | 35 | 90 | 149 | 261 |
| S100D, A190Q, E229S, S635E, T649K, I656V, N672D, I703L, G753E, S754E, A769D, L775A, D801G, K875T, N892Y, N1008D | 35 | 90 | 168 | 263 |
| E229S, D458S, K567R, S635E, N672D, G753E, S754E, A769D, L775A, D801G, K875T, N892Y | 35 | 90 | 168 | 266 |
| E229S, D458S, N672D, G753E, S754E, A769D, L775A, D801G, A843P, K875T, N892Y | 35 | 90 | 149 | 281 |
| E229S, T631N, N672D, I703L, P752K, G753E, A769D, L775A, D801G, K875T, N892Y | 35 | 90 | 149 | 284 |
| E229S, N440K, S582K, N672D, G753E, S754E, A769D, L775A, D801G, A843P, K875T, N892Y, N1008D | 35 | 90 | 149 | 296 |

TABLE 12

Half-life of purified variants: Temperature (T) 35° C., detergent concentration 95%

| Mutations | T (° C.) | Detergent (%) | Incubation time (h) | Half-life (h) |
|---|---|---|---|---|
| No mutations (Wild-type) | 35 | 95 | 1 | <0.2 |
| E229S, K360G, D458S, S582K, T631N, S635E, N672D, I703L, M728V, G753E, S754E, S757D, A769D, L775A, D801G, K875T, N892Y | 35 | 95 | 168 | 40 |
| E229S, D458S, S582K, T631N, S635E, N672D, M728V, G753E, S754E, S757D, A769D, L775A, D777R, V800P, D801G, K875T, N892Y | 35 | 95 | 168 | 27 |
| E229S, D458S, S582K, T631N, S635E, N672D, M728V, G753E, S754E, S757D, A769D, L775A, D801G, A843P, K875T, N892Y | 35 | 95 | 168 | 39 |
| E229S, D458S, S582K, T631N, S635E, N672D, M728V, G753E, S754E, S757D, A769D, L775A, D801G, A843P, K875T, N892Y | 35 | 95 | 168 | 46 |

TABLE 12-continued

Half-life of purified variants: Temperature (T) 35° C., detergent concentration 95%

| Mutations | T (° C.) | Detergent (%) | Incubation time (h) | Half-life (h) |
|---|---|---|---|---|
| E229S, D458S, S582K, T631N, S635E, T664K, N672D, M728V, G753E, S754E, S757D, A769D, L775A, D801G, K875T, N892Y | 35 | 95 | 168 | 41 |
| E229S, V352I, D458S, S582K, T631N, S635E, N672D, M728V, G753E, S754E, S757D, A769D, L775A, D801G, K875T, N892Y, K1016T | 35 | 95 | 168 | 43 |
| S100D, E229S, K360G, A624E, S635E, T649K, N672D, G753E, S754E, A769D, L775A, D777K, D801G, K875T, N892Y, K1016T | 35 | 95 | 168 | 54 |
| S100D, E229S, V352I, K360G, D458S, A624E, S635E, T649K, I656V, N672D, G753E, S754R, S757D, A769D, L775A, D777K, D801G, K875T, N892Y, K1016T | 35 | 95 | 168 | 42 |
| E229S, A624E, S635E, T649K, I656V, N672D, L748T, G753E, S754R, S757D, A769D, L775A, D777K, D801G, K875T, N892Y | 35 | 95 | 168 | 37 |
| E229S, S582K, A624E, S635E, T649K, I656V, N672D, G753E, S754R, S757D, A769D, L775A, D777K, V800P, D801G, K875T, N892Y | 35 | 95 | 168 | 38 |
| E229S, A624E, S635E, T649K, N672D, G753E, S754E, A769D, L775A, D777K, D801G, K875T, N892Y | 35 | 95 | 168 | 45 |
| E229S, A624E, S635E, T649K, I656V, N672D, G753E, S754E, S757D, A769D, L775A, D777R, D801G, A843P, K875T, N892Y | 35 | 95 | 168 | 55 |
| E229S, D458S, K567R, S582K, S635E, N672D, M728V, G753E, S754R, S757D, A769D, L775A, D777K, D801G, K875T, N892Y, K1016T | 35 | 95 | 168 | 23 |
| E229S, D458S, K567R, S582K, S635E, N672D, G753E, S754E, A769D, L775A, D777R, V800P, D801G, K875T, N892Y | 35 | 95 | 168 | 26 |
| E229S, D458S, K567R, S582K, S635E, N672D, G753E, S754E, A769D, L775A, D777R, D801G, K875T, N892Y, N1008D | 35 | 95 | 168 | 29 |
| E229S, D458S, K567R, S582K, S635E, T649K, N672D, G753E, S754E, A769D, L775A, D777K, D801G, K875T, N892Y | 35 | 95 | 168 | 29 |
| E229S, N399K, D458S, A492H, K567R, S582K, S635E, T649K, N672D, G753E, S754E, A769D, L775A, D777R, D801G, K875T, N892Y | 35 | 95 | 168 | 61 |
| E229S, D458S, K567R, S582K, S635E, N672D, G753E, S754E, S757D, A769D, L775A, D777R, D801G, K875T, N892Y | 35 | 95 | 168 | 23 |
| E229S, D458S, K567R, S582K, S635E, T664K, N672D, G753E, S754E, A769D, L775A, D777R, K792Y, D801G, K875T, N892Y | 35 | 95 | 168 | 25 |
| E229S, D458S, K567R, S582K, S635E, T664K, N672D, G753E, S754E, A769D, L775A, D777R, D801G, K875T, N892Y | 35 | 95 | 168 | 25 |
| E229S, D458S, K567R, S582K, S635E, N672D, M728V, G753E, S754E, A769D, L775A, D777R, D801G, K875T, N892Y | 35 | 95 | 168 | 30 |
| S100D, E229S, K360G, D458S, S582K, A624E, N672D, G753E, S754E, S757D, A769D, L775A, D801G, A843P, K875T, N892Y, N1008D | 35 | 95 | 168 | 60 |
| S100D, E229S, K360G, D458S, S582K, N672D, G753E, S754E, S757D, A769D, L775A, D801G, A843P, K875T, N892Y, N1008D | 35 | 95 | 168 | 50 |
| S100D, E229S, K360G, D458S, S582K, S635E, N672D, G753E, S754E, S757D, A769D, L775A, V800P, D801G, A843P, K875T, N892Y, N1008D | 35 | 95 | 168 | 51 |
| S100D, E229S, K360G, D458S, S582K, S635E, T649K, N672D, G753E, S754E, S757D, A769D, L775A, D801G, A843P, K875T, N892Y, N1008D | 35 | 95 | 168 | 59 |
| E229S, S635E, T649K, N672D, P752R, G753E, S754E, A769D, L775A, D777K, D801G, K875T, N892Y | 35 | 95 | 168 | 37 |
| E229S, N672D, P752R, G753E, S754E, S757D, A769D, L775A, D801G, A843P, K875T, N892Y | 35 | 95 | 168 | 47 |
| E229S, S635E, T649K, I656V, N672D, G753E, A769D, L775A, D801G, K875T, N892Y | 35 | 95 | 168 | 24 |
| S100D, E229S, K360G, D458S, S582K, N672D, G753E, S754E, A769D, L775A, D801G, K875T, N892Y, N1008D | 35 | 95 | 168 | 45 |
| A190Q, E229S, K360G, D458S, S582K, N672D, G753E, S754E, A769D, L775A, D801G, K875T, N892Y, N1008D | 35 | 95 | 168 | 41 |

TABLE 13

Half-life of purified variants: Temperature (T) 37° C., detergent concentration 90%

| Mutations | T (° C.) | Detergent (%) | Incubation time (h) | Half-life (h) |
|---|---|---|---|---|
| No mutations (Wild-type) | 37 | 90 | 1 | <0.2 |
| Q109R, A159P, E229S, V352I, S635E, T649K, N672D, I703L, G753E, S754E, S757D, A769T, L775A, D801G, K875T, N892Y | 37 | 90 | 120 | 29 |
| E229N, T631N, N672D, G753E, S754E, A769D, L775A, D801G, K875T, N892Y, N1008D | 37 | 90 | 120 | 40 |
| E229S, N440K, S582K, A624E, S635E, N672D, G753E, S754E, S757D, A769D, L775A, D801G, A843P, K875T, N892Y | 37 | 90 | 120 | 53 |
| E229S, I234V, T631N, N672D, I703L, P752K, G753E, A769D, L775A, D801G, K875T, N892Y | 37 | 90 | 120 | 63 |
| Q109R, A159P, E229S, S582K, S635Q, T649K, G753E, S754E, S757D, A769D, L775A, D801G, K875T, N892Y | 37 | 90 | 120 | 64 |
| Q109R, A159P, A190Q, E229S, G753E, S754E, S757D, A769D, L775A, D801G, K875T, N892Y | 37 | 90 | 120 | 65 |
| A159P, E229S, S635E, T649K, I656V, N672D, G753E, S754E, A769D, L775A, V800P, D801G, K875T, N892Y | 37 | 90 | 120 | 67 |
| T18D, Q89Y, E229S, S635E, T649K, I656V, N672D, G753E, S754E, A769D, L775A, D801G, K875T, N892Y | 37 | 90 | 120 | 69 |
| T18D, A190Q, E229S, S635E, T649K, I656V, N672D, G753E, S754E, A769D, L775A, D801G, K875T, N892Y | 37 | 90 | 120 | 70 |
| Q109R, A159P, E229S, T631N, G753E, S754E, S757D, A769D, L775A, D801G, K875T, N892Y | 37 | 90 | 120 | 71 |
| A58L, E229S, N440K, S582K, T631N, N672D, G753E, S754E, A769D, L775A, D801G, K875T, N892Y, N1008D | 37 | 90 | 120 | 71 |

TABLE 13-continued

Half-life of purified variants: Temperature (T) 37° C., detergent concentration 90%

| Mutations | T (° C.) | Detergent (%) | Incubation time (h) | Half-life (h) |
|---|---|---|---|---|
| E229S, S635E, T649K, I656V, N672D, G753E, S754E, A769D, L775A, V800P, D801G, K875T, N892Y | 37 | 90 | 120 | 72 |
| E229S, T631N, N672D, I703L, P752R, G753E, S754E, A769D, L775A, D801G, K875T, N892Y | 37 | 90 | 120 | 73 |
| T18D, Q109R, E229S, T631N, S635E, T649K, N672D, P752R, G753E, S754E, A769D, L775A, D801G, K875T, N892Y | 37 | 90 | 120 | 74 |
| A190Q, E229S, D458S, K567R, S635E, N672D, G753E, S754E, A769D, L775A, D801G, K875T, N892Y | 37 | 90 | 120 | 74 |
| Q109R, A159P, E229S, T631N, S635Q, T649K, G753E, S754E, S757D, A769D, L775A, D801G, K875T, N892Y | 37 | 90 | 120 | 77 |
| E229S, T631N, N672D, I703L, P752K, G753E, A769D, L775A, D801G, K875T, N892Y | 37 | 90 | 120 | 77 |
| E229S, T631N, N672D, I703L, P752K, G753E, A769D, L775A, D801G, K875T, N892Y, N1008D | 37 | 90 | 120 | 79 |
| Q89Y, E229S, D458S, T631N, N672D, G753E, S754E, S757D, A769D, L775A, D801G, K875T, N892Y | 37 | 90 | 120 | 80 |
| A190Q, E229S, D458S, T631N, N672D, G753E, S754E, A769D, L775A, D801G, K875T, N892Y | 37 | 90 | 120 | 80 |
| Q109R, E229S, T631N, N672D, M728V, P752R, G753E, S754E, S757D, A769D, L775A, D801G, K875T, N892Y | 37 | 90 | 120 | 82 |
| Q109R, A159P, E229S, T631N, S635Q, T649K, G753E, S754E, S757D, A769D, L775A, D801G, K875T, N892Y | 37 | 90 | 120 | 82 |
| Q109R, A159P, E229S, S635Q, T649K, G753E, S754E, S757D, A769D, L775A, D801G, K875T, N892Y | 37 | 90 | 120 | 82 |
| Q109R, A159P, E229S, S635E, T649K, N672D, I703L, M728V, G753E, S754E, S757D, A769T, L775A, D801G, K875T, N892Y | 37 | 90 | 120 | 83 |
| E229S, D458S, T631N, N672D, G753E, S754E, S757D, A769D, L775A, D801G, K875T, N892Y | 37 | 90 | 120 | 83 |
| E229S, D458S, S582K, T631N, N672D, M728V, G753E, S754E, S757D, A769D, L775A, D801G, K875T, N892Y | 37 | 90 | 120 | 84 |
| Q109R, E229S, S582K, T631N, S635E, T649K, N672D, P752R, G753E, S754E, A769D, L775A, D801G, K875T, N892Y | 37 | 90 | 120 | 84 |
| A190Q, E229S, D458S, T631N, S635E, N672D, G753E, S754E, A769D, L775A, D801G, K875T, N892Y | 37 | 90 | 120 | 84 |
| E229S, T631N, N672D, I703L, P752R, G753E, S754E, A769D, L775A, D801G, K875T, N892Y | 37 | 90 | 120 | 84 |
| E229S, S635E, T649K, I656V, N672D, P752K, G753E, S754E, A769D, L775A, V800P, D801G, K875T, N892Y | 37 | 90 | 120 | 84 |
| L46D, E229S, T631N, N672D, I703L, P752K, G753E, A769D, L775A, D801G, K875T, N892Y | 37 | 90 | 120 | 84 |
| A190Q, E229S, R284G, S635E, T649K, I656V, N672D, G753E, S754E, A769D, L775A, V800P, D801G, K875T, N892Y | 37 | 90 | 120 | 85 |
| T18D, A190Q, E229S, D458S, T631N, N672D, G753E, S754E, A769D, L775A, D801G, K875T, N892Y | 37 | 90 | 120 | 85 |
| E229S, S635E, T649K, I656V, N672D, G753E, S754E, A769D, L775A, V800P, D801G, A843P, K875T, N892Y | 37 | 90 | 120 | 86 |
| E229S, I234V, N440K, S582K, A624E, S635E, N672D, G753E, S754E, A769D, L775A, D801G, K875T, N892Y | 37 | 90 | 120 | 86 |
| Q109R, A159P, E229S, S635E, T649K, N672D, I703L, G753E, S754E, S757D, A769T, L775A, V800P, D801G, K875T, N892Y | 37 | 90 | 120 | 86 |
| Q109R, E229S, K360G, T631N, S635E, T649K, N672D, P752R, G753E, S754E, A769D, L775A, D801G, K875T, N892Y | 37 | 90 | 120 | 87 |
| E229S, S582K, T631N, N672D, I703L, P752K, G753E, A769D, L775A, D801G, K875T, N892Y | 37 | 90 | 120 | 87 |
| E229S, I234V, S582K, N672D, M728V, G753E, S754E, A769D, L775A, D801G, K875T, N892Y | 37 | 90 | 120 | 87 |
| E229S, A492L, S635E, T649K, I656V, N672D, G753E, S754E, A769D, L775A, V800P, D801G, K875T, N892Y | 37 | 90 | 120 | 87 |
| E229S, N440K, S582K, A624E, S635E, N672D, G753E, S754E, A769D, L775A, D777K, D801G, K875T, N892Y | 37 | 90 | 120 | 87 |
| L46D, E229S, N440K, S582K, T631N, N672D, G753E, S754E, A769D, L775A, D801G, K875T, N892Y, N1008D | 37 | 90 | 120 | 88 |
| Q109R, A159P, E229S, A624E, S635E, T649K, N672D, I703L, G753E, S754E, S757D, A769T, L775A, D801G, K875T, N892Y | 37 | 90 | 120 | 88 |
| E229S, N672D, G753E, S754E, A769D, L775A, D801G, K875T, N892Y | 37 | 90 | 120 | 88 |
| E229S, A492L, S635E, T649K, I656V, N672D, G753E, A769D, L775A, D801G, K875T, N892Y, N1008D | 37 | 90 | 120 | 88 |
| Q109R, A159P, E229S, T631N, S635E, T649K, N672D, I703L, G753E, S754E, S757D, A769T, L775A, D801G, K875T, N892Y | 37 | 90 | 120 | 88 |
| T18D, S100D, E229S, S635E, T649K, I656V, N672D, I703L, G753E, A769D, L775A, D801G, A843P, K875T, N892Y, N1008D | 37 | 90 | 120 | 88 |
| T18D, E229S, S582K, T664K, N672D, G753E, S754E, A769D, L775A, D801G, K875T, N892Y | 37 | 90 | 120 | 89 |
| Q109R, A159P, E229S, T631N, S635E, T649K, N672D, P752R, G753E, S754E, A769D, L775A, D801G, K875T, N892Y | 37 | 90 | 120 | 89 |
| A58L, E229S, S635E, T649K, I656V, N672D, G753E, S754E, S757D, A769D, L775A, D801G, K875T, N892Y | 37 | 90 | 120 | 91 |
| E229S, V352I, D458S, K567R, S635E, N672D, G753E, S754E, A769D, L775A, D801G, K875T, N892Y | 37 | 90 | 120 | 92 |
| E229S, S635E, T649K, I656V, N672D, P752R, G753E, S754E, A769D, L775A, D801G, K875T, N892Y, N1008D, K1016T | 37 | 90 | 120 | 92 |
| T18D, S100D, E229S, S635E, T649K, I656V, N672D, G753E, S754E, A769D, L775A, D801G, K875T, N892Y | 37 | 90 | 120 | 93 |
| T18D, E229S, A492L, S635E, T649K, I656V, N672D, G753E, S754E, A769D, L775A, D801G, K875T, N892Y | 37 | 90 | 120 | 93 |
| E229S, N440K, D458S, S582K, A624E, S635E, N672D, G753E, S754E, A769D, L775A, D801G, K875T, N892Y | 37 | 90 | 120 | 93 |
| T18D, E229S, Q372H, S582K, N672D, G753E, S754E, A769D, L775A, D801G, K875T, N892Y | 37 | 90 | 120 | 93 |

TABLE 13-continued

Half-life of purified variants: Temperature (T) 37° C., detergent concentration 90%

| Mutations | T (° C.) | Detergent (%) | Incubation time (h) | Half-life (h) |
|---|---|---|---|---|
| E229S, D458S, T631N, N672D, G753E, S754E, S757D, A769D, L775A, D801G, K875T, N892Y | 37 | 90 | 120 | 93 |
| S100D, E229S, N440K, S582K, A624E, S635E, N672D, G753E, S754E, A769D, L775A, D801G, K875T, N892Y | 37 | 90 | 120 | 93 |
| S100D, E229S, S635E, T649K, I656V, N672D, G753E, S754E, A769D, L775A, V800P, D801G, K875T, N892Y | 37 | 90 | 120 | 94 |
| E229S, I234V, S582K, N672D, I703L, G753E, S754E, A769D, L775A, D801G, K875T, N892Y | 37 | 90 | 120 | 95 |
| T18D, E229S, S582K, N672D, G753E, S754E, A769D, L775A, D801G, E856D, K875T, N892Y | 37 | 90 | 120 | 95 |
| Q109R, A159P, E229S, S635Q, T649K, G753E, S754E, S757D, A769D, L775A, D801G, A843P, K875T, N892Y | 37 | 90 | 120 | 95 |
| E229S, T631N, N672D, I703L, P752K, G753E, A769D, L775A, D801G, K875T, N892Y, K1016T | 37 | 90 | 120 | 96 |
| A159P, E229S, A492L, S635E, T649K, I656V, N672D, G753E, A769D, L775A, D801G, K875T, N892Y | 37 | 90 | 120 | 96 |
| E229S, T631N, N672D, I703L, P752K, G753E, A769D, L775A, D801G, A843P, K875T, N892Y | 37 | 90 | 120 | 96 |
| E229S, N440K, S582K, T631N, S635E, T649K, N672D, G753E, S754E, A769D, L775A, D801G, K875T, N892Y, N1008D | 37 | 90 | 120 | 96 |
| E229S, D458S, K567R, S582K, S635E, N672D, G753E, S754E, A769D, L775A, D777R, D801G, K875T, N892Y | 37 | 90 | 120 | 96 |
| T18D, E229S, S582K, N672D, G753E, S754E, A769D, L775A, D801G, K875T, N892Y, I900G | 37 | 90 | 120 | 97 |
| L46D, E229S, K360G, D458S, S582K, N672D, G753E, S754E, A769D, L775A, D801G, K875T, N892Y, N1008D | 37 | 90 | 120 | 97 |
| T18D, E229S, S582K, N672D, G753E, S754E, A769D, L775A, D801G, K819T, K875T, N892Y | 37 | 90 | 120 | 97 |
| S100D, E229S, K360G, D458S, S582K, N672D, G753E, S754E, A769D, L775A, D777R, V800P, D801G, K875T, N892Y, N1008D | 37 | 90 | 120 | 97 |
| E229S, D458S, K567R, S582K, S635E, N672D, G753E, S754E, A769D, L775A, D801G, K875T, N892Y | 37 | 90 | 120 | 98 |
| E229S, A624E, S635E, T649K, I656V, N672D, P752R, G753E, S754E, A769D, L775A, D801G, K875T, N892Y, N1008D | 37 | 90 | 120 | 100 |
| E229S, N440K, K567R, S582K, A624E, S635E, N672D, G753E, S754E, A769D, L775A, D801G, K875T, N892Y | 37 | 90 | 120 | 100 |
| T18D, E229S, S582K, N672D, G753E, S754E, P764V, A769D, L775A, D801G, K875T, N892Y | 37 | 90 | 120 | 100 |
| A190Q, E229S, A492L, S635E, T649K, I656V, N672D, G753E, A769D, L775A, D801G, K875T, N892Y | 37 | 90 | 120 | 100 |
| E229S, N440K, S582K, T631N, N672D, G753E, S754E, A769D, L775A, D801G, A843P, K875T, N892Y, N1008D | 37 | 90 | 120 | 100 |
| T18D, Q89Y, E229S, S582K, N672D, G753E, S754E, A769D, L775A, D801G, K875T, N892Y | 37 | 90 | 120 | 100 |
| S100D, Q109R, A159P, E229S, S635E, T649K, N672D, I703L, G753E, S754E, S757D, A769T, L775A, D801G, K875T, N892Y | 37 | 90 | 120 | 102 |
| Q109R, A159P, E229S, S635E, T649K, N672D, P752G, G753E, S754E, A769D, L775A, D801G, K875T, N892Y | 37 | 90 | 120 | 102 |
| T18D, E229S, S582K, N672D, G753E, S754E, A769D, L775A, D801G, P867S, K875T, N892Y | 37 | 90 | 120 | 102 |
| E229S, K567R, S635E, T649K, I656V, N672D, P752K, G753E, A769D, L775A, D801G, A843P, K875T, N892Y | 37 | 90 | 120 | 102 |
| E229S, D458S, S635E, T649K, I656V, N672D, G753E, S754E, A769D, L775A, V800P, D801G, K875T, N892Y | 37 | 90 | 120 | 104 |
| E229S, S635E, T649K, I656V, N672D, P752K, G753E, S754E, A769D, L775A, D801G, A843P, K875T, N892Y | 37 | 90 | 120 | 104 |
| Q109R, E229S, T631N, S635E, N672D, P752K, G753E, S754E, S757D, A769D, L775A, D801G, K875T, N892Y | 37 | 90 | 120 | 105 |
| E229S, A624E, S635E, T649K, I656V, N672D, G753E, S754R, S757D, A769D, L775A, D777D, D801G, K875T, N892Y | 37 | 90 | 120 | 106 |
| E229S, T631N, S635E, T649K, I656V, N672D, P752K, G753E, S757D, A769D, L775A, D801G, A843P, K875T, N892Y | 37 | 90 | 120 | 106 |
| E229S, D458S, S635E, T649K, I656V, N672D, G753E, S754E, S757D, A769D, L775A, D801G, K875T, N892Y | 37 | 90 | 120 | 106 |
| E229S, D458S, T631N, N672D, G753E, S754E, S757D, A769D, L775A, D777K, D801G, K875T, N892Y | 37 | 90 | 120 | 107 |
| E229S, A624E, S635E, T649K, I656V, N672D, G753E, S754E, S757D, A769D, L775A, D801G, K875T, N892Y | 37 | 90 | 120 | 107 |
| T18D, E229S, S582K, N672D, G753E, S754E, S757D, A769D, L775A, D801G, K875T, N892Y | 37 | 90 | 120 | 107 |
| E229S, I234V, D458S, S582K, N672D, G753E, S754E, A769D, L775A, D801G, K875T, N892Y | 37 | 90 | 120 | 108 |
| Q109R, E229S, K567R, T631N, N672D, P752R, G753E, S754E, S757D, A769D, L775A, D801G, K875T, N892Y | 37 | 90 | 120 | 109 |
| S100D, A190Q, E229S, D458S, T631N, N672D, G753E, S754E, A769D, L775A, D801G, K875T, N892Y | 37 | 90 | 120 | 109 |
| S100D, E229S, S582K, S635E, T649K, I656V, N672D, I703L, G753E, A769D, L775A, D801G, A843P, K875T, N892Y, N1008D | 37 | 90 | 120 | 109 |
| E229S, T631N, N672D, I703L, P752K, G753E, S754E, A769D, L775A, D801G, K875T, N892Y | 37 | 90 | 120 | 109 |
| A190Q, E229S, I234V, S582K, N672D, G753E, S754E, A769D, L775A, D801G, A843P, K875T, N892Y | 37 | 90 | 120 | 110 |
| E229S, D458S, T631N, N672D, G753E, S754E, A769D, L775A, D777R, D801G, K875T, N892Y | 37 | 90 | 120 | 111 |
| T18D, E229S, D458S, K567R, S582K, S635E, N672D, G753E, S754E, A769D, L775A, D801G, K875T, N892Y | 37 | 90 | 120 | 111 |
| E229S, N440K, D458S, S582K, T631N, N672D, G753E, S754E, A769D, L775A, D801G, K875T, N892Y, N1008D | 37 | 90 | 120 | 111 |
| E229S, D458S, K567R, S582K, T631N, S635E, N672D, G753E, S754E, A769D, L775A, D801G, K875T, N892Y | 37 | 90 | 120 | 112 |
| E229S, K360G, D458S, S582K, N672D, P752R, G753E, S754E, A769D, L775A, D801G, K875T, N892Y, N1008D | 37 | 90 | 120 | 112 |

TABLE 13-continued

Half-life of purified variants: Temperature (T) 37° C., detergent concentration 90%

| Mutations | T (° C.) | Detergent (%) | Incubation time (h) | Half-life (h) |
|---|---|---|---|---|
| E229S, D458S, S582K, T631N, N672D, G753E, S754E, S757D, A769D, L775A, D801G, K875T, N892Y | 37 | 90 | 120 | 112 |
| E229S, K360G, D458S, S582K, S635E, N672D, G753E, S754E, A769D, L775A, D801G, K875T, N892Y, N1008D | 37 | 90 | 120 | 112 |
| E229S, S582K, S635E, T649K, I656V, N672D, P752K, G753E, A769D, L775A, D801G, A843P, K875T, N892Y | 37 | 90 | 120 | 112 |
| E229S, D458S, K567R, S582K, S635E, N672D, G753E, S754E, A769D, L775A, D801G, K875T, N892Y, K1016T | 37 | 90 | 120 | 112 |
| E229S, T631N, N672D, P752R, G753E, S754E, A769D, L775A, D801G, A843P, K875T, N892Y | 37 | 90 | 120 | 113 |
| E229S, N440K, S582K, N672D, P752R, G753E, S754E, A769D, L775A, D801G, A843P, K875T, N892Y, N1008D | 37 | 90 | 120 | 113 |
| S100D, E229S, S635E, T649K, I656V, N672D, I703L, G753E, A769D, L775A, D777D, D801G, A843P, K875T, N892Y, N1008D | 37 | 90 | 120 | 114 |
| E229S, D458S, K567R, S582K, S635E, N672D, G753E, S754E, A769D, L775A, D777D, D801G, K875T, N892Y | 37 | 90 | 120 | 115 |
| E229S, D458S, K567R, T631N, S635E, N672D, G753E, S754E, A769D, L775A, D801G, K875T, N892Y | 37 | 90 | 120 | 115 |
| A190Q, E229S, D458S, T631N, N672D, G753E, S754E, A769D, L775A, D801G, K875T, N892Y | 37 | 90 | 120 | 115 |
| E229S, N440K, S582K, A624E, S635E, N672D, G753E, S754E, S757D, A769D, L775A, D801G, K875T, N892Y | 37 | 90 | 120 | 115 |
| A190Q, E229S, D458S, T631N, N672D, G753E, S754E, S757D, A769D, L775A, D801G, K875T, N892Y | 37 | 90 | 120 | 116 |
| Q109R, A159P, E229S, S635Q, T649K, N672D, G753E, S754E, S757D, A769D, L775A, D801G, K875T, N892Y | 37 | 90 | 120 | 116 |
| E229S, N440K, S582K, N672D, P752R, G753E, S754E, A769D, L775A, D801G, A843P, K875T, N892Y | 37 | 90 | 120 | 116 |
| A190Q, E229S, T631N, N672D, I703L, P752K, G753E, A769D, L775A, D801G, K875T, N892Y | 37 | 90 | 120 | 116 |
| T18D, E229S, S582K, N672D, G753E, S754E, A769D, L775A, D801G, K875T, N892Y | 37 | 90 | 120 | 117 |
| E229S, D458S, T631E, S635E, N672D, G753E, S754E, A769D, L775A, D801G, K875T, N892Y | 37 | 90 | 120 | 117 |
| E229S, A492L, S582K, S635E, T649K, I656V, N672D, G753E, A769D, L775A, D801G, K875T, N892Y | 37 | 90 | 120 | 118 |
| S100D, E229S, S635E, T649K, I656V, N672D, P752K, G753E, S754E, A769D, L775A, D801G, K875T, N892Y | 37 | 90 | 120 | 118 |
| E229S, K360G, D458S, S582K, N672D, G753E, S754E, A769D, L775A, V800P, D801G, K875T, N892Y, N1008D | 37 | 90 | 120 | 118 |
| E229S, A624E, S635E, T649K, I656V, N672D, M728V, G753E, S754R, S757D, A769D, L775A, D801G, K875T, N892Y | 37 | 90 | 120 | 118 |
| E229S, D458S, K567R, S635E, N672D, I703L, G753E, S754E, A769D, L775A, D801G, K875T, N892Y | 37 | 90 | 120 | 118 |
| Q109R, E229S, K360G, T631N, N672D, P752R, G753E, S754E, S757D, A769D, L775A, D801G, K875T, N892Y | 37 | 90 | 120 | 119 |
| E229S, K360G, D458S, K567R, S582K, S635E, N672D, G753E, S754E, A769D, L775A, D801G, K875T, N892Y | 37 | 90 | 120 | 119 |
| E229S, N440K, A492L, S582K, T631N, N672D, G753E, S754E, A769D, L775A, D801G, K875T, N892Y, N1008D | 37 | 90 | 120 | 120 |
| E229S, I234V, S582K, N672D, G753E, S754E, S757D, A769D, L775A, D801G, K875T, N892Y | 37 | 90 | 120 | 121 |
| E229S, N440K, A492L, S582K, A624E, S635E, N672D, G753E, S754E, A769D, L775A, D801G, K875T, N892Y | 37 | 90 | 120 | 121 |
| A159P, A190Q, E229S, I234V, S582K, N672D, G753E, S754E, A769D, L775A, D801G, K875T, N892Y | 37 | 90 | 120 | 122 |
| S100D, E229S, D458S, K567R, S635E, N672D, G753E, S754E, A769D, L775A, D801G, K875T, N892Y | 37 | 90 | 120 | 123 |
| A190Q, E229S, N440K, S582K, T631N, N672D, G753E, S754E, A769D, L775A, D801G, K875T, N892Y, N1008D | 37 | 90 | 120 | 124 |
| S100D, Q109R, E229S, R284G, T631N, S635E, T649K, N672D, P752R, G753E, S754E, A769D, L775A, D801G, K875T, N892Y | 37 | 90 | 120 | 125 |
| E229S, V352I, S635E, T649K, I656V, N672D, G753E, S754E, A769D, L775A, V800P, D801G, K875T, N892Y | 37 | 90 | 120 | 125 |
| T18D, Q109R, E229S, T631N, N672D, P752R, G753E, S754E, S757D, A769D, L775A, D801G, K875T, N892Y | 37 | 90 | 120 | 126 |
| S100D, A190Q, E229S, I234V, S582K, N672D, G753E, S754E, A769D, L775A, D801G, K875T, N892Y | 37 | 90 | 120 | 129 |
| S100D, E229S, K360G, D458S, S582K, N672D, G753E, S754E, A769D, L775A, D777K, D801G, K875T, N892Y, N1008D | 37 | 90 | 120 | 129 |
| E229S, K360G, D458S, A492L, S582K, N672D, G753E, S754E, A769D, L775A, D801G, K875T, N892Y, N1008D | 37 | 90 | 120 | 130 |
| E229S, K360G, D458S, S582K, N672D, G753E, S754E, A769D, L775A, D801G, K875T, N892Y, N1008D | 37 | 90 | 120 | 130 |
| S100D, A190Q, E229S, K360G, D458S, S582K, N672D, G753E, S754E, A769D, L775A, D801G, K875T, N892Y, N1008D | 37 | 90 | 120 | 132 |
| E229S, A492L, S635E, T649K, I656V, N672D, G753E, S757D, A769D, L775A, D801G, K875T, N892Y | 37 | 90 | 120 | 134 |
| E229S, A624E, S635E, T649K, I656V, N672D, G753E, S754R, S757D, A769D, L775A, D777K, D801G, K875T, N892Y | 37 | 90 | 120 | 135 |
| A190Q, E229S, S635E, T649K, I656V, N672D, P752K, G753E, A769D, L775A, D801G, A843P, K875T, N892Y | 37 | 90 | 120 | 135 |
| T18D, E229S, A624E, S635E, T649K, I656V, N672D, G753E, S754R, S757D, A769D, L775A, D777K, D801G, K875T, N892Y | 37 | 90 | 120 | 136 |
| E229S, S582K, S635E, N672D, P752R, G753E, S754E, A769D, L775A, D801G, K875T, N892Y, N1008D | 37 | 90 | 120 | 136 |
| A190Q, E229S, N440K, S582K, A624E, S635E, N672D, G753E, S754E, A769D, L775A, D801G, K875T, N892Y | 37 | 90 | 120 | 136 |
| E229S, S582K, S635E, T649K, I656V, N672D, M728V, G753E, S754R, S757D, A769D, L775A, D801G, K875T, N892Y | 37 | 90 | 120 | 137 |
| E229S, D458S, K567R, S582K, S635E, N672D, I703L, G753E, S754E, A769D, L775A, D801G, K875T, N892Y | 37 | 90 | 120 | 137 |

TABLE 13-continued

Half-life of purified variants: Temperature (T) 37° C., detergent concentration 90%

| Mutations | T (° C.) | Detergent (%) | Incubation time (h) | Half-life (h) |
|---|---|---|---|---|
| E229S, I234V, S582K, N672D, G753E, S754E, A769D, L775A, V800P, D801G, K875T, N892Y | 37 | 90 | 120 | 137 |
| E229S, S635E, T649K, I656V, N672D, P752K, G753E, S754E, S757D, A769D, L775A, D801G, A843P, K875T, N892Y | 37 | 90 | 120 | 137 |
| Q109R, E229S, T631N, N672D, P752R, G753E, S754E, S757D, A769D, L775A, D801G, K875T, N892Y, K1016T | 37 | 90 | 120 | 138 |
| E229S, D458S, A624E, S635E, T649K, I656V, N672D, G753E, S754E, S757D, A769D, L775A, D777K, D801G, K875T, N892Y | 37 | 90 | 120 | 138 |
| A190Q, E229S, K360G, D458S, S582K, N672D, G753E, S754E, A769D, L775A, D801G, K875T, N892Y, N1008D | 37 | 90 | 120 | 141 |
| S100D, E229S, N440K, S582K, T631N, N672D, G753E, S754E, A769D, L775A, D801G, K875T, N892Y, N1008D | 37 | 90 | 120 | 142 |
| S100D, E229S, K360G, D458S, S582K, N672D, G753E, S754E, A769D, L775A, D801G, A843P, K875T, N892Y, N1008D | 37 | 90 | 120 | 144 |
| E229S, I234V, A492L, N672D, G753E, S754E, A769D, L775A, D777K, D801G, K875T, N892Y | 37 | 90 | 120 | 145 |
| A190Q, E229S, K360G, D458S, S582K, T664K, N672D, G753E, S754E, A769D, L775A, D801G, K875T, N892Y, N1008D | 37 | 90 | 120 | 146 |
| A190Q, E229S, D458S, T631N, N672D, G753E, S754E, A769D, L775A, D801G, A843P, K875T, N892Y | 37 | 90 | 120 | 147 |
| E229S, N440K, S582K, S635E, N672D, G753E, S754E, A769D, L775A, D801G, A843P, K875T, N892Y, N1008D | 37 | 90 | 120 | 147 |
| E229S, A492L, S635E, T649K, I656V, N672D, P752R, G753E, S754E, A769D, L775A, D801G, K875T, N892Y, N1008D | 37 | 90 | 120 | 147 |
| T18D, E229S, S582K, N672D, G753E, S754E, A769D, L775A, D801G, K875T, N892Y, T902F | 37 | 90 | 120 | 149 |
| E229S, D458S, S582K, A624E, T631N, N672D, M728V, G753E, S754E, S757D, A769D, L775A, D801G, K875T, N892Y | 37 | 90 | 120 | 149 |
| E229S, D458S, T631E, N672D, G753E, S754E, S757D, A769D, L775A, D801G, K875T, N892Y | 37 | 90 | 120 | 151 |
| T18D, E229S, N440K, S582K, A624E, S635E, N672D, G753E, S754E, S757D, A769D, L775A, D801G, K875T, N892Y | 37 | 90 | 120 | 152 |
| E229S, N440K, S582K, A624E, N672D, P752R, G753E, S754E, A769D, L775A, D801G, K875T, N892Y, N1008D | 37 | 90 | 120 | 152 |
| E229S, N440K, S582K, A624E, T631N, S635E, N672D, G753E, S754E, S757D, A769D, L775A, D801G, K875T, N892Y | 37 | 90 | 120 | 153 |
| E229S, N440K, S582K, A624E, S635E, N672D, G738L, G753E, S754E, S757D, A769D, L775A, D801G, K875T, N892Y | 37 | 90 | 120 | 154 |
| E229S, I234V, A492L, S582K, N672D, M728V, G753E, S754E, A769D, L775A, D801G, K875T, N892Y | 37 | 90 | 120 | 157 |
| E229S, D458S, A492L, T631N, N672D, G753E, S754E, S757D, A769D, L775A, D801G, K875T, N892Y | 37 | 90 | 120 | 158 |
| A190Q, E229S, I234V, S582K, N672D, G753E, S754E, S757D, A769D, L775A, D801G, K875T, N892Y | 37 | 90 | 120 | 158 |
| E229S, N440K, S582K, N672D, P752R, G753E, S754E, S757D, A769D, L775A, D801G, K875T, N892Y, N1008D | 37 | 90 | 120 | 158 |
| E229S, S635E, T649K, I656V, N672D, G753E, S754R, S757D, A769D, L775A, D801G, A843P, K875T, N892Y | 37 | 90 | 120 | 159 |
| A190Q, E229S, N440K, S582K, A624E, S635E, N672D, G753E, S754E, S757D, A769D, L775A, D801G, K875T, N892Y | 37 | 90 | 120 | 162 |
| S100D, E229S, D458S, K567R, S582K, S635E, N672D, G753E, S754E, A769D, L775A, D801G, K875T, N892Y | 37 | 90 | 120 | 163 |
| E229S, S635E, N672D, P752R, G753E, S754E, A769D, L775A, D777K, D801G, K875T, N892Y | 37 | 90 | 120 | 169 |
| S100D, A190Q, E229S, K360G, D458S, S582K, N672D, G753E, S754E, A769D, L775A, D801G, K875T, N892Y, N1008D | 37 | 90 | 120 | 170 |
| S100D, E229S, K360G, D458S, S582K, N672D, G753E, S754E, A769D, L775A, D801G, K875T, N892Y, N1008D | 37 | 90 | 120 | 171 |
| E229S, D458S, S582K, T631N, S635E, N672D, M728V, G753E, S754E, S757D, A769D, L775A, D801G, K875T, N892Y | 37 | 90 | 120 | 172 |
| S100D, E229S, K360G, D458S, S582K, N672D, G753E, S754E, S757D, A769D, L775A, D801G, A843P, K875T, N892Y, N1008D | 37 | 90 | 120 | 174 |
| E229S, I234V, A492L, S582K, N672D, G753E, S754E, A769D, L775A, D801G, K875T, N892Y | 37 | 90 | 120 | 174 |
| E229S, D458S, S582K, T631E, N672D, G753E, S754E, A769D, L775A, D801G, K875T, N892Y | 37 | 90 | 120 | 175 |
| E229S, I234V, A492L, N672D, G753E, S754E, A769D, L775A, D777R, D801G, K875T, N892Y | 37 | 90 | 120 | 176 |
| S100D, E229S, K360G, D458S, S582K, N672D, G753E, S754E, S757D, A769D, L775A, D801G, A843P, K875T, N892Y | 37 | 90 | 120 | 179 |
| E229S, A624E, S635E, T649K, I656V, N672D, G753E, S754R, S757D, A769D, L775A, D777K, D801G, K875T, N892Y | 37 | 90 | 120 | 185 |
| S100D, E229S, K360G, D458S, S582K, N672D, G753E, S754E, S757D, A769D, L775A, D801G, A843P, K875T, N892Y, T915A, N1008D | 37 | 90 | 120 | 189 |
| T18D, E229S, D458S, T631N, N672D, M728V, G753E, S754E, S757D, A769D, L775A, D801G, K875T, N892Y | 37 | 90 | 120 | 191 |
| S100D, E229S, N440K, S582K, N672D, P752R, G753E, S754E, A769D, L775A, D801G, K875T, N892Y, N1008D | 37 | 90 | 120 | 192 |
| T18D, E229S, S582K, N672D, G753E, S754E, P764K, A769D, L775A, D801G, K875T, N892Y | 37 | 90 | 120 | 202 |
| E229S, D458S, T631N, N672D, G753E, S754E, A769D, L775A, D777K, D801G, K875T, N892Y | 37 | 90 | 120 | 203 |
| E229S, S582K, S635E, T649K, I656V, N672D, P752R, G753E, S754E, S757D, A769D, L775A, D801G, A843P, K875T, N892Y | 37 | 90 | 120 | 209 |
| E229S, A624E, S635E, T649K, I656V, N672D, G738L, G753E, S754R, S757D, A769D, L775A, D777K, D801G, K875T, N892Y | 37 | 90 | 120 | 210 |
| A159P, E229S, D458S, T631N, N672D, M728V, G753E, S754E, S757D, A769D, L775A, D801G, K875T, N892Y | 37 | 90 | 120 | 223 |
| A190Q, E229S, S582K, N672D, G753E, S754E, A769D, L775A, D801G, K875T, N892Y | 37 | 90 | 120 | 226 |

TABLE 13-continued

Half-life of purified variants: Temperature (T) 37° C., detergent concentration 90%

| Mutations | T (° C.) | Detergent (%) | Incubation time (h) | Half-life (h) |
|---|---|---|---|---|
| A190Q, E229S, K360G, D458S, S582K, N672D, G753E, S754E, S757D, A769D, L775A, D801G, K875T, N892Y, N1008D | 37 | 90 | 120 | 234 |

The invention claimed is:

1. A xanthan lyase variant, which
    (a) comprises a substitution at one or more positions selected from the group consisting of G753, S754, S757, A769, L775 and D801, wherein the numbering corresponds to SEQ ID NO: 2, and wherein
        (i) the substitution at position 753 is with Ala, Arg, Asn, Asp, Cys, Gln, Glu, His, Ile, Leu, Lys, Met, Phe, Pro, Ser, Thr, Trp, Tyr, or Val;
        (ii) the substitution at position 754 is with Ala, Arg, Asn, Asp, Cys, Gln, Glu, Gly, His, Ile, Leu, Lys, Met, Phe, Pro, Thr, Trp, Tyr, or Val
        (iii) the substitution at position 757 is with Ala, Arg, Asn, Asp, Cys, Gln, Glu, Gly, His, Ile, Leu, Lys, Met, Phe, Pro, Thr, Trp, Tyr, or Val,
        (iv) the substitution at position 769 is with Arg, Asn, Asp, Cys, Gln, Glu, Gly, His, Ile, Leu, Lys, Met, Phe, Pro, Ser, Thr, Trp, Tyr, or Val,
        (v) the substitution at position 775 is with Ala, Arg, Asn, Asp, Cys, Gln, Glu, Gly, His, Ile, Lys, Met, Phe, Pro, Ser, Thr, Trp, Tyr, or Val, and
        (vi) the substitution at position 801 is with Ala, Arg, Asn, Cys, Gln, Glu, Gly, His, Ile, Leu, Met, Phe, Pro, Ser, Thr, Trp, Tyr, or Val;
    (b) has at least 85% and less than 100% sequence identity to SEQ ID NO: 2; and
    (c) has xanthan lyase activity.

2. The xanthan lyase variant of claim 1, which comprises G753E, G753Q, or G753S.

3. The xanthan lyase variant of claim 1, which comprises S754E, S754L, S754Q, or S754R.

4. The xanthan lyase variant of claim 1, which comprises S757D, S757P, or S757E.

5. The xanthan lyase variant of claim 1, which comprises A769D, A769T, or A769R.

6. The xanthan lyase variant of claim 1, which comprises L775A, L775F, L775I, L775M, L775Q, L775S, or L775Y.

7. The xanthan lyase variant of claim 1, which comprises D801G.

8. The xanthan lyase variant of claim 1, which further comprises a substitution selected from the group consisting of G738L, K745R, P752R, P752K, D777R, P779V, Y782I, N786K, G789R, K792W, K792Y, K792V, K792A, N796Q, and A799H.

9. The xanthan lyase variant of claim 1, which further comprises a substitution at one or more positions selected from the group consisting of positions 89, 100, 190, 229, 234, 352, 360, 399, 440, 458, 492, 567, 582, 664, 672, 703, 728, 892, 1008 and 1016.

10. The xanthan lyase variant of claim 9, wherein the substitution is selected from the group consisting of Q89Y, S100D, A190Q, E229S, I234V, V352I, K360G, N399K, N440K, D458S, A492H, A492L, K567R, S582K, T664K, N672D, I703L, M728V, N892Y N1008D and K1016T.

11. The xanthan lyase variant of claim 1, which further comprises a substitution at one or more positions selected from the group consisting of:
    (a) amino acids 154 to 176,
    (b) amino acids 614 to 658,
    (c) amino acids 807 to 846,
    (d) amino acids 872 to 885, and
    (e) amino acids 903 to 1004.

12. The xanthan lyase variant of claim 11, further comprising a substitution at one or more positions selected from the group consisting of: 155, 159, 620, 624, 626, 631, 635, 649, 650, 656, 819, 824, 843, 875, 903, 911, 912, 915, 919, 921, 923, 925, 927, 928, 930, 933, 941, 966, 991 and 998.

13. The xanthan lyase variant of claim 12, wherein the substitution is selected from the group consisting of: Y155E, A159P, K620R, A624E, A626Q, T631N, S635E, S635T, T649V, T649K, Q650G, I656V, K819R, K824R, A843P, K875T, K875E, T903A, T903Q, A911M, A911V, A911S, A912T, A912I, A912Y, T915S, T915V, T915Q, T919D, T919F, T919G, T921R, T921S, T923D, T923H, T925D, T925Q, T925R, T927K, D928W, Y930F, Y930H, Y930L, D933M, G941D, G941E, A966P, N991D and V998K.

14. The xanthan lyase variant of claim 1, wherein the variant has at least 90% sequence identity to SEQ ID NO: 2.

15. The xanthan lyase variant of claim 1, wherein the variant has at least 95% sequence identity to SEQ ID NO: 2.

16. The xanthan lyase variant of claim 1, which comprises
    Q109R, E229S, K567R, G753E, S754E, A769T, L775A, K875T, N892Y;
    Q109R, E229S, S578K, G753E, S754E, A769T, L775A, K875T, N892Y;
    Q109R, E229S, S578K, A769T, L775A, K875T, N892Y;
    Q109R, E229S, T631N, G753E, S754E, A769T, L775A, K875T, N892Y;

Q109R, E229S, S635T, G753E, S754E, A769T, L775A, K875T, N892Y;
Q109R, E229S, N672D, G753E, S754E, A769T, L775A, K875T, N892Y;
Q109R, E229S, P752K, G753E, A769T, L775A, K875T, N892Y;
Q109R, E229S, P752K, S754E, A769T, L775A, K875T, N892Y;
Q109R, E229S, P752R, G753E, S754E, A769T, L775A, K875T, N892Y;
Q109R, E229S, G753E, S754E, A769E, L775A, K875T, N892Y;
Q109R, E229S, G753E, S754E, A769T, L775A, D801G, K875T, N892Y;
Q109R, E229S, G753E, S754E, A769T, L775A, A843P, K875T, N892Y;
Q109R, E229S, G753E, S754E, A769T, L775A, K875T, N892Y;
Q109R, E229S, G753E, S754E, A769T, L775A, K875T, N892Y, A932P;
Q109R, E229S, G753E, S754E, A769T, L775A, K875T, N892Y, K1016T;
Q109R, E229S, G753E, A769T, L775A, K875T, N892Y;
Q109R, E229S, A769D, L775A, K875T, N892Y;
Q109R, E229S, A769T, L775A, K792Y, K875T, N892Y;
Q109R, E229S, A769T, L775A, D801G, K875T, N892Y;
Q109R, N672D, G753E, S754E, A769T, L775A, K875T, N892Y;
Q109R, P752K, G753E, S754E, A769T, L775A, K875T, N892Y;
Q109R, P752K, G753E, A769T, L775A, K875T, N892Y;
Q109R, P752K, G753E, L775A, D801G, K875T;
Q109R, P752R, G753E, S754E, A769T, L775A, K875T, N892Y,
Q109R, P752R, G753E, A769T, L775A, K875T, N892Y;
Q109R, G753E, S754E, A769T, L775A, D801G, K875T, N892Y;
Q109R, G753E, S754E, A769T, L775A, K875T, N892Y;
Q109R, G753E, A769T, L775A, K875T, N892Y; or
A190Q, A769D, L775A, D801G, K875T, N892Y.

17. The xanthan lyase variant of claim 1, which comprises
E229N, S578K, A769D, L775A, K875T, N892Y;
E229N, G753E, L775A, D801G, K875T, N892Y;
E229N, A769D, L775A, D801G, K875T, N892Y;
E229S, K360R, S578K, P752K, G753E, S754E;
E229S, K360R, S578K, P752K, G753E, A769D, L775A, K875T, N892Y;
E229S, K360R, S578K, P752K, A769D, L775A, K875T, N892Y;
E229S, K360R, S578K, P752R, G753E, A769D, L775A, K875T, N892Y;
E229S, K360R, S578K, P752R, S754E, A769T, L775A, K875T, N892Y;
E229S, K360R, S578K, P752R, A769D, L775A, K875T, N892Y;
E229S, K360R, S578K, G753E, S754E, A769D, L775A, K875T, N892Y;
E229S, K360R, S578K, S754E, A769D, L775A, K875T, N892Y;
E229S, K360R, S578K, A769D, L775A, K792Y;
E229S, F419Y, S578K, G753E;
E229S, A492L, S578K, G753E;
E229S, A492L, S578K, G753E, S754E;
E229S, A492L, S578K, G753E, A769D;
E229S, A492L, S578K, G753E, L775A;
E229S, A492L, S578K, G753E, L775A, P779V;
E229S, A492L, S578K, G753E, L775A, K792Y;
E229S, A492L, S578K, G753E, D801G;
E229S, A492L, S578K, G753E, N1008D;
E229S, A492L, S578K, G753E, K1016T;
E229S, S578K, T631N, P752K, G753E, S754E;
E229S, S578K, T631N, G753E;
E229S, S578K, T631N, G753E, S754E;
E229S, S578K, T631N, G753E, A769D, A774V, L775A, P779V, K792Y;
E229S, S578K, T631N, G753E, A769D, K792Y;
E229S, S578K, T631N, G753E, A769T, L775A;
E229S, S578K, T631N, G753E, D801G;
E229S, S578K, T631N, G753E, D901A;
E229S, S578K, T631N, G753E, A912T;
E229S, S578K, T631N, G753E, K1016T;
E229S, S578K, P752K, S754E;
E229S, S578K, P752R, G753E;
E229S, S578K, P752R, S754E;
E229S, S578K, G753E;
E229S, S578K, G753E, S754E;
E229S, S578K, G753E, L775A, P779V;
E229S, S578K, G753E, A843P;
E229S, S578K, G753E, N892Y;
E229S, S578K, G753E, A912T;
E229S, S578K, G753E, N1008D;
E229S, S578K, S754E;
E229S, S578K, A769D, L775A, K875T, N892Y;
E229S, S578K, A769D, P779V;
E229S, S578K, A769D, K792Y;
E229S, S578K, L775A, P779V, K792Y;
E229S, S578K, L775A, K792Y; or
E229S, S578K, D801G.

18. The xanthan lyase variant of claim 1, which comprises
E229S, S578R, P752K, S754E, K792Y, N892Y, A912T;
E229S, S578R, P752R, G753E, K792Y, N892Y, A912T;
E229S, S578R, G753E, A769D, L775A, N892Y;
E229S, S578R, G753E, A769D, P779V, N892Y;
E229S, S578R, G753E, A769D, K792Y, N892Y;
E229S, S578R, A769D, L775A, K792Y, N892Y, A912T;
E229S, S578R, A769D, P779V, K792Y, N892Y;
E229S, S578R, A769S, K792Y, N892Y;
E229S, S578R, L775A, P779V, K792Y, N892Y;
E229S, S578R, L775A, K792Y, N892Y, A912T;
E229S, S578R, K792Y, D801G, N892Y;
E229S, G753E, L775A, D801G, K875T, N892Y;
E229S, A769D, L775A, D801G, K875T, N892Y;
E229S, A769D, L775A, K875T, N892Y; or
E229S, L775A, D801G, K875T, N892Y.

19. The xanthan lyase variant of claim 1, which comprises
T631N, A769D, L775A, D801G, K875T, N892Y;
S635T, A769D, L775A, D801G, K875T, N892Y;
N672D, G753E, L775A, D801G, K875T, N892Y;
N672D, A769D, L775A, D801G, K875T, N892Y;
P752K, G753E, S754E, A769D, L775A, D801G, K875T, N892Y;
P752K, G753E, S754E, L775A, D801G, K875T, N892Y;
P752K, G753E, L775A, D801G, K875T, N892Y;
P752R, G753E, S754E, A769D, L775A, D801G, K875T, N892Y;
P752R, G753E, A769D, L775A, D801G, K875T, N892Y;
P752R, G753E, L775A, D801G, K875T, N892Y;
P752R, S754E, L775A, D801G, K875T, N892Y;
G753E, S754E, L775A, D801G, K875T, N892Y;
G753E, A769D, L775A, D801G, K875T, N892Y;
G753E, L775A, D801G, K875T, N892Y;
G753E, L775A, D801G, K875T, N892Y, A912T;
G753E, L775A, D801G, K875T, N892Y, V998K;
A769D, L775A, D801G, A843P, K875T, N892Y;

A769D, L775A, D801G, K875T, N892Y;
A769D, L775A, D801G, K875T, N892Y, V998K; or
A769D, L775A, D801G, K875T, N892Y, N1008D.

20. A non-detergent composition comprising a xanthan lyase variant of claim 1.

21. A method of reducing viscosity of a xanthan gum-containing fluid, the method comprising contacting the xanthan gum-containing fluid with a composition comprising a xanthan lyase variant of claim 1.

* * * * *